(12) United States Patent
Tomlinson et al.

(10) Patent No.: US 9,066,925 B2
(45) Date of Patent: Jun. 30, 2015

(54) METHODS OF STIMULATING LIVER REGENERATION

(75) Inventors: Stephen Tomlinson, Mount Pleasant, SC (US); Songqing He, Charleston, SC (US); Carl Atkinson, Mount Pleasant, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 473 days.

(21) Appl. No.: 13/380,477

(22) PCT Filed: Jul. 2, 2010

(86) PCT No.: PCT/US2010/040973
§ 371 (c)(1),
(2), (4) Date: Mar. 19, 2012

(87) PCT Pub. No.: WO2011/003098
PCT Pub. Date: Jan. 6, 2011

(65) Prior Publication Data
US 2012/0171206 A1 Jul. 5, 2012

Related U.S. Application Data

(60) Provisional application No. 61/222,867, filed on Jul. 2, 2009.

(51) Int. Cl.
*A61K 39/00* (2006.01)
*A61K 39/385* (2006.01)
*A61K 38/39* (2006.01)
*A61K 38/17* (2006.01)

(52) U.S. Cl.
CPC ............ *A61K 38/39* (2013.01); *A61K 38/1709* (2013.01); *A61K 38/177* (2013.01)

(58) Field of Classification Search
None
See application file for complete search history.

(56) References Cited

U.S. PATENT DOCUMENTS

| | | | |
|---|---|---|---|
| 4,845,083 A | 7/1989 | Fortin et al. | |
| 4,883,784 A | 11/1989 | Kaneko | |
| 5,212,071 A | 5/1993 | Fearon et al. | |
| 5,260,203 A | 11/1993 | Ladner et al. | |
| 5,310,729 A | 5/1994 | Lernhardt | |
| 5,328,470 A | 7/1994 | Nabel et al. | |
| 5,331,090 A | 7/1994 | Lernhardt | |
| 5,472,939 A | 12/1995 | Fearon et al. | |
| 5,679,345 A | 10/1997 | Sanfilippo et al. | |
| 5,679,546 A | 10/1997 | Ko et al. | |
| 5,851,528 A | 12/1998 | Ko et al. | |
| 5,869,615 A | 2/1999 | Hourcade et al. | |
| 5,976,540 A | 11/1999 | Rittershaus et al. | |
| 5,981,481 A | 11/1999 | Fearon et al. | |
| 6,140,472 A | 10/2000 | Rosengard et al. | |
| 6,165,463 A | 12/2000 | Platz et al. | |
| 6,214,966 B1 | 4/2001 | Harris | |
| 6,224,866 B1 | 5/2001 | Barbera-Guillem | |
| 6,248,365 B1 | 6/2001 | Romisch et al. | |
| 6,291,239 B1 | 9/2001 | Prodinger et al. | |
| 6,355,245 B1 | 3/2002 | Evans et al. | |
| 6,368,596 B1 | 4/2002 | Ghetie et al. | |
| 6,432,679 B1 | 8/2002 | Mond et al. | |
| 6,458,360 B1 | 10/2002 | Fearon et al. | |
| 6,503,947 B1 | 1/2003 | Lipton et al. | |
| 6,521,450 B1 | 2/2003 | Atkinson et al. | |
| 6,572,856 B1 | 6/2003 | Taylor et al. | |
| 6,820,011 B2 | 11/2004 | Chen et al. | |
| 6,897,290 B1 | 5/2005 | Atkinson et al. | |
| 6,962,903 B2 | 11/2005 | Allison | |
| 7,407,475 B2 | 8/2008 | Allison | |
| 7,423,128 B2 | 9/2008 | Gazit-Bornstein et al. | |
| 7,439,331 B2 | 10/2008 | Fung et al. | |
| 7,576,182 B1 | 8/2009 | Goddard et al. | |
| 7,635,676 B2 | 12/2009 | Allison | |
| 7,635,678 B2 | 12/2009 | Allison | |
| 7,635,679 B2 | 12/2009 | Fumero et al. | |
| 7,635,680 B2 | 12/2009 | Allison | |
| 7,645,739 B2 | 1/2010 | Allison | |
| 7,759,304 B2 | 7/2010 | Gilkeson et al. | |
| 7,964,105 B2 | 6/2011 | Moss | |
| 7,964,705 B2 | 6/2011 | Emlen et al. | |
| 7,999,082 B2 | 8/2011 | Holers et al. | |
| 8,007,804 B2 | 8/2011 | Tomlinson et al. | |
| 2002/0015701 A1 | 2/2002 | Gupta-Bansal et al. | |

(Continued)

FOREIGN PATENT DOCUMENTS

| | | |
|---|---|---|
| CA | 1340879 A | 1/2000 |
| EP | 0358130 A2 | 3/1990 |

(Continued)

OTHER PUBLICATIONS

Tang "Exogenous biliverdin ameliorates ischemia-reperfusion injury in small-for-size rat liver grafts" Transplantation Proceedings, 39, 1338-1344 (2007).*
Yang et al. "The role of complement C3 in intracerebral hemorrhage-induced brain injury" J. Cerebral Blood Flow & Metabolism (2006), 26, pp. 1490-1495.*
Fondevila et al. "The membrane attack complex (C5b-9) in liver cold ischemia and reperfusion injury" Liver Transpl. 2008, 14(8), pp. 1133-1141.*
Qin et al.,"The complement system in liver diseases," Cell Mol Immunol. 3(5):333-340 (2006).
"Monoclonal antibody to human C3(C3d), Catalog No. A207," Quidel Corporation Product Catalog, <http://www.quidel.com/products/product_detail.php?prod=73&group=2>, retrieved on Apr. 25, 2013 (2 pages).
"Monoclonal antibody to human C3d (neo), Catalog No. A250," Quidel Corporation Product Catalog, <http://www.quidel.com/products/product_detail.php?prod=160&group=2>, retrieved on Dec. 26, 2013 (2 pages).

(Continued)

*Primary Examiner* — Daniel E Kolker
*Assistant Examiner* — James Rogers
(74) *Attorney, Agent, or Firm* — Clark & Elbing LLP; Kristina Bieker-Brady; Todd Armstrong

(57) ABSTRACT

Provided herein are methods and compositions, including pharmaceutical compositions, for stimulating liver regeneration after partial hepatectomy, massive liver resection and toxic injury, or following liver transplantation, including small-for-size liver transplantation, by inhibiting activation of complement.

19 Claims, 32 Drawing Sheets

(56) References Cited

U.S. PATENT DOCUMENTS

| | | |
|---|---|---|
| 2002/0081293 A1 | 6/2002 | Fung et al. |
| 2002/0103346 A1 | 8/2002 | Vogel et al. |
| 2003/0077273 A1 | 4/2003 | Linnik et al. |
| 2003/0165509 A1 | 9/2003 | Ghetie et al. |
| 2003/0180292 A1 | 9/2003 | Hanna et al. |
| 2003/0198636 A1 | 10/2003 | Gupta-Bansal et al. |
| 2003/0235582 A1 | 12/2003 | Singh et al. |
| 2004/0005538 A1 | 1/2004 | Chen et al. |
| 2004/0014782 A1 | 1/2004 | Krause |
| 2004/0191252 A1 | 9/2004 | Taylor et al. |
| 2004/0219156 A1 | 11/2004 | Goldenberg et al. |
| 2004/0229827 A1 | 11/2004 | Steward et al. |
| 2005/0002128 A1 | 1/2005 | Ito et al. |
| 2005/0032128 A1 | 2/2005 | Halperin |
| 2005/0107319 A1 | 5/2005 | Bansal |
| 2005/0169915 A1 | 8/2005 | Do Couto et al. |
| 2005/0232920 A1 | 10/2005 | Fung et al. |
| 2005/0255552 A1 | 11/2005 | Flynn et al. |
| 2005/0260198 A1 | 11/2005 | Holers et al. |
| 2005/0265995 A1 | 12/2005 | Tomlinson et al. |
| 2006/0002944 A1 | 1/2006 | Ashkenazi et al. |
| 2006/0014681 A1 | 1/2006 | Chen et al. |
| 2006/0134098 A1 | 6/2006 | Bebbington et al. |
| 2006/0178308 A1 | 8/2006 | Schwaeble et al. |
| 2006/0263819 A1 | 11/2006 | Hageman et al. |
| 2006/0276388 A1 | 12/2006 | Christa et al. |
| 2006/0292141 A1 | 12/2006 | Holers et al. |
| 2007/0003544 A1 | 1/2007 | Hanna |
| 2007/0020647 A1 | 1/2007 | Hageman et al. |
| 2007/0065433 A1 | 3/2007 | Mollnes et al. |
| 2007/0134260 A1 | 6/2007 | Feger et al. |
| 2007/0172483 A1 | 7/2007 | Schwaeble et al. |
| 2007/0183970 A1 | 8/2007 | Goldenberg et al. |
| 2007/0224197 A1 | 9/2007 | Chen et al. |
| 2008/0029911 A1 | 2/2008 | Jeon et al. |
| 2008/0075720 A1 | 3/2008 | Holers et al. |
| 2008/0102040 A1 | 5/2008 | Holers et al. |
| 2008/0118506 A1 | 5/2008 | An et al. |
| 2008/0221011 A1 | 9/2008 | Gilkeson et al. |
| 2008/0267980 A1 | 10/2008 | Tomlinson et al. |
| 2008/0299114 A1 | 12/2008 | Emlen et al. |
| 2009/0081211 A1 | 3/2009 | Campagne |
| 2009/0087907 A1 | 4/2009 | Pebay et al. |
| 2009/0123469 A1 | 5/2009 | Campagne et al. |
| 2009/0175847 A1 | 7/2009 | Barghorn et al. |
| 2009/0175875 A1 | 7/2009 | Etemad-Gilbertson et al. |
| 2009/0304706 A1 | 12/2009 | Lu et al. |
| 2011/0014614 A1 | 1/2011 | Liew |
| 2011/0015127 A1 | 1/2011 | Gilkeson et al. |
| 2011/0163412 A1 | 7/2011 | Park |
| 2011/0286938 A1 | 11/2011 | Thurman et al. |
| 2011/0293605 A1 | 12/2011 | Sathish et al. |
| 2011/0318337 A1 | 12/2011 | Emlen et al. |
| 2012/0014952 A1 | 1/2012 | Tomlinson et al. |
| 2012/0015871 A1 | 1/2012 | Tomlinson et al. |
| 2012/0015872 A1 | 1/2012 | Tomlinson et al. |
| 2012/0135430 A1 | 5/2012 | Zhang et al. |
| 2012/0171206 A1 | 7/2012 | Tomlinson et al. |
| 2013/0029912 A1 | 1/2013 | Holers et al. |
| 2013/0129728 A1 | 5/2013 | Holers et al. |
| 2013/0190477 A1 | 7/2013 | Kovacs et al. |

FOREIGN PATENT DOCUMENTS

| | | |
|---|---|---|
| EP | 0402226 A1 | 12/1990 |
| EP | 0402266 A2 | 12/1990 |
| EP | 1336618 A1 | 8/2003 |
| EP | 1336618 A1 * | 8/2003 |
| JP | 05507197 A | 10/1993 |
| JP | 09502985 A | 3/1997 |
| JP | 2002-534959 A | 10/2002 |
| WO | WO-91/16437 A1 | 10/1991 |
| WO | WO-96/12742 A1 | 5/1996 |
| WO | WO-98/07835 A2 | 2/1998 |
| WO | WO-99/42133 A1 | 8/1999 |
| WO | WO-99/44625 A1 | 9/1999 |
| WO | WO-00/21559 A2 | 4/2000 |
| WO | WO-00/34317 A2 | 6/2000 |
| WO | WO-00/34317 A3 | 8/2000 |
| WO | WO-00/67796 A1 | 11/2000 |
| WO | WO-01/47963 A2 | 7/2001 |
| WO | WO-02/068579 A2 | 9/2002 |
| WO | WO-2004/022096 A1 | 3/2004 |
| WO | WO-2004/031240 A1 | 4/2004 |
| WO | WO-2004/045520 A2 | 6/2004 |
| WO | WO-2004/103288 A2 | 12/2004 |
| WO | WO-2004/106369 A2 | 12/2004 |
| WO | WO-2005/003159 A1 | 1/2005 |
| WO | WO-2005/014618 A2 | 2/2005 |
| WO | WO-2005/023195 A2 | 3/2005 |
| WO | WO-2005/044998 A2 | 5/2005 |
| WO | WO-2005/069970 A2 | 8/2005 |
| WO | WO-2005/072479 A2 | 8/2005 |
| WO | WO-2005/077417 A1 | 8/2005 |
| WO | WO-2006/012621 A2 | 2/2006 |
| WO | WO-2006/030220 A1 | 3/2006 |
| WO | WO-2006/055178 A2 | 5/2006 |
| WO | WO-2006/062716 A2 | 6/2006 |
| WO | WO-2006/083533 A2 | 8/2006 |
| WO | WO-2006/088950 A2 | 8/2006 |
| WO | WO-2006/122257 A2 | 11/2006 |
| WO | WO-2006/128006 A1 | 11/2006 |
| WO | WO-2007/011363 A2 | 1/2007 |
| WO | WO-2007/029008 A2 | 3/2007 |
| WO | WO-2007/032876 A2 | 3/2007 |
| WO | WO-2007/035857 A2 | 3/2007 |
| WO | WO-2007/056227 A2 | 5/2007 |
| WO | WO-2007/112403 A2 | 10/2007 |
| WO | WO-2007/129895 A2 | 11/2007 |
| WO | WO-2007/149567 A2 | 12/2007 |
| WO | WO-2008/140653 A2 | 11/2008 |
| WO | WO-2008/154251 A2 | 12/2008 |
| WO | WO-2009/029669 A1 | 3/2009 |
| WO | WO-2009/056631 A2 | 5/2009 |
| WO | WO-2009061910 A1 | 5/2009 |
| WO | WO-2009/110918 A1 | 9/2009 |
| WO | WO-2010/015608 A1 | 2/2010 |
| WO | WO-2010/091183 A2 | 8/2010 |
| WO | WO-2010/136311 A2 | 12/2010 |
| WO | WO-2011/057158 A1 | 5/2011 |
| WO | WO-2011/143637 A1 | 11/2011 |
| WO | WO-2011/163412 A1 | 12/2011 |
| WO | WO-2013/117035 A1 | 8/2013 |
| WO | WO-2013/177035 A2 | 11/2013 |

OTHER PUBLICATIONS

"Monoclonal antibody to human factor B (Ba), Catalog No. A225," Quidel Corporation Product Catalog, <http://www.quidel.com/products/product_detail.php?group=2&prod=82>, retrieved on Aug. 4, 2008 (2 pages).

"Monoclonal antibody to human factor B (Bb), Catalog No. A227," Quidel Corporation Product Catalog, <http://www.quidel.com/products/product_detail.php?group=2&prod=83>, retrieved on Aug. 4, 2008 (2 pages).

Abbas, et al., eds., *Cellular and Molecular Immunology*. W.B. Saunders Company, 54 (1991).

Abe et al., "Contribution of anaphylatoxin C5a to late airway responses after repeated exposure of antigen to allergic rats," J Immunol. 167:4651-4660 (2001).

Abrahamsen et al., "Differential mediator release from basophils of allergic and non-allergic asthmatic patients after stimulation with anti-IgE and C5a," Clin Exp Allergy. 31:368-378 (2001).

Abrahmsén et al., "Engineering subtilisin and its substrates for efficient ligation of peptide bonds in aqueous solution," Biochemistry. 30:4151-4159 (1991).

Aguado et al., "Monoclonal antibodies against complement 3 neoantigens for detection of immune complexes and complement activation. Relationship between immune complex levels, state of C3, and numbers of receptors for C3b," J Clin Invest. 76:1418-26 (1985).

Ahearn et al., "Disruption of the Cr2 locus results in a reduction in B-1a cells and in an imparied B cell response to T-dependent antigen," Immunity. 4(3):251-262 (1996).

(56) References Cited

OTHER PUBLICATIONS

Ahearn et al., "Epstein-Barr virus (EBV) infection of murine L cells expressing recombinant human EBV/C3d receptor," Proc Natl Acad Sci USA. 85:9307-11 (1988).
Ahearn et al., "Structure and function of the complement receptors, CR1 (CD35) and CR2 (CD21)," Adv Immunol. 46:183-219 (1989).
Alexander et al., "Complement-dependent apoptosis and inflammatory gene changes in murine lupus cerebritis," J Immunol. 175(12):8312-8319 (2005).
Amsterdam et al., "Limitation of reperfusion injury by a monoclonal antibody to C5a during myocardial infarction in pigs," Am J Physiol. 268(1):H448-57 (1995).
Anderson et al., "Activation of complement pathways after contusion-induced spinal cord injury," J Neurotrauma. 21:1831-1846 (2004).
Andrews et al., "Spontaneous murine Lupus-like syndromes. Clinical and immunopathological manifestations in several strains," J Exp Med. 148:1198-215 (1978).
Arumugam et al., "Complement mediators in ischemia-reperfusion injury," Clin Chim Acta. 374:33-45 (2006).
Arumugam et al., "Protective effect of a human C5a receptor antagonist against hepatic ischaemia-reperfusion injury to rats," J Hepatol. 40:934-41 (2004).
Aslam et al., "Folded-back solution structure of monomeric factor H of human complement by synchrotron X-ray and neutron scattering, analytical ultracentrifugation and constrained molecular modelling," J Mol Biol. 309(5):1117-1138 (2001).
Asokan et al., "Characterization of human complement receptor type 2 (CR2/CD21) as a receptor for IFN-alpha: a potential role in systemic lupus erythematosus," J Immunol. 177:383-94 (2006).
Atkinson et al., "Complement-dependent P-selectin expression and injury following ischemic stroke," J Immunol. 177:7266-74 (2006).
Atkinson et al., "Targeted complement inhibition by C3d recognition ameliorates tissue injury without apparent increase in susceptibility to infection," J Clin Invest. 115(9):2444-53 (2005).
Atkinson et al., "Targeted complement inhibitors protect against posttransplant cardiac ischemia and reperfusion injury and reveal an important role for the alternative pathway of complement activation," J Immunol. 185:7007-13 (2010).
Atkinson et al., "Targeted inhibition of the alternative complement pathway delays the onset of antibody-mediated rejection in a mouse heterotopic heart transplant model," Mol Immunol. 44:3944, Abstract No. P24 (2007).
Attwood, "The babel of bioinformatics," Science. 290:471-3 (2000).
Aubry et al., "CD21 is a ligand for CD23 and regulates IgE production," Nature. 358(6386):505-507 (1992).
Aubry et al., "CD23 interacts with a new functional extracytoplasmic domain involving N-linked oligosaccharides on CD21," J Immunol. 152:5806-13 (1994).
Author manuscript of Clark et al., "Evidence for non-traditional activation of complement factor C3 during murine liver regeneration," available in PMC Jun. 1, 2009, published in final edited form as: Mol Immunol. 45(11):3125-32 (2008) (15 pages).
Author manuscript of Habermann et al., "Increased serum levels of complement C3a anaphylatoxin indicate the presence of colorectal tumors," available in PMC Sep. 8, 2008, published in final edited form as: Gastroenterol. 131(4):1020-9 (2006) (17 pages).
Author manuscript of Huang et al., "A novel targeted inhibitor of the alternative pathway of complement and its therapeutic application in ischemia/reperfusion injury," available in PMC Nov. 25, 2009, published in final edited form as: J Immunol. 181(11): 8068-8076 (2008) (19 pages).
Baechler et al., "Interferon-inducible gene expression signature in peripheral blood cells of patients with severe lupus," Proc Natl Acad Sci USA. 100:2610-5 (2003).
Bagshawe et al., "A cytotoxic agent can be generated selectively at cancer sites," Br J Cancer. 58:700-703 (1988).
Bagshawe, "Towards generating cytotoxic agents at cancer sites," Br J Cancer. 60:275-281(1989).
Baldo et al., "The adipsin-acylation stimulating protein system and regulation of intracellular triglyceride synthesis," J Clin Invest. 92:1543-47 (1993).
Banda et al., "Targeted inhibition of the complement alternative pathway with complement receptor 2 and factor H attenuates collagen antibody-induced arthritis in mice," J Immunol. 183:5928-37 (2009).
Baranyi et al., "Cell-surface bound complement regulatory activity is necessary for the in vivo survival of KDH-8 rat hepatoma," Immunology. 82(4):522-8 (1994).
Barlow et al., "Solution structure of a pair of complement modules by nuclear magnetic resonance," J Mol Biol. 232:268-284 (1993).
Barnum, "Inhibition of complement as a therapeutic approach in inflammatory central nervous system (CNS) disease," Mol Med. 5:569-582 (1999).
Battelli et al., "T lymphocyte killing by a xanthine-oxidase-containing immunotoxin," Cancer Immunol Immunother. 35:421-425 (1992).
Becherer et al., "Segment spanning residues 727-768 of the complement C3 sequence contains a neoantigenic site and accommodates the binding of CR1, Factor H, and factor B," Biochemistry. 31:1787-1794 (1992).
Bellander et al., "Activation of the complement cascade and increase of clusterin in the brain following a cortical contusion in the adult rat," J Neurosurg. 85:468-475 (1996).
Bellander et al., "Complement activation in the human brain after traumatic head injury," J Neurotrauma. 18:1295-1311 (2001).
Bendayan, "Possibilities of false Immunocytochemical results generated by the use of monoclonal antibodies: The example of the anti-proinsulin antibody," J Histochem Cytochem. 43:881-886 (1995).
Bendig, "Humanization of rodent monoclonal antibodies by CDR grafting," Methods: A Companion to Methods in Enzymology. 8:83-93 (1995).
Benvenuti et al., "Crystallization of soluble proteins in vapor diffusion for X-ray crystallography," Nat Protoc. 2(7):1633-1651 (2007).
Bergelson et al., "Decay-accelerating factor (CD55), a glycosylphosphatidylinositol-anchored complement regulatory protein, is a receptor for several echoviruses," Proc Nat Acad Sci USA. 91(13):6245-9 (1994).
Beste et al., "Small antibody-like proteins with prescribed ligand specificities derived from the lipocalin fold," Proc Natl Acad Sci USA. 96:1898-1903 (1999).
Bjornson et al., "Complement is activated in the upper respiratory tract during influenza virus infection," Am Rev Respir Dis. 143:1062-1066 (1991).
Blank et al., "Hemoglobin interference from in vivo hemolysis," Clin Chem. 31(9):1566-9 (1985).
Blease et al., "Chemokines and their role in airway hyper-reactivity," Respir Res. 1:54-61 (2000).
Bohnsack et al., "CR2 ligands modulate human B cell activation," J Immunol. 141:2569-76 (1988).
Boos et al., "Murine complement C4 is not required for experimental autoimmune encephalomyelitis," Glia. 49:158-160 (2004).
Boross et al., "Boosting antibody therapy with complement," Blood. 119(25):5945-5947 (2012).
Bost et al., "Antibodies against a peptide sequence within the HIV envelope protein crossreacts with human interleukin-2," Immunol Invest. 17:577-586 (1988).
Brandis, "Acid-Base Physiology," <http://www.anaesthesiamcq.com/AcidBaseBook/ab4_4.php>, retrieved on Sep. 19, 2011 (2 pages).
Brauer et al., "Functional activity of anti-C6 antibodies elicited in C6-deficient rats reconstituted by liver allografts. Ability to inhibit hyperacute rejection of discordant cardiac xenografts," Transplantation 61(4):588-94 (1996).
Brodsky, "How I treat paroxysmal nocturnal hemoglobinuria," Blood. 113(26):6522-7 (2009).
Brown et al., "Molecular and cellular mechanisms of receptor-mediated endocytosis," DNA Cell Biol. 10:399-409 (1991).
Bykov, "Complement system and alcoholic liver disease," University of Helsinki 1-69 (2008).

(56) References Cited

OTHER PUBLICATIONS

Caldas et al., "Humanization of the anti-CD18 antibody 6.7: An unexpected effect of a framework residue in binding to antigen," Mol Immunol. 39:941-952 (2003).
Camargo et al., "Interleukin-6 protects liver against warm ischemia/reperfusion injury and promotes hepatocyte proliferation in the rodent," Hepatology. 26:1513-20 (1997).
Cambier, "Signalling processes in haematopoietic cells: positive and negative signal co-operativity in the immune system: the BCR, Fc gamma RIIB, CR2 paradigm," Biochem Soc Trans. 25(2):441-445 (1997).
Caragine et al., "A tumor-expressed inhibitor of the early but not late complement lytic pathway enhances tumor growth in a rat model of human breast cancer," Cancer Res. 62(4):1110-5 (2002).
Cardarelli et al., "A nonfucosylated human antibody to CD19 with potent B-cell depletive activity for therapy of B-cell malignancies," Cancer Immunol Immunother. 59(2):257-65 (2010).
Carel et al., "Structural requirements for C3d,g/Epstein-Barr virus receptor (CR2/CD21) ligand binding, internalization, and viral infection," J Biol Chem. 265(21):12293-9 (1990).
Carroll, "The role of complement and complement receptors in induction and regulation of immunity," Annu Rev Immunol. 16:545-568 (1998).
Carroll, The role of complement in B cell activation and tolerance. *Advances in Immunology*. Dixon,74:61-88 (2000).
Carter et al., "CD19: lowering the threshold for antigen receptor stimulation of B lymphocytes," Science. 256:105-7 (1992).
Carter et al., "Polymeric C3dg primes human B lymphocytes for proliferation induced by anti-IgM," J Immunol. 143(6):1755-60 (1989).
Carter et al., "Synergistic interaction between complement receptor type 2 and membrane IgM on B lymphocytes," J Immunol. 141:457-63 (1988).
Casale et al., "Direct evidence of a role for mast cells in the pathogenesis of antigen-induced bronchoconstriction," J Clin Invest. 80:1507-1511 (1987).
Casarsa et al., "Intracerebroventricular injection of the terminal complement complex causes inflammatory reaction in the rat brain," Eur J Immunol. 33:1260-1270 (2003).
Casasnovas et al., "Crystal structure of two CD46 domains reveals an extended measles virus-binding surface," EMBO J. 18(11):2911-2922 (1999).
Chaney, "Corticosteroids and cardiopulmonary bypass: A review of clinical investigations," CHEST. 121:921-931 (2002).
Chavez-Cartaya et al., "Regulation of the complement cascade by soluble complement receptor type 1. Protective effect in experimental liver ischemia and reperfusion," Transplantation. 59:1047-52 (1995).
Chen et al., "An experimental model of closed head injury in mice: pathophysiology, histopathology, and cognitive deficits," J. Neurotrauma 13: 557-568, 1996.
Chen et al., "CD59 expressed on a tumor cell surface modulates decay-accelerating factor expression and enhances tumor growth in a rat model of human neuroblastoma," Cancer Res. 60(11):3013-8 (2000).
Chen et al., "Gene therapy for brain tumors: regression of experimental gliomas by adenovirus-mediated gene transfer in vivo," Proc Natl Acad Sci USA. 91:3054-3057 (1994).
Chien et al., "Significant structural and functional change of an antigen-binding site by a distant amino acid substitution: proposal of a structural mechanism," Proc Natl Acad Sci USA. 86:5532-5536 (1989).
Choi et al., "Inhalation delivery of proteins from ethanol suspensions," Proc Natl Acad Sci. 98(20):11103-11107 (2001).
Christiansen et al., "A functional analysis of recombinant soluble CD46 in vivo and a comparison with recombinant soluble forms of CD55 and CD35 in vitro," Eur J Immunol. 26(3):578-85 (1996).
Chàrdes et al., "Efficient amplification and direct sequencing of mouse variable regions from any immunoglobulin gene Family," FEBS Lett. 452:386-394 (1999).

Cieslewicz et al., "The late, but not early, asthmatic response is dependent on IL-5 and correlates with eosinophil infiltration," J. Clin Invest. 104: 301-308, 1999.
Clardy et al., "In vitro inhibition of complement activation using a monoclonal antibody (McAb) directed against human Factor B (FB), Abstract No. 1969," Pediatric Res. 31:331 A (1992).
Clardy, "Complement activation by whole endotoxin is blocked by a monoclonal antibody to factor B," Infect Immun. 62(10):4549-4555, 1994.
Clark, "Antibodies for therapeutic applications," <http://www.path.cam.ac.uk/~mrc7/humanisation/antibodies.html>, retrieved Jun. 1, 2002 (5 pages).
Clark, "Antibody humanisation for therapeutic applications," <http://www.path.cam.ac.uk/~mrc7/humanisation/index.html>, printed Jun. 1, 2002 (4 pages).
Clavien et al., "Strategies for safer liver surgery and partial liver transplantation," N Engl J Med. 356:1545-59 (2007).
Clemenza et al., "Structure-guided identification of C3d residues essential for its binding to complement receptor 2 (CD21)," J Immunol. 165:3839-3848 (2000).
Cole et al., "Beyond lysis: how complement influences cell fate," Clin Sci (Lond). 104:455-466 (2003).
Cole et al., Complement regulator loss on apoptotic neuronal cells causes increased complement activation and promotes both phagocytosis and cell lysis, Mol Immunol. 43:1953-1964 (2006).
Collard et al., "Complement activation following oxidative stress," Mol Immunol. 36:941-948 (1999).
Colvin, "Antibody-mediated renal allograft rejection: diagnosis and pathogenesis," J Am Soc Nephrol. 18(4):1046-56 (2007).
Cooper et al., "Immunobiology of CR2, the B lymphocyte receptor for Epstein-Barr virus and the C3d complement fragment," Ann Rev Immunol. 6:85-113 (1988).
CRASH trial collaborators, "Effect of intravenous corticosteroids on death within 14 days in 10008 adults with clinically significant head injury (MRC CRASH trial): Randomised placebo-controlled trial," Lancet. 364:1321-1328 (2004).
Crumm et al., "Adenine necleotide changes in the remnant liver: an early signal for regeneration after partial hepatectomy," Hepatology. 48:898-908 (2008).
Cudney, "Protein crystallization and dumb luck," The Rigaku Journal. 16(1):1-7 (1999).
Czermak et al., "Complement, cytokines, and adhesion molecule expression in inflammatory reactions," Proc Assoc Am Physicians. 110(5):306-312 (1998).
Daha et al., "Stabilization of the amplification convertase of complement by monoclonal antibodies directed against human factor B," J Immun. 132(5):2538-42 (1984).
Dahm et al., "Small-for-size syndrome after partial liver transplantation: definition, mechanisms of disease and clinical implications," Am J Transplant. 5:2605-10 (2005).
Davies et al., "CD59, a Ly-6-Like protein expressed in human lymphoid cells, regulates the action of the complement membrane attack complex on homologous cells," J Exp Med. 170(3):637-54 (1989).
De Broe et al., "Pathophysiology of hemodialysis-associated hypoxemia," Adv Nephrol Necker Hosp. 18:297-315, Abstract Only (1989).
De Córdoba et al., "The human complement factor H: functional roles, genetic variations and disease associations," Molec Immunol. 41:355-67 (2004).
Declaration of Joshua M. Thurman for U.S. Appl. No. 11/057,047, executed Apr. 16, 2008 (3 pages).
Declaration of Vernon Michael Holers for U.S. Appl. No. 11/057,047, executed Aug. 31, 2009 (68 pages).
Delaglio et al., "NMRPipe: a multidimensional spectral processing system based on UNIX pipes," J Biomol NMR. 6:277-93 (1995).
Delcayre et al., "Epstein Barr virus/complement C3d receptor is an interferon alpha receptor," EMBO J. 10:919-26 (1991).
Delcayre et al., "Inhibition of Epstein-Barr virus-mediated capping of CD21/CR2 by alpha interferon (IFN-alpha): immediate antiviral activity of IFN-alpha during the early phase of infection," J Virol. 67:2918-21 (1993).

(56) References Cited

OTHER PUBLICATIONS

Dempsey et al., "C3d of complement as a molecular adjuvant: bridging innate and acquired immunity," Science. 271:348-350 (1996).
Desai et al., "Demonstration of C5 cleaving activity in bronchoalveolar fluids and cells: A mechanism of acute and chronic alveolitis," J Exp Pathol. (3):201-216 (1984).
Dev et al., "Electrochemotherapy—A novel method of cancer treatment," Cancer Treat Rev. 20:105-115 (1994).
Diaz et al., "Leukocytes and mediators in bronchoalveolar lavage during allergen-induced late-phase asthmatic reactions," Am Rev Respir Dis. 139:1383-1389 (1989).
Diefenbach et al., "Mutation of residues in the C3dg region of human complement component C3 corresponding to a proposed binding site for complement receptor type 2 (CR2, CD21) does not abolish binding of iC3b or C3dg to CR2," J Immunol. 154(5):2303-2320 (1995).
Dierich et al., "Structural and functional relationships among receptors and regulators of the complement system," Mol Immunol. 25(11):1043-1051 (1988).
Dilillo et al., "Selective and efficient inhibition of the alternative pathway of complement by a mAb that recognizes C3b/iC3b," Mol Immunol. 43:1010-9 (2006).
Dobbie et al., "Epitope specificities and quantitative and serologic aspects of monoclonal complement (C3c and C3d) antibodies," Transfusion. 27(6):453-459 (1987).
Dominguez et al., "HADDOCK: a protein-protein docking approach based on biochemical or biophysical information," J Am Chem Soc. 125:1731-7 (2003).
Drenth, Crystalling a Protein. *Principles of Protein X-Ray Crystallography*. Springer-Verlag, 1-21 (1999).
Drouin et al., "A protective role for the fifth complement component (C5) in allergic airway disease," Am J Respir Crit Care Med. 173:852-857 (2006).
Drouin et al., "Expression of the complement anaphylatoxin C3a and C5a receptors on bronchial epithelial and smooth muscle cells in models of sepsis and asthma," J Immunol. 166:2025-2032 (2001).
Duits et al., "Selective enhancement of Leu-Cam expression by Interleukin 6 during differentiation of human promonocytic U937 cells," Scand J Immunol. 33(2):151-9 (1991).
Duranski et al., "Cytoprotective effects of nitrite during in vivo ischemia-reperfusion of the heart and liver," J Clin Invest. 115(5):1232-40 (2005).
Dutkowski et al., "Novel short-term hypothermic oxygenated perfusion (HOPE) system prevents injury in rat liver graft from non-heart beating donor," Ann Surg. 244(6):968-76, discussion 976-7 (2006).
Dutton et al., "Traumatic Brain Injury," Curr Opin Crit Care. 9:503-509 (2003).
Dörig et al., "The human CD46 molecule is a receptor for measles virus (Edmonston strain)," Cell. 75(2):295-305 (1993).
EBI Accession No. CQ729676, <http://ibis/IBIS/exam/dbfetch.jsp?id=EM_PAT:CQ729676>retrieved on Jan. 3, 2011(1 page).
EBI Accession No. CQ729676. Retrieved on Jan. 3, 2011 (1 page).
Edberg et al., "Quantitative analyses of the binding of soluble complement-fixing antibody/dsDNA immune complexes to CR1 on human red blood cells," J Immunol. 139:3739-47 (1987).
Edwards et al., "Complement factor H polymorphism and age-related macular degeneration," Science. 308:421-4 (2005).
Eldadah et al., "Caspase pathways, neuronal apoptosis, and CNS injury," J Neurotrauma 17:811-829 (2000).
Elf et al., "Prevention of secondary insults in neurointensive care of traumatic brain injury," Eur J of Trauma. 29:74-80 (2003).
Elvington et al., "A targeted complement-dependent strategy to improve the outcome of mAb therapy, and characterization in a murine model of metastatic cancer," Blood. 119(25):6043-6051 (2012).
Elward et al., "CD46 plays a key role in tailoring innate immune recognition of apoptotic and necrotic cells," J Biol Chem. 280:36342-36354 (2005).
Extended European Search Report and Written Opinion for European Application No. 11781394.9, dated Sep. 19, 2013 (11 pages).

Extended European Search Report for European Application No. 10829204.6, dated Mar. 5, 2013 (9 pages).
Extended European Search Report for European Patent Application No. 10188613.3, dated May 31, 2011 (10 pages).
Fabrikant, "The kinetics of cellular proliferation in regenerating liver," J Cell Biol. 36(3):551-65 (1968).
Farkas et al., "A neuronal C5a receptor and an associated apoptotic signal transduction pathway," J Physiol. 507:679-687 (1998).
Fausto, "Involvement of the innate immune system in liver regeneration and injury," J Hepatol. 45:347-9 (2006).
Fearon et al., "The CD19/CR2/TAPA-1 complex of B lymphocytes: Linking natural to acquired immunity," Annu Rev Immunol. 13:127-149 (1995).
Fearon, "The complement system and adaptive immunity," Semin Immunol. 10(5):355-361 (1998).
Felderhoff-Mueser et al., "Pathways leading to apoptotic neurodegeneration following trauma to the developing rat brain," Neurobiol Dis. 11:231-245 (2002).
Ferreira et al., "Factor H-mediated cell surface protection from complement is critical for the survival of PNH erythrocytes," Blood. 110(6):2190-2 (2007).
Figueroa et al., "Infectious diseases associated with complement deficiencies," Clin Microbiol Rev. 4:359-395 (1991).
Fingeroth et al., "Characterization of a T-lymphocyte Epstein-Barr virus/C3d receptor (CD21)," J Virol. 62:1442-7 (1988).
Fingeroth et al., "Epstein-Barr virus receptor of human B lymphocytes is the C3d receptor CR2," Proc Natl Acad Sci USA. 81(14):4510-4514 (1984).
Fingeroth et al., "Identification of murine complement receptor type 2," Proc Natl Acad Sci USA. 86(1):242-246 (1989).
Fiorini et al., "Development of an unbiased method for the estimation of liver steatosis," Clin Transplant. 18:700-6 (2004).
Fishelson et al., "Regulation of the alternative pathway of complement by pH," J Immunol. 138(10):3392-5 (1987).
Fondevila et al., "The membrane attack complex (C5b-9) in liver cold ischemia and reperfusion injury," Liver Transpl. 14:1133-41 (2008).
Franco-Gou et al., "Protection of reduced-size liver for transplantation," Am J Transplant. 4(9):1408-20 (2004).
Frank, "Complement: A brief review," J Allergy Clin Immunol. 84:411-420 (1989).
Friedlander, "Apoptosis and caspases in neurodegenerative diseases," N Engl J Med. 348:1365-1375 (2003).
Fritzinger et al., "Functional characterization of human C3/cobra venom factor hybrid proteins for therapeutic complement depletion," Develop Comp Immunol. 33(1):105-16 (2009).
Fritzinger et al., "Molecular cloning and derived primary structure of cobra venom factor," Proc Natl Acad Sci USA. 91:12775-12779 (1994); correction 92: 7065 (1995).
Frémeaux-Bacchi et al., "Soluble CD21 induces activation and differentiation of human monocytes through binding to membrane CD23," Eur J Immunol. 28:4268-4274 (1998).
Fujisaku et al., "Genomic organization and polymorphisms of the human C3d/Epstein-Barr virus receptor," J Biol Chem. 264:2118-25 (1989).
Fukuoka et al., "Molecular cloning of murine decay accelerating factor by immunoscreening," International Immunology. 8:379-385 (1996).
Gaetz, "The neurophysiology of brain injury," Clin Neurophysiology. 115:4-18 (2004).
Gerard et al., "Complement in allergy and asthma," Curr Opin Immunol. 14:705-708 (2002).
German et al., "Systemic complement depletion inhibits experimental cerebral vasospasm," Neurosurgery. 39:141-145, discussion 145-146, Abstract Only (1996).
Ghajar, "Traumatic brain injury," Lancet. 356:923-929 (2000).
Gilkeson, "Role of complement factor B in the pathogenesis of SLE, Project No. 5R01AI047469-05," <<http://projectreporter.nih.gov/pr_Prj_info_desc_dtls.cfm?icde=0&aid=6712799&print=yes>>, retrieved on Apr. 25, 2011 (2 pages).
Girardi et al., "Complement C5a receptors and neutrophils mediate fetal injury in the antiphospholipid syndrome," J Clin Invest. 112(11):1644-54 (2003).

(56) References Cited

OTHER PUBLICATIONS

Girardi et al., "Complement C5a receptors and neutrophils mediate fetal injury in the Antiphospholipid Syndrome," J. Clin. Invest. Corrigendum. 113:646 (2004).
Girardi et al., (Dec. 2003) "Complement C5a receptors and neutrophils mediate fetal injury in the Antiphospholipid Syndrome," J. Clin. Invest. 112(11):1644-1654.
Giusti, et al. "Somatic diversification of S107 from an antiphosphocholine to an anti-DNA autoantibody is due to a single base change in its heavy chain variable region," Proc Natl Acad Sci USA. 84:2926-2930 (1987).
Glovsky et al., "Is complement activation a factor in bronchial asthma?" Int Arch Allergy Immunol. 118:330-332 (1999).
Glovsky, et al., "Complement determinations in human disease," Ann Allergy, Asthma Immunol. 93(6):513-523 (2004).
Gomez et al., "Role of ischaemic preconditioning in liver regeneration following major liver resection and transplantation," World J Gastroenterol. 13(5):657-70 (2007).
Goodford, "A computational procedure for determining energetically favorable binding sites on biologically important macromolecules," J. Med. Chem. 28: 849-857, 1985.
Gordon, "B-cell signalling via the C-type lectins CD23 and CD72," Immunol Today. 15(9):411-417 (1994).
Greene et al., "Partial hepatectomy in the mouse: technique and perioperative management," J Invest Surg. 16:99-102 (2003).
Greenspan et al., "Defining epitopes: It's not as easy as it seems," Nat Biotechnol. 17:936-937 (1999).
Grzesiek et al., "Improved 3D triple-resonance NMR techniques applied to a 31-kDa protein," J Magn Reson. 96:432-40 (1992).
Guthridge et al., "Epitope mapping using the X-ray crystallographic structure of complement receptor type 2 (CR2)/CD21: Identification of a highly inhibitory monoclonal antibody that directly recognizes the CR2-C3d interface," J Immunol. 167:5758-5766 (2001).
Guthridge et al., "Structural studies in solution of the recombinant N-terminal pair of short consensus/complement repeat domains of complement receptor type 2 (CR2/CD21) and interactions with its ligand C3dg," Biochemistry. 40:5931-5941 (2001).
Gönczi et al., "The severity of clinical symptoms in ragweed-allergic patients is related to the extent of ragweed-induced complement activation in their sera," Allergy. 52:1110-1114 (1997).
Haan et al., "Different functional domains in the cytoplasmic tail of glycoprotein B are involved in Epstein-Barr virus-induced membrane fusion," Virology. 290:106-14 (2001).
Haddad et al., "Depletion of glycoprotein gp85 from virosomes made with Epstein-Barr virus proteins abolishes their ability to fuse with virus receptor-bearing cells," J Virol. 63:4998-5005 (1989).
Hageman et al., "A common haplotype in the complement regulatory gene factor H (HF1/CFH) predisposes individuals to age-related macular degeneration," Proc Natl Acad Sci USA. 102(20):7227-32 (2005).
Haines et al., "Complement factor H variant increases the risk of age-related macular degeneration," Science. 308(5720):419-21 (2005).
Hall, "Cooperative Interaction of Factor B and other complement components with mononuclear cells in the antibody-independent lysis of xenogeneic erythrocytes," J Exp Med. 156:834-843 (1982).
Ham et al., "Studies on destruction of red blood cells. II. Chronic hemolytic anemia with paroxysmal nocturnal hemoglobinuria: certain immunological aspects of the hemolytic mechanism with special reference to serum complement," J Clin Invest. 18:657-72 (1939).
Hampton Research, Catalog, 5 & 7 (2001).
Hampton Research, Crystal Screen User Guide, 27632 El Lazo Road, Laguna Niguel, California, 1991 (4 pages).
Hannan et al., "Mutational analysis of the complement receptor type 2 (CR2/CD21)-C3d interaction reveals a putative charged SCR1 binding site for C3d," J Mol Biol. 346(3):845-58 (2005).
Hannan et al., "Structure of complement receptor (CR) 2 and CR2-C3d complexes," Biochem Soc Trans. 30:983-9 (2002).
Harada et al., "Antithrombin reduces ischemia/reperfusion injury of rat liver by increasing the hepatic level of prostacyclin," Blood. 93:157-64 (1999).
Harlow et al., Proteolytic Fragments of Antibodies. *Antibodies: A Laboratory Manuel.* 626-629 (1988).
Harris et al., "Tailoring anti-complement therapeutics," Biochem Soc Trans. 30(6):1019-26 (2002).
Hautekeete et al., "Microvesicular steatosis of the liver," Acta Clin Belg. 45(5):311-326 (1990). Abstract Only.
Hawlisch et al., "The anaphylatoxins bridge innate and adaptive immune responses in allergic asthma," Mol Immunol. 41:123-131 (2004).
He et al., "Delivery of antioxidative enzyme genes protects against ischemia/reperfusion-induced liver injury in mice," Liver Transpl. 12:1869-79 (2006).
Hebell et al., "Suppression of the immune response by a soluble complement receptor of B lymphocytes," Science. 254:102-105 (1991).
Heinen et al., "Factor H-related protein 1 (CFHR-1) inhibits complement C5 convertase activity and terminal complex formation," Blood. 114(12):2439-47 (2009).
Helling et al., "Partial hepatectomy with or without endotoxin does not promote apoptosis in the rat liver," J Surg Res. 116:1-10 (2004).
Helling, "Liver failure following partial hepatectomyn" HPB (Oxford). 8:165-74 (2006).
Heyman, "Regulation of antibody responses via antibodies, complement, and Fc receptors," Ann Rev Immunol. 18:709-737 (2000).
Hicks et al., "Vaccinia virus complement control protein enhances functional recovery after traumatic brain injury," J. Neurotrauma. 19:705-714 (2002).
Higgins et al., "A soluble chimeric complement inhibitory protein that possesses both decay-accelerating and factor I cofactor activities," J Immunol. 158(6):2872-81 (1997).
Higgins et al., "Experimental pathology of the liver. 1. Restoration of the liver of the white rat following partial surgical removal," Arch Pathol. 12:186-202 (1931).
Hill et al., "Sustained response and long-term safety of eculizumab in paroxysmal nocturnal hemoglobinuria," Blood. 106:2559-65 (2005).
Hill, "Eculizumab for the treatment of paroxysmal nocturnal hemoglobinuria," Clin Adv Hematol Oncol. 3(11):849-50 (2005).
Hillmen et al., "Effect of eculizumab on hemolysis and transfusion requirements in patients with paroxysmal nocturnal hemoglobinuria," N Engl J Med. 350(6):552-9 (2004).
Hogaboam et al., "Mannose-binding lectin deficiency alters the development of fungal asthma: Effects on airway response, inflammation, and cytokine profile," J Leukoc Biol. 75:805-814 (2004).
Holers et al., "The alternative pathway of complement in disease: Opportunities for therapeutic targeting," Mol. Immunol. 41:147-152 (2004).
Holers, "Phenotypes of Complement Knockouts," Immunopharmacology. 49:125-131 (2000).
Holers, "The complement system as a therapeutic target in autoimmunity," Clin Immunol. 107:140-151 (2003).
Holers, "The spectrum of complement alternative pathway-mediated diseases," Immunol Rev. 223:300-316 (2008).
Holers, Complement Receptors. *The Year in Immunology 1988. Cellular, Molecular and Clinical Aspects.* Cruse et al., 4:231-240 (1989).
Holers, Complement. *Clinical Immunology, Principles and Practice.* Mosby ed. 363-91 (1996).
Holgate et al., "The bronchial epithelium as a key regulator of airway inflammation and remodelling in asthma," Clin Exp Allergy. 29:90-95 (1999).
Holm et al., "Functional mapping and single chain construction of the anti-cytokeratin 8 monoclonal antibody TS1," Mol. Immunol. 44:1075-1084 (2007).
Homeister et al., "Soluble complement receptor type 1 prevents human complement-mediated damage of the rabbit isolated heart," J Immunol. 150(3):1055-1064 (1993).
Hori et al., "Crry, a complement regulatory protein, modulates renal interstitial disease induced by proteinuria," Kidney Int. 56:2096-2106 (1999).

(56) References Cited

OTHER PUBLICATIONS

Hourcade et al., "Analysis of the short consensus repeats of human complement factor B by site-directed mutagenesis," J. Biol. Chem. 270(34): 19716-19722, 1995.
Hourcade et al., "Mutations of the type A domain of complement factor B that promote high-affinity C3b-binding," J. Immunol. 162: 2906-2911, 1999.
Hsu et al., "Chronic progression of tubulointerstitial damage in proteinuric renal disease is mediated by complement activation: a therapeutic role for complement inhibitors?" J Am Soc Nephrol. 14:S186-91 (2003).
Huang et al., "A novel targeted inhibitor of the alternative pathway of complement," Mol Immunol. 44(16):3947 (Abstract Only: No. P31) (2007).
Huang et al., "Insights into the human CD59 complement binding interface toward engineering new therapeutics," J Biol Chem. 280(40):34073-9 (2005).
Hughes et al., "Monoclonal antibody targeting of liposomes to mouse lung in vivo," Cancer Res. 49(22):6214-20 (1989).
Humar et al., "Liver regeneration after adult living donor and deceased donor split-liver transplants," Liver Transpl. 10(3):374-8 (2004).
Humbles et al., "A role for the C3a anaphylatoxin receptor in the effector phase of asthma," Nature 406:998-1001 (2000).
Humblet et al., "3D database searching and docking strategies," Topics in Drug Design and Discovery. *Annual Reports in Medicinal Chemistry*. Bristol et al., 28:275-284 (1993).
Höpken et al., "The C5a chemoattractant receptor mediates mucosal defence to infection," Nature. 383:86-89 (1996).
Iida et al., "Identification of the membrane receptor for the complement fragment C3d by means of a monoclonal antibody," J Exp Med. 158:1021-33 (1983).
Iimuro et al., "NFkappaB prevents apoptosis and liver dysfunction during liver regeneration," J Clin Invest. 101(4):802-11 (1998).
Imai et al., "Enhancement of antibody-dependent mechanisms of tumor cell lysis by a targeted activator of complement," Cancer Res. 67(19):9535-9541 (2007).
International Preliminary Report on Patentability and Written Opinion for International Application No. PCT/US2011/041517, dated Dec. 28, 2012 (11 pages).
International Preliminary Report on Patentability and Written Opinion of the International Searching Authority for International Application No. PCT/US2010/040973, dated Jan. 4, 2012 (8 pages).
International Search Report for PCT Application No. PCT/US2008/003381, mailed Feb. 11, 2009 (3 pages).
International Search Report for International Application No. PCT/US2003/36459, mailed Sep. 15, 2004 (2 pages).
International Search Report for International Application No. PCT/US2007/014602, mailed on Mar. 6, 2008 (5 pages).
International Search Report for International Application No. PCT/US2010/040973, mailed Oct. 14, 2010 (5 pages).
International Search Report for International Application No. PCT/US2010/055745, mailed Feb. 4, 2011 (3 pages).
International Search Report for International Application No. PCT/US2011/036552, mailed Jul. 26, 2011 (7 pages).
International Search Report for International Application No. PCT/US2011/041517, mailed Nov. 10, 2011 (8 pages).
International Search Report for PCT Application No. PCT/US2005/04346, mailed Jul. 7, 2005 (2 pages).
International Search Report for PCT Application No. PCT/US2006/020460, mailed Aug. 29, 2006 (3 pages).
International Search Report mailed on Aug. 29, 2006, for International Application No. PCT/US2006/020460, filed on May 26, 2006 (3 pages).
International Search Report mailed on Feb. 11, 2009, for International Application No. PCT/US2008/003381, filed on Mar. 14, 2008 (3 pages).
International Search Report mailed on Jul. 7, 2005, for International Application No. PCT/US2005/004346, filed on Feb. 10, 2005 (2 pages).

Irvin et al., "Airways hyperreactivity and inflammation produced by aerosolization of human C5A des arg$^{1-3}$," Am Rev Respir Dis. 134:777-783 (1986).
Jackson et al., "Pl3K/Akt activation is critical for early hepatic regeneration after partial hepatectomy," Am J Physiol Gastrointest Liver Physiol. 294:G1401-10 (2008).
Jacobson et al., "Clinical and immunologic features of transient cold agglutinin-hemolytic anemia," Am J Med. 54:514-21 (1973).
Jaeschke et al., "Role of neutrophils in acute inflammatory livery injury," Liver Int. 26:912-919 (2006).
Jagels et al., "C3a and C5a enhance granulocyte adhesion to endothelial and epithelial cell monolayers: Epithelial and endothelial priming is required for C3a-induced eosinophil adhesion," Immunopharmacology. 46:209-222 (2000).
Janssen et al., "Structure of C3b reveals conformational changes that underlie complement activity," Nature. 444:213-216 (2006).
Janssen et al., "Structure of compstatin in complex with complement component C3c reveals a new mechanism of complement inhibition," J Biol Chem. 282:29241-7 (2007).
Janzi et al., "Serum microarrays for large scale screening of protein levels," Mol Cell Proteomics. 4(12):1942-7 (2005).
Jin et al., "Interleukin-6 inhibits oxidative injury and necrosis after extreme liver resection," Hepatology. 46:802-12 (2007).
Jin et al., "Paradoxical effects of short- and long-term interleukin-6 exposure on liver injury and repair," Hepatology. 43:474-84 (2006).
Johswich et al., "Ligand specificity of the anaphylatoxin C5L2 receptor and its regulation on myeloid and epithelial cell lines," J Biol Chem. 281(51):39088-95 (2006).
Jozsi et al., "Attachment of the soluble complement regulator factor H to cell and tissue surfaces: relevance for pathology," Histol Hitopathol. 19:251-8 (2004).
Juhl et al., "Complement killing of human neuroblastoma cells: A cytotoxic monoclonal antibody and its F(ab')2-cobra venom factor conjugate are equally cytotoxic," *Mol Immunol*. 27(10):957-964 (1990).
Kaczorowski et al., "Effect of Soluble Complement Receptor-1 on Neutrophil Accumulation After Traumatic Brain Injury in Rats," J Cereb Blood Flow Metab. 15:860-864 (1995).
Kadry et al., "Liver regeneration after adult living donor and deceased donor split-liver transplants," Liver Transpl. 10(8):1078 (2004).
Kalant et al., "C5L2 is a functional receptor for acylation-stimulating protein," J Biol Chem 208(25):23936-44 (2005).
Kalant et al., "The chemoattractant receptor-like protein C5L2 binds the C3a des-Arg77/acylation-stimulating protein," J Biol Chem 278(13):11123-9 (2003).
Kalli et al., "Interaction of iC3b with recombinant isotypic and chimeric forms of CR2," J Immunol. 147(2):590-594 (1991).
Kang et al., "A novel anti-human Factor B monoclonal antibody inhibits Factor D-mediated associate and cleavage of Factor B," Abstract No. 191, Immunopharmacology. 49:68 (2000).
Kaplan, "Eculizumab Alexion," Curr Opin Investig Drugs. 3(7):1017-23 (2002).
Karp et al., "Identification of complement factor 5 as a susceptibility locus for experimental allergic asthma," Nat Immunol. 1(3):221-226 (2000).
Kasamatsu et al., "Experimental acute lung injury in guinea pigs after aerosol challenge with sonicated Pseudomonas aeruginosa whole cells," Arerugi 42(10):1616-1622 (1993) English translation of abstract only.
Keeling et al., "Local neutrophil influx following lateral fluid-percussion brain injury in rats is associated with accumulation of complement activation fragments of the third component (C3) of the complement system," J Neuroimmunol. 105:20-30 (2000).
Khurana et al., "Crystal structure of 2,5-diketo-D-gluconic acid reductase A complexed with NADPH at 2.1-A resolution," Proc Natl Aced Sci 95:6768-6773 (1998).
Kildsgaard et al., "A critical evaluation of the putative role of C3adesArg (ASP) in lipid metabolism and hyperapobetalipoproteinemia," Mol Immunol. 36:869-76 (1999).
Klein et al., "Complement factor H polymorphism in age-related macular degeneration," Science. 308(5720):385-9 (2005).

(56) References Cited

OTHER PUBLICATIONS

Kodani et al., "Intratracheal administration of anaphylatoxin C5a potentiates antigen-induced pulmonary reactions through the prolonged production of cysteinyl-leukotrienes," Immunopharmacology. 49:263-274 (2000).
Kolb et al., "Ba and Bb fragments of Factor B activation: fragment production, biological activities, neoepitope expression and quantitation in clinical samples," Complement Inflamm. 6(3):175-204 (1989).
Kolb et al., "Ba and Bb fragments of factor B activation: Fragment production, biological activities, neoepitope expression and quantitation in clinical samples," Complement Inflamm. 6:175-204 (1989).
Koski et al., "Cytolysis of nucleated cells by complement: cell death displays multi-hit characteristics," Proc Natl Acad Sci USA. 80:3816-3820 (1983).
Kossmann et al., "Elevated levels of the complement components C3 and factor B in ventricular cerebrospinal fluid of patients with traumatic brain injury," J Neuroimmunol. 73:63-69 (1997).
Kovacs et al., "Biophysical investigations of complement receptor 2 (CD21 and CR2)-ligand interactions reveal amino acid contacts unique to each receptor-ligand pair," J Biol Chem. 285:27251-8 (2010).
Kovacs et al., "Mapping of the C3d ligand binding site on complement receptor 2 (CR2/CD21) using nuclear magnetic resonance and chemical shift analysis," J Biol Chem. 284(14):9513-20 (2009).
Kroshus et al., "A recombinant soluble chimeric complement inhibitor composed of human CD46 and CD55 reduces acute cardiac tissue injury in models of pig-to-human heart transplantation," Transplantation. 69(11):2282-9 (2000).
Kroshus et al., "Complement inhibition with an anti-C5 monoclonal antibody prevents acute cardiac tissue injury in an ex vivo model of pig-to-human xenotransplantation," Transplantation. 60(11):1194-202 (1995).
Krug et al., "Complement factors C3a and C5a are increased in bronchoalveolar lavage fluid after segmental allergen provocation in subjects with asthma," Am J Respir Crit Care Med. 164:1841-1843 (2001).
Krushkal et al., "Evolutionary relationships among proteins encoded by the regulator of complement activation gene cluster," Mol Biol Evol. 17(11):1718-30 (2000).
Kuby et al., Antigens. *Immunology (2nd edition)*. W H Freeman and Company, 85-96 (1994).
Kulik et al., "Pathogenic natural antibodies recognizing Annexin IV are required to develop intestinal ischaemia-reperfusion injury and are selected during development in a CR2/CD21-dependent manner," Mol. Immunology. 45:4110, Abstract 045 (2008).
Kulkarni et al., "Neuroprotection from complement-mediated inflammatory damage," Ann N Y Acad Sci. 1035:147-164 (2004).
Kundrot, "Which strategy for a protein crystallization project?" Cell Mol Life Science. 61(5):525-536 (2004).
Kuraya et al., "Expression of the complement regulatory proteins CD21, CD55, and CD59 on Burkitt lymphoma lines: Their role in sensitivity to human serum-meidated lysis," Eur J Immunol. 22(7):1871-1876 (1992).
Kurucz et al., Current animal models of bronchial asthma, Curr Pharm Des. 12(25):3175-3194 (2006).
Kuttner-Kondo et al., "Characterization of the active sites in decay-accelerating factor," J Immunol. 167(4):2164-2171 (2001).
Kyrkanides et al., "Enhanced glial activation and expression of specific CNS inflammation-related molecules in aged versus young rats following cortical stab injury," J Neuroimmunol. 119:269-277 (2001).
Köhl et al., "A regulatory role for the C5a anaphylatoxin in type 2 immunity in asthma," J Clin Invest. 116(3):783-796 (2006).
La Flamme et al., "Lack of C3 affects Th2 response development and the sequelae of chemotherapy in schistosomiasis," J Immunol. 170:470-6 (2003).
Lambrecht, "An unexpected role for the anaphylatoxin C5a receptor in allergic sensitization," J Clin Invest. 1 16(3):628-632 (2006).
Lambris et al., "Mapping of the C3d receptor (CR2)-binding site and a neoantigenic site in the C3d domain of the third component of complement," Proc Natl Acad Sci USA. 82(12):4235-4239 (1985).
Langlois et al., "Complement activation occurs through both classical and alternative pathways prior to onset and resolution of adult respiratory distress syndrome," Clin. Immunol. Immunopathol. 47:152-163, 1988.
Larsen et al., "A differential effect of C5a and C5a des Arg in the induction of pulmonary inflammation," Am J Pathol. 100:179-192 (1980).
Law et al., "Action of the C3b-inactivator of the cell-bound C3b," J Immunol. 122(3):759-65 (1979).
Law et al., Complement. *In Focus*. Male, vii-ix (1995).
Lederman et al., "A single amino acid substitution in a common African allele of the CD4 molecule ablates binding of the monoclonal antibody, OKT4," Mol Immunol. 28(11):1171-1181 (1991).
Lehmann et al., "Complement inhibition by soluble complement receptor type 1 improves microcirculation after rat liver transplantation," Transplantation. 66:717-22 (1998).
Lehmann et al., "Impact of inhibition of complement by sCR1 on hepatic microcirculation after warm ischemia," Microvasc Res. 62:284-92 (2001).
Leinhase et al., "Pharmacological complement inhibition at the C3 convertase level promotes neuronal survival, neuroprotective intracerebral gene expression, and neurological outcome after traumatic brain injury," Exp. Neurol. 199:454-464 (2006).
Leinhase et al., "Reduced neuronal cell death after experimental brain injury in mice lacking a functional alternative pathway of complement activation," BMC Neurosci. 7:55 (2006).
Leivo et al., "C3d fragment of complement interacts with laminin and binds to basement membranes of glomerulus and trophoblast," J Cell Biol. 103:1091-100 (1986).
Lemanske, "Asthma therapies revisited: what have we learned?" Proc Am Thorac Soc. 6:312-315 (2009).
Lemoli et al., "Immunological effects of omalizumab in chronic urticaria: a case report," J Invest Allergol Clin Immunol. 20(3):252-4 (2010).
Leslie et al., "Complement Receptors," Encyclopedia of Life Sciences, Nature Publishing Group. (2001) (9 pages).
Leu et al., "Triggering of interferon γ-primed macrophages by various known complement activators for nonspecific tumor cytotoxicity," *Cell Immunol*. 106:114-121 (1987).
Li et al., "Beta-Endorphin omission analogs: Dissociation of immunoreactivity from other biological activities." Proc Natl Acad Sci USA. 77(6):3211-3214 (1980).
Linton et al., "Therapeutic efficacy of a novel membrane-targeted complement regulator in antigen-induced arthritis in the rat," Arthritis Rheum. 43(11):2590-7 (2000).
Liszewski et al., "Complement inhibitors as therapeutic agents," Clin Immunol Newsletter. 17(12):168-73 (1997).
Litzinger et al., "Biodistribution and immunotargetability of ganglioside-stabilized dioleoylphosphatidylethanolamine liposomes," Biochimica et Biophysica Acta. 1104:179-87 (1992).
Lowell et al., "Mapping of the Epstein-Barr virus and C3dg binding sites to a common domain on complement receptor type 2," J Exp Med. 170(6):1931-1946 (1989).
Lukacs et al., "Complement-dependent immune complex-induced bronchial inflammation and hyperreactivity," Am J Physiol Lung Cell Mol Physiol. 280:L512-L518 (2001).
Luqman et al., "The antileukemia activity of a human anti-CD40 antagonist antibody, HCD122, on human chronic lymphocytic leukemia cells," Blood. 112(3):711-20 (2008).
Luxembourg et al., "Modulation of signaling via the B cell antigen receptor by CD21, the receptor for C3dg and EBV," J Immunol. 153:4448-57 (1994).
Lyubarsky et al., "Recovery phase of the murine rod photoresponse reconstructed from electroretinographic recordings," J Neurosci. 16(2):563-571 (1996).
Lyubchenko et al., "Coligation of the B cell receptor with complement receptor type 2 (CR2/CD21) using its natural ligand C3dg: activation without engagement of an inhibitory signaling pathway," J Immunol. 174:3264-72 (2005).

(56) References Cited

OTHER PUBLICATIONS

MacCallum et al., "Antibody-antigen interactions: Contact analysis and binding site topography," J Mol Biol. 262(5):732-45 (1996).
Mache et al., "Complement inhibitor eculizumab in atypical hemolytic uremic syndrome," Clin J Am Soc Nephrol. 4(8):1312-6 (2009).
MacLaren et al., "Adipokines and the immune system: an adipocentric view," Adv Exp Med Biol. 632:1-21 (2008).
Marciano et al., "Neuron-specific mRNA complexity responses during hippocampal apoptosis after traumatic brain injury," J Neurosci. 24:2866-2876 (2004).
Mariuzza et al., The structural basis of antigen-antibody recognition, Annu Rev Biophys Chem. 16:139-159 (1987).
Markiewski et al., "C3a and C3b activation products of the third component of complement (C3) are critical for normal liver recovery after toxic injury," J Immunol. 173:747-754 (2004).
Marshall et al., "A new classification of head injury based on computerized tomography," J. Neurosurg. 75:S14-S20 (1991).
Martin et al., "Determination of the role for CD21 during Epstein-Barr virus infection of B-lymphoblastoid cells," J Virol. 68(8):4716-4726 (1994).
Martin et al., "Determination of the structural basis for selective binding of Epstein-Barr virus to human complement receptor type 2," J Exp Med. 174:1299-1311 (1991).
Maruo et al., "Generation of anaphylatoxins through proteolytic processing of C3 and C5 by house dust mite protease," J Allergy Clin Immunol. 100(2):253-260 (1997).
Maslowska et al., "Novel roles for acylation stimulating protein/C3adesArg: a review of recent in vitro and in vivo evidence," Vitam Horm. 70:309-32 (2005).
Mastellos et al., "A novel role of complement: mice deficient in the fifth component of complement (C5) exhibit impaired liver regeneration," J Immunol. 166(4):2479-86 (2001).
Mastellos et al., "Novel monoclonal antibodies against mouse C3 interfering with complement activation: description of fine specificity and applications to various immunoassays," Mol Immunol. 40(16):1213-21 (2004).
Matis et al., "Complement-specific antibodies: designing novel anti-inflammatories," Nat Med. 1(8):839-842 (1995).
Matsumoto et al., "Abrogation of the alternative complement pathway by targeted deletion of murine factor B," Proc Natl Acad Sci USA. 94(16):8720-8725 (1997).
Matsumoto et al., "Intersection of the complement and immune systems: A signal transduction complex of the B lymphocyte-containing complement receptor type 2 and CD19," J Exp Med. 173(1):55-64 (1991).
Matsuo et al., "Complement in renal tubulointerstitial injuries," Proceedings of the 35th Complement Symposium 21-22 (1998).
Maulik et al., "Molecular biotechnology: therapeutic applications and strategies," Wiley-Liss, Inc., pp. v-viii (Table of Contents Only), 1996.
McArthur et al., "Moderate and severe traumatic brain injury: epidemiologic, imaging and neuropathologic perspectives," Brain Pathol. 14:185-194 (2004).
McPherson, "Current approaches to macromolecular crystallization," Eur J Biochem. 189(1):1-23 (1990).
Mendrick et al., "I. induction of proteinuria in the rat by a monoclonal antibody against SGP-115/107," Kidney Int. 33:818-30 (1988).
Mendrick et al., "Monoclonal antibodies against rat glomerular antigens: production and specificity," Lab Invest. 49(1):107-17 (1983).
Meri et al., "Structural composition and functional characterization of soluble CD59: heterogeneity of the oligosaccharide and glycophosphoinositol (GPI) anchor revealed by laser-desorption mass spectrometric analysis," Biochem J. 316(3):923-35 (1996).
Mohamad et al., "Mitochondrial apoptotic pathways," Biocell. 29(2):149-161 (2005).
Moir et al., "B cells of HIV-1-infected patients bind virions through CD21-complement interactions and transmit infectious virus to activated T cells," J Exp Med. 192(5):637-646 (2000).
Mold et al., "Activation of the alternative complement pathway by EBV and the viral envelope glycoprotein, gp350," J Immunol. 140(11):3867-3874 (1988).
Molesworth et al., "Epstein-Barr virus gH is essential for penetration of B cells but also plays a role in attachment of virus to epithelial cells," J Virol. 74(14):6324-32 (2000).
Molina et al., "Analysis of C3b/C3d binding sites and factor I cofactor regions within mouse complement receptor 1 and 2," J Immunol. 153(2):789-795 (1994).
Molina et al., "Analysis of Epstein-Barr virus-binding sites on complement receptor 2 (CR2/CD21) using human-mouse chimeras and peptides," J Biol Chem. 266(19-20):12173-9 (1991).
Molina et al., "Characterization of a complement receptor 2 (CR2, CD21) ligand binding site for C3. An initial model of ligand interaction with two linked short consensus repeat modules," J Immunol. 154:5426-5435 (1995).
Molina et al., "Markedly impaired humoral immune response in mice deficient in complement receptors 1 and 2," Proc Natl Acad Sci USA. 93:3357-3361 (1996).
Mollnes et al., "Identification of a human C5 beta-chain epitope exposed in the native complement component but concealed in the SC5b-9 complex," Scand J Immunol. 28:307-12 (1988).
Moongkarndi et al., "Immunological and functional properties of two monoclonal antibodies against human C5," Immunobiol. 165:323 (1983).
Moongkarndi et al., "Monoclonal antibodies against the fifth component of human complement," Immunobiol. 162:397 (1982).
Moore et al., "Hydrodynamic, electron microscopic, and ligand-binding analysis of the Epstein-Barr virus/C3dg receptor (CR2)," J Biol Chem. 264:20576-82 (1989).
Moore et al., "Inhibition of Epstein-Barr virus infection In Vitro and In Vivo by soluble CR2 (CD21) containing two short consensus repeats," J Virol. 65(7):3559-3565 (1991).
Moore et al., "Molecular cloning of the cDNA encoding the Epstein-Barr virus/C3d receptor (complement receptor type 2) of human B lymphocytes," Proc Natl Acad Sci USA. 84:9194-8 (1987).
Moran et al., "Human recombinant soluble decay accelerating factor inhibits complement activation in vitro and in vivo," J Immunol. 149:1736-1743 (1992).
Morgan et al., "Expression of complement in the brain: Role in health and disease," Immunol Today. 17(10):461-466 (1996).
Morgan, "Clinical complementology: recent progress and future trends," Eur J Clin Invest. 24(4):219-28 (1994).
Morgan, "Regulation of the complement membrane attack pathway," Crit Rev Immunol. 19(3):173-198 (1999).
Morikis et al., "The electrostatic nature of C3d-complement receptor 2 association," J Immunol. 172:7537-47 (2004).
Mukherjee et al., "Allergic asthma: Influence of genetic and environmental factors," J Biol Chem. 286(38):32883-32889 (2011).
Mullen et al., "Structure of the Epstein-Barr virus gp42 protein bound to the MHC class II receptor HLA-DR1," Mol Cell. 9:375-85 (2002).
Mulligan et al., "Endothelial targeting and enhanced antiinflammatory effects of complement inhibitors possessing sialyl Lewisx moieties," J Immunol 162(8):4952-9 (1999).
Murray et al., "Functional bioactive recombinant acylation stimulating protein is distinct from C3a anaphylatoxin," J Lipid Res. 38:2492-501 (1997).
Murray et al., "Mice lacking acylation stimulating protein (ASP) have delayed postprandial triglyceride clearance," J Lipid Res. 40:1671-6 (1999).
Murray et al., "Reduced body weight, adipose tissue, and leptin levels despite increased energy intake in female mice lacking acylation-stimulating protein," Endocrinology. 141(3):1041-9 (2000).
Müller-Eberhard, "Molecular organization and function of the complement system," Ann Rev Biochem. 57:321-47 (1988).
Nagar et al., "X-ray crystal structure of C3d: A C3 fragment and ligand for complement receptor 2," Science. 280(5367):1277-81 (1998).
Nagata et al., "Activation of human serum complement with allergens," J Allergy Clin Immunol. 80(1):24-32 (1987).

(56) References Cited

OTHER PUBLICATIONS

Nagy et al., "The development of asthma in children infected with *Chlamydia pneumoniae* is dependent on the modifying effect of mannose-binding lectin," J Allergy Clin Immunol. 112:729-734 (2003).
Nataf et al., "Attenuation of experimental autoimmune demyelination in complement-deficient mice," J Immunol. 165(10):5867-5873 (2000).
Nataf et al., "Complement anaphylatoxin receptors on neurons: New tricks for old receptors?" Trends Neurosci. 22(9):397-402 (1999).
NCBI Blast for Accession No. NP_001006659.1. Retrieved on Dec. 26, 2013 (5 pages).
NCBI Blast for Accession No. NP_031784.1. Retrieved on Dec. 26, 2013 (4 pages).
NCBI Blast for GenBank Accession No. U09969. Retrieved on Nov. 15, 2013 (3 pages).
NCBI Blast for UniProtKB/Swiss-Prot Accession No. O55186. Retrieved on Nov. 13, 2013 (5 pages).
NCBI Blast for UniProtKB/Swiss-Prot Accession No. P00746. Retrieved on Nov. 13, 2013 (14 pages).
NCBI Blast for UniProtKB/Swiss-Prot Accession No. P00751. Retrieved on Nov. 13, 2013 (1 page).
NCBI Blast for UniProtKB/Swiss-Prot Accession No. P01024. Retrieved on Nov. 13, 2013 (29 pages).
NCBI Blast for UniProtKB/Swiss-Prot Accession No. P01027. Retrieved on Nov. 13, 2013 (13 pages).
NCBI Blast for UniProtKB/Swiss-Prot Accession No. P03953. Retrieved on Nov. 13, 2013 (6 pages).
NCBI Blast for UniProtKB/Swiss-Prot Accession No. P04004. Retrieved on Nov. 13, 2013 (14 pages).
NCBI Blast for UniProtKB/Swiss-Prot Accession No. P04186. Retrieved on Nov. 13, 2013 (9 pages).
NCBI Blast for UniProtKB/Swiss-Prot Accession No. P05155. Retrieved on Nov. 13, 2013 (29 pages).
NCBI Blast for UniProtKB/Swiss-Prot Accession No. P06909. Retrieved on Nov. 13, 2013 (19 pages).
NCBI Blast for UniProtKB/Swiss-Prot Accession No. P08173. Retrieved on Nov. 13, 2013 (4 pages).
NCBI Blast for UniProtKB/Swiss-Prot Accession No. P08603. Retrieved on Nov. 13, 2013 (1 page).
NCBI Blast for UniProtKB/Swiss-Prot Accession No. P10909. Retrieved on Nov. 13, 2013 (21 pages).
NCBI Blast for UniProtKB/Swiss-Prot Accession No. P11680. Retrieved on Nov. 13, 2013 (5 pages).
NCBI Blast for UniProtKB/Swiss-Prot Accession No. P13987. Retrieved on Nov. 13, 2013 (16 pages).
NCBI Blast for UniProtKB/Swiss-Prot Accession No. P15529. Retrieved on Nov. 13, 2013 (30 pages).
NCBI Blast for UniProtKB/Swiss-Prot Accession No. P17927. Retrieved on Nov. 13, 2013 (1 page).
NCBI Blast for UniProtKB/Swiss-Prot Accession No. P27918. Retrieved on Nov. 13, 2013 (13 pages).
NCBI Blast for UniProtKB/Swiss-Prot Accession No. P29788. Retrieved on Nov. 13, 2013 (10 pages).
NCBI Blast for UniProtKB/Swiss-Prot Accession No. P58019. Retrieved on Nov. 13, 2013 (5 pages).
NCBI Blast for UniProtKB/Swiss-Prot Accession No. P97290. Retrieved on Nov. 13, 2013 (6 pages).
NCBI Blast for UniProtKB/Swiss-Prot Accession No. Q06890. Retrieved on Nov. 13, 2013 (9 pages).
NCBI Blast for UniProtKB/Swiss-Prot Accession No. Q61475. Retrieved on Nov. 13, 2013 (11 pages).
NCBI Blast for UniProtKB/Swiss-Prot Accession No. Q9P296. Retrieved on Nov. 13, 2013 (9 pages).
NCBI Protein Database Accession No. P08173. Retrieved Feb. 18, 2014 (4 pages).
NCBI Protein Database Accession No. P13987. Retrieved Feb. 18, 2014 (12 pages).
NCBI Protein Database Accession No. P15529. Retrieved Feb. 18, 2014 (21 pages).
NCBI Protein Database Accession No. P58019. Retrieved Feb. 18, 2014 (4 pages).
Nemerow et al., "Identification and characterization of the Epstein-Barr virus receptor on human B lymphocytes and its relationship to the C3d complement receptor (CR2)," J Virol. 55(2):347-51 (1985).
Nemerow et al., "Identification of an epitope in the major envelope protein of Epstein-Barr virus that mediates viral binding to the B lymphocyte EBV receptor (CR2)," Cell. 56:369-77 (1989).
Nemerow et al., "Identification of gp350 as the viral glycoprotein mediating attachment of Epstein-Barr virus (EBV) to the EBV/C3d receptor of B cells: sequence homology of gp350 and C3 complement fragment C3d," J Virol. 61(5):1416-20 (1987).
Ngo et al., Computational Complexity, Protein Structure Prediction, and the Levinthal Paradox. *The Protein Folding Problem and Tertiary Structure Prediction*. Merz et al., 491-495 (1994).
Niemann et al., "The use of monoclonal antibodies as probes of the three-dimensional structure of human complement factor D," J Immunol. 132(2):809-15 (1984).
Nozaki et al., "Drusen complement components C3a and C5a promote choroidal neovascularization," Proc Natl Acad Sci USA. 103(7):2328-2333 (2006).
O'Barr et al., "Neuronal expression of a functional receptor for the C5a complement activation fragment," J Immunol. 166(6):4154-4162 (2001).
Oglesby et al., "Membrane cofactor protein (CD46) protects cells from complement-mediated attack by an intrinsic mechanism," J Exp Med. 175:1547-51 (1992).
Ohlsson et al., "Complement activation after lumbosacral ventral root avulsion injury," Neurosci Lett. 394(3):179-183 (2006).
Ohlsson et al., "Complement activation following optic nerve crush in the adult rat," J. Neurotrauma. 20:895-904(2003).
Okano, "Epstein-Barr virus infection and its role in the expanding spectrum of human diseases," Acta Paediatr. 87:11-18 (1998).
Padlan et al., "Structure of an antibody-antigen complex: crystal structure of the HyHEL-10 Fab-lysozyme complex," Proc Natl Acad Sci USA. 86(15):5938-5942 (1989).
Paglialunga et al., "Reduced adipose tissue triglyceride synthesis and increased muscle fatty acid oxidation in C5L2 knockout mice," J Endocrinol. 194:293-304 (2007).
Paixao-Cavalcante et al., "Factor H facilitates the clearance of GBM bound iC3b by controlling C3 activation in fluid phase," Mol Immunol. 46:1942-50 (2009).
Pascual et al., "A monoclonal antibody which blocks the function of factor D of human complement," J Immunol Methods. 127:263-9 (1990).
Pascual et al., "Inhibition of complement alternative pathway in mice with Fab antibody to recombinant adipsin/factor D," Eur J Immunol. 23:1389-92 (1993).
Patel et al., "Pexelizumab: a novel therapy for myocardial ischemia-reperfusion," Drugs Today (Barc). 41(3):165-70 (2005).
Peng et al., "Role of C5 in the development of airway inflammation, airway hyperresponsiveness, and ongoing airway response," J. Clin. Invest. 115(6):1590-1600(2005).
Peng et al., Abstract 200: "Contribution of complement component C5 in the development of airway inflammation, maintaining airway hyperresponsiveness and sustaining an ongoing asthmatic attack," Abstracts/Mol Immunol. 41:292 (2004).
Peng et al., Late-breaking abstracts presented at scientific sessions AAAAI 62nd annual meeting, Mar. 3-7, "Blocking intrapulmonary activation of complement cascade on the development of airway hyperresponsiveness: Utility in sight?" Abstract LB2:720 (2006).
Pervushin et al., "Attenuated T2 relaxation by mutual cancellation of dipole-dipole coupling and chemical shift anisotropy indicates an avenue to NMR structures of very large biological macromolecules in solution," Proc Natl Acad Sci USA. 94:12366-71 (1997).
Peters et al., "The Bb fragment of complement factor B acts as a B cell growth factor." J Exp Med. 169(4):1225-1235 (1988).
Petersen et al., "The mannan-binding lectin pathway of complement activation: biology and disease association," Mol Immunol. 38:133-49 (2001).
Piatesi et al., "Immunological optimization of a generic hydrophobic pocket for high affinity hapten binding and Diels-Alder activity," Chembiochem. 5(4):460-466 (2004).

(56) References Cited

OTHER PUBLICATIONS

Pietersz et al., "Antibody conjugates for the treatment of cancer," Immunolog Reviews. 129:57-80 (1992).
Pillay et al., "Administration of vaccinia virus complement control protein shows significant cognitive improvement in a mild injury model," Ann. N.Y. Acad. Sci. 1056:450-461(2005).
Poznansky et al., "The difference between human C3F and C3S results from a single amino acid change from an asparagine to an aspartate residue at position 1216 on the α-chain of the complement component C3," J Immunol. 143(4):1254-1258 (1989).
Preissner, "Structure and biological role of vitronectin," Annu Rev Cell Biol. 7:275-310 (1991).
Prodeus et al., "A critical role for complement in maintenance of self-tolerance," Immunity. 9(5):721-731 (1998).
Prodinger et al., "Characterization of C3dg binding to to a recess formed between short consensus repeats 1 and 2 of complement receptor type 2 (CR2; CD21)," J Immunol. 161:4604-4610 (1998).
Prota et al., "The crystal structure of human CD21: Implications for Epstein-Barr virus and C3d binding," Proc Natl Acad Sci USA. 99:10641-6 (2002).
Qiu et al., "Upregulation of the fas receptor death-inducing signaling complex after traumatic brain injury in mice and humans," J. Neurosci. 22(9):3504-3511(2002).
Quigg et al., "Blockade of antibody-induced glomerulonephritis with Crry-Ig, a soluble murine complement inhibitor," J Immunol. 160(9):4553-60 (1998).
Quigg et al., "Production and fuctional analysis of rat CD59 and chimeric CD59-Crry as active soluble proteins in Pichia pastoris," Immunol. 99(1):46-53 (2000).
Rabinovici et al., "Role of complement in endotoxin/platelet-activating factor-induced lung injury," J Immunol. 149(5):1744-50 (1992).
Rader et al., "A phage display approach for rapid antibody humanization: Designed combinatorial V gene libraries," Proc Natl Sci USA. 95:8910-8915 (1998).
Raghupathi et al., "BCL-2 overexpression attenuates cortical cell loss after traumatic brain injury in transgenic mice," J. Cereb. Blood Flow Metab. 18:1259-1269(1998).
Raghupathi et al., "Mild traumatic brain injury induces apoptotic cell death in the cortex that is preceded by decreases in cellular Bcl-2 immunoreactivity," Neuroscience. 110(4):605-616(2002).
Raghupathi et al., "Temporal alterations in cellular bax: Bcl-2 ratio following traumatic brain injury in the rat," J. Neurotrauma. 20(5):421-435(2003).
Raghupathi, "Cell death mechanisms following traumatic brain injury," Brain Pathol. 14:215-222(2004).
Ramer et al., "Setting the stage for functional repair of spinal cord injuries: A cast of thousands," Spinal Cord. 43:134-161(2005).
Ramm et al., "Transmembrane channel formation by complement: functional analysis of the No. of C5b6, C7, C8, and C9 molecules required for a single channel," Pro Natl Acad Sci. 79(15):4751-5 (1982).
Rancan et al., "Central nervous system-targeted complement inhibition mediates neuroprotection after closed head injury in transgenic mice," J. Cereb. Blood Flow. Metab. 23(9):1070-1074(2003).
Rao et al., "OKB7, a monoclonal antibody that reacts at or near the C3d binding site of human CR2," Cell Immunol. 93(2):549-555 (1985).
Rebhun et al., "Proteins of the complement system and acute phase reactants in sera of patients with spinal cord injury," Ann. Allergy 66:335-338(1991).
Reeck et al., "Homology in proteins and nucleic acids: A terminology muddle and a way out of it," Cell. 50:667 (1987).
Rehrig et al., "Complement inhibitor, complement receptor 1-related gene/protein y-lg attenuates intestinal damage after the onset of mesenteric ischemia/reperfusion injury in mice," J Immunol. 167:5921-7 (2001).
Reynolds et al., "Vaccinia Virus Complement Control Protein Reduces Inflammation and Improves Spinal Cord Integrity Following Spinal Cord Injury," Ann. NY. Acad Sci. 1035:165-178(2004).
Ricklin et al., "Complement-targeted therapeutics," Nat Biotechnol. 25(11):1265-75 (2007).
Rinder et al., "Blockade of C5a and C5b-9 generation inhibits leukocyte and platelet activation during extracorporeal circulation," J Clin Invest. 96(3):1564-72 (1995).
Rink et al., "Evidence of apoptotic cell death after experimental traumatic brain injury in the rat," Am. J. Pathol. 147(6):1575-1583(1995).
Rioux, "TP-10 AVANT immunotherapeutics," Curr Opin Invest Drugs 2(3):364-71 (2001).
Risitano et al., "Complement fraction 3 binding on erythrocytes as additional mechanism of disease in paroxysmal nocturnal hemoglobinuria patients treated by eculizumab," Blood. 113(17):4094-4100 (2009) (25 pages).
Risitano et al., "Paroxysmal nocturnal hemoglobinuria: pathophysiology, natural history and treatment options in the era of biological agents," Biologics. 2(2):205-222 (2008).
Risitano et al., "The complement receptor 2/factor H fusion protein TT30 protects paroxysmal nocturnal hemoglobinuria erythroctyes from complement-mediated hemolysis and C3 fragment opsonization," Blood. 119(26):6307-6316 (2012).
Risitano et al., "TT30, a novel regulator of the complement alternative pathway (CAP), inhibits hemolysis of paroxysmal nocturnal hemoglobinuria (PNH) erythrocytes and prevents upstream C3 binding on their surface in an in vitro model," <https://ash.confex.com/ash/2009/webprogram/Paper19102.html>, retrieved on Dec. 26, 2013 (2 pages).
Rittershaus et al., "Recombinant glycoproteins that inhibit complement activation and also bind the selectin adhesion molecules," J Biol Chem. 274(16):11237-44 (1999).
Robbins et al., "Complement activation by cigarette smoke," Am J. Physiol. 260:L254-L259 (1991).
Roffler et al., "Anti-neoplastic glucuronide prodrug treatment of human tumor cells targeted with a monoclonal antibody-enzyme conjugate," Biochem Pharmacol. 42:2062-2065 (1991).
Rohrer et al., "A targeted inhibitor of the alternative complement pathway reduces angiogenesis in a mouse model of age-related macular degeneration," Invest Ophthalmol Vis Sci. 50(7):3056-3064 (2009).
Rohrer et al., "Eliminating complement factor D reduces photoreceptor susceptibility to light-induced damage," Invest Ophthalmol Vis Sci. 48(11):5282-9 (2007).
Rohrer et al., "Role of neurotrophin receptor TrkB in the maturation of rod photoreceptors and establishment of synaptic transmission to the inner retina," J Neurosci. 19(20):8919-8930 (1999).
Rood et al., "Reduction of early graft loss after intraportal porcine islet transplantation in monkeys," Transplantation. 83(2):202-210 (2007) Abstract Only.
Roof et al., "Gender differences in acute CNS trauma and stroke: Neuroprotective effects of estrogen and progesterone," J Neurotrauma. 17(5):367-388(2000).
Ross et al., "Macrophage cytoskeleton association with CR3 and CR4 regulates receptor mobility and phagocytosis of iC3b-opsonized erythrocytes," J Leukoc Biol. 51(20):109-117 (1992).
Rother et al., "Discovery and development of the complement inhibitor eculizumab for the treatment of paroxysmal nocturnal hemoglobinuria," Nat Biotechnol. 25(11):1256-64, 1488 (2007).
Rothlein et al., "The requirement for lymphocyte function-associated antigen 1 in homotypic leukocyte adhesion stimulated by phorbol ester," J Exp Med. 163(5):1132-49 (1986).
Rounioja et al., "Mechanism of acute fetal cardiovascular depression after maternal inflammatory challenge in mouse," Am J Pathol. 166(6):1585-1592 (2005).
Royo et al., "Pharmacology of traumatic brain injury," Current Opinion in Pharmacology. 3:27-32(2003).
Rudikoff et al., "Single amino acid subsitution altering antigen-binding specificity," Proc Natl Acad Sci USA. 79(6):1979-19783 (1982).
Rudikoff et al., "Single amino acid substitution altering antigen-binding specificity," Proc Natl Acad Sci USA. 79(6):1979-1983 (1982).

(56) References Cited

OTHER PUBLICATIONS

Rushmere et al., "Production and functional characterization of a soluble recombinant form of mouse CD59," Immunol. 99(2):326-32 (2000).
Sahu et al., "Identification of multiple sites of interaction between heparin and the complement system," Mol Immunol. 30(7):679-84 (1993).
Salerno et al., "A soluble chimeric inhibitor of C3 and C5 convertases, complement activation blocker-2, prolongs graft survival in pig-to-rhesus monkey heart transplantation," Xenotransplantation. 9(2):125-34 (2002).
Sambrook et al., Analysis of genomic DNA by Southern hybridization. *Molecular Cloning: A Laboratory Manual.* Second Edition, Cold Spring Harbor Labs Press: Cold Spring Harbor, NY, pp. 9.31-9.62(1989).
Santiago-Raber et al., "Type-I interferon receptor deficiency reduces lupus-like disease in NZB mice," J Exp Med. 197:777-88 (2003).
Sarnaik et al., "Periodic transfusions for sickle cell anemia and CNS infarction," Am J Dis Child. 133(12):1254-7 (1979).
Satoh et al., "Energy metabolism regeneration in transgenic mouse liver expressing creatine kinase after major hepatectomy," Gastroenterology. 101:1166-74 (1996).
Sauerland et al., "A CRASH landing in severe head injury," Lancet. 364(9442):1291-1292 (2004).
Schmidt et al., "Closed head injury—an inflammatory disease?," Brain Res. Rev. 48(2):388-399(2005).
Schmidt et al., "The role of neuroinflammation in traumatic brain injury," Eur. J. Trauma. 3:135-149(2004).
Schreiber et al., Abstract No. 042 "Complement anaphylatoxin C5a and C5a receptor are fundamental to neutrophil activation and glomerulonephritis induced by anti-neutrophil cytoplasmic antibodies," Abstracts/Mol Immunol. 45:4109(2008).
Schwarzenbacher et al., "Crystal structure of human b2-glycoprotein I: implications for phospholipid binding and the antiphospholipid syndrome," EMBO J. 18:6228-39 (1999).
Scola et al., "The human complement fragment receptor, C5L2, is a recycling decoy receptor," Mol Immunol. 46:1149-62 (2009).
Selzner et al., "Failure of regeneration of the steatotic rat liver: disruption at two different levels in the regeneration pathway," Hepatology. 31:35-42 (2000).
Senter et al., "Generation of 5-fluorouracil from 5-fluorocytosine by monoclonal antibody-cytosine deaminase conjugates," Bioconjugate Chem. 2:447-451 (1991).
Senter et al., "Generation of cytotoxic agents by targeted enzymes," Bioconjugate Chem. 4:3-9 (1993).
Sewell et al., "Complement C3 and C5 play critical roles in traumatic brain cryoinjury: blocking effects on neutrophil extravasation by C5a receptor antagonist," *J. Neuroimmunol.* 155: 55-63, 2004.
Seya et al., "Limited proteolysis of complement protein C3b by regulatory enzyme C3b inactivator: Isolation and characterization of a biologically active fragment, C3d,g," J Biochem. 97(1):373-382 (1985).
Shacka et al., "Regulation of neuronal cell death and neurodegeneration by members of the Bcl-2 family: Therapeutic implications," Curr Drug Targets CNS Neurol Disord. 4(1):25-39 (2005).
Sharkey et al., "Biodistribution and radiation dose estimates for yttrium- and iodine-labeled monoclonal antibody IgG and fragments in nude mice bearing human colonic tumor xenografts," Cancer Res. 50:2330-2336 (1990).
Sharkey et al., "Rapid blood clearance of immunoglobulin G2a and immunoglobulin G2b in nude mice," Cancer Res. 51:3102-3107 (1991).
Sharma et al., "Identification of three physically and functionally distinct binding sites for C3b in human complement Factor H by deletion mutagenesis," Proc Natl Acad Sci USA. 93(20):10996-11001 (1996).
Sheerin et al., "Leaked protein and interstitial damage in the kidney: is complement the missing link?" Clin Exp Immunol. 130(1):1-3 (2002).
Sigala et al., "Histological and lipid peroxidation changes after administration of 2-acetylaminofluorene in a rat liver injury model following selective periportal and pericentral damage," Toxicology. 196:155-63 (2004).
Singhrao et al., "Spontaneous classical pathway activation and deficiency of membrane regulators render human neurons susceptible to complement lysis," *Am. J. Pathol.* 157: 905-918, 2000.
Sinha et al., Abstract No. 043 "The receptor for complement anaphylatoxin C5a protects against the development of airway hyperresponsiveness in allergic asthma by inhibiting cysteinyl leukotriene pathway," Abstracts/Mol Immunol. 45:4109-4110 (2008).
Skjodt et al., "MBL/Ficolin assocaited protein-1 (MAP-1) may function as a local lectin pathway specific complement inhibitor," Mol Immunol. 47:2229-30 (2010).
Skolnick et al., "From genes to protein structure and function: novel applications of computational approaches in the genomic era," Trends Niotechnol. 18(1):34-39 (2000).
Smith et al., "Membrane-targeted complement inhibitors," Mol Immunol. 38:249-55 (2001).
Sokoloff et al., "Targeting of cancer cells with monoclonal antibodies specific for C3b(ii)," Cancer Immunol and Immunother. 49(10):551-62 (2000).
Song et al., "Complement receptor 2-mediated targeting of complement inhibitors to sites of complement activation," J Clin Invest. 111(12):1875-1885 (2003).
Spriggs et al., "The extracellular domain of the Epstein-Barr virus BZLF2 protein binds the HLA-DR beta chain and inhibits antigen presentation," J Virol. 70:5557-63 (1996).
Stahel et al., "Experimental closed head injury: Analysis of neurological outcome, blood-brain barrier dysfunction, intracranial neutrophil infiltration, and neuronal cell death in mice deficient in genes for pro-inflammatory cytokines," J. Cereb. Blood Flow Metab. 20:369-380(2000).
Stahel et al., "Intracerebral complement C5a receptor (CD88) expression is regulated by TNF and lymphotoxin-α following closed head injury in mice," J. Neuroimmunol. 109:164-172(2000).
Stahel et al., "Intrathecal levels of complement-derived soluble membrane attack complex (sC5b-9) correlate with blood-brain barrier dysfunction in patients with traumatic brain injury," J. Neurotrauma. 18(8): 773-781(2001).
Stahel et al., "The role of the complement system in traumatic brain injury," *Brain Res. Rev.* 27: 243-256, 1998.
Strauss et al., "Common patterns of Bcl-2 family gene expression in two traumatic brain injury models," Neurotox. Res. 6(4):333-342(2004).
Strey et al., "The proinflammatory mediators C3a and C5a are essential for liver regeneration," J Exp Med. 198(6):913-23 (2003).
Stribling et al., "Aerosol gene delivery in vivo," Proc. Natl. Acad. Sci. USA. 89:11277-11281(1992).
Stryer et al., Levels of Structure in Protein Architecture. *Biochemistry (3rd edition).* W H Freeman Company, 31-33 (1998).
Sugita et al., "Recombinant soluble CD59 inhibits reative haemolysis with complement," Immunol. 82(1):34-41 (1994).
Supplementary European Search Report for European Application No. 03796403.8, mailed Jul. 3, 2006 (4 pages).
Supplementary European Search Report for European Application No. 06771303.2, dated Oct. 28, 2011 (5 pages).
Supplementary European Search Report for European Patent Application No. EP11798880.8, dated Jan. 7, 2014 (13 pages).
Supplementary Partial European Search Report for European Application No. 03796403.8, mailed Apr. 3, 2006 (3 pages).
Supplementary Partial European Search Report for European Application No. 05722948.6, dated Jun. 24, 2008 (6 pages).
Szakonyi et al., "Structure of complement receptor 2 in complex with its C3d ligand," Science. 292:1725-1728 (2001).
Szakonyi et al., "Structure of the Epstein-Barr virus major envelope glycoprotein," Nature Struct Mol Biol. 13:996-1001 (2006).
Takafuji et al., "Degranulation from human eosinophils stimulated with C3a and C5a," Int Arch Allergy Immunol. 104(Suppl 1):27-29 (1994).
Takahashi et al., "Mouse complement receptors type 1 (CR1;CD35) and type 2 (CR2;CD21): expression on normal B cell subpopulations

(56) References Cited

OTHER PUBLICATIONS and decreased levels during the development of autoimmunity in MRL/lpr mice," J Immunol. 159:1557-69 (1997).
Takahashi et al., "Solubilization of antigen-antibody complexes: a new function of complement as a regulator of immune reactions," Prog Allergy. 27:134-166 (1980).
Takeda et al., "Number of hits necessary for complement-mediated hemolysis," Microbiol Immunol. 30(5):461-8 (1986).
Tamerius et al., "Detection of a neoantigen on human C3bi and C3d by monoclonal antibody," J Immunol. 135(3):2015-2019 (1985).
Tanaka et al., "Murine monoclonal anti-Ba antibody that enhances haemolytic activity of Factor B," Immunology. 73(4):383-387(1991).
Tanhehco et al., "The anti-factor D antibody, MAb 166-32, inhibits the alternative pathway of the human complement system," Transplant Proc. 31(55):2168-71 (1999).
Tanner et al., "Epstein-Barr virus gp350/220 binding to the B lymphocyte C3d receptor mediates adsorption, capping, and endocytosis," Cell. 50:203-13 (1987).
Tatusova et al., "Blast 2 Sequences, a new tool for comparing protein and nucleotide sequences," FEMS Microbiol Lett. 174(2):247-250 (1999).
Taub, "Liver regeneration: from myth to mechanism," Nat Rev Mol Cell Biol. 5:836-47 (2004).
Taube et al., "Factor B of the alternative complement pathway regulates development of airway hyperresponsiveness and inflammation," Proc Natl Acad Sci USA. 103(21):8084-8049 (2006).
Taube et al., "Inhibition of complement activation decreases airway inflammation and hyperresponsiveness," Am J Respir Cri. Care Med. 168:1333-1341 (2003).
Teasdale et al., "Assessment of coma and impaired consciousness," Lancet. 2:81-4 (1974).
Ten et al., "The signal transduction pathway of CD23 (FceRIIb) targets IkB kinase," J Immunol. 163(7):3851-7 (1999).
Teoh et al., "Dual role of tumor necrosis factor-alpha in hepatic ischemia-reperfusion injury: studies in tumor necrosis factor-alpha gene knockout mice," Hepatology. 39:412-21 (2004).
Thomas et al., "Inhibition of complement activity by humanized anti-C5 antibody and single-chain Fv," Mol Immunol. 33(17-18):1389-401 (1996).
Thurman et al., "A novel inhibitor of the alternative compliment pathway prevents antiphospholipid antibody-induced pregnancy loss in mice," Mol Immunol. 42(1):87-97 (2005).
Thurman et al., "A novel inhibitor of the alternative pathway of complement protects mice from ischemic acute renal failure," American Nephrology Society Meeting, Abstract (1 page), 2007.
Thurman et al., "Acute tubular necrosis is characterized by activation of the alternative pathway of complement," Kidney Int. 67:524-530 (2005).
Thurman et al., "Complement activation through the alternative pathway is necessary for the development of airway hyperresponsiveness (AHR) and inflammation in a model of human asthma," Mol Immunol., 41:319, Abstract No. 256, 2005.
Thurman et al., "Lack of functional alternative complement pathway ameliorates ischemic acute renal failure in mice," J Immunol. 170:1517-1523, 2003.
Thurman et al., "The central role of the alternative complement pathway in human disease," J Immunol. 176(3):1305-1310 (2006).
Thurman et al., "Treatment with an inhibitory monoclonal antibody to mouse factor B protects mice from induction of apoptosis and renal ischemia/reperfusion injury," J Am Soc Nephrol. 17(3):707-715 (2006).
Tian et al., "Kupffer cell-dependent TNF-alpha signaling mediates injury in the arterialized small-for-size liver transplantation in the mouse," Proc Natl Acad Sci USA. 103(12):4598-603 (2006).
Tolnay et al., "Complement receptor 2 in the regulation of the immune response," Clin Immunol Immunopathol. 88:123-32 (1998).
Tosic et al., "Preparation of monoclonal antibodies to C3b by immunization with C3b(i)-sepharose," J Immunol Methods. 120:241-9 (1989).

Tsutsumi et al., "Site-specific chemical modification with polyethylene glycol of recombinant immunotoxin anti-Tac(Fv)-PE38 (LMB-2) improves antitumor activity and reduces animal toxicity and immunogenicity," Proc Natl Acad Sci USA. 97(15):8548-53 (2000).
Tuveson et al., "Molecular interactions of complement receptors on B lymphocytes: a CR1/CR2 complex distinct from the CR2/CD19 complex," J Exp Med. 173:1083-9 (1991).
Ueda et al., "Probing functional sites on complement protein B with monoclonal antibodies," J. Immunol. 138: 1143-1149, 1987.
Van Beek et al., "Activation of the complement in the central nervous system: Roles in neurodegeneration and neuroprotection," Ann. N.Y. Acad. Sci. 992:56-71(2003).
van der Eisen et al., "A crystal structure of the complex between human complement receptor 2 and its ligand C3d," Science. 332:608-611 (2011).
Van Harmelen et al., "Mechanisms involved in the regulation of free fatty acid release from isolated human fat cells by acylation-stimulating protein and insulin," J Biol Chem. 274(26):18243-51 (1999).
Varsano et al., "Generation of complement C3 and expression of cell membrane complement inhibitory proteins by human bronchial epithelium cell line," Thorax. 55:364-369 (2000).
Versey et al., "Activation of complement in relation to disease," J. Clin. Pathol., 28, Suppl. (Assoc. Clin. Pathol) 6: 38-44, 1975.
Vos et al., "EFNS guideline on mild traumatic brain injury: report of an EFNS task force," Eur. J. Neurol. 9:207-219(2002).
Vranken et al., "The CCPN data model for NMR spectroscopy: development of a software pipeline," Proteins. 59:687-96 (2005).
Wang et al., "Amelioration of Lupus-like autoimmune disease in NZB/W $F_1$ mice after treatment with a blocking monoclonal antibody specific for complement component C5," Proc Natl Acad Sci USA. 93(16):8563-8 (1996).
Wang et al., "Anti-C5 monoclonal antibody therapy prevents collagen-induced arthritis and ameoliorates established disease," Proc Natl Acad Sci USA. 92(19):8955-9 (1995).
Ward et al., "Decay-accelerating factor CD55 is identified as the receptor for echovirus 7 using CELICS, a rapid immuno-focal cloning method," EMBO J. 13(21):5070-4 (1994).
Watanabe et al., "Co-protective effect of Crry and CD59 in rat kidney against complement attack," Proceedings of the Joint Academic Meeting of the Complement Symposium and Japanese Society for Host Defense Research, 37(11):19-20 (2000).
Watanabe et al., "Modulation of renal disease in MRL/lpr mice genetically deficient in the alternative complement pathway factor B," J Immunol. 164(2):786-794 (2000).
Weis et al., "Identification of a 145,000 Mr membrane protein as the C3d receptor (CR2) of human B lymphocytes," Proc Natl Acad Sci USA. 81:881-5 (1984).
Weis et al., "Identification of a partial cDNA clone for the C3d/Epstein-Barr virus receptor of human B lymphocytes: homology with the receptor for fragments C3b and C4b of the third and fourth components of complement," Proc Natl Acad Sci USA. 83:5639-43 (1986).
Weis et al., "Structure of the human B lymphocyte receptor for C3d and the Epstein-Barr virus and relatedness to other members of the family of C3/C4 binding proteins," J Exp Med. 167:1047-66 (1988).
Weisman et al., "Soluble human complement receptor type 1: in vivo inhibitor of complement suppressing post-ischemic myocardial inflammation and necrosis," Science. 249(4965):146-151 (1990).
Whiss, "Pexelizumab Alexion," Curr Opin Investig Drugs. 3(6):870-7 (2002).
Wiles et al., "NMR studies of a viral protein that mimics the regulators of complement activation," J Mol Biol. 272(2):253-265 (1997).
Williams et al., "In situ DNA fragmentation occurs in white matter up to 12 months after head injury in man," Acta Neuropathol. 102:581-590 (2001).
Winkelstein et al., "The role of C3 as an opsonin in the early stages of infection," Proc Soc Exp Biol Med. 149:397-401 (1975).
Wiseman et al., "Rapid measurement of binding constants and heats of binding using a new titration calorimeter," Anal Biochem. 179:131-7 (1989).

(56) References Cited

OTHER PUBLICATIONS

Wittekind et al., "A high sensitivity 3D NMR experiment to correlate amide-proton and nitrogen resonances with the alpha-carbon and beta-carbon resonances in proteins," J Magn Reson. 101:201-5 (1993).
Wong et al., "Apoptosis and traumatic brain injury," Neurocrit Care. 3:177-182 (2005).
Wullaert et al., "Hepatic tumor necrosis factor signaling and nuclear factor-kappaB: effects on liver homeostasis and beyond," Endocr Rev. 28(4):365-86 (2007).
Xia et al., "Acylation-stimulating protein (ASP) deficiency induces obesity resistance and increased energy expenditure in ob/ob mice," J Biol Chem. 277:45874-9 (2002).
Xiong et al., "Formation of complement membrane attack complex in mammalian cerebral cortex evokes seizures and neurodegeneration," J Neurosci. 23:955-960 (2003).
Xu, Y. et al., (1997) "Contribution of the complement control protein modules of C2 in C4b binding assessed by analysis of C2/factor B chimeras," J. Immunol. 158: 5958-5965, 1997.
Yakovlev et al., "Activation of CPP32-like caspases contributes to neuronal apoptosis and neurological dysfunction after traumatic brain injury," J Neurosci. 17:7415-7424 (1997).
Yamaji et al., "Up-regulation of hepatic heme oxygenase-1 expression by locally induced interleukin-6 in rats administered carbon tetrachloride intraperitoneally," Toxicol Lett. 179:124-9 (2008).
Yang et al., "An engineered complement receptor 1 composed of two functional domains can protect against immune-mediated hemolysis," Protein Expr Purif. 66(1):28-34 (2009).
Yao et al., "Progesterone differentially regulates pro- and anti-apoptotic gene expression in cerebral cortex following traumatic brain injury in rats," J Neurotrauma. 22:656-668 (2005).
Yatsiv et al., "Elevated intracranial IL-18 in humans and mice after traumatic brain injury and evidence of neuroprotective effects of IL-18-binding protein after experimental closed head injury," J Cereb Blood Flow Metab. 22:971-978 (2002).
Yatsiv et al., "Erythropoietin is neuroprotective, improves functional recovery, and reduces neuronal apoptosis and inflammation in a rodent model of experimental closed head injury," FASEB J. 19:1701-1703 (2005).
Young et al., "Isolating the Epstein-Barr virus gp350/220 binding site on complement receptor type 2 (CR2/CD21)," J Biol Chem. 282(50):36614-25 (2007).
Young et al., "Molecular basis of the interaction between complement receptor type 2 (CR2/CD21) and Epstein-Barr virus glycoprotein gp350," J Virol. 82:11217-27 (2008).
Younger et al., "Detrimental effects of complement activation in hemorrhagic shock," J Appl Physiol. 90:441-446 (2001).
Yu et al., "Protection of human breast cancer cells from complement-mediated lysis by expression of heterologous CD59," Clin Exp Immunol. 115(1):13-8 (1999).
Zhang et al., "Bench-to-bedside review: Apoptosis/programmed cell death triggered by traumatic brain injury," Crit Care. 9(1):66-75 (2005).
Zhang et al., "Immunophysical exploration of C3d-CR2(CCP1-2) interaction using molecular dynamics and electrostatics," J Mol Biol. 369:567-83 (2007).
Zhang et al., "Targeting of functional antibody-CD59 fusion proteins to a cell surface," J Clin Invest. 103(1):55-61 (1999).
Zhang et al., "Targeting of functional antibody-decay-accelerating factor fusion proteins to a cell surface," J Biol Chem. 276(29):27290-5 (2001).
Zhong et al., "NIM811, a mitochondrial permeability transition inhibitor, prevents mitochondrial depolarization in small-for-size rat liver grafts," Am J Transplant. 7:1103-11 (2007).
Zhu et al., "Inhibition of tumor growth and metastasis by targeting tumor-associated angiogenesis with antagonists to the receptors of vascular endothelial growth factor," Invest New Drugs. 17(3):195-212 (1999).
Zipfel, "Complement factor H: physiology and pathophysiology," Semin Thromb Hemost. 27(3):191-9 (2001).
Zuiderweg et al., "Heteronuclear three-dimensional NMR spectroscopy of the inflammatory protein C5a," Biochemistry. 28:2387-91 (1989).
International Search Report for PCT Application No. PCT/US2013/041811, mailed Nov. 12, 2013 (3 pages).
Tang et al, "Exogenous biliverdin ameliorates ischemia-reperfusion injury in small-for-size rat liver grafts," Transplant Proc. 39(5):1338-44 (2007).
Yang et al., "The role of complement C3 in intracerebral hemorrhage-induced brain injury," J Cereb Blood Flow Metab. 26(12): 1490-5 (2006).
Weaver, "Animal studies paint misleading picture," <http://www.nature.com/news/2010/100330/full/news.2010.158.html>, retrieved on Sep. 14, 2014 (3 pages) (2010).
Leu et al., "Triggering of interferon gamma-primed macrophages by various known complement activators for nonspecific tumor cytotoxicity," Cell Immunol. 106(1):114-121 (1987).
International Preliminary Report on Patentability and Written Opinion of the International Searching Authority for International Application No. PCT/US2007/014602, dated Dec. 22, 2008 (6 pages).
International Preliminary Report on Patentability and Written Opinion of the International Searching Authority for International Application No. PCT/US2011/036552, dated Nov. 20, 2012 (9 pages).
International Preliminary Report on Patentability and Written Opinion of the International Searching Authority for International Application No. PCT/US2010/055745, dated May 8, 2012 (6 pages).
International Search Report for International Application No. PCT/US2011/041517, completed Oct. 11, 2011 (8 pages).
Supplementary European Search Report for European Application No. 10794833.3 , completed Nov. 28, 2013 (8 pages).
He et al., "A complement-dependent balance between hepatic ischemia/reperfusion injury and liver regeneration in mice," J Clin Invest. 119(8):2304-16 (2009).

* cited by examiner

SEQUENCE LISTING

<160> NUMBER OF SEQ ID NOS: 20

<210> SEQ ID NO 1
<211> LENGTH: 1087
<212> TYPE: PRT
<213> ORGANISM: Homo sapiens

<400> SEQUENCE: 1

Met Gly Ala Ala Gly Leu Leu Gly Val Phe Leu Ala Leu Val Ala Pro
1               5                   10                  15

Gly Val Leu Gly Ile Ser Cys Gly Ser Pro Pro Ile Leu Asn Gly
            20                  25                  30

Arg Ile Ser Tyr Tyr Ser Thr Pro Ile Ala Val Gly Thr Val Ile Arg
            35                  40                  45

Tyr Ser Cys Ser Gly Thr Phe Arg Leu Ile Gly Glu Lys Ser Leu Leu
        50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
            100                 105                 110

Ser Val Thr Phe Ala Cys Lys Thr Asn Phe Ser Met Asn Gly Asn Lys
            115                 120                 125

Ser Val Trp Cys Gln Ala Asn Asn Met Trp Gly Pro Thr Arg Leu Pro
        130                 135                 140

Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
                165                 170                 175

Leu Ser Val Thr Tyr Ser Cys Glu Ser Gly Tyr Leu Leu Val Gly Glu
            180                 185                 190

Lys Ile Ile Asn Cys Leu Ser Ser Gly Lys Trp Ser Ala Val Pro Pro
        195                 200                 205

Thr Cys Glu Glu Ala Arg Cys Lys Ser Leu Gly Arg Phe Pro Asn Gly
    210                 215                 220

Lys Val Lys Glu Pro Pro Ile Leu Arg Val Gly Val Thr Ala Asn Phe
225                 230                 235                 240

Phe Cys Asp Glu Gly Tyr Arg Leu Gln Gly Pro Pro Ser Ser Arg Cys
                245                 250                 255

Val Ile Ala Gly Gln Gly Val Ala Trp Thr Lys Met Pro Val Cys Glu
            260                 265                 270

Glu Ile Phe Cys Pro Ser Pro Pro Ile Leu Asn Gly Arg His Ile
        275                 280                 285

Gly Asn Ser Leu Ala Asn Val Ser Tyr Gly Ser Ile Val Thr Tyr Thr
    290                 295                 300

Cys Asp Pro Asp Pro Glu Glu Gly Val Asn Phe Ile Leu Ile Gly Glu
305                 310                 315                 320

Ser Thr Leu Arg Cys Thr Val Asp Ser Gln Lys Thr Gly Thr Trp Ser
                325                 330                 335

Gly Pro Ala Pro Arg Cys Glu Leu Ser Thr Ser Ala Val Gln Cys Pro
            340                 345                 350

His Pro Gln Ile Leu Arg Gly Arg Met Val Ser Gly Gln Lys Asp Arg
        355                 360                 365

-continued

Tyr Thr Tyr Asn Asp Thr Val Ile Phe Ala Cys Met Phe Gly Phe Thr
370                 375                 380

Leu Lys Gly Ser Lys Gln Ile Arg Cys Asn Ala Gln Gly Thr Trp Glu
385                 390                 395                 400

Pro Ser Ala Pro Val Cys Glu Lys Glu Cys Gln Ala Pro Pro Asn Ile
            405                 410                 415

Leu Asn Gly Gln Lys Glu Asp Arg His Met Val Arg Phe Asp Pro Gly
            420                 425                 430

Thr Ser Ile Lys Tyr Ser Cys Asn Pro Gly Tyr Val Leu Val Gly Glu
            435                 440                 445

Glu Ser Ile Gln Cys Thr Ser Glu Gly Val Trp Thr Pro Pro Val Pro
450                 455                 460

Gln Cys Lys Val Ala Ala Cys Glu Ala Thr Gly Arg Gln Leu Leu Thr
465                 470                 475                 480

Lys Pro Gln His Gln Phe Val Arg Pro Asp Val Asn Ser Ser Cys Gly
                485                 490                 495

Glu Gly Tyr Lys Leu Ser Gly Ser Val Tyr Gln Glu Cys Gln Gly Thr
            500                 505                 510

Ile Pro Trp Phe Met Glu Ile Arg Leu Cys Lys Glu Ile Thr Cys Pro
            515                 520                 525

Pro Pro Pro Val Ile Tyr Asn Gly Ala His Thr Gly Ser Ser Leu Glu
530                 535                 540

Asp Phe Pro Tyr Gly Thr Thr Val Thr Tyr Thr Cys Asn Pro Gly Pro
545                 550                 555                 560

Glu Arg Gly Val Glu Phe Ser Leu Ile Gly Glu Ser Thr Ile Arg Cys
                565                 570                 575

Thr Ser Asn Asp Gln Glu Arg Gly Thr Trp Ser Gly Pro Ala Pro Leu
            580                 585                 590

Cys Lys Leu Ser Leu Leu Ala Val Gln Cys Ser His Val His Ile Ala
            595                 600                 605

Asn Gly Tyr Lys Ile Ser Gly Lys Glu Ala Pro Tyr Phe Tyr Asn Asp
            610                 615                 620

Thr Val Thr Phe Lys Cys Tyr Ser Gly Phe Thr Leu Lys Gly Ser Ser
625                 630                 635                 640

Gln Ile Arg Cys Lys Arg Asp Asn Thr Trp Asp Pro Glu Ile Pro Val
            645                 650                 655

Cys Glu Lys Gly Cys Gln Pro Pro Gly Leu His His Gly Arg His
            660                 665                 670

Thr Gly Gly Asn Thr Val Phe Phe Val Ser Gly Met Thr Val Asp Tyr
            675                 680                 685

Thr Cys Asp Pro Gly Tyr Leu Leu Val Gly Asn Lys Ser Ile His Cys
690                 695                 700

Met Pro Ser Gly Asn Trp Ser Pro Ser Ala Pro Arg Cys Glu Glu Thr
705                 710                 715                 720

Cys Gln His Val Arg Gln Ser Leu Gln Glu Leu Pro Ala Gly Ser Arg
            725                 730                 735

Val Glu Leu Val Asn Thr Ser Cys Gln Asp Gly Tyr Gln Leu Thr Gly
            740                 745                 750

His Ala Tyr Gln Met Cys Gln Asp Ala Glu Asn Gly Ile Trp Phe Lys
            755                 760                 765

Lys Ile Pro Leu Cys Lys Val Ile His Cys His Pro Pro Pro Val Ile
770                 775                 780

Val Asn Gly Lys His Thr Gly Met Met Ala Glu Asn Phe Leu Tyr Gly

Asn Glu Val Ser Tyr Glu Cys Asp Gln Gly Phe Tyr Leu Leu Gly Glu
785             790              795             800
                    805              810             815

Lys Asn Cys Ser Ala Glu Val Ile Leu Lys Ala Trp Ile Leu Glu Arg
                    820              825             830

Ala Phe Pro Gln Cys Leu Arg Ser Leu Cys Pro Asn Pro Glu Val Lys
                    835              840             845

His Gly Tyr Lys Leu Asn Lys Thr His Ser Ala Tyr Ser His Asn Asp
                    850              855             860

Ile Val Tyr Val Asp Cys Asn Pro Gly Phe Ile Met Asn Gly Ser Arg
865                 870              875             880

Val Ile Arg Cys His Thr Asp Asn Thr Trp Val Pro Gly Val Pro Thr
                    885              890             895

Cys Ile Lys Lys Ala Phe Ile Gly Cys Pro Pro Pro Lys Thr Pro
                    900              905             910

Asn Gly Asn His Thr Gly Gly Asn Ile Ala Arg Phe Ser Pro Gly Met
                    915              920             925

Ser Ile Leu Tyr Ser Cys Asp Gln Gly Tyr Leu Val Val Gly Glu Pro
930                 935              940

Leu Leu Leu Cys Thr His Glu Gly Thr Trp Ser Gln Pro Ala Pro His
945                 950              955             960

Cys Lys Glu Val Asn Cys Ser Ser Pro Ala Asp Met Asp Gly Ile Gln
                    965              970             975

Lys Gly Leu Glu Pro Arg Lys Met Tyr Gln Tyr Gly Ala Val Val Thr
                    980              985             990

Leu Glu Cys Glu Asp Gly Tyr Met Leu Glu Gly Ser Pro Gln Ser Gln
                    995              1000            1005

Cys Gln Ser Asp His Gln Trp Asn Pro Pro Leu Ala Val Cys Arg Ser
        1010            1015            1020

Arg Ser Leu Ala Pro Val Leu Cys Gly Ile Ala Ala Gly Leu Ile Leu
1025            1030            1035            1040

Leu Thr Phe Leu Ile Val Ile Thr Leu Tyr Val Ile Ser Lys His Arg
                1045            1050            1055

Glu Arg Asn Tyr Tyr Thr Asp Thr Ser Gln Lys Glu Ala Phe His Leu
                1060            1065            1070

Glu Ala Arg Glu Val Tyr Ser Val Asp Pro Tyr Asn Pro Ala Ser
        1075            1080            1085

<210> SEQ ID NO 2
<211> LENGTH: 128
<212> TYPE: PRT
<213> ORGANISM: Homo sapiens

<400> SEQUENCE: 2

Ile Ser Cys Gly Ser Pro Pro Ile Leu Asn Gly Arg Ile Ser Tyr
1               5                   10              15

Tyr Ser Thr Pro Ile Ala Val Gly Thr Val Ile Arg Tyr Ser Cys Ser
                    20              25              30

Gly Thr Phe Arg Leu Ile Gly Glu Lys Ser Leu Leu Cys Ile Thr Lys
                    35              40              45

Asp Lys Val Asp Gly Thr Trp Asp Lys Pro Ala Pro Lys Cys Glu Tyr
            50              55              60

Phe Asn Lys Tyr Ser Ser Cys Pro Glu Pro Ile Val Pro Gly Gly Tyr
65              70              75              80

```
Lys Ile Arg Gly Ser Thr Pro Tyr Arg His Gly Asp Ser Val Thr Phe
                85                  90                  95
Ala Cys Lys Thr Asn Phe Ser Met Asn Gly Asn Lys Ser Val Trp Cys
            100                 105                 110
Gln Ala Asn Asn Met Trp Gly Pro Thr Arg Leu Pro Thr Cys Val Ser
        115                 120                 125

<210> SEQ ID NO 3
<211> LENGTH: 128
<212> TYPE: PRT
<213> ORGANISM: Homo sapiens

<400> SEQUENCE: 3

Met Gly Ile Gln Gly Gly Ser Val Leu Phe Gly Leu Leu Leu Val Leu
  1               5                  10                  15
Ala Val Phe Cys His Ser Gly His Ser Leu Gln Cys Tyr Asn Cys Pro
             20                  25                  30
Asn Pro Thr Ala Asp Cys Lys Thr Ala Val Asn Cys Ser Ser Asp Phe
         35                  40                  45
Asp Ala Cys Leu Ile Thr Lys Ala Gly Leu Gln Val Tyr Asn Lys Cys
     50                  55                  60
Trp Lys Phe Glu His Cys Asn Phe Asn Asp Val Thr Thr Arg Leu Arg
 65                  70                  75                  80
Glu Asn Glu Leu Thr Tyr Tyr Cys Cys Lys Lys Asp Leu Cys Asn Phe
                 85                  90                  95
Asn Glu Gln Leu Glu Asn Gly Gly Thr Ser Leu Ser Glu Lys Thr Val
            100                 105                 110
Leu Leu Leu Val Thr Pro Phe Leu Ala Ala Ala Trp Ser Leu His Pro
        115                 120                 125

<210> SEQ ID NO 4
<211> LENGTH: 483
<212> TYPE: PRT
<213> ORGANISM: Murine

<400> SEQUENCE: 4

Met Glu Val Ser Ser Arg Ser Ser Glu Pro Leu Asp Pro Val Trp Leu
  1               5                  10                  15
Leu Val Ala Phe Gly Arg Gly Gly Val Lys Leu Glu Val Leu Leu Leu
             20                  25                  30
Phe Leu Leu Pro Phe Thr Leu Gly Glu Leu Arg Gly Leu Gly Leu Lys
         35                  40                  45
His Gly His Thr Val His Arg Glu Pro Ala Val Asn Arg Leu Cys Ala
     50                  55                  60
Asp Ser Lys Arg Trp Ser Gly Leu Pro Val Ser Ala Gln Arg Pro Phe
 65                  70                  75                  80
Pro Met Gly His Cys Pro Ala Pro Ser Gln Leu Pro Ser Ala Lys Pro
                 85                  90                  95
Ile Asn Leu Thr Asp Glu Ser Met Phe Pro Ile Gly Thr Tyr Leu Leu
            100                 105                 110
Tyr Glu Cys Leu Pro Gly Tyr Ile Lys Arg Gln Phe Ser Ile Thr Cys
        115                 120                 125
Lys Gln Asp Ser Thr Trp Thr Ser Ala Glu Asp Lys Cys Ile Arg Lys
    130                 135                 140
Gln Cys Lys Thr Pro Ser Asp Pro Glu Asn Gly Leu Val His Val His
145                 150                 155                 160
```

-continued

Thr Gly Ile Gln Phe Gly Ser Arg Ile Asn Tyr Thr Cys Asn Gln Gly
                    165                 170                 175

Tyr Arg Leu Ile Gly Ser Ser Ala Val Cys Val Ile Thr Asp Gln
            180                 185                 190

Ser Val Asp Trp Asp Thr Glu Ala Pro Ile Cys Glu Trp Ile Pro Cys
        195                 200                 205

Glu Ile Pro Pro Gly Ile Pro Asn Gly Asp Phe Phe Ser Ser Thr Arg
    210                 215                 220

Glu Asp Phe His Tyr Gly Met Val Val Thr Tyr Arg Cys Asn Thr Asp
225                 230                 235                 240

Ala Arg Gly Lys Ala Leu Phe Asn Leu Val Gly Glu Pro Ser Leu Tyr
                245                 250                 255

Cys Thr Ser Asn Asp Gly Glu Ile Gly Val Trp Ser Gly Pro Pro Pro
                260                 265                 270

Gln Cys Ile Glu Leu Asn Lys Cys Thr Pro Pro Tyr Val Glu Asn
        275                 280                 285

Ala Val Met Leu Ser Glu Asn Arg Ser Leu Phe Ser Leu Arg Asp Ile
        290                 295                 300

Val Glu Phe Arg Cys His Pro Gly Phe Ile Met Lys Gly Ala Ser Ser
305                 310                 315                 320

Val His Cys Gln Ser Leu Asn Lys Trp Glu Pro Glu Leu Pro Ser Cys
                325                 330                 335

Phe Lys Gly Val Ile Cys Arg Leu Pro Gln Glu Met Ser Gly Phe Gln
                340                 345                 350

Lys Gly Leu Gly Met Lys Lys Glu Tyr Tyr Tyr Gly Glu Asn Val Thr
            355                 360                 365

Leu Glu Cys Glu Asp Gly Tyr Thr Leu Glu Gly Ser Ser Gln Ser Gln
    370                 375                 380

Cys Gln Ser Asp Gly Ser Trp Asn Pro Leu Leu Ala Lys Cys Val Ser
385                 390                 395                 400

Arg Ser Ile Ser Gly Leu Ile Val Gly Ile Phe Ile Gly Ile Ile Val
                405                 410                 415

Phe Ile Leu Val Ile Ile Val Phe Ile Trp Met Ile Leu Lys Tyr Lys
                420                 425                 430

Lys Arg Asn Thr Thr Asp Glu Lys Tyr Lys Glu Val Gly Ile His Leu
            435                 440                 445

Asn Tyr Lys Glu Asp Ser Cys Val Arg Leu Gln Ser Leu Leu Thr Ser
        450                 455                 460

Gln Glu Asn Ser Ser Thr Thr Ser Pro Ala Arg Asn Ser Leu Thr Gln
465                 470                 475                 480

Glu Val Ser

<210> SEQ ID NO 5
<211> LENGTH: 1231
<212> TYPE: PRT
<213> ORGANISM: Homo sapiens

<400> SEQUENCE: 5

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

-continued

```
Ile Tyr Lys Cys Arg Pro Gly Tyr Arg Ser Leu Gly Asn Val Ile Met
     50                  55                  60
Val Cys Arg Lys Gly Glu Trp Val Ala Leu Asn Pro Leu Arg Lys Cys
 65                  70                  75                  80
Gln Lys Arg Pro Cys Gly His Pro Gly Asp Thr Pro Phe Gly Thr Phe
                 85                  90                  95
Thr Leu Thr Gly Gly Asn Val Phe Glu Tyr Gly Val Lys Ala Val Tyr
             100                 105                 110
Thr Cys Asn Glu Gly Tyr Gln Leu Leu Gly Glu Ile Asn Tyr Arg Glu
             115                 120                 125
Cys Asp Thr Asp Gly Trp Thr Asn Asp Ile Pro Ile Cys Glu Val Val
130                 135                 140
Lys Cys Leu Pro Val Thr Ala Pro Glu Asn Gly Lys Ile Val Ser Ser
145                 150                 155                 160
Ala Met Glu Pro Asp Arg Glu Tyr His Phe Gly Gln Ala Val Arg Phe
                 165                 170                 175
Val Cys Asn Ser Gly Tyr Lys Ile Glu Gly Asp Glu Glu Met His Cys
             180                 185                 190
Ser Asp Asp Gly Phe Trp Ser Lys Glu Lys Pro Lys Cys Val Glu Ile
             195                 200                 205
Ser Cys Lys Ser Pro Asp Val Ile Asn Gly Ser Pro Ile Ser Gln Lys
     210                 215                 220
Ile Ile Tyr Lys Glu Asn Glu Arg Phe Gln Tyr Lys Cys Asn Met Gly
225                 230                 235                 240
Tyr Glu Tyr Ser Glu Arg Gly Asp Ala Val Cys Thr Glu Ser Gly Trp
                 245                 250                 255
Arg Pro Leu Pro Ser Cys Glu Glu Lys Ser Cys Asp Asn Pro Tyr Ile
             260                 265                 270
Pro Asn Gly Asp Tyr Ser Pro Leu Arg Ile Lys His Arg Thr Gly Asp
             275                 280                 285
Glu Ile Thr Tyr Gln Cys Arg Asn Gly Phe Tyr Pro Ala Thr Arg Gly
     290                 295                 300
Asn Thr Ala Lys Cys Thr Ser Thr Gly Trp Ile Pro Ala Pro Arg Cys
305                 310                 315                 320
Thr Leu Lys Pro Cys Asp Tyr Pro Asp Ile Lys His Gly Gly Leu Tyr
                 325                 330                 335
His Glu Asn Met Arg Arg Pro Tyr Phe Pro Val Ala Val Gly Lys Tyr
             340                 345                 350
Tyr Ser Tyr Tyr Cys Asp Glu His Phe Glu Thr Pro Ser Gly Ser Tyr
             355                 360                 365
Trp Asp His Ile His Cys Thr Gln Asp Gly Trp Ser Pro Ala Val Pro
     370                 375                 380
Cys Leu Arg Lys Cys Tyr Phe Pro Tyr Leu Glu Asn Gly Tyr Asn Gln
385                 390                 395                 400
Asn Tyr Gly Arg Lys Phe Val Gln Gly Lys Ser Ile Asp Val Ala Cys
                 405                 410                 415
His Pro Gly Tyr Ala Leu Pro Lys Ala Gln Thr Thr Val Thr Cys Met
             420                 425                 430
Glu Asn Gly Trp Ser Pro Thr Pro Arg Cys Ile Arg Val Lys Thr Cys
             435                 440                 445
Ser Lys Ser Ser Ile Asp Ile Glu Asn Gly Phe Ile Ser Glu Ser Gln
     450                 455                 460
Tyr Thr Tyr Ala Leu Lys Glu Lys Ala Lys Tyr Gln Cys Lys Leu Gly
```

-continued

```
            465                 470                 475                 480
        Tyr Val Thr Ala Asp Gly Glu Thr Ser Gly Ser Ile Thr Cys Gly Lys
                            485                 490                 495
        Asp Gly Trp Ser Ala Gln Pro Thr Cys Ile Lys Ser Cys Asp Ile Pro
                            500                 505                 510
        Val Phe Met Asn Ala Arg Thr Lys Asn Asp Phe Thr Trp Phe Lys Leu
                            515                 520                 525
        Asn Asp Thr Leu Asp Tyr Glu Cys His Asp Gly Tyr Glu Ser Asn Thr
                            530                 535                 540
        Gly Ser Thr Thr Gly Ser Ile Val Cys Gly Tyr Asn Gly Trp Ser Asp
        545                 550                 555                 560
        Leu Pro Ile Cys Tyr Glu Arg Glu Cys Glu Leu Pro Lys Ile Asp Val
                            565                 570                 575
        His Leu Val Pro Asp Arg Lys Lys Asp Gln Tyr Lys Val Gly Glu Val
                            580                 585                 590
        Leu Lys Phe Ser Cys Lys Pro Gly Phe Thr Ile Val Gly Pro Asn Ser
                            595                 600                 605
        Val Gln Cys Tyr His Phe Gly Leu Ser Pro Asp Leu Pro Ile Cys Lys
                            610                 615                 620
        Glu Gln Val Gln Ser Cys Gly Pro Pro Glu Leu Leu Asn Gly Asn
        625                 630                 635                 640
        Val Lys Glu Lys Thr Lys Glu Glu Tyr Gly His Ser Glu Val Val Glu
                            645                 650                 655
        Tyr Tyr Cys Asn Pro Arg Phe Leu Met Lys Gly Pro Asn Lys Ile Gln
                            660                 665                 670
        Cys Val Asp Gly Glu Trp Thr Thr Leu Pro Val Cys Ile Val Glu Glu
                            675                 680                 685
        Ser Thr Cys Gly Asp Ile Pro Glu Leu Glu His Gly Trp Ala Gln Leu
                            690                 695                 700
        Ser Ser Pro Pro Tyr Tyr Tyr Gly Asp Ser Val Glu Phe Asn Cys Ser
        705                 710                 715                 720
        Glu Ser Phe Thr Met Ile Gly His Arg Ser Ile Thr Cys Ile His Gly
                            725                 730                 735
        Val Trp Thr Gln Leu Pro Gln Cys Val Ala Ile Asp Lys Leu Lys Lys
                            740                 745                 750
        Cys Lys Ser Ser Asn Leu Ile Ile Leu Glu Glu His Leu Lys Asn Lys
                            755                 760                 765
        Lys Glu Phe Asp His Asn Ser Asn Ile Arg Tyr Arg Cys Arg Gly Lys
                            770                 775                 780
        Glu Gly Trp Ile His Thr Val Cys Ile Asn Gly Arg Trp Asp Pro Glu
        785                 790                 795                 800
        Val Asn Cys Ser Met Ala Gln Ile Gln Leu Cys Pro Pro Pro Pro Gln
                            805                 810                 815
        Ile Pro Asn Ser His Asn Met Thr Thr Thr Leu Asn Tyr Arg Asp Gly
                            820                 825                 830
        Glu Lys Val Ser Val Leu Cys Gln Glu Asn Tyr Leu Ile Gln Glu Gly
                            835                 840                 845
        Glu Glu Ile Thr Cys Lys Asp Gly Arg Trp Gln Ser Ile Pro Leu Cys
        850                 855                 860
        Val Glu Lys Ile Pro Cys Ser Gln Pro Pro Gln Ile Glu His Gly Thr
        865                 870                 875                 880
        Ile Asn Ser Ser Arg Ser Ser Gln Glu Ser Tyr Ala His Gly Thr Lys
                            885                 890                 895
```

-continued

```
Leu Ser Tyr Thr Cys Glu Gly Gly Phe Arg Ile Ser Glu Glu Asn Glu
                900                 905                 910
Thr Thr Cys Tyr Met Gly Lys Trp Ser Ser Pro Gln Cys Glu Gly
            915                 920                 925
Leu Pro Cys Lys Ser Pro Glu Ile Ser His Gly Val Val Ala His
        930                 935                 940
Met Ser Asp Ser Tyr Gln Tyr Gly Glu Glu Val Thr Tyr Lys Cys Phe
945                 950                 955                 960
Glu Gly Phe Gly Ile Asp Gly Pro Ala Ile Ala Lys Cys Leu Gly Glu
                965                 970                 975
Lys Trp Ser His Pro Pro Ser Cys Ile Lys Thr Asp Cys Leu Ser Leu
            980                 985                 990
Pro Ser Phe Glu Asn Ala Ile Pro Met Gly Glu Lys Lys Asp Val Tyr
        995                 1000                1005
Lys Ala Gly Glu Gln Val Thr Tyr Thr Cys Ala Thr Tyr Tyr Lys Met
    1010                1015                1020
Asp Gly Ala Ser Asn Val Thr Cys Ile Asn Ser Arg Trp Thr Gly Arg
1025                1030                1035                1040
Pro Thr Cys Arg Asp Thr Ser Cys Val Asn Pro Pro Thr Val Gln Asn
                1045                1050                1055
Ala Tyr Ile Val Ser Arg Gln Met Ser Lys Tyr Pro Ser Gly Glu Arg
                1060                1065                1070
Val Arg Tyr Gln Cys Arg Ser Pro Tyr Glu Met Phe Gly Asp Glu Glu
                1075                1080                1085
Val Met Cys Leu Asn Gly Asn Trp Thr Glu Pro Pro Gln Cys Lys Asp
                1090                1095                1100
Ser Thr Gly Lys Cys Gly Pro Pro Pro Ile Asp Asn Gly Asp Ile
1105                1110                1115                1120
Thr Ser Phe Pro Leu Ser Val Tyr Ala Pro Ala Ser Ser Val Glu Tyr
                1125                1130                1135
Gln Cys Gln Asn Leu Tyr Gln Leu Glu Gly Asn Lys Arg Ile Thr Cys
                1140                1145                1150
Arg Asn Gly Gln Trp Ser Glu Pro Pro Lys Cys Leu His Pro Cys Val
                1155                1160                1165
Ile Ser Arg Glu Ile Met Glu Asn Tyr Asn Ile Ala Leu Arg Trp Thr
                1170                1175                1180
Ala Lys Gln Lys Leu Tyr Ser Arg Thr Gly Glu Ser Val Glu Phe Val
1185                1190                1195                1200
Cys Lys Arg Gly Tyr Arg Leu Ser Ser Arg Ser His Thr Leu Arg Thr
                1205                1210                1215
Thr Cys Trp Asp Gly Lys Leu Glu Tyr Pro Thr Cys Ala Lys Arg
                1220                1225                1230

<210> SEQ ID NO 6
<211> LENGTH: 76
<212> TYPE: PRT
<213> ORGANISM: Homo sapiens

<400> SEQUENCE: 6

Ser Val Gln Leu Thr Glu Lys Arg Met Asp Lys Val Gly Lys Tyr Pro
  1               5                  10                  15
Lys Glu Leu Arg Lys Cys Cys Glu Asp Gly Met Arg Glu Asn Pro Met
                20                  25                  30
Arg Phe Ser Cys Gln Arg Arg Thr Arg Phe Ile Ser Leu Gly Glu Ala
```

```
                35                  40                  45
Cys Lys Lys Val Phe Leu Asp Cys Cys Asn Tyr Ile Thr Glu Leu Arg
         50                  55                  60

Arg Gln His Ala Arg Ala Ser His Leu Gly Leu Ala
 65                  70                  75
```

<210> SEQ ID NO 7
<211> LENGTH: 337
<212> TYPE: PRT
<213> ORGANISM: Homo sapiens

<400> SEQUENCE: 7

```
Met Gly Asn Asp Ser Val Ser Tyr Glu Tyr Gly Asp Tyr Ser Asp Leu
  1               5                  10                  15

Ser Asp Arg Pro Val Asp Cys Leu Asp Gly Ala Cys Leu Ala Ile Asp
             20                  25                  30

Pro Leu Arg Val Ala Pro Leu Pro Leu Tyr Ala Ala Ile Phe Leu Val
         35                  40                  45

Gly Val Pro Gly Asn Ala Met Val Ala Trp Val Ala Gly Lys Val Ala
 50                  55                  60

Arg Arg Arg Val Gly Ala Thr Trp Leu His Leu Ala Val Ala Ala Asp
 65                  70                  75                  80

Leu Leu Cys Cys Leu Ser Leu Pro Ile Leu Ala Val Pro Ile Ala Arg
                 85                  90                  95

Gly Gly His Trp Pro Tyr Gly Ala Val Gly Cys Arg Ala Leu Pro Ser
            100                 105                 110

Ile Ile Leu Leu Thr Met Tyr Ala Ser Val Leu Leu Leu Ala Ala Leu
            115                 120                 125

Ser Ala Asp Leu Cys Phe Leu Ala Leu Gly Pro Ala Trp Trp Ser Thr
130                 135                 140

Val Gln Arg Ala Cys Gly Val Gln Val Ala Cys Gly Ala Ala Trp Thr
145                 150                 155                 160

Leu Ala Leu Leu Leu Thr Val Pro Ser Ala Ile Tyr Arg Arg Leu His
                165                 170                 175

Gln Glu His Phe Pro Ala Arg Leu Gln Cys Val Val Asp Tyr Gly Gly
            180                 185                 190

Ser Ser Ser Thr Glu Asn Ala Val Thr Ala Ile Arg Phe Leu Phe Gly
            195                 200                 205

Phe Leu Gly Pro Leu Val Ala Val Ala Ser Cys His Ser Ala Leu Leu
210                 215                 220

Cys Trp Ala Ala Arg Arg Cys Arg Pro Leu Gly Thr Ala Ile Val Val
225                 230                 235                 240

Gly Phe Phe Val Cys Trp Ala Pro Tyr His Leu Leu Gly Leu Val Leu
                245                 250                 255

Thr Val Ala Ala Pro Asn Ser Ala Leu Leu Ala Arg Ala Leu Arg Ala
            260                 265                 270

Glu Pro Leu Ile Val Gly Leu Ala Leu Ala His Ser Cys Leu Asn Pro
            275                 280                 285

Met Leu Phe Leu Tyr Phe Gly Arg Ala Gln Leu Arg Arg Ser Leu Pro
            290                 295                 300

Ala Ala Cys His Trp Ala Leu Arg Glu Ser Gln Gly Gln Asp Glu Ser
305                 310                 315                 320

Val Asp Ser Lys Lys Ser Thr Ser His Asp Leu Val Ser Glu Met Glu
                325                 330                 335
```

Val

<210> SEQ ID NO 8
<211> LENGTH: 123
<212> TYPE: PRT
<213> ORGANISM: Murine

<400> SEQUENCE: 8

Met Arg Ala Gln Arg Gly Leu Ile Leu Leu Leu Leu Leu Ala Val
1               5                   10                  15

Phe Cys Ser Thr Ala Val Ser Leu Thr Cys Tyr His Cys Phe Gln Pro
            20                  25                  30

Val Val Ser Ser Cys Asn Met Asn Ser Thr Cys Ser Pro Asp Gln Asp
                35                  40                  45

Ser Cys Leu Tyr Ala Val Ala Gly Met Gln Val Tyr Gln Arg Cys Trp
        50                  55                  60

Lys Gln Ser Asp Cys His Gly Glu Ile Ile Met Asp Gln Leu Glu Glu
65                  70                  75                  80

Thr Lys Leu Lys Phe Arg Cys Cys Gln Phe Asn Leu Cys Asn Lys Ser
                85                  90                  95

Asp Gly Ser Leu Gly Lys Thr Pro Leu Leu Gly Thr Ser Val Leu Val
            100                 105                 110

Ala Ile Leu Asn Leu Cys Phe Leu Ser His Leu
        115                 120

<210> SEQ ID NO 9
<211> LENGTH: 129
<212> TYPE: PRT
<213> ORGANISM: Murine

<400> SEQUENCE: 9

Met Arg Ala Gln Arg Gly Leu Ile Leu Leu Leu Leu Leu Ala Val
1               5                   10                  15

Phe Cys Ser Thr Ala Val Ser Leu Lys Cys Tyr Asn Cys Phe Gln Phe
            20                  25                  30

Val Ser Ser Cys Lys Ile Asn Thr Thr Cys Ser Pro Asn Leu Asp Ser
                35                  40                  45

Cys Leu Tyr Ala Val Ala Gly Arg Gln Val Tyr Gln Gln Cys Trp Lys
        50                  55                  60

Leu Ser Asp Cys Asn Ser Asn Tyr Ile Met Ser Arg Leu Asp Val Ala
65                  70                  75                  80

Gly Ile Gln Ser Lys Cys Cys Gln Trp Gly Leu Cys Asn Lys Asn Leu
                85                  90                  95

Asp Gly Leu Glu Glu Pro Asn Asn Ala Glu Thr Ser Ser Leu Arg Lys
            100                 105                 110

Thr Ala Leu Leu Gly Thr Ser Val Leu Val Ala Ile Leu Lys Phe Cys
        115                 120                 125

Phe

<210> SEQ ID NO 10
<211> LENGTH: 1234
<212> TYPE: PRT
<213> ORGANISM: Murine

<400> SEQUENCE: 10

Met Arg Leu Ser Ala Arg Ile Ile Trp Leu Ile Leu Trp Thr Val Cys
1               5                   10                  15

```
Ala Ala Glu Asp Cys Lys Gly Pro Pro Arg Glu Asn Ser Glu Ile
            20                  25                  30

Leu Ser Gly Ser Trp Ser Glu Gln Leu Tyr Pro Glu Gly Thr Gln Ala
        35                  40                  45

Thr Tyr Lys Cys Arg Pro Gly Tyr Arg Thr Leu Gly Thr Ile Val Lys
    50                  55                  60

Val Cys Lys Asn Gly Lys Trp Val Ala Ser Asn Pro Ser Arg Ile Cys
65                  70                  75                  80

Arg Lys Lys Pro Cys Gly His Pro Gly Asp Thr Pro Phe Gly Ser Phe
                85                  90                  95

Arg Leu Ala Val Gly Ser Gln Phe Glu Phe Gly Ala Lys Val Val Tyr
            100                 105                 110

Thr Cys Asp Asp Gly Tyr Gln Leu Leu Gly Glu Ile Asp Tyr Arg Glu
        115                 120                 125

Cys Gly Ala Asp Gly Trp Ile Asn Asp Ile Pro Leu Cys Glu Val Val
    130                 135                 140

Lys Cys Leu Pro Val Thr Glu Leu Glu Asn Gly Arg Ile Val Ser Gly
145                 150                 155                 160

Ala Ala Glu Thr Asp Gln Glu Tyr Tyr Phe Gly Gln Val Val Arg Phe
                165                 170                 175

Glu Cys Asn Ser Gly Phe Lys Ile Glu Gly His Lys Glu Ile His Cys
            180                 185                 190

Ser Glu Asn Gly Leu Trp Ser Asn Glu Lys Pro Arg Cys Val Glu Ile
        195                 200                 205

Leu Cys Thr Pro Pro Arg Val Glu Asn Gly Asp Gly Ile Asn Val Lys
    210                 215                 220

Pro Val Tyr Lys Glu Asn Glu Arg Tyr His Tyr Lys Cys Lys His Gly
225                 230                 235                 240

Tyr Val Pro Lys Glu Arg Gly Asp Ala Val Cys Thr Gly Ser Gly Trp
                245                 250                 255

Ser Ser Gln Pro Phe Cys Glu Glu Lys Arg Cys Ser Pro Pro Tyr Ile
            260                 265                 270

Leu Asn Gly Ile Tyr Thr Pro His Arg Ile Ile His Arg Ser Asp Asp
        275                 280                 285

Glu Ile Arg Tyr Glu Cys Asn Tyr Gly Phe Tyr Pro Val Thr Gly Ser
    290                 295                 300

Thr Val Ser Lys Cys Thr Pro Thr Gly Trp Ile Pro Val Pro Arg Cys
305                 310                 315                 320

Thr Leu Lys Pro Cys Glu Phe Pro Gln Phe Lys Tyr Gly Arg Leu Tyr
                325                 330                 335

Tyr Glu Glu Ser Leu Arg Pro Asn Phe Pro Val Ser Ile Gly Asn Lys
            340                 345                 350

Tyr Ser Tyr Lys Cys Asp Asn Gly Phe Ser Pro Pro Ser Gly Tyr Ser
        355                 360                 365

Trp Asp Tyr Leu Arg Cys Thr Ala Gln Gly Trp Glu Pro Glu Val Pro
    370                 375                 380

Cys Val Arg Lys Cys Val Phe His Tyr Val Glu Asn Gly Asp Ser Ala
385                 390                 395                 400

Tyr Trp Glu Lys Val Tyr Val Gln Gly Gln Ser Leu Lys Val Gln Cys
                405                 410                 415

Tyr Asn Gly Tyr Ser Leu Gln Asn Gly Gln Asp Thr Met Thr Cys Thr
            420                 425                 430

Glu Asn Gly Trp Ser Pro Pro Lys Cys Ile Arg Ile Lys Thr Cys
```

```
            435                 440                 445
Ser Ala Ser Asp Ile His Ile Asp Asn Gly Phe Leu Ser Glu Ser Ser
450                 455                 460

Ser Ile Tyr Ala Leu Asn Arg Glu Thr Ser Tyr Arg Cys Lys Gln Gly
465                 470                 475                 480

Tyr Val Thr Asn Thr Gly Glu Ile Ser Gly Ser Ile Thr Cys Leu Gln
                485                 490                 495

Asn Gly Trp Ser Pro Gln Pro Ser Cys Ile Lys Ser Cys Asp Met Pro
            500                 505                 510

Val Phe Glu Asn Ser Ile Thr Lys Asn Thr Arg Thr Trp Phe Lys Leu
        515                 520                 525

Asn Asp Lys Leu Asp Tyr Glu Cys Leu Val Gly Phe Glu Asn Glu Tyr
    530                 535                 540

Lys His Thr Lys Gly Ser Ile Thr Cys Thr Tyr Tyr Gly Trp Ser Asp
545                 550                 555                 560

Thr Pro Ser Cys Tyr Glu Arg Glu Cys Ser Val Pro Thr Leu Asp Arg
                565                 570                 575

Lys Leu Val Val Ser Pro Arg Lys Glu Lys Tyr Arg Val Gly Asp Leu
            580                 585                 590

Leu Glu Phe Ser Cys His Ser Gly His Arg Val Gly Pro Asp Ser Val
        595                 600                 605

Gln Cys Tyr His Phe Gly Trp Ser Pro Gly Phe Pro Thr Cys Lys Gly
    610                 615                 620

Gln Val Ala Ser Cys Ala Pro Pro Leu Glu Ile Leu Asn Gly Glu Ile
625                 630                 635                 640

Asn Gly Ala Lys Lys Val Glu Tyr Ser His Gly Glu Val Val Lys Tyr
                645                 650                 655

Asp Cys Lys Pro Arg Phe Leu Leu Lys Gly Pro Asn Lys Ile Gln Cys
            660                 665                 670

Val Asp Gly Asn Trp Thr Thr Leu Pro Val Cys Ile Glu Glu Arg
        675                 680                 685

Thr Cys Gly Asp Ile Pro Glu Leu Glu His Gly Ser Ala Lys Cys Ser
    690                 695                 700

Val Pro Pro Tyr His His Gly Asp Ser Val Glu Phe Ile Cys Glu Glu
705                 710                 715                 720

Asn Phe Thr Met Ile Gly His Gly Ser Val Ser Cys Ile Ser Gly Lys
                725                 730                 735

Trp Thr Gln Leu Pro Lys Cys Val Ala Thr Asp Gln Leu Glu Lys Cys
            740                 745                 750

Arg Val Leu Lys Ser Thr Gly Ile Glu Ala Ile Lys Pro Lys Leu Thr
        755                 760                 765

Glu Phe Thr His Asn Ser Thr Met Asp Tyr Lys Cys Arg Asp Lys Gln
    770                 775                 780

Glu Tyr Glu Arg Ser Ile Cys Ile Asn Gly Lys Trp Asp Pro Glu Pro
785                 790                 795                 800

Asn Cys Thr Ser Lys Thr Ser Cys Pro Pro Pro Gln Ile Pro Asn
                805                 810                 815

Thr Gln Val Ile Glu Thr Thr Val Lys Tyr Leu Asp Gly Glu Lys Leu
            820                 825                 830

Ser Val Leu Cys Gln Asp Asn Tyr Leu Thr Gln Asp Ser Glu Glu Met
        835                 840                 845

Val Cys Lys Asp Gly Arg Trp Gln Ser Leu Pro Arg Cys Ile Glu Lys
    850                 855                 860
```

-continued

Ile Pro Cys Ser Gln Pro Pro Thr Ile Glu His Gly Ser Ile Asn Leu
865                 870                 875                 880

Pro Arg Ser Ser Glu Glu Arg Arg Asp Ser Ile Glu Ser Ser Ser His
            885                 890                 895

Glu His Gly Thr Thr Phe Ser Tyr Val Cys Asp Asp Gly Phe Arg Ile
            900                 905                 910

Pro Glu Glu Asn Arg Ile Thr Cys Tyr Met Gly Lys Trp Ser Thr Pro
            915                 920                 925

Pro Arg Cys Val Gly Leu Pro Cys Gly Pro Pro Ser Ile Pro Leu
            930                 935                 940

Gly Thr Val Ser Leu Glu Leu Glu Ser Tyr Gln His Gly Glu Glu Val
945                 950                 955                 960

Thr Tyr His Cys Ser Thr Gly Phe Gly Ile Asp Gly Pro Ala Phe Ile
            965                 970                 975

Ile Cys Glu Gly Gly Lys Trp Ser Asp Pro Pro Lys Cys Ile Lys Thr
            980                 985                 990

Asp Cys Asp Val Leu Pro Thr Val Lys Asn Ala Ile Ile Arg Gly Lys
            995                 1000                1005

Ser Lys Lys Ser Tyr Arg Thr Gly Glu Gln Val Thr Phe Arg Cys Gln
            1010                1015                1020

Ser Pro Tyr Gln Met Asn Gly Ser Asp Thr Val Thr Cys Val Asn Ser
1025                1030                1035                1040

Arg Trp Ile Gly Gln Pro Val Cys Lys Asp Asn Ser Cys Val Asp Pro
            1045                1050                1055

Pro His Val Pro Asn Ala Thr Ile Val Thr Arg Thr Lys Asn Lys Tyr
            1060                1065                1070

Leu His Gly Asp Arg Val Arg Tyr Glu Cys Asn Lys Pro Leu Glu Leu
            1075                1080                1085

Phe Gly Gln Val Glu Val Met Cys Glu Asn Gly Ile Trp Thr Glu Lys
1090                1095                1100

Pro Lys Cys Arg Asp Ser Thr Gly Lys Cys Gly Pro Pro Pro Pro Ile
1105                1110                1115                1120

Asp Asn Gly Asp Ile Thr Ser Leu Ser Leu Pro Val Tyr Glu Pro Leu
            1125                1130                1135

Ser Ser Val Glu Tyr Gln Cys Gln Lys Tyr Tyr Leu Leu Lys Gly Lys
            1140                1145                1150

Lys Thr Ile Thr Cys Thr Asn Gly Lys Trp Ser Glu Pro Pro Thr Cys
            1155                1160                1165

Leu His Ala Cys Val Ile Pro Glu Asn Ile Met Glu Ser His Asn Ile
            1170                1175                1180

Ile Leu Lys Trp Arg His Thr Glu Lys Ile Tyr Ser His Ser Gly Glu
1185                1190                1195                1200

Asp Ile Glu Phe Gly Cys Lys Tyr Gly Tyr Tyr Lys Ala Arg Asp Ser
            1205                1210                1215

Pro Pro Phe Arg Thr Lys Cys Ile Asn Gly Thr Ile Asn Tyr Pro Thr
            1220                1225                1230

Cys Val

<210> SEQ ID NO 11
<211> LENGTH: 2039
<212> TYPE: PRT
<213> ORGANISM: Homo sapiens

<400> SEQUENCE: 11

-continued

```
Met Gly Ala Ser Ser Pro Arg Ser Pro Glu Pro Val Gly Pro Pro Ala
 1               5                  10                  15
Pro Gly Leu Pro Phe Cys Cys Gly Gly Ser Leu Leu Ala Val Val Val
            20                  25                  30
Leu Leu Ala Leu Pro Val Ala Trp Gly Gln Cys Asn Ala Pro Glu Trp
        35                  40                  45
Leu Pro Phe Ala Arg Pro Thr Asn Leu Thr Asp Glu Phe Glu Phe Pro
    50                  55                  60
Ile Gly Thr Tyr Leu Asn Tyr Glu Cys Arg Pro Gly Tyr Ser Gly Arg
65                  70                  75                  80
Pro Phe Ser Ile Ile Cys Leu Lys Asn Ser Val Trp Thr Gly Ala Lys
                85                  90                  95
Asp Arg Cys Arg Arg Lys Ser Cys Arg Asn Pro Pro Asp Pro Val Asn
            100                 105                 110
Gly Met Val His Val Ile Lys Gly Ile Gln Phe Gly Ser Gln Ile Lys
        115                 120                 125
Tyr Ser Cys Thr Lys Gly Tyr Arg Leu Ile Gly Ser Ser Ser Ala Thr
    130                 135                 140
Cys Ile Ile Ser Gly Asp Thr Val Ile Trp Asp Asn Glu Thr Pro Ile
145                 150                 155                 160
Cys Asp Arg Ile Pro Cys Gly Leu Pro Pro Thr Ile Thr Asn Gly Asp
                165                 170                 175
Phe Ile Ser Thr Asn Arg Glu Asn Phe His Tyr Gly Ser Val Val Thr
            180                 185                 190
Tyr Arg Cys Asn Pro Gly Ser Gly Gly Arg Lys Val Phe Glu Leu Val
            195                 200                 205
Gly Glu Pro Ser Ile Tyr Cys Thr Ser Asn Asp Asp Gln Val Gly Ile
        210                 215                 220
Trp Ser Gly Pro Ala Pro Gln Cys Ile Ile Pro Asn Lys Cys Thr Pro
225                 230                 235                 240
Pro Asn Val Glu Asn Gly Ile Leu Val Ser Asp Asn Arg Ser Leu Phe
                245                 250                 255
Ser Leu Asn Glu Val Val Glu Phe Arg Cys Gln Pro Gly Phe Val Met
            260                 265                 270
Lys Gly Pro Arg Arg Val Lys Cys Gln Ala Leu Asn Lys Trp Glu Pro
        275                 280                 285
Glu Leu Pro Ser Cys Ser Arg Val Cys Gln Pro Pro Pro Asp Val Leu
    290                 295                 300
His Ala Glu Arg Thr Gln Arg Asp Lys Asp Asn Phe Ser Pro Gly Gln
305                 310                 315                 320
Glu Val Phe Tyr Ser Cys Glu Pro Gly Tyr Asp Leu Arg Gly Ala Ala
                325                 330                 335
Ser Met Arg Cys Thr Pro Gln Gly Asp Trp Ser Pro Ala Ala Pro Thr
            340                 345                 350
Cys Glu Val Lys Ser Cys Asp Asp Phe Met Gly Gln Leu Leu Asn Gly
        355                 360                 365
Arg Val Leu Phe Pro Val Asn Leu Gln Leu Gly Ala Lys Val Asp Phe
    370                 375                 380
Val Cys Asp Glu Gly Phe Gln Leu Lys Gly Ser Ser Ala Ser Tyr Cys
385                 390                 395                 400
Val Leu Ala Gly Met Glu Ser Leu Trp Asn Ser Ser Val Pro Val Cys
                405                 410                 415
```

```
Glu Gln Ile Phe Cys Pro Ser Pro Val Ile Pro Asn Gly Arg His
            420                 425                 430

Thr Gly Lys Pro Leu Glu Val Phe Pro Phe Gly Lys Ala Val Asn Tyr
            435                 440                 445

Thr Cys Asp Pro His Pro Asp Arg Gly Thr Ser Phe Asp Leu Ile Gly
            450                 455                 460

Glu Ser Thr Ile Arg Cys Thr Ser Asp Pro Gln Gly Asn Gly Val Trp
465                 470                 475                 480

Ser Ser Pro Ala Pro Arg Cys Gly Ile Leu Gly His Cys Gln Ala Pro
            485                 490                 495

Asp His Phe Leu Phe Ala Lys Leu Lys Thr Gln Thr Asn Ala Ser Asp
            500                 505                 510

Phe Pro Ile Gly Thr Ser Leu Lys Tyr Glu Cys Arg Pro Glu Tyr Tyr
            515                 520                 525

Gly Arg Pro Phe Ser Ile Thr Cys Leu Asp Asn Leu Val Trp Ser Ser
            530                 535                 540

Pro Lys Asp Val Cys Lys Arg Lys Ser Cys Lys Thr Pro Pro Asp Pro
545                 550                 555                 560

Val Asn Gly Met Val His Val Ile Thr Asp Ile Gln Val Gly Ser Arg
            565                 570                 575

Ile Asn Tyr Ser Cys Thr Thr Gly His Arg Leu Ile Gly His Ser Ser
            580                 585                 590

Ala Glu Cys Ile Leu Ser Gly Asn Ala Ala His Trp Ser Thr Lys Pro
            595                 600                 605

Pro Ile Cys Gln Arg Ile Pro Cys Gly Leu Pro Pro Thr Ile Ala Asn
            610                 615                 620

Gly Asp Phe Ile Ser Thr Asn Arg Glu Asn Phe His Tyr Gly Ser Val
625                 630                 635                 640

Val Thr Tyr Arg Cys Asn Pro Gly Ser Gly Gly Arg Lys Val Phe Glu
            645                 650                 655

Leu Val Gly Glu Pro Ser Ile Tyr Cys Thr Ser Asn Asp Asp Gln Val
            660                 665                 670

Gly Ile Trp Ser Gly Pro Ala Pro Gln Cys Ile Ile Pro Asn Lys Cys
            675                 680                 685

Thr Pro Pro Asn Val Glu Asn Gly Ile Leu Val Ser Asp Asn Arg Ser
            690                 695                 700

Leu Phe Ser Leu Asn Glu Val Val Glu Phe Arg Cys Gln Pro Gly Phe
705                 710                 715                 720

Val Met Lys Gly Pro Arg Arg Val Lys Cys Gln Ala Leu Asn Lys Trp
            725                 730                 735

Glu Pro Glu Leu Pro Ser Cys Ser Arg Val Cys Gln Pro Pro Pro Asp
            740                 745                 750

Val Leu His Ala Glu Arg Thr Gln Arg Asp Lys Asp Asn Phe Ser Pro
            755                 760                 765

Gly Gln Glu Val Phe Tyr Ser Cys Glu Pro Gly Tyr Asp Leu Arg Gly
            770                 775                 780

Ala Ala Ser Met Arg Cys Thr Pro Gln Gly Asp Trp Ser Pro Ala Ala
785                 790                 795                 800

Pro Thr Cys Glu Val Lys Ser Cys Asp Asp Phe Met Gly Gln Leu Leu
            805                 810                 815

Asn Gly Arg Val Leu Phe Pro Val Asn Leu Gln Leu Gly Ala Lys Val
            820                 825                 830

Asp Phe Val Cys Asp Glu Gly Phe Gln Leu Lys Gly Ser Ser Ala Ser
```

-continued

```
            835                 840                 845
Tyr Cys Val Leu Ala Gly Met Glu Ser Leu Trp Asn Ser Ser Val Pro
850                 855                 860
Val Cys Glu Gln Ile Phe Cys Pro Ser Pro Val Ile Pro Asn Gly
865                 870             875                 880
Arg His Thr Gly Lys Pro Leu Glu Val Phe Pro Gly Lys Ala Val
                885                 890                 895
Asn Tyr Thr Cys Asp Pro His Pro Asp Arg Gly Thr Ser Phe Asp Leu
                900                 905                 910
Ile Gly Glu Ser Thr Ile Arg Cys Thr Ser Asp Pro Gln Gly Asn Gly
                915                 920                 925
Val Trp Ser Ser Pro Ala Pro Arg Cys Gly Ile Leu Gly His Cys Gln
930                 935                 940
Ala Pro Asp His Phe Leu Phe Ala Lys Leu Lys Thr Gln Thr Asn Ala
945                 950                 955                 960
Ser Asp Phe Pro Ile Gly Thr Ser Leu Lys Tyr Glu Cys Arg Pro Glu
                965                 970                 975
Tyr Tyr Gly Arg Pro Phe Ser Ile Thr Cys Leu Asp Asn Leu Val Trp
                980                 985                 990
Ser Ser Pro Lys Asp Val Cys Lys Arg Lys Ser Cys Lys Thr Pro Pro
                995                 1000                1005
Asp Pro Val Asn Gly Met Val His Val Ile Thr Asp Ile Gln Val Gly
                1010                1015                1020
Ser Arg Ile Asn Tyr Ser Cys Thr Thr Gly His Arg Leu Ile Gly His
1025                1030                1035                1040
Ser Ser Ala Glu Cys Ile Leu Ser Gly Asn Thr Ala His Trp Ser Thr
                1045                1050                1055
Lys Pro Pro Ile Cys Gln Arg Ile Pro Cys Gly Leu Pro Pro Thr Ile
                1060                1065                1070
Ala Asn Gly Asp Phe Ile Ser Thr Asn Arg Glu Asn Phe His Tyr Gly
                1075                1080                1085
Ser Val Val Thr Tyr Arg Cys Asn Leu Gly Ser Arg Gly Arg Lys Val
                1090                1095                1100
Phe Glu Leu Val Gly Glu Pro Ser Ile Tyr Cys Thr Ser Asn Asp Asp
1105                1110                1115                1120
Gln Val Gly Ile Trp Ser Gly Pro Ala Pro Gln Cys Ile Ile Pro Asn
                1125                1130                1135
Lys Cys Thr Pro Pro Asn Val Glu Asn Gly Ile Leu Val Ser Asp Asn
                1140                1145                1150
Arg Ser Leu Phe Ser Leu Asn Glu Val Val Glu Phe Arg Cys Gln Pro
                1155                1160                1165
Gly Phe Val Met Lys Gly Pro Arg Arg Val Lys Cys Gln Ala Leu Asn
                1170                1175                1180
Lys Trp Glu Pro Glu Leu Pro Ser Cys Ser Arg Val Cys Gln Pro Pro
1185                1190                1195                1200
Pro Glu Ile Leu His Gly Glu His Thr Pro Ser His Gln Asp Asn Phe
                1205                1210                1215
Ser Pro Gly Gln Glu Val Phe Tyr Ser Cys Glu Pro Gly Tyr Asp Leu
                1220                1225                1230
Arg Gly Ala Ala Ser Leu His Cys Thr Pro Gln Gly Asp Trp Ser Pro
                1235                1240                1245
Glu Ala Pro Arg Cys Ala Val Lys Ser Cys Asp Asp Phe Leu Gly Gln
                1250                1255                1260
```

```
Leu Pro His Gly Arg Val Leu Phe Pro Leu Asn Leu Gln Leu Gly Ala
1265                1270                1275                1280

Lys Val Ser Phe Val Cys Asp Glu Gly Phe Arg Leu Lys Gly Ser Ser
            1285                1290                1295

Val Ser His Cys Val Leu Val Gly Met Arg Ser Leu Trp Asn Asn Ser
        1300                1305                1310

Val Pro Val Cys Glu His Ile Phe Cys Pro Asn Pro Pro Ala Ile Leu
    1315                1320                1325

Asn Gly Arg His Thr Gly Thr Pro Ser Gly Asp Ile Pro Tyr Gly Lys
1330                1335                1340

Glu Ile Ser Tyr Thr Cys Asp Pro His Pro Asp Arg Gly Met Thr Phe
1345                1350                1355                1360

Asn Leu Ile Gly Glu Ser Thr Ile Arg Cys Thr Ser Asp Pro His Gly
            1365                1370                1375

Asn Gly Val Trp Ser Ser Pro Ala Pro Arg Cys Glu Leu Ser Val Arg
        1380                1385                1390

Ala Gly His Cys Lys Thr Pro Glu Gln Phe Pro Phe Ala Ser Pro Thr
    1395                1400                1405

Ile Pro Ile Asn Asp Phe Glu Phe Pro Val Gly Thr Ser Leu Asn Tyr
    1410                1415                1420

Glu Cys Arg Pro Gly Tyr Phe Gly Lys Met Phe Ser Ile Ser Cys Leu
1425                1430                1435                1440

Glu Asn Leu Val Trp Ser Ser Val Glu Asp Asn Cys Arg Arg Lys Ser
            1445                1450                1455

Cys Gly Pro Pro Pro Glu Pro Phe Asn Gly Met Val His Ile Asn Thr
        1460                1465                1470

Asp Thr Gln Phe Gly Ser Thr Val Asn Tyr Ser Cys Asn Glu Gly Phe
    1475                1480                1485

Arg Leu Ile Gly Ser Pro Ser Thr Thr Cys Leu Val Ser Gly Asn Asn
    1490                1495                1500

Val Thr Trp Asp Lys Lys Ala Pro Ile Cys Glu Ile Ile Ser Cys Glu
1505                1510                1515                1520

Pro Pro Pro Thr Ile Ser Asn Gly Asp Phe Tyr Ser Asn Asn Arg Thr
            1525                1530                1535

Ser Phe His Asn Gly Thr Val Val Thr Tyr Gln Cys His Thr Gly Pro
        1540                1545                1550

Asp Gly Glu Gln Leu Phe Glu Leu Val Gly Glu Arg Ser Ile Tyr Cys
    1555                1560                1565

Thr Ser Lys Asp Asp Gln Val Gly Val Trp Ser Ser Pro Pro Pro Arg
    1570                1575                1580

Cys Ile Ser Thr Asn Lys Cys Thr Ala Pro Glu Val Glu Asn Ala Ile
1585                1590                1595                1600

Arg Val Pro Gly Asn Arg Ser Phe Phe Ser Leu Thr Glu Ile Ile Arg
            1605                1610                1615

Phe Arg Cys Gln Pro Gly Phe Val Met Val Gly Ser His Thr Val Gln
        1620                1625                1630

Cys Gln Thr Asn Gly Arg Trp Gly Pro Lys Leu Pro His Cys Ser Arg
    1635                1640                1645

Val Cys Gln Pro Pro Pro Glu Ile Leu His Gly Glu His Thr Leu Ser
    1650                1655                1660

His Gln Asp Asn Phe Ser Pro Gly Gln Glu Val Phe Tyr Ser Cys Glu
1665                1670                1675                1680
```

```
Pro Ser Tyr Asp Leu Arg Gly Ala Ala Ser Leu His Cys Thr Pro Gln
            1685                1690                1695

Gly Asp Trp Ser Pro Glu Ala Pro Arg Cys Thr Val Lys Ser Cys Asp
        1700                1705                1710

Asp Phe Leu Gly Gln Leu Pro His Gly Arg Val Leu Leu Pro Leu Asn
        1715                1720                1725

Leu Gln Leu Gly Ala Lys Val Ser Phe Val Cys Asp Glu Gly Phe Arg
        1730                1735                1740

Leu Lys Gly Arg Ser Ala Ser His Cys Val Leu Ala Gly Met Lys Ala
1745                1750                1755                1760

Leu Trp Asn Ser Ser Val Pro Val Cys Glu Gln Ile Phe Cys Pro Asn
            1765                1770                1775

Pro Pro Ala Ile Leu Asn Gly Arg His Thr Gly Thr Pro Phe Gly Asp
            1780                1785                1790

Ile Pro Tyr Gly Lys Glu Ile Ser Tyr Ala Cys Asp Thr His Pro Asp
            1795                1800                1805

Arg Gly Met Thr Phe Asn Leu Ile Gly Glu Ser Ser Ile Arg Cys Thr
            1810                1815                1820

Ser Asp Pro Gln Gly Asn Gly Val Trp Ser Pro Ala Pro Arg Cys
1825                1830                1835                1840

Glu Leu Ser Val Pro Ala Ala Cys Pro His Pro Pro Lys Ile Gln Asn
            1845                1850                1855

Gly His Tyr Ile Gly Gly His Val Ser Leu Tyr Leu Pro Gly Met Thr
            1860                1865                1870

Ile Ser Tyr Thr Cys Asp Pro Gly Tyr Leu Leu Val Gly Lys Gly Phe
            1875                1880                1885

Ile Phe Cys Thr Asp Gln Gly Ile Trp Ser Gln Leu Asp His Tyr Cys
            1890                1895                1900

Lys Glu Val Asn Cys Ser Phe Pro Leu Phe Met Asn Gly Ile Ser Lys
1905                1910                1915                1920

Glu Leu Glu Met Lys Lys Val Tyr His Tyr Gly Asp Tyr Val Thr Leu
            1925                1930                1935

Lys Cys Glu Asp Gly Tyr Thr Leu Glu Gly Ser Pro Trp Ser Gln Cys
            1940                1945                1950

Gln Ala Asp Asp Arg Trp Asp Pro Pro Leu Ala Lys Cys Thr Ser Arg
            1955                1960                1965

Ala His Asp Ala Leu Ile Val Gly Thr Leu Ser Gly Thr Ile Phe Phe
            1970                1975                1980

Ile Leu Leu Ile Ile Phe Leu Ser Trp Ile Ile Leu Lys His Arg Lys
1985                1990                1995                2000

Gly Asn Asn Ala His Glu Asn Pro Lys Glu Val Ala Ile His Leu His
            2005                2010                2015

Ser Gln Gly Gly Ser Ser Val His Pro Arg Thr Leu Gln Thr Asn Glu
            2020                2025                2030

Glu Asn Ser Arg Val Leu Pro
            2035

<210> SEQ ID NO 12
<211> LENGTH: 392
<212> TYPE: PRT
<213> ORGANISM: Homo sapiens

<400> SEQUENCE: 12

Met Glu Pro Pro Gly Arg Arg Glu Cys Pro Phe Pro Ser Trp Arg Phe
1               5                   10                  15
```

```
Pro Gly Leu Leu Leu Ala Ala Met Val Leu Leu Tyr Ser Phe Ser
            20                  25                  30

Asp Ala Cys Glu Glu Pro Pro Thr Phe Glu Ala Met Glu Leu Ile Gly
        35                  40                  45

Lys Pro Lys Pro Tyr Tyr Glu Ile Gly Glu Arg Val Asp Tyr Lys Cys
    50                  55                  60

Lys Lys Gly Tyr Phe Tyr Ile Pro Pro Leu Ala Thr His Thr Ile Cys
65                  70                  75                  80

Asp Arg Asn His Thr Trp Leu Pro Val Ser Asp Ala Cys Tyr Arg
                85                  90                  95

Glu Thr Cys Pro Tyr Ile Arg Asp Pro Leu Asn Gly Gln Ala Val Pro
            100                 105                 110

Ala Asn Gly Thr Tyr Glu Phe Gly Tyr Gln Met His Phe Ile Cys Asn
        115                 120                 125

Glu Gly Tyr Tyr Leu Ile Gly Glu Glu Ile Leu Tyr Cys Glu Leu Lys
    130                 135                 140

Gly Ser Val Ala Ile Trp Ser Gly Lys Pro Pro Ile Cys Glu Lys Val
145                 150                 155                 160

Leu Cys Thr Pro Pro Lys Ile Lys Asn Gly Lys His Thr Phe Ser
            165                 170                 175

Glu Val Glu Val Phe Glu Tyr Leu Asp Ala Val Thr Tyr Ser Cys Asp
        180                 185                 190

Pro Ala Pro Gly Pro Asp Pro Phe Ser Leu Ile Gly Glu Ser Thr Ile
    195                 200                 205

Tyr Cys Gly Asp Asn Ser Val Trp Ser Arg Ala Ala Pro Glu Cys Lys
210                 215                 220

Val Val Lys Cys Arg Phe Pro Val Val Glu Asn Gly Lys Gln Ile Ser
225                 230                 235                 240

Gly Phe Gly Lys Lys Phe Tyr Tyr Lys Ala Thr Val Met Phe Glu Cys
            245                 250                 255

Asp Lys Gly Phe Tyr Leu Asp Gly Ser Asp Thr Ile Val Cys Asp Ser
        260                 265                 270

Asn Ser Thr Trp Asp Pro Pro Val Pro Lys Cys Leu Lys Val Leu Pro
    275                 280                 285

Pro Ser Ser Thr Lys Pro Pro Ala Leu Ser His Ser Val Ser Thr Ser
290                 295                 300

Ser Thr Thr Lys Ser Pro Ala Ser Ser Ala Ser Gly Pro Arg Pro Thr
305                 310                 315                 320

Tyr Lys Pro Pro Val Ser Asn Tyr Pro Gly Tyr Pro Lys Pro Glu Glu
            325                 330                 335

Gly Ile Leu Asp Ser Leu Asp Val Trp Val Ile Ala Val Ile Val Ile
        340                 345                 350

Ala Ile Val Val Gly Val Ala Val Ile Cys Val Val Pro Tyr Arg Tyr
    355                 360                 365

Leu Gln Arg Arg Lys Lys Gly Thr Tyr Leu Thr Asp Glu Thr His
370                 375                 380

Arg Glu Val Lys Phe Thr Ser Leu
385                 390

<210> SEQ ID NO 13
<211> LENGTH: 381
<212> TYPE: PRT
<213> ORGANISM: Homo sapiens
```

```
<400> SEQUENCE: 13

Met Thr Val Ala Arg Pro Ser Val Pro Ala Leu Pro Leu Leu Gly
  1               5                  10                  15

Glu Leu Pro Arg Leu Leu Leu Val Leu Leu Cys Leu Pro Ala Val
             20                  25                  30

Trp Gly Asp Cys Gly Leu Pro Pro Asp Val Pro Asn Ala Gln Pro Ala
             35                  40                  45

Leu Glu Gly Arg Thr Ser Phe Pro Glu Asp Thr Val Ile Thr Tyr Lys
 50                  55                  60

Cys Glu Glu Ser Phe Val Lys Ile Pro Gly Glu Lys Asp Ser Val Ile
 65                  70                  75                  80

Cys Leu Lys Gly Ser Gln Trp Ser Asp Ile Glu Glu Phe Cys Asn Arg
                 85                  90                  95

Ser Cys Glu Val Pro Thr Arg Leu Asn Ser Ala Ser Leu Lys Gln Pro
                100                 105                 110

Tyr Ile Thr Gln Asn Tyr Phe Pro Val Gly Thr Val Val Glu Tyr Glu
                115                 120                 125

Cys Arg Pro Gly Tyr Arg Arg Glu Pro Ser Leu Ser Pro Lys Leu Thr
130                 135                 140

Cys Leu Gln Asn Leu Lys Trp Ser Thr Ala Val Glu Phe Cys Lys Lys
145                 150                 155                 160

Lys Ser Cys Pro Asn Pro Gly Glu Ile Arg Asn Gly Gln Ile Asp Val
                165                 170                 175

Pro Gly Gly Ile Leu Phe Gly Ala Thr Ile Ser Phe Ser Cys Asn Thr
                180                 185                 190

Gly Tyr Lys Leu Phe Gly Ser Thr Ser Ser Phe Cys Leu Ile Ser Gly
                195                 200                 205

Ser Ser Val Gln Trp Ser Asp Pro Leu Pro Glu Cys Arg Glu Ile Tyr
210                 215                 220

Cys Pro Ala Pro Pro Gln Ile Asp Asn Gly Ile Ile Gln Gly Glu Arg
225                 230                 235                 240

Asp His Tyr Gly Tyr Arg Gln Ser Val Thr Tyr Ala Cys Asn Lys Gly
                245                 250                 255

Phe Thr Met Ile Gly Glu His Ser Ile Tyr Cys Thr Val Asn Asn Asp
                260                 265                 270

Glu Gly Glu Trp Ser Gly Pro Pro Pro Glu Cys Arg Gly Lys Ser Leu
                275                 280                 285

Thr Ser Lys Val Pro Pro Thr Val Gln Lys Pro Thr Thr Val Asn Val
290                 295                 300

Pro Thr Thr Glu Val Ser Pro Thr Ser Gln Lys Thr Thr Lys Thr
305                 310                 315                 320

Thr Thr Pro Asn Ala Gln Ala Thr Arg Ser Thr Pro Val Ser Arg Thr
                325                 330                 335

Thr Lys His Phe His Glu Thr Thr Pro Asn Lys Gly Ser Gly Thr Thr
                340                 345                 350

Ser Gly Thr Thr Arg Leu Leu Ser Gly His Thr Cys Phe Thr Leu Thr
                355                 360                 365

Gly Leu Leu Gly Thr Leu Val Thr Met Gly Leu Leu Thr
370                 375                 380

<210> SEQ ID NO 14
<211> LENGTH: 390
<212> TYPE: PRT
<213> ORGANISM: Murine
```

<400> SEQUENCE: 14

```
Met Ile Arg Gly Arg Ala Pro Arg Thr Arg Pro Ser Pro Pro Pro
 1               5                  10                  15

Leu Leu Pro Leu Leu Ser Leu Ser Leu Leu Leu Leu Ser Pro Thr Val
                 20                  25                  30

Arg Gly Asp Cys Gly Pro Pro Asp Ile Pro Asn Ala Arg Pro Ile
             35                  40                  45

Leu Gly Arg His Ser Lys Phe Ala Glu Gln Ser Lys Val Ala Tyr Ser
 50                  55                  60

Cys Asn Asn Gly Phe Lys Gln Val Pro Asp Lys Ser Asn Ile Val Val
 65                  70                  75                  80

Cys Leu Glu Asn Gly Gln Trp Ser Ser His Glu Thr Phe Cys Glu Lys
                 85                  90                  95

Ser Cys Val Ala Pro Glu Arg Leu Ser Phe Ala Ser Leu Lys Lys Glu
                 100                 105                 110

Tyr Leu Asn Met Asn Phe Phe Pro Val Gly Thr Ile Val Glu Tyr Glu
                 115                 120                 125

Cys Arg Pro Gly Phe Arg Lys Gln Pro Pro Leu Pro Gly Lys Ala Thr
                 130                 135                 140

Cys Leu Glu Asp Leu Val Trp Ser Pro Val Ala Gln Phe Cys Lys Lys
145                 150                 155                 160

Lys Ser Cys Pro Asn Pro Lys Asp Leu Asp Asn Gly His Ile Asn Ile
                 165                 170                 175

Pro Thr Gly Ile Leu Phe Gly Ser Glu Ile Asn Phe Ser Cys Asn Pro
                 180                 185                 190

Gly Tyr Arg Leu Val Gly Val Ser Ser Thr Phe Cys Ser Val Thr Gly
                 195                 200                 205

Asn Thr Val Asp Trp Asp Asp Glu Phe Pro Val Cys Thr Glu Ile His
                 210                 215                 220

Cys Pro Glu Pro Pro Lys Ile Asn Asn Gly Ile Met Arg Gly Glu Ser
225                 230                 235                 240

Asp Ser Tyr Thr Tyr Ser Gln Val Val Thr Tyr Ser Cys Asp Lys Gly
                 245                 250                 255

Phe Ile Leu Val Gly Asn Ala Ser Ile Tyr Cys Thr Val Ser Lys Ser
                 260                 265                 270

Asp Val Gly Gln Trp Ser Ser Pro Pro Arg Cys Ile Glu Lys Ser
                 275                 280                 285

Lys Val Pro Thr Lys Pro Thr Ile Asn Val Pro Ser Thr Gly Thr
                 290                 295                 300

Pro Ser Thr Pro Gln Lys Pro Thr Thr Glu Ser Val Pro Asn Pro Gly
305                 310                 315                 320

Asp Gln Pro Thr Pro Gln Lys Pro Ser Thr Val Lys Val Ser Ala Thr
                 325                 330                 335

Gln His Val Pro Val Thr Lys Thr Thr Val Arg His Pro Ile Arg Thr
                 340                 345                 350

Ser Thr Asp Lys Gly Glu Pro Asn Thr Gly Gly Asp Arg Tyr Ile Tyr
                 355                 360                 365

Gly His Thr Cys Leu Ile Thr Leu Thr Val Leu His Val Met Leu Ser
                 370                 375                 380

Leu Ile Gly Tyr Leu Thr
385                 390
```

```
<210> SEQ ID NO 15
<211> LENGTH: 449
<212> TYPE: PRT
<213> ORGANISM: Homo sapiens

<400> SEQUENCE: 15

Met Met Lys Thr Leu Leu Phe Val Gly Leu Leu Thr Trp Glu
 1               5                  10                  15

Ser Gly Gln Val Leu Gly Asp Gln Thr Val Ser Asp Asn Glu Leu Gln
                20                  25                  30

Glu Met Ser Asn Gln Gly Ser Lys Tyr Val Asn Lys Glu Ile Gln Asn
            35                  40                  45

Ala Val Asn Gly Val Lys Gln Ile Lys Thr Leu Ile Glu Lys Thr Asn
        50                  55                  60

Glu Glu Arg Lys Thr Leu Leu Ser Asn Leu Glu Glu Ala Lys Lys Lys
 65                  70                  75                  80

Lys Glu Asp Ala Leu Asn Glu Thr Arg Glu Ser Glu Thr Lys Leu Lys
                85                  90                  95

Glu Leu Pro Gly Val Cys Asn Glu Thr Met Met Ala Leu Trp Glu Glu
            100                 105                 110

Cys Lys Pro Cys Leu Lys Gln Thr Cys Met Lys Phe Tyr Ala Arg Val
        115                 120                 125

Cys Arg Ser Gly Ser Gly Leu Val Gly Arg Gln Leu Glu Glu Phe Leu
130                 135                 140

Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
                165                 170                 175

Gln Asp His Phe Ser Arg Ala Ser Ser Ile Ile Asp Glu Leu Phe Gln
            180                 185                 190

Asp Arg Phe Phe Thr Arg Glu Pro Gln Asp Thr Tyr His Tyr Leu Pro
        195                 200                 205

Phe Ser Leu Pro His Arg Arg Pro His Phe Phe Pro Lys Ser Arg
210                 215                 220

Ile Val Arg Ser Leu Met Pro Phe Ser Pro Tyr Glu Pro Leu Asn Phe
225                 230                 235                 240

His Ala Met Phe Gln Pro Phe Leu Glu Met Ile His Glu Ala Gln Gln
                245                 250                 255

Ala Met Asp Ile His Phe His Ser Pro Ala Phe Gln His Pro Pro Thr
            260                 265                 270

Glu Phe Ile Arg Glu Gly Asp Asp Arg Thr Val Cys Arg Glu Ile
        275                 280                 285

Arg His Asn Ser Thr Gly Cys Leu Arg Met Lys Asp Gln Cys Asp Lys
290                 295                 300

Cys Arg Glu Ile Leu Ser Val Asp Cys Ser Thr Asn Asn Pro Ser Gln
305                 310                 315                 320

Ala Lys Leu Arg Arg Glu Leu Asp Glu Ser Leu Gln Val Ala Glu Arg
                325                 330                 335

Leu Thr Arg Lys Tyr Asn Glu Leu Leu Lys Ser Tyr Gln Trp Lys Met
            340                 345                 350

Leu Asn Thr Ser Ser Leu Leu Glu Gln Leu Asn Glu Gln Phe Asn Trp
        355                 360                 365

Val Ser Arg Leu Ala Asn Leu Thr Gln Gly Glu Asp Gln Tyr Tyr Leu
370                 375                 380
```

```
Arg Val Thr Thr Val Ala Ser His Thr Ser Asp Ser Asp Val Pro Ser
385                 390                 395                 400

Gly Val Thr Glu Val Val Lys Leu Phe Asp Ser Asp Pro Ile Thr
            405                 410                 415

Val Thr Val Pro Val Glu Val Ser Arg Lys Asn Pro Lys Phe Met Glu
            420                 425                 430

Thr Val Ala Glu Lys Ala Leu Gln Glu Tyr Arg Lys Lys His Arg Glu
            435                 440                 445

Glu

<210> SEQ ID NO 16
<211> LENGTH: 448
<212> TYPE: PRT
<213> ORGANISM: Murine

<400> SEQUENCE: 16

Met Lys Ile Leu Leu Cys Val Ala Leu Leu Ile Trp Asp Asn
 1               5                  10                  15

Gly Met Val Leu Gly Glu Gln Glu Val Ser Asp Asn Glu Leu Gln Glu
            20                  25                  30

Leu Ser Thr Gln Gly Ser Arg Tyr Ile Asn Lys Glu Ile Gln Asn Ala
            35                  40                  45

Val Gln Gly Val Lys His Ile Lys Thr Leu Ile Glu Lys Thr Asn Ala
 50                  55                  60

Glu Arg Lys Ser Leu Leu Asn Ser Leu Glu Glu Ala Lys Lys Lys Lys
 65                  70                  75                  80

Glu Asp Ala Leu Glu Asp Thr Arg Asp Ser Glu Met Lys Leu Lys Ala
                 85                  90                  95

Phe Pro Glu Val Cys Asn Glu Thr Met Met Ala Leu Trp Glu Glu Cys
                100                 105                 110

Lys Pro Cys Leu Lys His Thr Cys Met Lys Phe Tyr Ala Arg Val Cys
                115                 120                 125

Arg Ser Gly Ser Gly Leu Val Gly Gln Gln Leu Glu Glu Phe Leu Asn
130                 135                 140

Gln Ser Ser Pro Phe Tyr Phe Trp Met Asn Gly Asp Arg Ile Asp Ser
145                 150                 155                 160

Leu Leu Glu Ser Asp Arg Gln Gln Ser Gln Val Leu Asp Ala Met Gln
                165                 170                 175

Asp Ser Phe Ala Arg Ala Ser Gly Ile Ile Asp Thr Leu Phe Gln Asp
                180                 185                 190

Arg Phe Phe Ala Arg Glu Leu His Asp Pro His Tyr Phe Ser Pro Ile
                195                 200                 205

Gly Phe Pro His Lys Arg Pro His Phe Leu Tyr Pro Lys Ser Arg Leu
            210                 215                 220

Val Arg Ser Leu Met Ser Pro Ser His Tyr Gly Pro Pro Ser Phe His
225                 230                 235                 240

Asn Met Phe Gln Pro Phe Glu Met Ile His Gln Ala Gln Gln Ala
                245                 250                 255

Met Asp Val Gln Leu His Ser Pro Ala Phe Gln Phe Pro Asp Val Asp
                260                 265                 270

Phe Leu Arg Glu Gly Glu Asp Asp Arg Thr Val Cys Lys Glu Ile Arg
                275                 280                 285

Arg Asn Ser Thr Gly Cys Leu Lys Met Lys Gly Gln Cys Glu Lys Cys
            290                 295                 300
```

```
Gln Glu Ile Leu Ser Val Asp Cys Ser Thr Asn Asn Pro Ala Gln Ala
305                 310                 315                 320

Asn Leu Arg Gln Glu Leu Asn Asp Ser Leu Gln Val Ala Glu Arg Leu
            325                 330                 335

Thr Glu Gln Tyr Lys Glu Leu Leu Gln Ser Phe Gln Ser Lys Met Leu
        340                 345                 350

Asn Thr Ser Ser Leu Leu Glu Gln Leu Asn Asp Gln Phe Asn Trp Val
        355                 360                 365

Ser Gln Leu Ala Asn Leu Thr Gln Gly Glu Asp Lys Tyr Tyr Leu Arg
    370                 375                 380

Val Ser Thr Val Thr Thr His Ser Ser Asp Ser Glu Val Pro Ser Arg
385                 390                 395                 400

Val Thr Glu Val Val Lys Leu Phe Asp Ser Asp Pro Ile Thr Val
                405                 410                 415

Val Leu Pro Glu Glu Val Ser Lys Asp Asn Pro Lys Phe Met Asp Thr
            420                 425                 430

Val Ala Glu Lys Ala Leu Gln Glu Tyr Arg Arg Lys Ser Arg Ala Glu
            435                 440                 445

<210> SEQ ID NO 17
<211> LENGTH: 478
<212> TYPE: PRT
<213> ORGANISM: Homo sapiens

<400> SEQUENCE: 17

Met Ala Pro Leu Arg Pro Leu Leu Ile Leu Ala Leu Leu Ala Trp Val
1               5                   10                  15

Ala Leu Ala Asp Gln Glu Ser Cys Lys Gly Arg Cys Thr Glu Gly Phe
            20                  25                  30

Asn Val Asp Lys Lys Cys Gln Cys Asp Glu Leu Cys Ser Tyr Tyr Gln
        35                  40                  45

Ser Cys Cys Thr Asp Tyr Thr Ala Glu Cys Lys Pro Gln Val Thr Arg
    50                  55                  60

Gly Asp Val Phe Thr Met Pro Glu Asp Glu Tyr Thr Val Tyr Asp Asp
65                  70                  75                  80

Gly Glu Glu Lys Asn Asn Ala Thr Val His Glu Gln Val Gly Gly Pro
                85                  90                  95

Ser Leu Thr Ser Asp Leu Gln Ala Gln Ser Lys Gly Asn Pro Glu Gln
            100                 105                 110

Thr Pro Val Leu Lys Pro Glu Glu Glu Ala Pro Ala Pro Glu Val Gly
        115                 120                 125

Ala Ser Lys Pro Glu Gly Ile Asp Ser Arg Pro Glu Thr Leu His Pro
    130                 135                 140

Gly Arg Pro Gln Pro Pro Ala Glu Glu Glu Leu Cys Ser Gly Lys Pro
145                 150                 155                 160

Phe Asp Ala Phe Thr Asp Leu Lys Asn Gly Ser Leu Phe Ala Phe Arg
                165                 170                 175

Gly Gln Tyr Cys Tyr Glu Leu Asp Glu Lys Ala Val Arg Pro Gly Tyr
            180                 185                 190

Pro Lys Leu Ile Arg Asp Val Trp Gly Ile Glu Gly Pro Ile Asp Ala
        195                 200                 205

Ala Phe Thr Arg Ile Asn Cys Gln Gly Lys Thr Tyr Leu Phe Lys Gly
    210                 215                 220

Ser Gln Tyr Trp Arg Phe Glu Asp Gly Val Leu Asp Pro Asp Tyr Pro
225                 230                 235                 240
```

```
Arg Asn Ile Ser Asp Gly Phe Asp Gly Ile Pro Asp Asn Val Asp Ala
                245                 250                 255

Ala Leu Ala Leu Pro Ala His Ser Tyr Ser Gly Arg Glu Arg Val Tyr
            260                 265                 270

Phe Phe Lys Gly Lys Gln Tyr Trp Glu Tyr Gln Phe Gln His Gln Pro
        275                 280                 285

Ser Gln Glu Glu Cys Glu Gly Ser Ser Leu Ser Ala Val Phe Glu His
    290                 295                 300

Phe Ala Met Met Gln Arg Asp Ser Trp Glu Asp Ile Phe Glu Leu Leu
305                 310                 315                 320

Phe Trp Gly Arg Thr Ser Ala Gly Thr Arg Gln Pro Gln Phe Ile Ser
                325                 330                 335

Arg Asp Trp His Gly Val Pro Gly Gln Val Asp Ala Ala Met Ala Gly
                340                 345                 350

Arg Ile Tyr Ile Ser Gly Met Ala Pro Arg Pro Ser Leu Ala Lys Lys
                355                 360                 365

Gln Arg Phe Arg His Arg Asn Arg Lys Gly Tyr Arg Ser Gln Arg Gly
        370                 375                 380

His Ser Arg Gly Arg Asn Gln Asn Ser Arg Arg Pro Ser Arg Ala Thr
385                 390                 395                 400

Trp Leu Ser Leu Phe Ser Ser Glu Glu Ser Asn Leu Gly Ala Asn Asn
                405                 410                 415

Tyr Asp Asp Tyr Arg Met Asp Trp Leu Val Pro Ala Thr Cys Glu Pro
                420                 425                 430

Ile Gln Ser Val Phe Phe Phe Ser Gly Asp Lys Tyr Tyr Arg Val Asn
            435                 440                 445

Leu Arg Thr Arg Arg Val Asp Thr Val Asp Pro Pro Tyr Pro Arg Ser
        450                 455                 460

Ile Ala Gln Tyr Trp Leu Gly Cys Pro Ala Pro Gly His Leu
465                 470                 475

<210> SEQ ID NO 18
<211> LENGTH: 478
<212> TYPE: PRT
<213> ORGANISM: Murine

<400> SEQUENCE: 18

Met Ala Pro Leu Arg Pro Phe Phe Ile Leu Ala Leu Val Ala Trp Val
1               5                   10                  15

Ser Leu Ala Asp Gln Glu Ser Cys Lys Gly Arg Cys Thr Gln Gly Phe
            20                  25                  30

Met Ala Ser Lys Lys Cys Gln Cys Asp Glu Leu Cys Thr Tyr Tyr Gln
            35                  40                  45

Ser Cys Cys Ala Asp Tyr Met Glu Gln Cys Lys Pro Gln Val Thr Arg
    50                  55                  60

Gly Asp Val Phe Thr Met Pro Glu Asp Tyr Trp Ser Tyr Asp Tyr
65                  70                  75                  80

Val Glu Glu Pro Lys Asn Asn Thr Asn Thr Gly Val Gln Pro Glu Asn
                85                  90                  95

Thr Ser Pro Pro Gly Asp Leu Asn Pro Arg Thr Asp Gly Thr Leu Lys
            100                 105                 110

Pro Thr Ala Phe Leu Asp Pro Glu Glu Gln Pro Ser Thr Pro Ala Pro
        115                 120                 125

Lys Val Glu Gln Gln Glu Glu Ile Leu Arg Pro Asp Thr Thr Asp Gln
```

```
                    130                 135                 140
Gly Thr Pro Glu Phe Pro Glu Glu Leu Cys Ser Gly Lys Pro Phe
145                 150                 155                 160

Asp Ala Phe Thr Asp Leu Lys Asn Gly Ser Leu Phe Ala Phe Arg Gly
                    165                 170                 175

Gln Tyr Cys Tyr Glu Leu Asp Glu Thr Ala Val Arg Pro Gly Tyr Pro
                180                 185                 190

Lys Leu Ile Gln Asp Val Trp Gly Ile Glu Gly Pro Ile Asp Ala Ala
                195                 200                 205

Phe Thr Arg Ile Asn Cys Gln Gly Lys Thr Tyr Leu Phe Lys Gly Ser
210                 215                 220

Gln Tyr Trp Arg Phe Glu Asp Gly Val Leu Asp Pro Gly Tyr Pro Arg
225                 230                 235                 240

Asn Ile Ser Glu Gly Phe Ser Gly Ile Pro Asp Asn Val Asp Ala Ala
                245                 250                 255

Phe Ala Leu Pro Ala His Arg Tyr Ser Gly Arg Glu Arg Val Tyr Phe
                260                 265                 270

Phe Lys Gly Lys Gln Tyr Trp Glu Tyr Glu Phe Gln Gln Gln Pro Ser
            275                 280                 285

Gln Glu Glu Cys Glu Gly Ser Ser Leu Ser Ala Val Phe Glu His Phe
290                 295                 300

Ala Leu Leu Gln Arg Asp Ser Trp Glu Asn Ile Phe Glu Leu Leu Phe
305                 310                 315                 320

Trp Gly Arg Ser Ser Asp Gly Ala Arg Glu Pro Gln Phe Ile Ser Arg
                325                 330                 335

Asn Trp His Gly Val Pro Gly Lys Val Asp Ala Ala Met Ala Gly Arg
                340                 345                 350

Ile Tyr Val Thr Gly Ser Leu Ser His Ser Ala Gln Ala Lys Lys Gln
                355                 360                 365

Lys Ser Lys Arg Arg Ser Arg Lys Arg Tyr Arg Ser Arg Arg Gly Arg
370                 375                 380

Gly His Arg Arg Ser Gln Ser Ser Asn Ser Arg Ser Ser Arg Ser
385                 390                 395                 400

Ile Trp Phe Ser Leu Phe Ser Ser Glu Glu Ser Gly Leu Gly Thr Tyr
                405                 410                 415

Asn Asn Tyr Asp Tyr Asp Met Asp Trp Leu Val Pro Ala Thr Cys Glu
                420                 425                 430

Pro Ile Gln Ser Val Tyr Phe Phe Ser Gly Asp Lys Tyr Tyr Arg Val
                435                 440                 445

Asn Leu Arg Thr Arg Arg Val Asp Ser Val Asn Pro Pro Tyr Pro Arg
450                 455                 460

Ser Ile Ala Gln Tyr Trp Leu Gly Cys Pro Thr Ser Glu Lys
465                 470                 475

<210> SEQ ID NO 19
<211> LENGTH: 500
<212> TYPE: PRT
<213> ORGANISM: Homo sapiens

<400> SEQUENCE: 19

Met Ala Ser Arg Leu Thr Leu Leu Thr Leu Leu Leu Leu Leu Leu Ala
1               5                   10                  15

Gly Asp Arg Ala Ser Ser Asn Pro Asn Ala Thr Ser Ser Ser Ser Gln
                20                  25                  30
```

-continued

```
Asp Pro Glu Ser Leu Gln Asp Arg Gly Glu Gly Lys Val Ala Thr Thr
             35                  40                  45

Val Ile Ser Lys Met Leu Phe Val Glu Pro Ile Leu Glu Val Ser Ser
 50                  55                  60

Leu Pro Thr Thr Asn Ser Thr Thr Asn Ser Ala Thr Lys Ile Thr Ala
 65                  70                  75                  80

Asn Thr Thr Asp Glu Pro Thr Thr Gln Pro Thr Thr Glu Pro Thr Thr
                 85                  90                  95

Gln Pro Thr Ile Gln Pro Thr Gln Thr Thr Gln Leu Pro Thr Asp
                 100                 105                 110

Ser Pro Thr Gln Pro Thr Thr Gly Ser Phe Cys Pro Gly Pro Val Thr
                 115                 120                 125

Leu Cys Ser Asp Leu Glu Ser His Ser Thr Glu Ala Val Leu Gly Asp
    130                 135                 140

Ala Leu Val Asp Phe Ser Leu Lys Leu Tyr His Ala Phe Ser Ala Met
145                 150                 155                 160

Lys Lys Val Glu Thr Asn Met Ala Phe Ser Pro Phe Ser Ile Ala Ser
                165                 170                 175

Leu Leu Thr Gln Val Leu Leu Gly Ala Gly Glu Asn Thr Lys Thr Asn
                180                 185                 190

Leu Glu Ser Ile Leu Ser Tyr Pro Lys Asp Phe Thr Cys Val His Gln
        195                 200                 205

Ala Leu Lys Gly Phe Thr Thr Lys Gly Val Thr Ser Val Ser Gln Ile
    210                 215                 220

Phe His Ser Pro Asp Leu Ala Ile Arg Asp Thr Phe Val Asn Ala Ser
225                 230                 235                 240

Arg Thr Leu Tyr Ser Ser Pro Arg Val Leu Ser Asn Asn Ser Asp
                245                 250                 255

Ala Asn Leu Glu Leu Ile Asn Thr Trp Val Ala Lys Asn Thr Asn Asn
                260                 265                 270

Lys Ile Ser Arg Leu Leu Asp Ser Leu Pro Ser Asp Thr Arg Leu Val
                275                 280                 285

Leu Leu Asn Ala Ile Tyr Leu Ser Ala Lys Trp Lys Thr Thr Phe Asp
    290                 295                 300

Pro Lys Lys Thr Arg Met Glu Pro Phe His Phe Lys Asn Ser Val Ile
305                 310                 315                 320

Lys Val Pro Met Met Asn Ser Lys Lys Tyr Pro Val Ala His Phe Ile
                325                 330                 335

Asp Gln Thr Leu Lys Ala Lys Val Gly Gln Leu Gln Leu Ser His Asn
                340                 345                 350

Leu Ser Leu Val Ile Leu Val Pro Gln Asn Leu Lys His Arg Leu Glu
        355                 360                 365

Asp Met Glu Gln Ala Leu Ser Pro Ser Val Phe Lys Ala Ile Met Glu
    370                 375                 380

Lys Leu Glu Met Ser Lys Phe Gln Pro Thr Leu Leu Thr Leu Pro Arg
385                 390                 395                 400

Ile Lys Val Thr Thr Ser Gln Asp Met Leu Ser Ile Met Glu Lys Leu
                405                 410                 415

Glu Phe Phe Asp Phe Ser Tyr Asp Leu Asn Leu Cys Gly Leu Thr Glu
                420                 425                 430

Asp Pro Asp Leu Gln Val Ser Ala Met Gln His Gln Thr Val Leu Glu
                435                 440                 445

Leu Thr Glu Thr Gly Val Glu Ala Ala Ala Ala Ser Ala Ile Ser Val
```

```
            450                 455                 460
Ala Arg Thr Leu Leu Val Phe Glu Val Gln Gln Pro Phe Leu Phe Val
465                 470                 475                 480

Leu Trp Asp Gln Gln His Lys Phe Pro Val Phe Met Gly Arg Val Tyr
                485                 490                 495

Asp Pro Arg Ala
            500

<210> SEQ ID NO 20
<211> LENGTH: 504
<212> TYPE: PRT
<213> ORGANISM: Murine

<400> SEQUENCE: 20

Met Ala Ser Arg Leu Thr Pro Leu Thr Leu Leu Leu Leu Leu Leu Ala
 1               5                  10                  15

Gly Asp Arg Ala Phe Ser Asp Pro Glu Ala Thr Ser His Ser Thr Gln
                20                  25                  30

Asp Pro Leu Glu Ala Gln Ala Lys Ser Arg Glu Ser Phe Pro Glu Arg
            35                  40                  45

Asp Asp Ser Trp Ser Pro Pro Glu Pro Thr Val Leu Pro Ser Thr Trp
50                  55                  60

Pro Thr Thr Ser Val Ala Ile Thr Ile Thr Asn Asp Thr Met Gly Lys
65                  70                  75                  80

Val Ala Asn Glu Ser Phe Ser Gln His Ser Gln Pro Ala Ala Gln Leu
                85                  90                  95

Pro Thr Asp Ser Pro Gly Gln Pro Pro Leu Asn Ser Ser Ser Gln Pro
            100                 105                 110

Ser Thr Ala Ser Asp Leu Pro Thr Gln Ala Thr Thr Glu Pro Phe Cys
        115                 120                 125

Pro Glu Pro Leu Ala Gln Cys Ser Asp Ser Asp Arg Asp Ser Ser Glu
130                 135                 140

Ala Lys Leu Ser Glu Ala Leu Thr Asp Phe Ser Val Lys Leu Tyr His
145                 150                 155                 160

Ala Phe Ser Ala Thr Lys Met Ala Lys Thr Asn Met Ala Phe Ser Pro
                165                 170                 175

Phe Ser Ile Ala Ser Leu Leu Thr Gln Val Leu Leu Gly Ala Gly Asp
            180                 185                 190

Ser Thr Lys Ser Asn Leu Glu Ser Ile Leu Ser Tyr Pro Lys Asp Phe
        195                 200                 205

Ala Cys Val His Gln Ala Leu Lys Gly Phe Ser Ser Lys Gly Val Thr
210                 215                 220

Ser Val Ser Gln Ile Phe His Ser Pro Asp Leu Ala Ile Arg Asp Thr
225                 230                 235                 240

Tyr Val Asn Ala Ser Gln Ser Leu Tyr Gly Ser Ser Pro Arg Val Leu
                245                 250                 255

Gly Pro Asp Ser Ala Ala Asn Leu Glu Leu Ile Asn Thr Trp Val Ala
            260                 265                 270

Glu Asn Thr Asn His Lys Ile Arg Lys Leu Leu Asp Ser Leu Pro Ser
        275                 280                 285

Asp Thr Arg Leu Val Leu Leu Asn Ala Val Tyr Leu Ser Ala Lys Trp
290                 295                 300

Lys Ile Thr Phe Glu Pro Lys Lys Met Met Ala Pro Phe Phe Tyr Lys
305                 310                 315                 320
```

-continued

```
Asn Ser Met Ile Lys Val Pro Met Met Ser Ser Val Lys Tyr Pro Val
            325                 330                 335

Ala Gln Phe Asp Asp His Thr Leu Lys Ala Lys Val Gly Gln Leu Gln
            340                 345                 350

Leu Ser His Asn Leu Ser Phe Val Ile Val Val Pro Val Phe Pro Lys
            355                 360                 365

His Gln Leu Lys Asp Val Glu Lys Ala Leu Asn Pro Thr Val Phe Lys
        370                 375                 380

Ala Ile Met Lys Lys Leu Glu Leu Ser Lys Phe Leu Pro Thr Tyr Leu
385                 390                 395                 400

Thr Met Pro His Ile Lys Val Lys Ser Ser Gln Asp Met Leu Ser Val
                405                 410                 415

Met Glu Lys Leu Glu Phe Phe Asp Phe Thr Tyr Asp Leu Asn Leu Cys
            420                 425                 430

Gly Leu Thr Glu Asp Pro Asp Leu Gln Val Ser Ala Met Lys His Glu
            435                 440                 445

Thr Val Leu Glu Leu Thr Glu Ser Gly Val Glu Ala Ala Ala Ala Ser
        450                 455                 460

Ala Ile Ser Phe Gly Arg Ser Leu Pro Ile Phe Glu Val Gln Arg Pro
465                 470                 475                 480

Phe Leu Phe Leu Leu Trp Asp Gln Gln His Arg Phe Pro Val Phe Met
                485                 490                 495

Gly Arg Val Tyr Asp Pro Arg Gly
                500
```

METHODS OF STIMULATING LIVER REGENERATION

CROSS-REFERENCE TO RELATED APPLICATIONS

This application is a National Phase application under 35 U.S.C. §371 of International Application No. PCT/US2010/040973 filed Jul. 2, 2010 which claims priority to U.S. Provisional Application No. 61/222,867, filed on Jul. 2, 2009, the disclosures of which are incorporated herein by reference in their entireties.

STATEMENT OF RIGHTS TO INVENTIONS MADE UNDER FEDERALLY SPONSORED RESEARCH

This invention was made in part during work supported by Grant No. R01 HL86576 and Grant No. C06 RR015455 from the National Institutes of Health. The government may have certain rights in the invention.

TECHNICAL FIELD

This application pertains to methods and compositions, including pharmaceutical compositions, for stimulating liver regeneration after partial hepatectomy, massive liver resection and toxic injury, or following liver transplantation, including small-for-size liver transplantation

BACKGROUND

Liver resection has become an increasingly safe procedure, but certain procedures remain high-risk, such as massive liver resection (i.e., 70% or more) and small-for-size (SFS) liver transplantation (1-3). Massive hepatic resection is the only option for some patients with primary or secondary liver tumors. With regard to SFS transplantation, the use of partial liver grafts has the potential to significantly reduce the donor shortage by allowing the donor organ to be split between two recipients. In addition, living donor liver transplantation is emerging as an option for some patients, a procedure requiring liver resection and regeneration in the donor and regeneration in the recipient.

The failure of a partial liver to regenerate is considered a critical contributing factor in post-surgical primary liver dysfunction and liver failure, and minimal viable liver volume required for regeneration, following either massive liver resection or SFS transplantation, is an important concept (1-3). Impaired liver regeneration and liver dysfunction has been strongly linked to the extent of hepatic ischemia reperfusion injury (IRI), an unavoidable consequence of the surgical procedures, and studies in rodent models have shown that small liver fragments and SFS grafts are more susceptible to IRI (3-7). Although the precise mechanisms responsible for liver dysfunction and failure in small liver remnants and SFS grafts are not well understood, complement appears to play an important role in both IRI and liver regeneration.

Complement is an important component of immunity, but inappropriate and excessive activation of the complement system is involved in numerous pathological conditions, including IRI. Complement activation products that mediate tissue injury are generated at various points in the complement pathway. Complement activation on a cell surface results in the cleavage of serum C3 and the covalent attachment of C3 fragments that serve as opsonins for immune effector cells. C3 cleavage also results in the generation of C3a, a soluble peptide that is a potent anaphylatoxin. Later in the pathway, serum C5 is cleaved to release soluble C5a, another potent anaphylatoxin and chemoattractant with a wide range of bioactive properties. Cleavage of C5 also initiates formation of the membrane attack complex (MAC), a cytolytic protein complex that assembles in cell membranes, ultimately resulting in cell lysis.

The disclosures of all publications, protein or nucleic acid sequences, accession numbers referring to protein or nucleic acid sequences in public sequence databases, patent applications and patents cited in this specification are hereby incorporated herein by reference in their entirety, as if each individual publication, patent application, or patent were specifically and individually indicated to be incorporated by reference. In particular, all publications cited herein are expressly incorporated by reference for the purpose of describing and disclosing compositions and methodologies which might be used in connection with the invention. Although the invention described herein has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

BRIEF SUMMARY OF THE INVENTION

In certain embodiments, the invention provides a method of stimulating liver regeneration in an individual in need thereof, the method comprising administering to the individual a composition in an amount effective to reduce activation of terminal complement and formation of the membrane attack complex (MAC) in the individual. In certain embodiments, the individual is a mammal. In certain embodiments, the mammal is a human. In certain embodiments, the individual has undergone a partial hepatectomy. In certain embodiments, the individual has undergone a liver transplant. In certain embodiments, the liver transplant is a small-for-size liver transplant. In certain embodiments, the individual is a live liver donor.

In certain embodiments, the composition is a complement inhibitor. In certain embodiments, the complement inhibitor is selected from the group consisting of a targeted complement inhibitor, or a non-targeted complement inhibitor. In certain embodiments, the targeted complement inhibitor is a fusion protein comprising: a complement receptor 2 (CR2) portion comprising CR2 (SEQ ID NO:1) or a biologically active fragment thereof; and a complement inhibitor portion, wherein the complement inhibitor portion is selected from the group consisting of human CD59 (SEQ ID NO:3), mouse CD59, isoform A (SEQ ID NO:8), mouse CD59, isoform B (SEQ ID NO:9) and a biologically active fragment thereof.

In certain embodiments, the CR2 portion comprises at least the first two N-terminal short consensus repeat (SCR) domains of CR2 (SEQ ID NO:2). In certain embodiments, the CR2 portion comprises at least the first four N-terminal short consensus repeat (SCR) domains of CR2 (amino acids 23-271 of SEQ ID NO:1). In certain embodiments, the complement inhibitor portion comprises full-length human CD59 (SEQ ID NO:3), full-length mouse CD59, isoform A (SEQ ID NO:8), or full-length mouse CD59, isoform B (SEQ ID NO:9). In certain embodiments, the complement inhibitor portion comprises the extracellular domain of human CD59 (amino acids 26-102 of SEQ ID NO:3), the extracellular domain of full-length mouse CD59 protein, isoform A (amino acids 24-96 of SEQ ID NO:8), or the extracellular domain of full-length mouse CD59 protein, isoform B (amino acids 24-104 of SEQ ID NO:9). In certain embodiments, the complement inhibitor portion comprises the extracellular domain of human CD59 (amino acids 26-102 of SEQ ID NO:3) lacking its GPI anchor and/or the amino acid to which it is attached (i.e., Asn-102), the extracellular domain of full-length mouse CD59 protein, isoform A (amino acids 24-96 of SEQ ID NO:8) lacking its GPI anchor and/or the amino acid to which it is attached (i.e., Ser-96), or the extracellular domain of full-length mouse CD59 protein, isoform B (amino acids 24-104 of SEQ ID NO:9) lacking its GPI anchor and/or the amino acid to which it is attached (i.e., Asn-104).

In certain embodiments, the targeted complement inhibitor comprises a fusion protein comprising at least the first two N-terminal SCR domains of CR2 and the extracellular domain of human CD59 lacking its GPI anchor. In certain embodiments, the targeted complement inhibitor comprises a fusion protein comprising at least the first two N-terminal SCR domains of CR2 and the extracellular domain of human CD59 lacking its GPI anchor and/or the amino acid to which it is attached (i.e., Asn-102). In certain embodiments, the targeted complement inhibitor comprises a fusion protein comprising at least the first four N-terminal SCR domains of CR2 and the extracellular domain of human CD59 lacking its GPI anchor. In certain embodiments, the targeted complement inhibitor comprises a fusion protein comprising at least the first four N-terminal SCR domains of CR2 and the extracellular domain of human CD59 lacking its GPI anchor and/or the amino acid to which it is attached (i.e., Asn-102).

In certain embodiments, the non-targeted complement inhibitor is selected from the group consisting of an anti-C5 antibody or antigen-binding fragment thereof, clusterin, and vitronectin. In certain embodiments, the non-targeted complement inhibitor is an anti-C5 antibody or antigen-binding fragment thereof is polyclonal, monoclonal, chimeric, or humanized. In certain embodiments, the antigen-binding fragments are selected from the group consisting of Fab, Fab', and F(ab')$_2$ fragments. In certain embodiments, the anti-C5 antibody or antigen-binding fragment thereof is humanized. In certain embodiments, the humanized anti-C5 antibody or antigen-binding fragment thereof is eculizumab or pexelizumab.

In certain embodiments, the non-targeted complement inhibitor is human clusterin protein (SEQ ID NO:15) or mouse clusterin protein (SEQ ID NO:16). In certain embodiments, the non-targeted complement inhibitor comprises a homolog of a human or mouse clusterin protein or a biologically active fragment thereof. In certain embodiments, the non-targeted complement inhibitor is human vitronectin protein (SEQ ID NO:17) or mouse vitronectin protein (SEQ ID NO:18). In certain embodiments, the non-targeted complement inhibitor comprises a homolog of a human or mouse vitronectin protein or a biologically active fragment thereof.

Accumulated survival rate 7 days after 70% PHx. For all determinations from A to E, $^{\#\#\#}$P<0.01 vs. normal saline group; **P<0.01 vs. all other PHx groups. Results expressed as Mean±SD, n=6 for all groups. For F, P<0.01 compared to NS and CR2-Crry 0.08 mg treatment groups, n=20.

Figure 6:
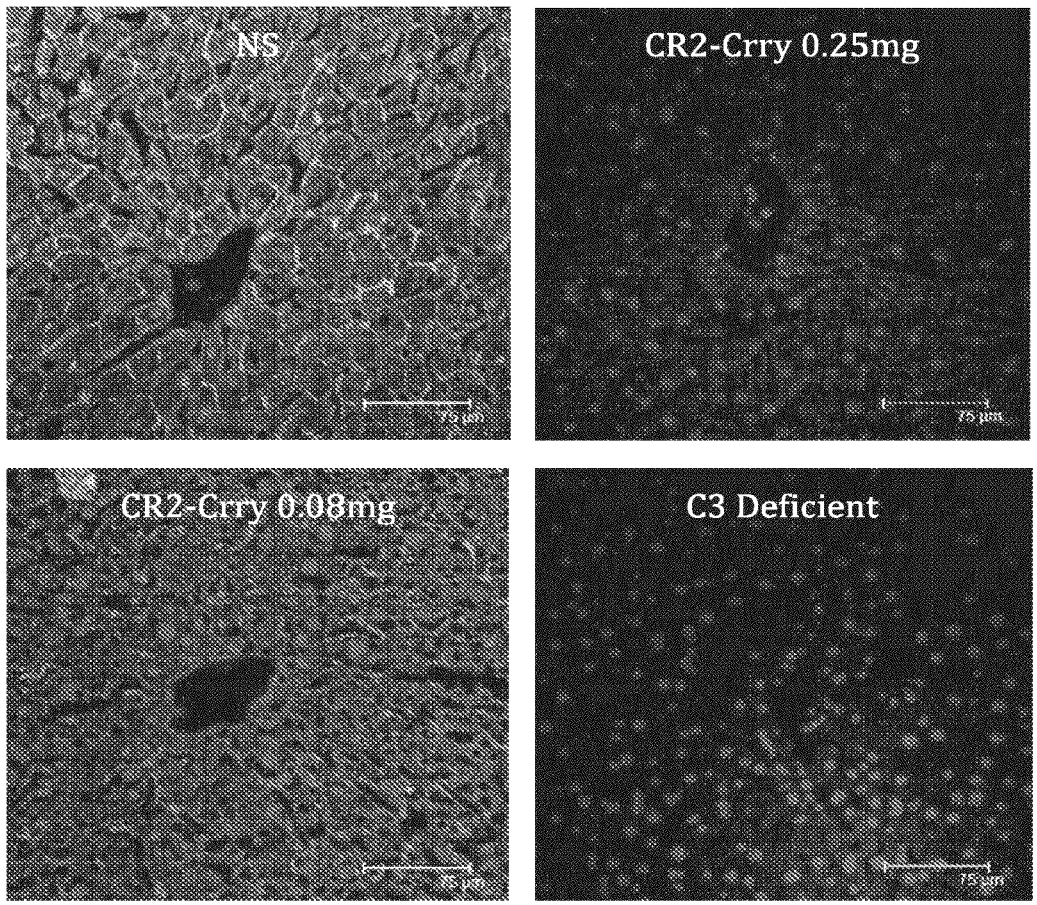

FIG. 6 shows that treatment of mice with CR2-Crry following PHx results in a dose-dependent decrease in hepatic C3d deposition. Wild-type mice were treated with normal saline (A) or CR2-Crry at a dose of 0.25 mg (B) or 0.08 mg (C) immediately after surgery. C3$^{-/-}$ mice (D) received no treatment. At 48 hours after PHx, livers were removed and sections analyzed for C3d deposition by immunofluorescence microscopy. Complement deposition was localized to the central lobular areas and was associated with hepatocyte and sinusoidal endothelial cells in wild-type mice. C3 deposition was reduced in mice treated with 0.08 mg CR2-Crry and was absent in mice treated with 0.25 mg CR2-Crry and in C3$^{-/-}$ mice. Representative images, n=3.

Figure 7:
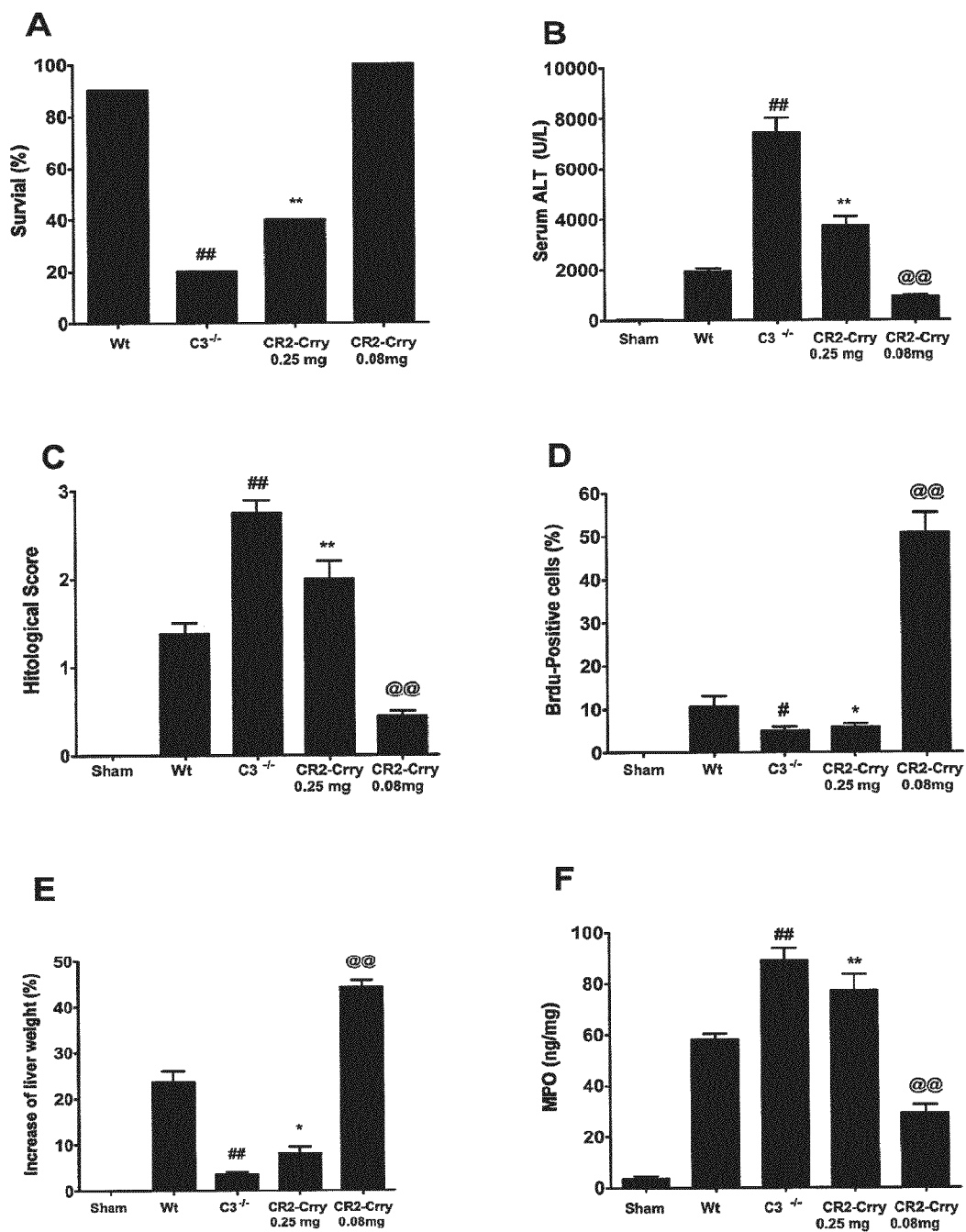

FIG. 7 shows the opposing effects of high and low dose complement inhibition on hepatic injury and regeneration in a model incorporating both IRI and PHx. Mice were treated with normal saline or CR2-Crry at a dose of either 0.25 mg or 0.08 mg immediately after surgery. C3$^{-/-}$ mice received no treatment. All determinations were made 48 hours post-I/R and PHx. (A) Mouse survival. (B) Serum ALT levels. (C) Histological quantification of hepatic necrosis and injury determined on scale of 0-4. (D) Assessment of regeneration by BrdU incorporation. (E) Restitution of liver weight. (F) MPO content in liver samples. $^{\#}$P<0.05, $^{\#\#}$P<0.01 vs. wild-type group; **P<0.01 vs. wild-type group (similar to wild-type NS group); $^{@@}$P<0.01 vs. all other groups. Results expressed as Mean±SD, n=6-10.

Figure 8:
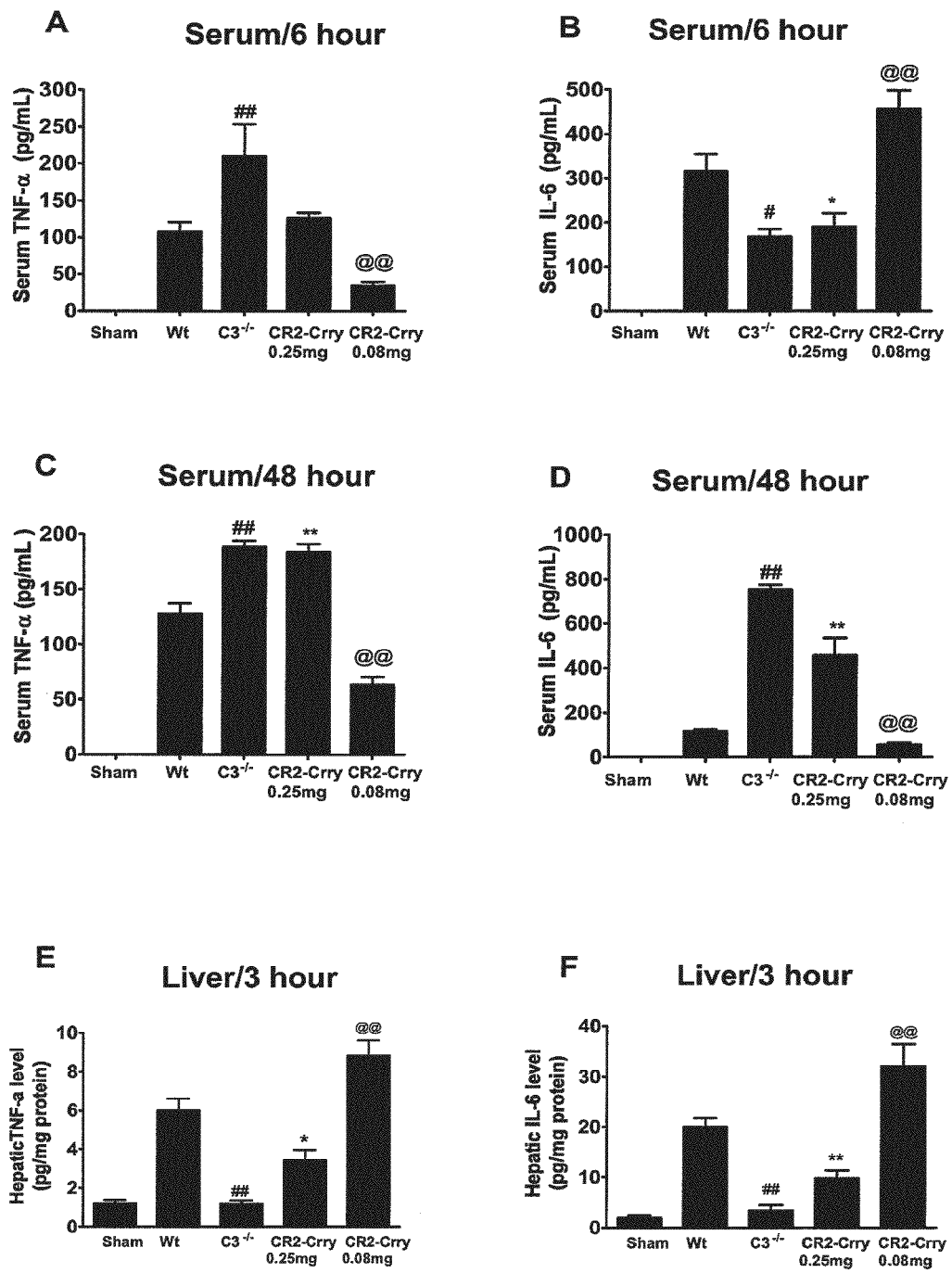

FIG. 8 shows the effect of C3 deficiency and complement inhibition on hepatic and serum levels of TNFa and IL-6 following IRI+PHx. Mice were treated with normal saline or CR2-Crry at a dose of either 0.25 mg or 0.08 mg immediately after surgery. C3$^{-/-}$ mice received no treatment. (A) Serum TNFa levels 6 hours post-PHx. (B) Serum IL-6 levels 6 hours post-PHx. (C) Serum TNFa levels 48 hours post-PHx. (D) Serum IL-6 levels 48 hours post-PHx. (E) Hepatic TNFa levels 3 hours post-PHx. (F) Hepatic IL-6 levels 3 hours post-PHx. Low dose CR2-Crry treatment was associated with high hepatic levels of IL-6 and TNFa early post-PHx relative to other groups, and lower relative serum cytokine levels by 48 h post-PHx. $^{\#}$P<0.05, $^{\#\#}$P<0.01 vs. wild-type group; *P<0.05, **P<0.01 vs. wild-type group (similar to wild-type NS group); $^{@@}$P<0.01 vs. CR2-Crry 0.25 mg and C3$^{-/-}$ groups. Results expressed as Mean±SD, n=6 for all groups.

Figure 9:
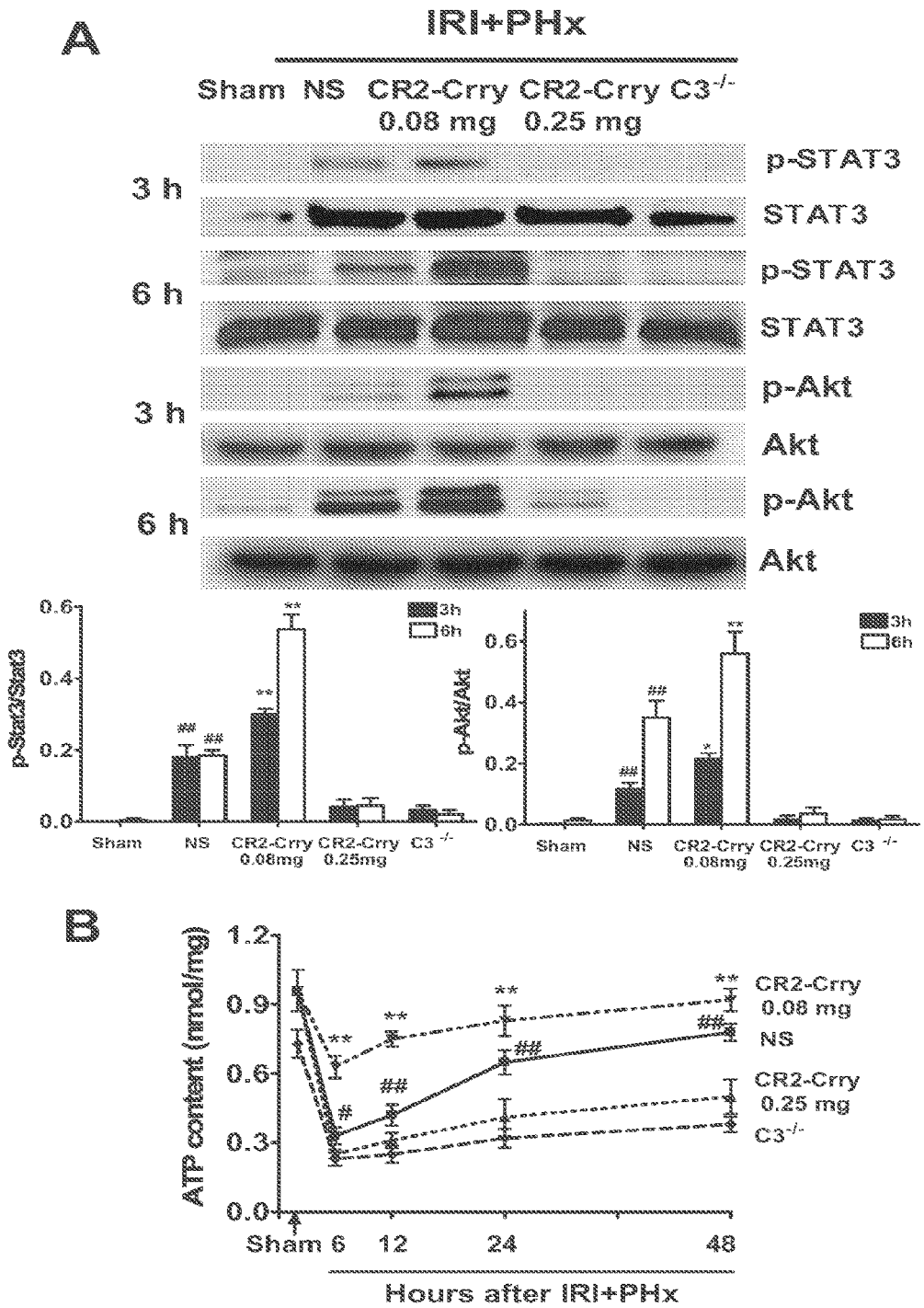

FIG. 9 shows the opposing effects of high and low dose complement inhibition on STAT3 and Akt activation and on hepatic ATP levels following IRI+PHx. Mice were treated with normal saline or CR2-Crry at a dose of either 0.25 mg or 0.08 mg immediately after surgery. C3$^{-/-}$ mice received no treatment. (A) Western blot analysis of STAT3 and Akt phosphorylation using liver samples taken 3 hours and 6 hours post-IRI+PHx. Low dose complement inhibition with CR2-Crry was associated with increased STAT3 and Akt activation. In contrast, expression of p-STAT3 and p-Akt was significantly reduced in mice treated with high dose CR2-Crry and in C3$^{-/-}$ mice. (B) ATP content in liver tissue samples taken at different time points after IRI+PHx. Low dose complement inhibition with CR2-Crry was associated with less ATP depletion and higher overall ATP levels compared to all other groups. **P<0.01 vs. all other IRI+PHx groups; $^{\#}$P<0.05, $^{\#\#}$P<0.01 vs. CR2-Crry 0.25 mg group and C3$^{-/-}$ group. N=4-6 for all groups.

Figure 10:
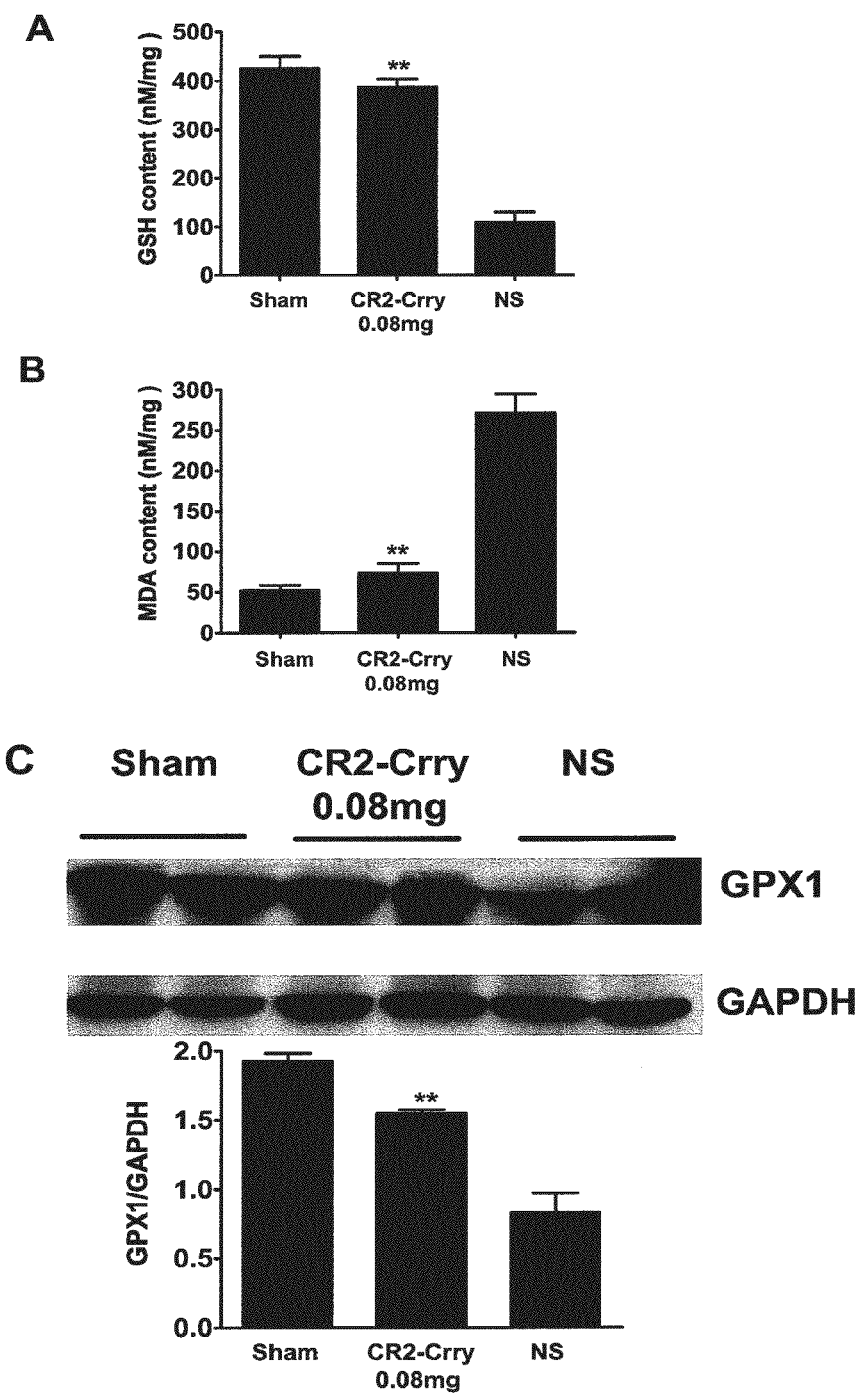

FIG. 10 shows that low dose CR2-Crry treatment after IRI+PHx decreases levels of markers for oxidative stress. (A) glutathione (GSH) and (B) malondialdehyde (MDA) content 6 hours after IRI+PHx as determined spectrophotometrically and expressed as nmol/mg protein in liver samples. (C) Western blot analysis of glutathione peroxidase 1 (GPX1), demonstrating that low dose CR2-Crry treatment prevents relative decrease in GPX1 levels after IRI+PHx. Western blot data quantitated by image analysis of autoradiograms. For all data, Mean±SD. **P<0.01 vs. NS group, n=4.

Figure 11:
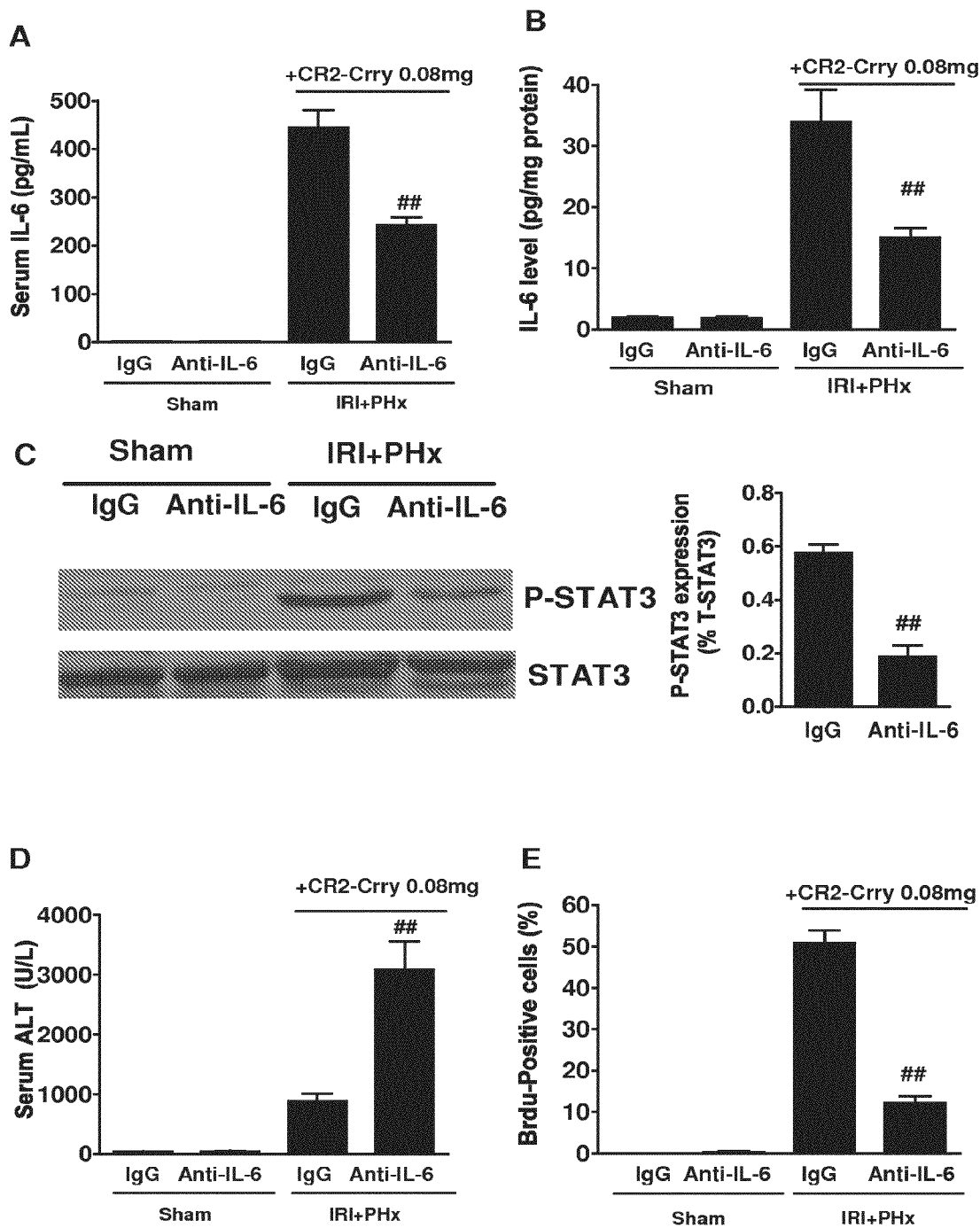

FIG. 11 shows that IL-6 blockade reverses protective effect of low dose complement inhibition following IRI+PHx. Mice were treated with 0.08 mg CR2-Crry and either anti-mouse IL-6 antibody or control IgG immediately after IRI+PHx. (A) Serum IL-6 levels at 6 hours post-PHx (B) Hepatic IL-6 levels at 3 hours post-PHx. (C) Western blot analysis of phosphorylated form of STAT3 (p-STAT3) at 3 hours post-PHx together with densitometric quantification. p-STAT3 levels were strongly reduced in mice treated with anti-IL-6 antibodies. (D) Serum ALT levels at 48 hours post-PHx. (E) BrdU incorporation at 48 hours post-PHx. Data are expressed as the Mean±SD, n=4. $^{\#\#}$P<0.01 vs. the IgG control IRI+PHx group.

Figure 12:
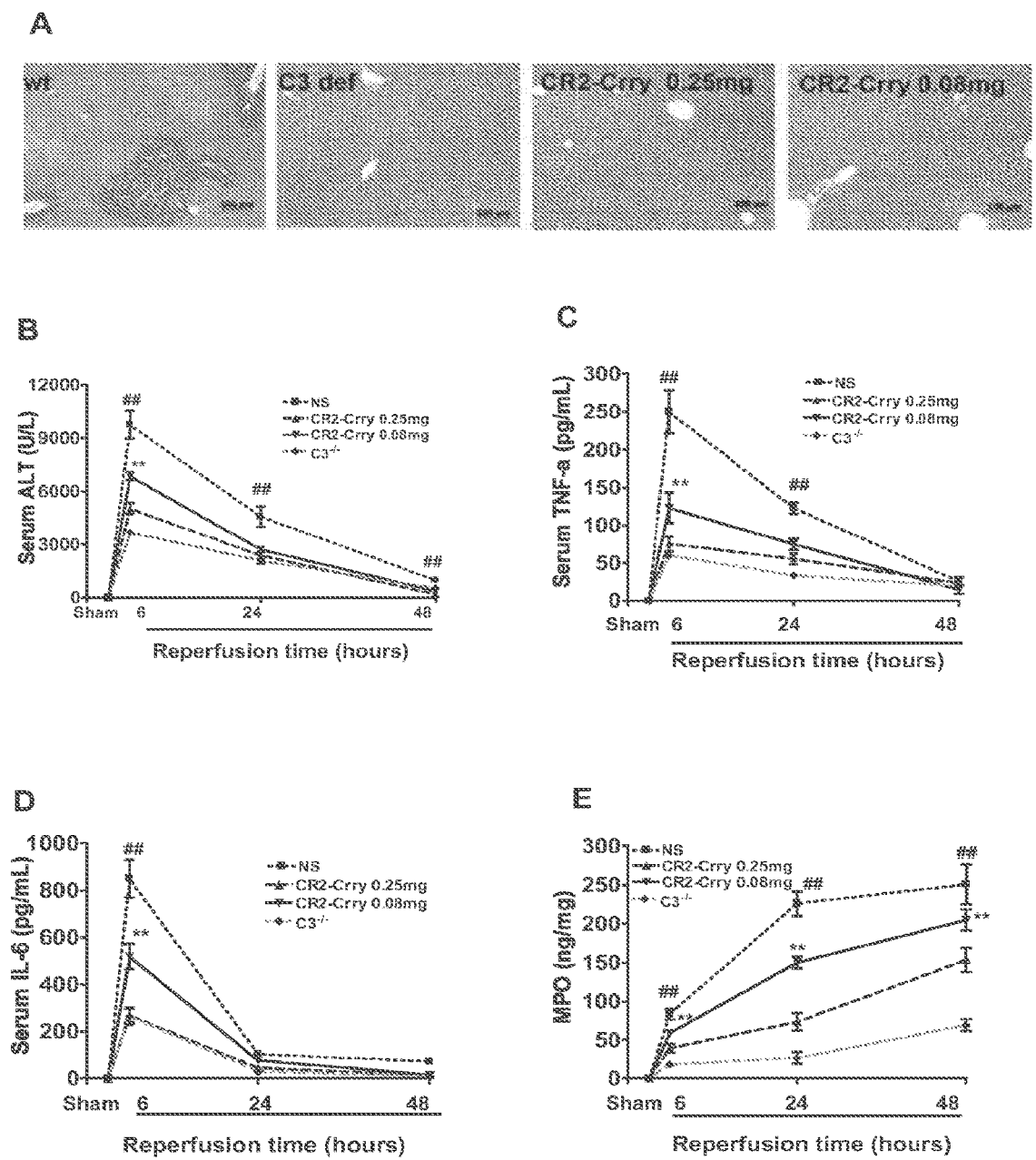

FIG. 12 shows that complement deficiency and inhibition protects against hepatic injury and inflammation following ischemia and reperfusion in a partial inflow occlusion model. Determinations were performed using liver or serum samples prepared after 90 minutes ischemia and indicated time of reperfusion in C3$^{-/-}$ mice or wild-type mice treated with normal saline (NS) or CR2-Crry (either 0.25 or 0.08 mg dose). (A) Representative H&E stained sections at 6 hours post-reperfusion. (B) Serum ALT levels. (C) Serum TNFa levels. (D) Serum IL-6 levels. (E) MPO content in liver samples normalized by total protein content. Results expressed as Mean±SD, n=4-6. $^{\#\#}$P<0.01 vs. all other IRI groups; **P<0.01 vs. CR2-Crry 0.25 mg group and C3$^{-/-}$ group.

Figure 13:
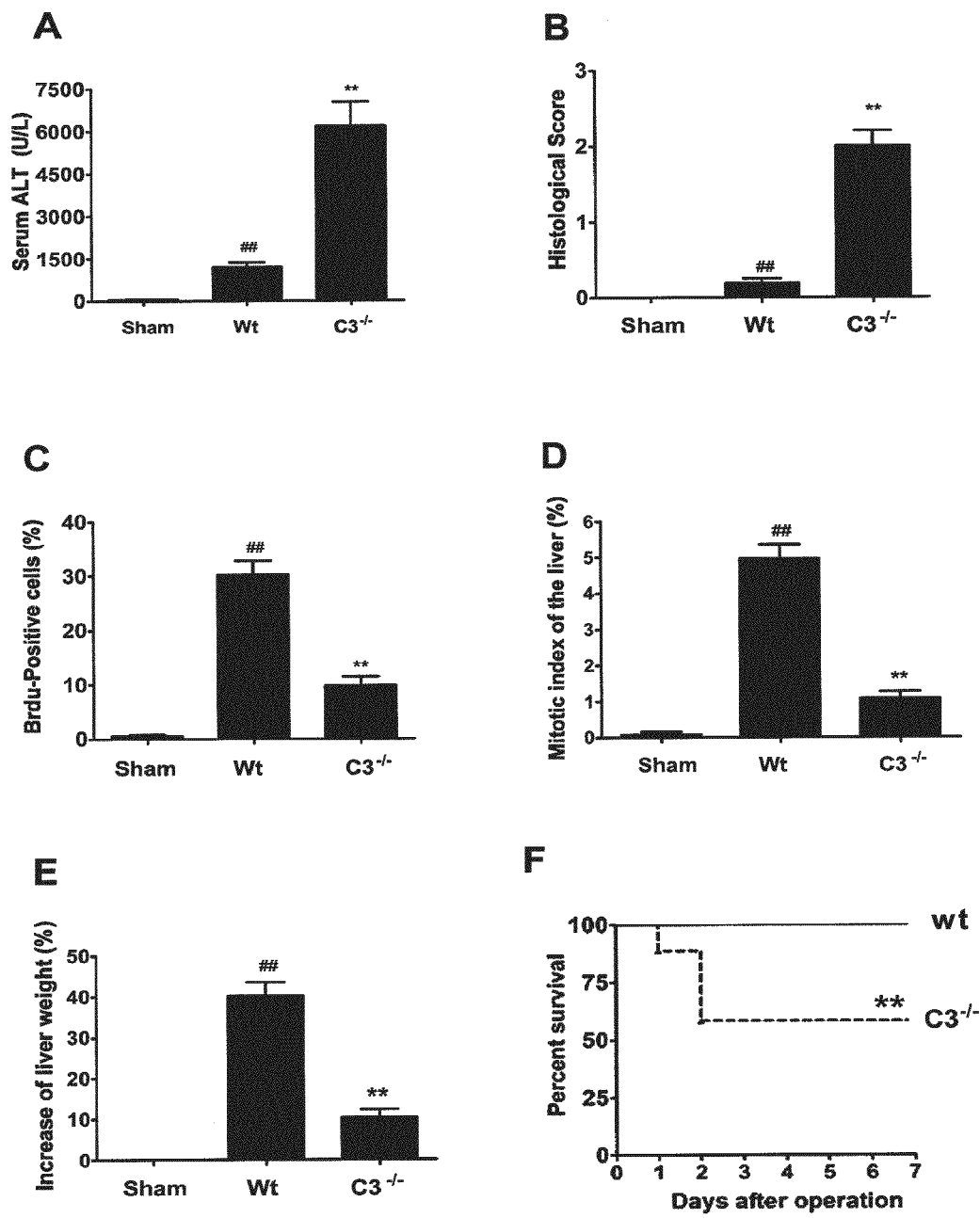

FIG. 13 shows that complement deficiency increases hepatic injury and inhibits regeneration following 70% PHx. All determinations made at 48 hours post-PHx. (A) Serum ALT levels. (B) Histological quantification of hepatic necrosis and injury determined on scale of 0-4. Assessment of liver regeneration by (C) BrdU incorporation, (D) mitotic index and, (E) restitution of liver weight. From A to E, n=6 for all groups. Results expressed as Mean±SD, $^{\#\#}$P<0.01 vs. sham group; $^{\#}$P<0.01 vs. wild-type PHx group. (F) Accumulative survival rate 7 days after 70% PHx. n=36/group, P<0.01.

Figure 14:
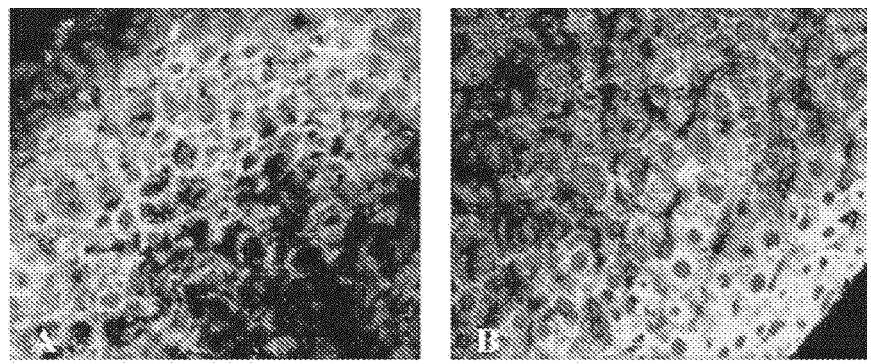

FIG. 14 shows that the distribution and intensity of hepatic C3d staining is not significantly different in wild-type and C5L2-deficient mice following PHx. Wild-type (A) or C5L2-deficient mice (B) were subjected to 70% PHx and livers isolated 48 later for anti-C3d immunofluorescence microscopy. Note the presence of C3d (green) in hepatocytes and around hepatocyte membranes. Images are representative of n=3.

Figure 15:
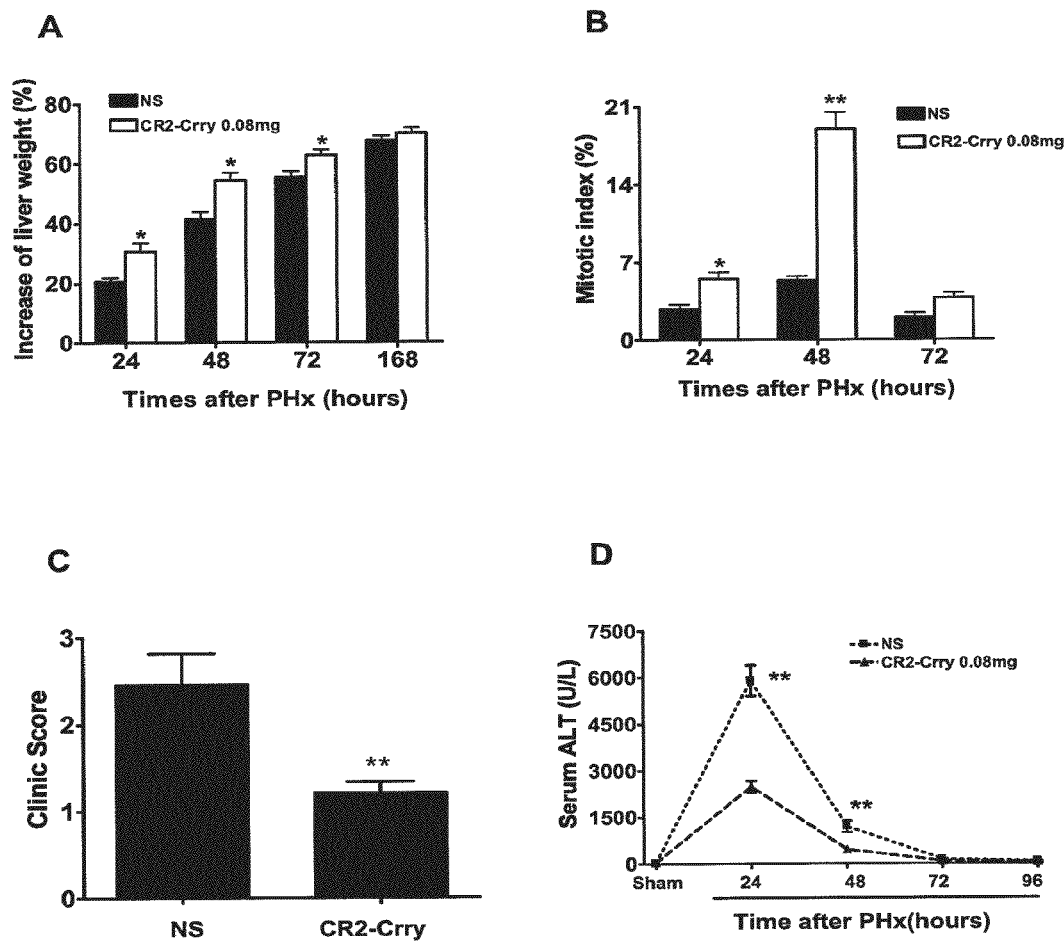

FIG. 15 shows that low dose CR2-Crry treatment decreases liver injury and improves liver regeneration following PHx. Wild-type mice were treated with normal saline (NS) or 0.08 mg CR2-Crry immediately after surgery. (A) The increase of liver weight at various times post-PHx showed that mass recovery in mice treated with low dose CR2-Crry was improved compared to NS control group. (B) The mitotic index was increased in mice treated with low dose CR2-Crry compared to NS treated mice. (C) 48 hour morbidity on a scale of 0-9 (see Example 1, Materials and Methods). (D)

Serum ALT levels. Results expressed as Mean±SD, *P<0.05; **P<0.01. n=4-6 mice for each time point in A, B, D, and n=12 in C.

Figure 16:
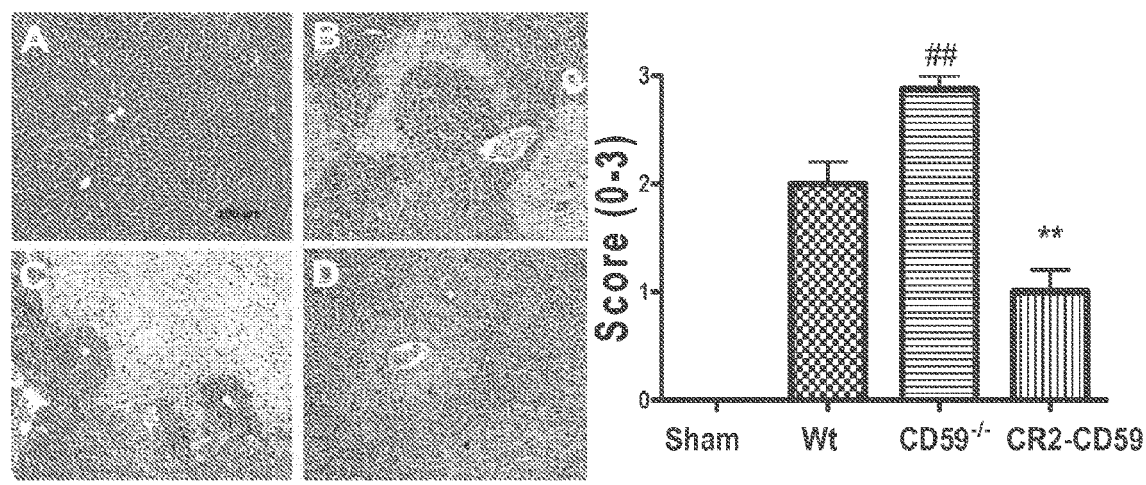

FIG. 16 shows the results of histological examination of liver subjected to 30 minutes ischemia and 6 hours reperfusion. A: Sham; B: WT; C: CD59$^{-/-}$; D: CD59$^{-/-}$+CR2-CD59. Quantification of histological evidence of hepatic injury demonstrated the IRI in CD59$^{-/-}$ animals was associated with a significant increase in liver damage compared to WW mice ($^{\#\#}$P<0.01). Reconstitution with 0.4 mg CR2-CD59 significantly decreased liver injury (**P<0.01). Sham operated animals in all cases had a histology score of 0 (n=6).

Figure 17:
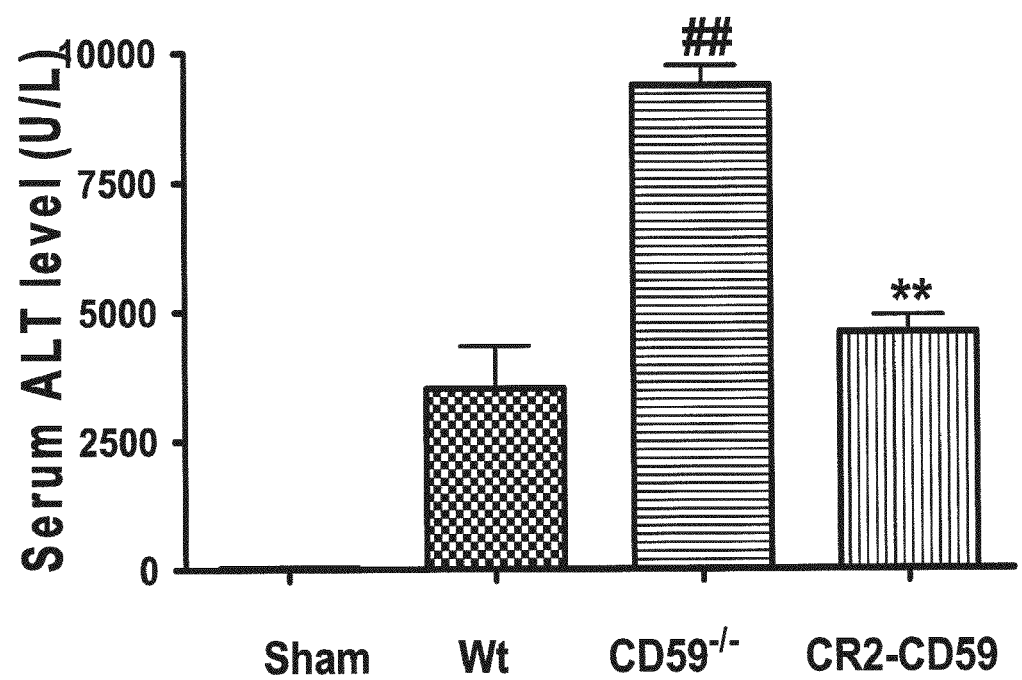

FIG. 17 shows that IRI induces a significant increase in serum alanine aminotransferase (ALT) in CD59$^{-/-}$ mice compared to wild-type mice ($^{\#\#}$P<0.01). Reconstitution with 0.4 mg CR2-CD59 significantly decreased ALT levels in CD59$^{-/-}$ mice after IRI (**P<0.01)(n=6).

Figure 18:
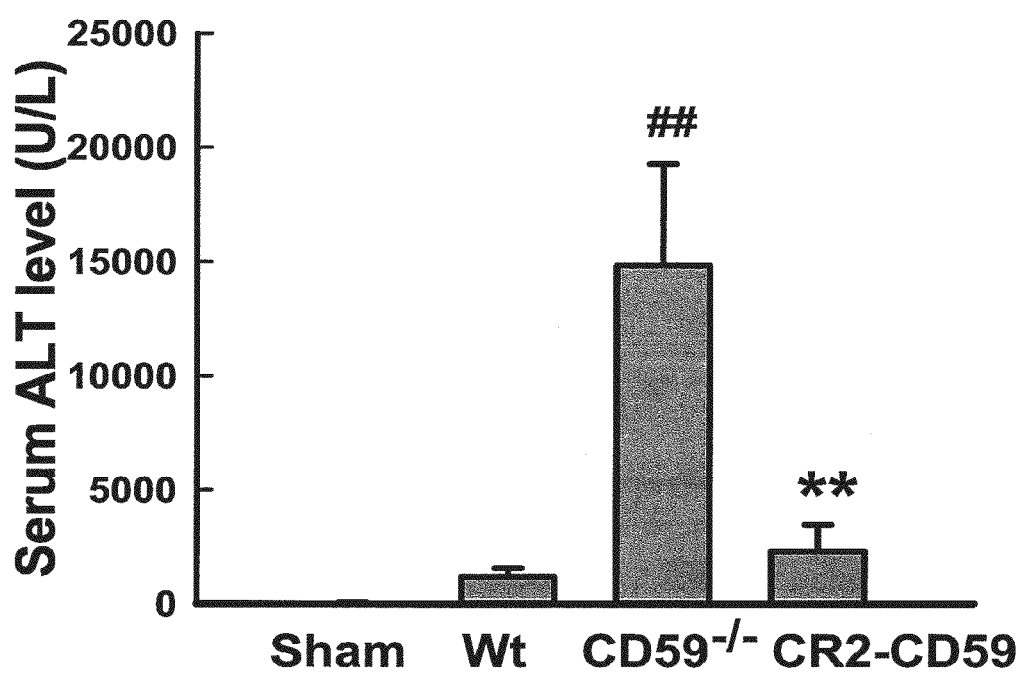

FIG. 18 shows that serum ALT levels significantly increased in the livers of CD59$^{-/-}$ mice 48 hours after undergoing 70% PHx compared to serum ALT levels in the livers of wild-type mice undergoing the same procedure ($^{\#\#}$P<0.01). Reconstitution of CD59$^{-/-}$ animals with 0.2 mg CR2-CD59 significantly decreased serum ALT levels (**P<0.01)(n=6).

Figure 19:
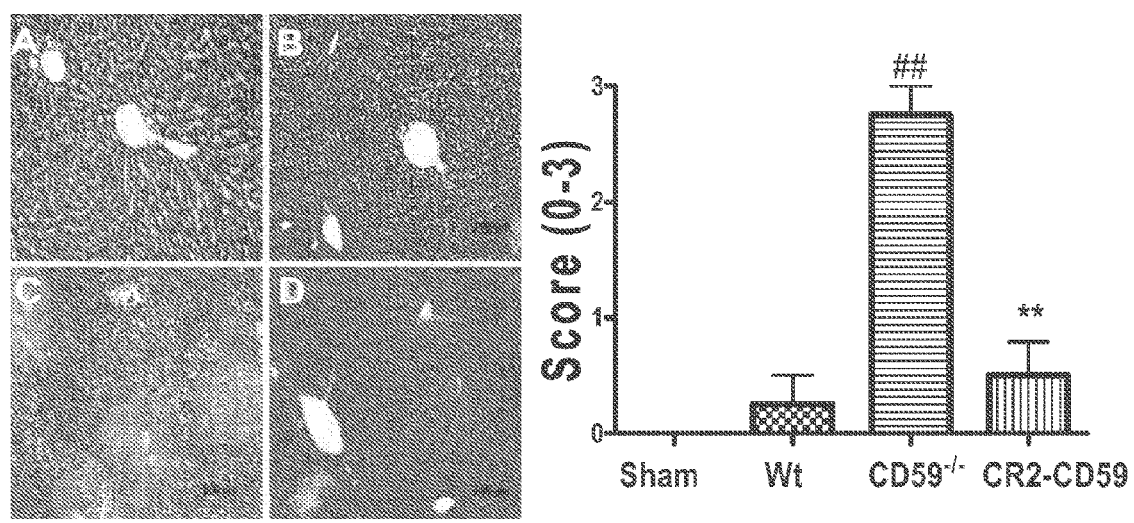

FIG. 19 shows that extensive necrosis was detected in the livers of CD59$^{-/-}$ mice 48 hours after undergoing 70% PHx. (A: Sham operated, B: WT, C: CD59$^{-/-}$, D: reconstituted with CR2-CD59; H&E staining, 100× magnification). Quantification of histological evidence of hepatic injury showed the 70% PHx in CD59$^{-/-}$ animals was associated with a significant increase in liver damage ($^{\#\#}$P<0.01). Again, reconstitution with 0.2 mg CR2-CD59 significantly decreased parenchyma damage (**P<0.01). Sham operated animals in all cases had histology scores of 0 (n=6).

Figure 20:
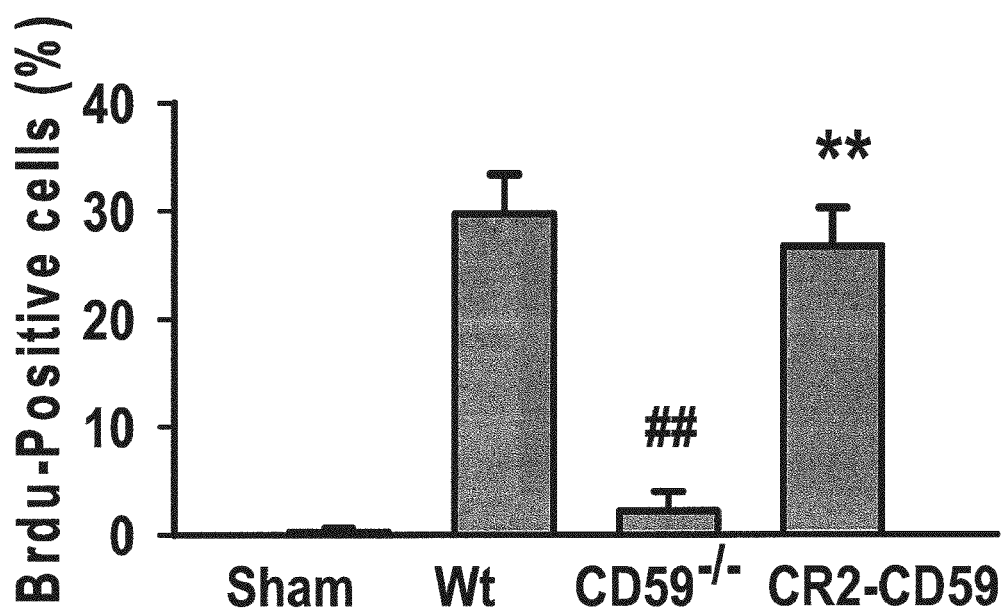

FIG. 20 shows that 70% PHx almost completely abolished hepatic regeneration as measured by BrdU incorporation in CD59$^{-/-}$ mice 48 hours after 70% PHx ($^{\#\#}$P<0.01) compared to wild-type animals or in CD59–/– animals reconstituted with 0.2 mg CR2-CD59, as shown by a marked increase in the number of BrdU+ cells (**P<0.01).

Figure 21:
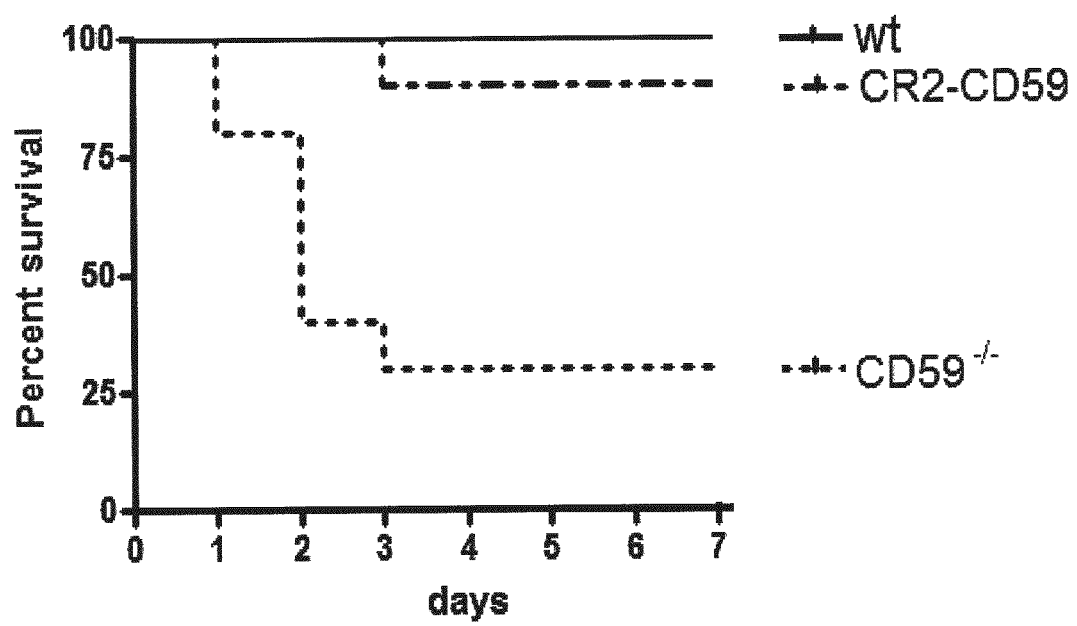

FIG. 21 shows that the 7-day survival rate for CD59$^{-/-}$ mice following 70% PHx was only 30% (3/10), compared to 100% for wild-type mice (10/10)(P<0.01). CR2-CD59 treatment significantly improved survival rate of CD59$^{-/-}$ animals from 30% (3/10) to 90% (9/10)(P<0.01).

Figure 22:
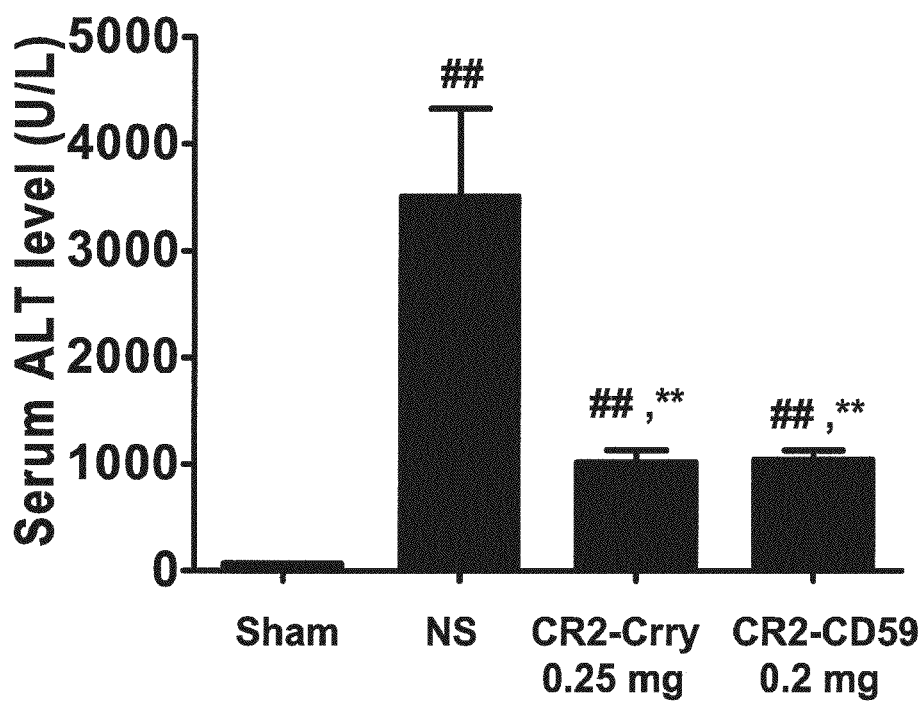

FIG. 22 shows that serum ALT levels significantly increased in wild-type mice following hepatic IRI compared to the sham-operated group ($^{\#\#}$P<0.01). Treatment with targeted complement inhibitors (either 0.25 mg CR2-Crry or 0.20 mg CR2-CD59) post-IRI decreased serum ALT levels compared to the normal saline (NS) group (**P<0.01)(n=4).

Figure 23:
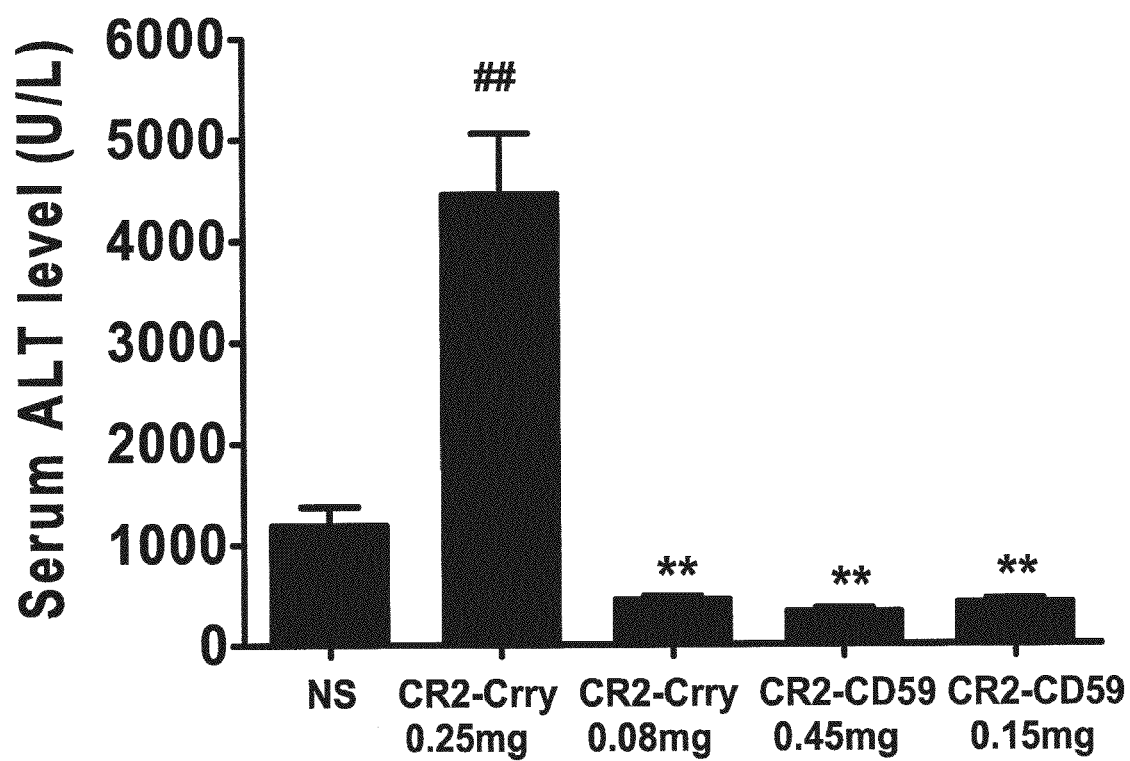

FIG. 23 shows that treatment with a 0.45 mg dose of CR2-CD59 or a 0.15 mg dose of CR2-CD59 significantly decreased ALT levels in wild-type mice 48 hours after 70% PHx compared to the NS control ($^{\#\#,**}$P<0.01)(n=4).

Figure 24:
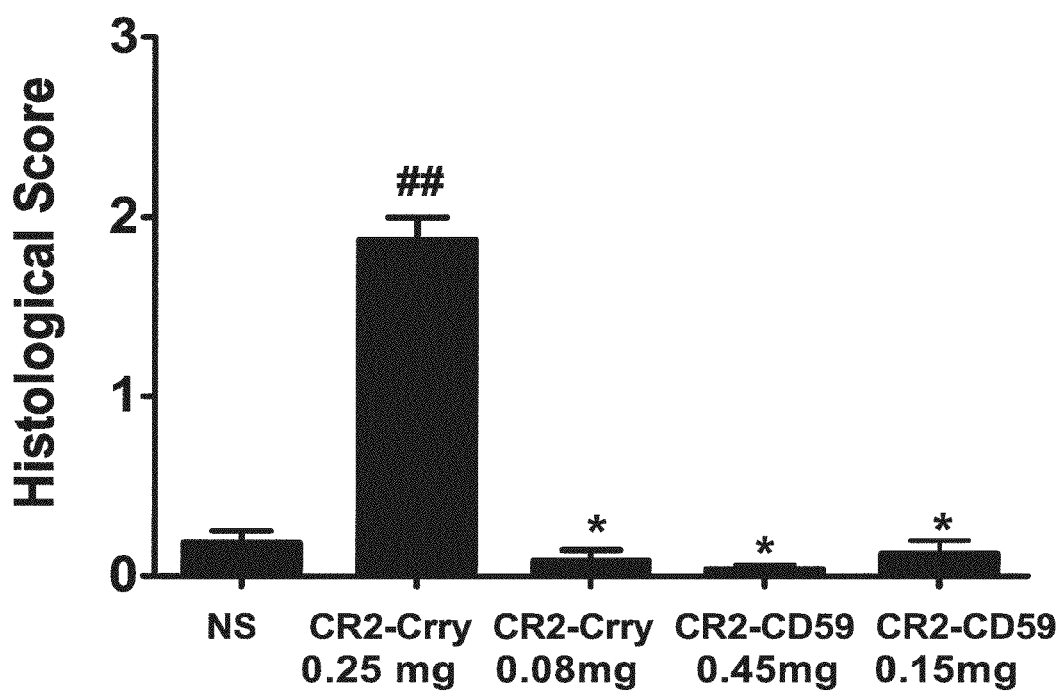

FIG. 24 shows histological quantification of hepatic necrosis and injury determined on scale of 0-4. Animals were treated with NS, 0.25 mg CR2-Crry, 0.08 mg CR2-Crry, 0.45 mg CR2-CD59, or 0.15 mg CR2-CD59 immediately after 70% PHx ($^{\#\#}$P<0.01 compared to the NS group; *P<0.05 compared to the NS group. Results expressed as Mean±SD (n=4-6).

Figure 25:
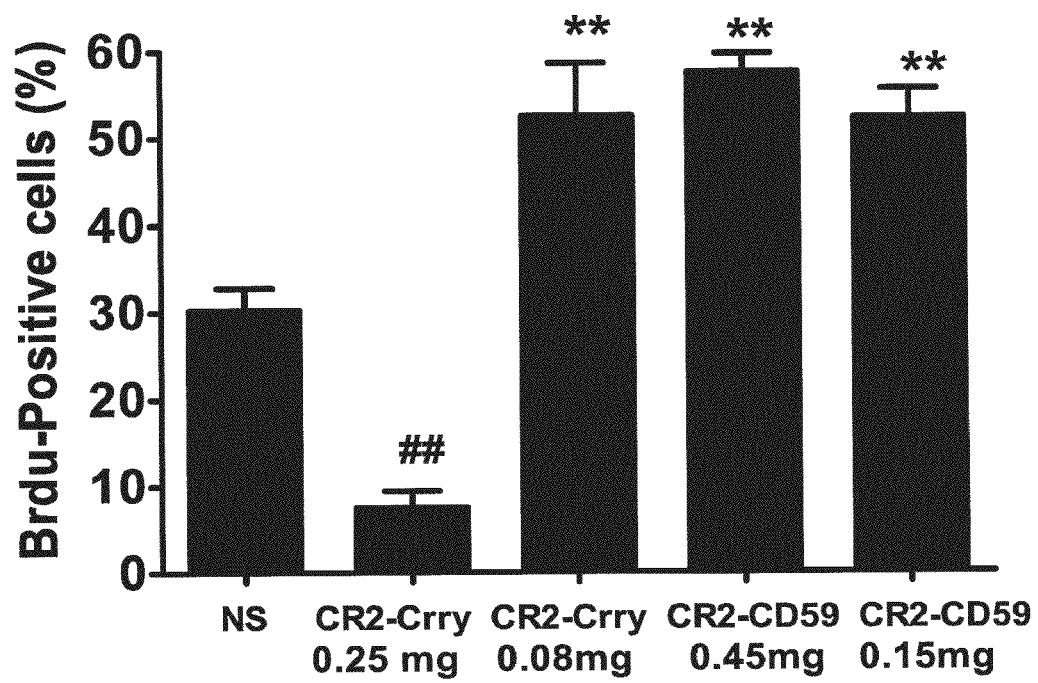

FIG. 25 shows that treatment with 0.45 mg or 0.15 mg CR2-CD59 immediately after 70% PHx improves liver regeneration, as shown by a marked increase in the number of BrdU+ cells ($^{\#\#}$P<0.01 compared to NS group; **P<0.01 compared to NS group (n=4-6).

Figure 26:
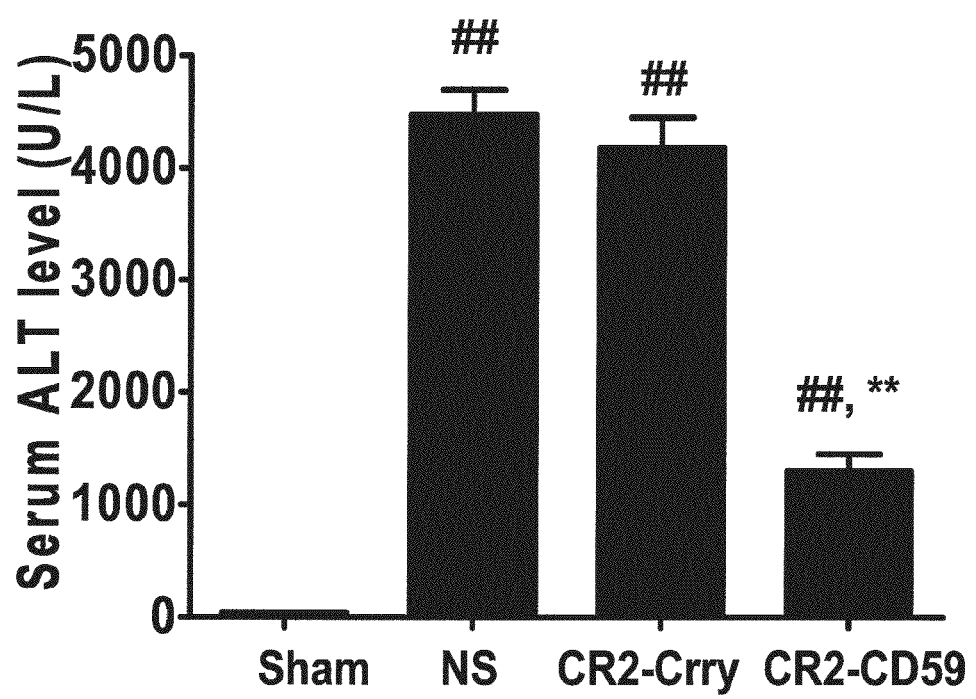

FIG. 26 shows that serum ALT levels increase significantly in wild-type mice 6 hours after undergoing 90% PHx ($^{\#\#}$P<0.01, compared to the sham-operated group). Treatment with 0.1 mg CR2-CD59 immediately after surgery significantly decreased serum ALT levels (**P<0.01)(n=4).

Figure 27:
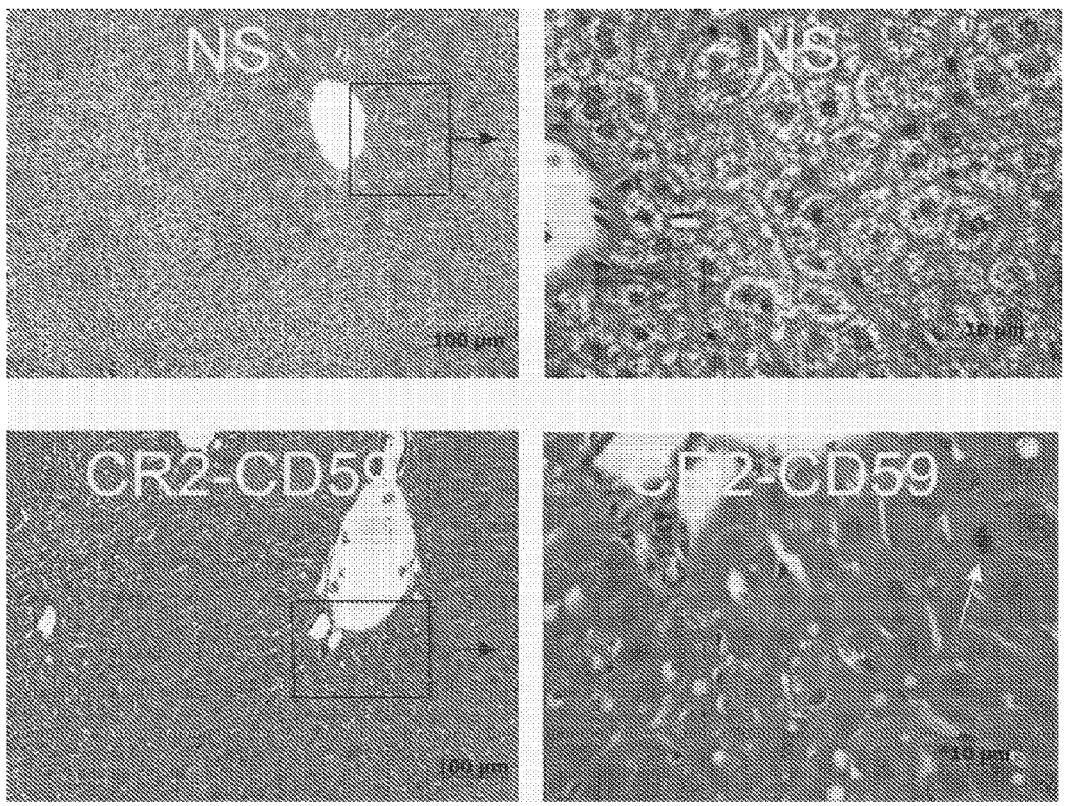

FIG. 27 shows hemotoxylin & eosin (H&E)-stained sections of liver tissue that revealed extensive histological change characterized by severe microvesicular steatosis of hepatocytes in the remnant liver 24 hours after 90% PHx in the CR2-Crry-treated and control groups, while the histological changes observed in the 90%-hepatectomized mice treated with 0.1 mg CR2-CD59 were significantly less extensive.

Figure 28:
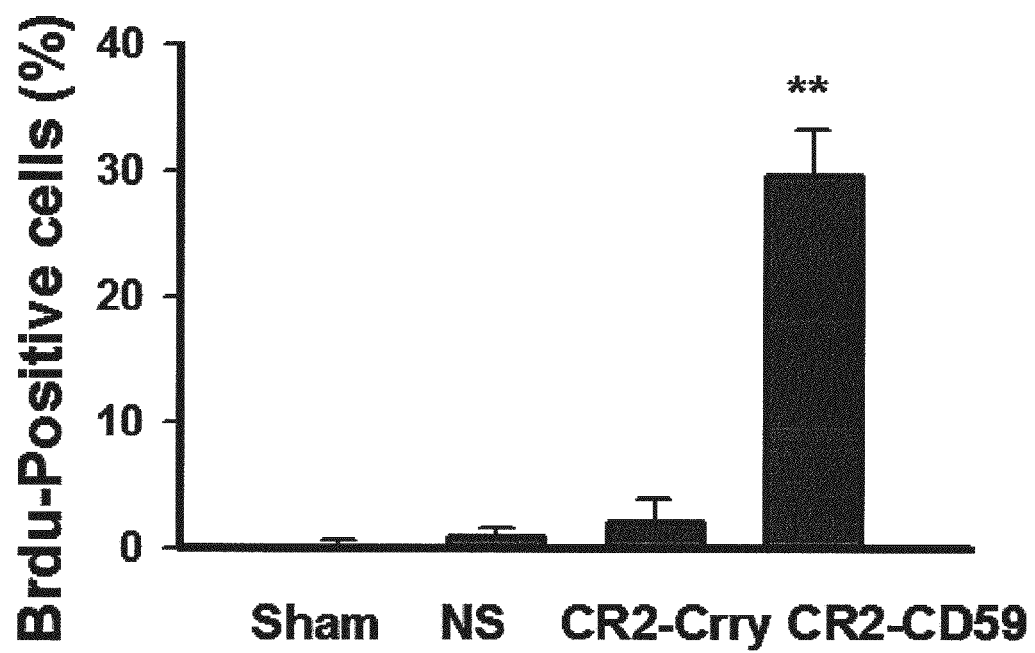

FIG. 28 shows that BrdU incorporation in wild-type mice was almost abolished 24 hours after 90% PHx. Treatment with 0.1 mg CR2-CD59 improved liver regeneration as shown by a marked increase in the number of BrdU+ cells (**P<0.01 compared to other groups).

Figure 29:
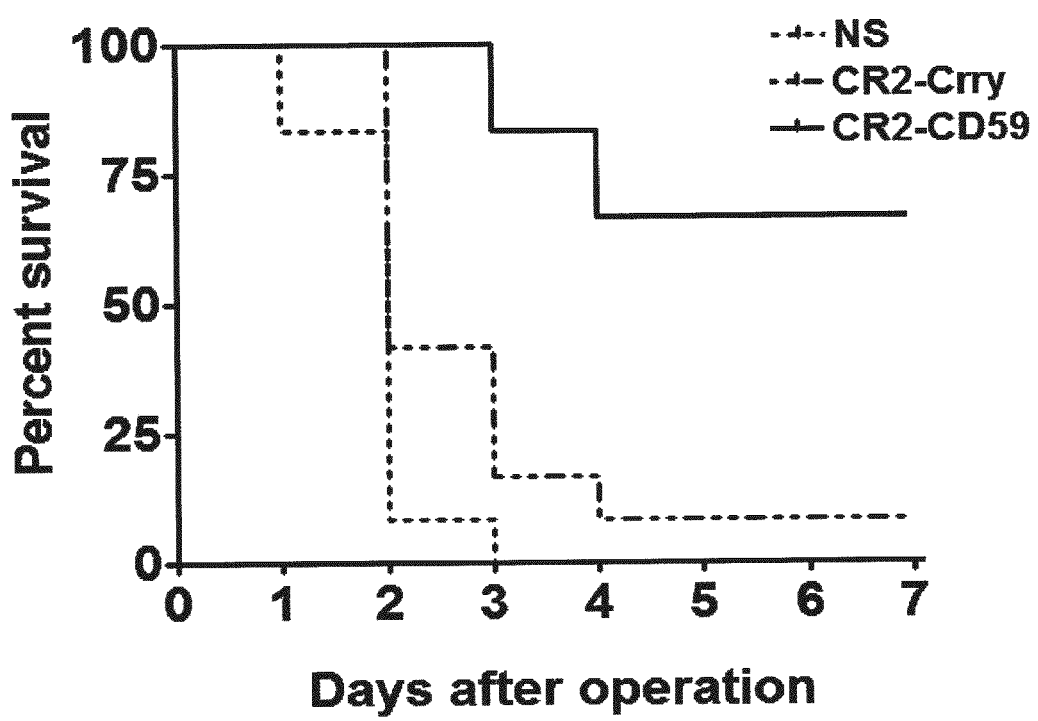

FIG. 29 shows that treatment of wild-type mice with a 0.1 mg dose of CR2-CD59 immediately following 90% PHx significantly increased the 7-day survival rate compared to other groups (P<0.01).

Figure 30:
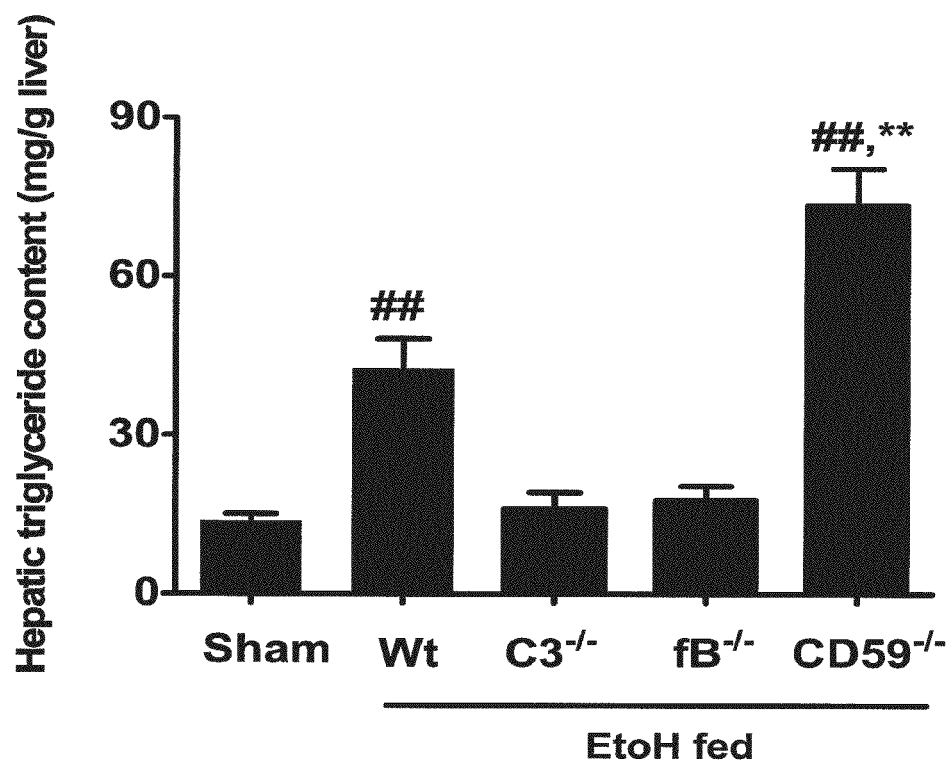

FIG. 30 shows hepatic triglyceride levels in wild-type and factor B$^{-/-}$, C3$^{-/-}$, and CD59$^{-/-}$ knockout mice after ethanol feeding and 70% PHx as described in the Examples. ($^{\#\#}$P<0.01 compared to sham-operated animals; **P<0.01 compared to wild-type animals)(n=6).

Figure 31:
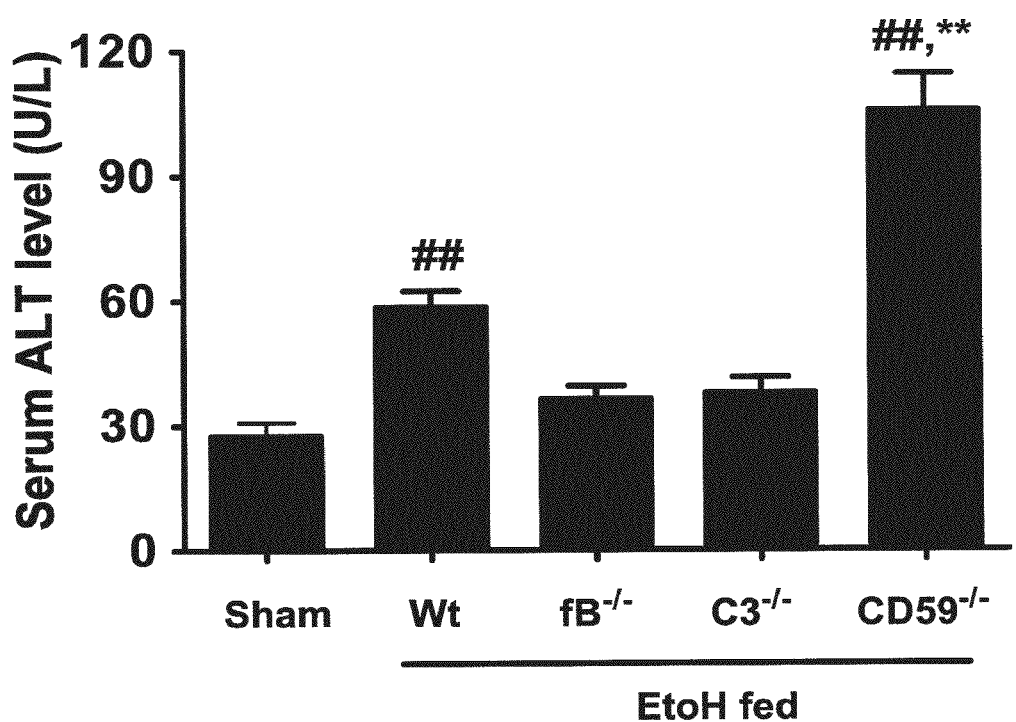

FIG. 31 shows serum ALT levels in wild-type and factor B$^{-/-}$, C3$^{-/-}$, and CD59$^{-/-}$ knockout mice after ethanol feeding and 70% PHx ($^{\#\#}$P<0.01 compared to sham-operated animals; **P<0.01 compared to wild-type animals)(n=6).

Figure 32:
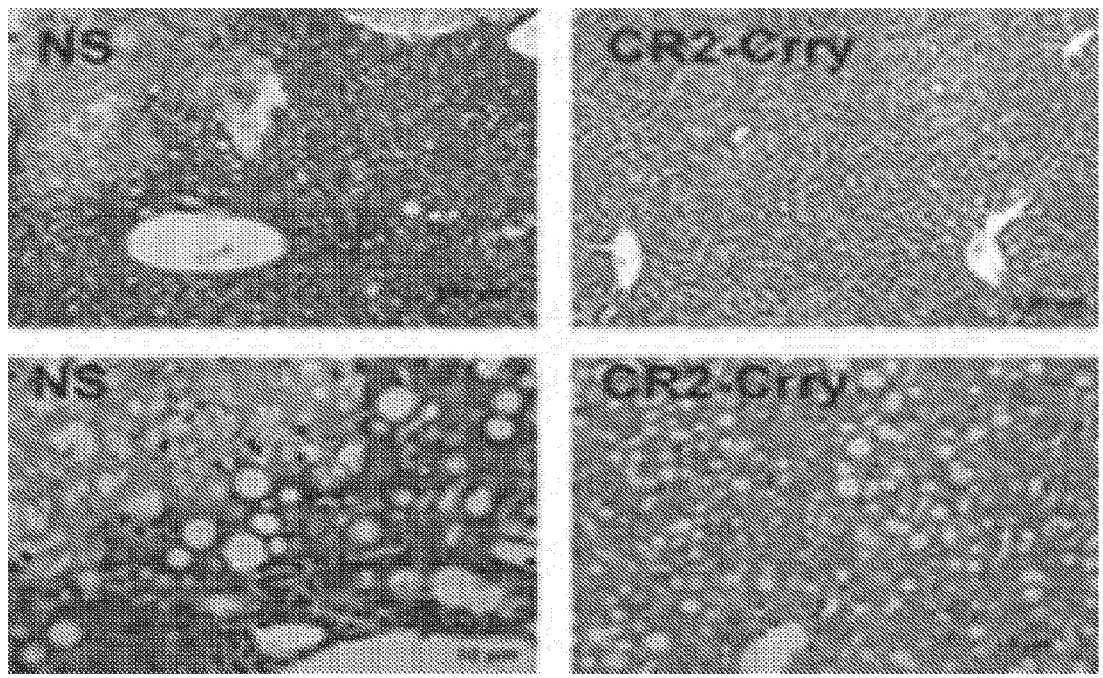

FIG. 32 shows H&E-stained sections of liver tissue from ethanol-fed animals undergoing 70% PHx revealing extensive histological change characterized by massive necrosis and severe steatosis of hepatocytes in the remnant liver 48 hours after 70% hepatectomy in the NS control group. The histological changes observed in the ethanol fed, 70% PHx animals treated with CR2-Crry were significantly less extensive.

BRIEF DESCRIPTION OF THE SEQUENCES

SEQ ID NO:1 is the complete amino acid sequence of human complement receptor 2 (CR2).

SEQ ID NO:2 is the complete amino acid sequence of short consensus repeat (SCR) domains 1 and 2 of human CR2.

SEQ ID NO:3 is the amino acid sequence of human CD59 protein.

SEQ ID NO:4 is the complete amino acid sequence of mouse complement receptor 1-related gene/protein y (Crry).

SEQ ID NO:5 is the amino acid sequence of human factor H.

SEQ ID NO:6 is the amino acid sequence of human ASP/C3adesArg.

SEQ ID NO:7 is the amino acid sequence of the human ASP/C3adesArg receptor (C5L2).

SEQ ID NO:8 is the amino acid sequence of mouse CD59A protein.

SEQ ID NO:9 is the amino acid sequence of mouse CD59B protein.

SEQ ID NO:10 is the amino acid sequence of mouse factor H.

SEQ ID NO:11 is the amino acid sequence of human complement receptor 1 (CR1).

SEQ ID NO:12 is the amino acid sequence of human membrane cofactor protein (MCP).

SEQ ID NO:13 is the amino acid sequence of human decay accelerating factor (DAF/CD55).

SEQ ID NO:14 is the amino acid sequence of mouse decay accelerating factor (DAF/CD55).

SEQ ID NO:15 is the amino acid sequence of human clusterin protein.

SEQ ID NO:16 is the amino acid sequence of mouse clusterin protein.

SEQ ID NO:17 is the amino acid sequence of human vitronectin protein.

SEQ ID NO:18 is the amino acid sequence of mouse vitronectin protein.

SEQ ID NO:19 is the amino acid sequence of human C1-inhibitor protein.

SEQ ID NO:20 is the amino acid sequence of mouse C1-inhibitor protein.

DETAILED DESCRIPTION OF THE INVENTION

Although complement inhibition represents a potential therapeutic strategy to protect against hepatic IRI, the important role of complement in liver regeneration suggests that complement inhibition might not be a viable therapeutic strategy in the context of liver resection and SFS liver transplantation, even though IRI is associated with impaired regeneration. The data from the Examples presented herein provide a better understanding of complement-dependent mechanisms and the relative contribution of complement in IRI compared to hepatic regeneration, as well as the relationship between hepatic IRI and regeneration. The data also suggests complement modulatory approaches to improve outcome following massive liver resection or SFS liver transplantation.

Failure of the liver to regenerate following massive liver resection or small-for-size liver transplantation often leads to liver dysfunction and organ or transplant failure. Hepatic ischemia and subsequent reperfusion (I/R) that injures the liver and impairs regeneration is unavoidable during such complex surgical procedures. The pathogenic mechanisms involved in IRI are complex and multifaceted, but it is clear that activation of complement is a key initiating event. Both C3 deficiency and complement inhibition protect against hepatic injury and inflammation following I/R.

It has been shown that C3 and C5 deficiency results in impaired liver regeneration following either toxic injury or partial hepatectomy (PHx, analogous to liver resection). Roles for complement activation products C3a and C5a in regeneration have been shown by the use of C3a receptor (C3aR)-deficient mice, treatment of mice with C3aR and C5aR antagonists, and reconstitution experiments (13-15). Data indicate that C3a and C5a contribute to the early priming events of the proliferative response via an effect on TNFa and IL-6 expression and the subsequent activation of the transcription factors NF-κB and STAT3 (14).

A significant increase in hepatosteatosis is associated with C3 deficiency (see Examples). Because the C3 cleavage product C3a plays a role in liver regeneration, and because a degraded form of C3a, acylation stimulating protein (ASP, or C3adesArg), plays a role in lipid metabolism, we examined the effect of ASP/C3adesArg reconstitution in $C3^{-/-}$ mice following PHx. Previous studies have shown that the hepatic proliferative response is restored in $C3^{-/-}$ mice reconstituted with multiple doses of C3a (14) and that liver regeneration is impaired in $C3aR^{-/-}$ mice (13). ASP/C3adesArg does not bind to C3aR, however. The only known receptor for ASP/C3adesArg, C5L2 (23-26, 34, 35), also binds C3a (and C5a/C5adesArg) and plays an important role in triglyceride synthesis and clearance (25, 26). Administration of 15 μg ASP/C3adesArg to $C3^{-/-}$ mice after PHx significantly reduced hepatosteatosis, protected against injury, restored BrdU incorporation (a measure of cell proliferation) to the level seen in wild-type mice and reversed the decrease in STAT3 phosphorylation seen in $C3^{-/-}$ mice. Thus, the involvement of complement in the proliferative response can be independent of C3aR signaling, showing that ASP/C3adesArg plays a key role in hepatoprotection and liver regeneration following PHx.

Unexpectedly, reconstitution of $C3^{-/-}$ mice with a high dose of ASP/C3adesArg (50 μg) following PHx failed to restore liver regeneration and induced severe injury. Moreover, wild-type mice treated with either a low or high dose of ASP/C3adesArg exhibited a significant increase in liver injury with impaired regeneration compared to untreated wild-type animals. While both C3a and ASP/C3adesArg play a role in liver regeneration, both peptides also have proinflammatory properties, although removal of the C-terminal Arg from C3a inactivates certain of them (26, 38). The significant increases seen in liver MPO activity and in serum levels of TNFa and IL-6 associated with high dose ASP/C3adesArg treatment in $C3^{-/-}$ mice testifies to the proinflammatory properties of ASP/C3adesArg, indicating that there is a threshold of complement activation, C3a, and ASP/C3adesArg production for optimal liver regeneration following PHx. Indeed, while TNFa and IL-6 play important roles in liver regeneration, these cytokines apparently play dual roles in injury vs. hepatoprotection and regeneration (27, 39). Although IL-6 dependent processes are associated mainly with protective responses, TNFa expression is clearly associated with inflammation and injury, and these cytokines can modulate expression of each other.

Thus, we have identified a complement-dependent balance in the link between IRI and impaired liver regeneration, suggesting there is a threshold of complement activation, C3a, and ASP/C3adesArg production for optimal liver regeneration following PHx, above which increased levels of C3a, ASP/C3adesArg, and other complement activation products, tip the balance toward injury and impairment of regeneration. These findings suggest that patients undergoing massive liver resection or small-for-size liver transplantation may benefit from modulated complement inhibition.

Complement Regulatory Proteins

A number of endogenous soluble and membrane-bound proteins that regulate complement have been identified. These complement regulatory proteins include, but are not limited to, membrane cofactor protein (MCP), decay accelerating factor (DAF/CD55), CD59, mouse complement receptor 1-related gene/protein y (Crry), human complement receptor 1 (CR1) and factor H.

Membrane cofactor protein, also referred to as CD46 (MCP/CD46) (SEQ ID NO:12), is a widely distributed C3b/C4b-binding cell surface glycoprotein which inhibits complement activation on host cells. Like several other complement regulatory proteins, MCP comprises several approximately 60 amino acid repeating motifs termed short consensus repeats (SCR). Beginning at its amino-terminus, MCP is composed of four SCR domains, a serine/threonine/proline-rich region, an area of undefined function, a transmembrane hydrophobic domain, a cytoplasmic anchor and cytoplasmic tail.

Decay accelerating factor, also referred to as CD55 (DAF/CD55) (SEQ ID NO:13 and SEQ ID NO:14), is a ~70 kilo-Dalton (kDa) membrane-bound glycoprotein which inhibits complement activation on host cells. Like several other complement regulatory proteins, DAF comprises several approximately 60 amino acid repeating motifs termed short consensus repeats (SCR). Beginning at its amino-terminus, DAF comprises four SCR domains, a heavily O-glycosylated serine/threonine-rich domain, and a glycosylphosphatidylinositol anchor. DAF prevents assembly or accelerates decay of both the C3- and C5-convertases of the alternative and classical complement pathways.

CD59 (SEQ ID NO:3, SEQ ID NO:8 and SEQ ID NO:9) is a membrane-bound inhibitor of complement that blocks assembly of the MAC by binding to C8 and C9 but does not affect generation of complement opsonins or C3a and C5a. Soluble forms of CD59 (sCD59) have been produced, but they generally have low functional activity in vitro, particularly in the presence of serum, suggesting that unmodified sCD59 has little or no therapeutic efficacy. See, e.g., S. Meri et al., "Structural composition and functional characterization of soluble CD59: heterogeneity of the oligosaccharide and glyophosphoinositol (GPI) anchor revealed by laser-desorption mass spectrometric analysis," Biochem. J.: 923-935 (1996).

The mouse protein complement receptor 1-related gene/protein y (Crry) (SEQ ID NO:4) is a membrane-bound inhibitor of complement that regulates complement activation by serving as a cofactor for complement factor I, a serine protease which cleaves C3b and C4b deposited on host tissue. Crry also acts as a decay-accelerating factor, preventing the formation of C4bC2a and C3bBb, the amplification convertases of the complement cascade.

Complement receptor 1 (CR1) (SEQ ID NO:11) protein is the main system for processing and clearance of complement-opsonized immune complexes. CR1 negatively regulates the complement cascade, mediates immune adherence and phagocytosis, and inhibits both the classic and alternative complement pathways. The CR1 protein has a 47 amino acid signal peptide, an extracellular domain of 1930 amino acids, a 25 amino acid transmembrane domain and a 43 amino acid C-terminal cytoplasmic region. The large extracellular domain of CR1, which has 25 potential N-glycosylation sites, can be divided into 30 short consensus repeat (SCR) domains (also known as complement control protein repeats or sushi domains), each having 60 to 70 amino acids. The 30 SCR domains are further grouped into four longer regions termed long homologous repeats (LHRs) each encoding approximately 45 kDa of protein and designated LHR-A, -B, -C, and -D.

Factor H (SEQ ID NO:5 and SEQ ID NO:10) is a plasma glycoprotein composed of 20 SCR domains of approximately 60 amino acids, arranged in a continuous fashion like a string of beads, separated by short linker sequences of 2-6 amino acids each. Factor H binds to C3b, accelerates the decay of the alternative pathway C3-convertase (C3bBb), and acts as a cofactor for the proteolytic inactivation of C3b. In the presence of factor H, C3b proteolysis results in the cleavage of C3b. Factor H has at least three distinct binding domains for C3b, located within SCRs 1-4, SCRs 5-8, and SCRs 19-20. Each site of factor H binds to a distinct region within the C3b protein: the N-terminal sites bind to native C3b; the second site, located in the middle region of factor H, binds to the C3c fragment and the site located within SCR19 and 20 binds to the C3d region. Factor H also contains binding sites for heparin, located within SCR 7, SCRs 5-12, and SCR 20, partially overlapping the C3b binding sites. The domains for the complement inhibitory activity of factor H are located within SCR1-4, the first four N-terminal SCR domains.

Targeted delivery of complement inhibitors to sites of complement activation and disease can improve their efficacy. Since complement plays an important role in host defense and the shaping of immunity, as well as in immune homeostatic mechanisms such as immune complex catabolism and apoptotic cell clearance, targeted delivery of complement inhibitors reduces potentially serious side effects resulting from systemic complement inhibition, particularly long-term complement inhibition.

Complement protein C3 is a zymogen. Intact C3 circulates at high concentrations (1-2 mg/ml). M. Janzi et al., Mol. Cell. Proteomics (2005) 4(12):1942-1947. During complement activation, whole C3 is cleaved to form C3b which becomes covalently bound to target surfaces. Endogenous complement regulatory proteins inactivate tissue-bound C3b to form iC3b and eventually the 35 kilodalton ("kD") C3d fragment. The C3d fragment remains fixed to tissues and serves as a durable marker of complement-mediated inflammation. I. Leivo et al., J. Cell. Biol. (1986) 103:1091-1100.

Human complement receptor 2, also referred to as CD21 (CR2/CD21) (SEQ ID NO:1 and SEQ ID NO:2), is a ~145 kD transmembrane protein of the C3 binding protein family comprising 15 or 16 short consensus repeat (SCR) domains, structural units characteristic of such proteins. CR2 is expressed on mature B cells and follicular dendritic cells, and plays an important role in humoral immunity. J. Hannan et al., Biochem. Soc. Trans. (2002) 30:983-989; K. A. Young et al., J. Biol. Chem. (2007) 282(50):36614-36625. CR2 protein does not bind intact C3 protein, but binds its breakdown products, including the C3b, iC3b, and C3d cleavage fragments, via a binding site located within the first two amino-terminal short consensus repeats ("SCRs 1-2") of the CR2 protein. Consequently, the SCR1-2 domain of CR2 discriminates between cleaved (i.e., activated) forms of C3 and intact circulating C3. As a targeting group, SCRs 1-2 of CR2 are therefore able to discriminate between circulating C3 and the C3 fragments generated during complement activation. Although the affinity of CR2 for C3d is only 620-658 nM (J. Hannan et al., Biochem. Soc. Trans. (2002) 30:983-989; J. M. Guthridge et al., Biochem. (2001) 40:5931-5941), the avidity of CR2 for clustered C3d makes it an effective method of targeting molecules to sites of complement activation.

Cleavage of C3 results initially in the generation and deposition of C3b on the activating cell surface. The C3b fragment is involved in the generation of enzymatic complexes that amplify the complement cascade. On a cell surface, C3b is rapidly converted to inactive iC3b, particularly when deposited on a host surface containing regulators of complement activation (i.e., most host tissue). Even in the absence of membrane-bound complement regulators, substantial levels of iC3b are formed because of the action of serum factor H. iC3b is subsequently digested to the membrane-bound fragments C3dg and then C3d by factor I and other proteases, but this process is relatively slow. Thus, the C3 ligands for CR2 are relatively long lived once they are generated and will be present in high concentrations at sites of complement activation.

DEFINITIONS

General reference to "the composition" or "compositions" includes and is applicable to compositions of the invention.

As used herein, the singular form of the articles "a," "an," and "the" includes plural references unless indicated otherwise. For example, the phrase "a biologically active CR2 fragment" includes one or more biologically active CR2 fragments.

Reference to "about" a value or parameter herein includes (and describes) embodiments that are directed to that value or parameter per se. For example, description referring to "about X" includes description of "X."

It is understood that aspects and embodiments of the invention described herein include consisting and/or consisting essentially of aspects and embodiments.

As used herein, the term "individual" refers to a vertebrate, preferably a mammal, more preferably a human. Mammals include, but are not limited to, research animals, domestic animals, farm animals, sport animals, pets, primates, mice and rats. In certain embodiments, the individual is human. In certain embodiments, the individual is an individual other than a human. In certain embodiments, the individual is an animal model for the study of a disease in which the alternative complement pathway is implicated.

Compositions

Provided herein are compositions for use in methods of stimulating liver regeneration. In certain embodiments, the compositions comprise targeted complement inhibitors. In certain embodiments, the compositions comprise non-targeted complement inhibitors. In certain embodiments, the targeted and non-targeted complement inhibitors inhibit the classical complement pathway and the alternative complement pathway. In certain embodiments, the targeted and non-targeted complement inhibitors specifically inhibit the alternative complement pathway. In certain embodiments, the targeted and non-targeted complement inhibitors inhibit terminal complement and formation of the membrane attack complex (MAC).

In certain embodiments, the compositions comprise ASP/C3adesArg antagonists. In certain embodiments, the compositions comprise ASP/C3adesArg receptor (C5L2) antagonists.

Targeted Complement Inhibitors

In certain embodiments, the targeted complement inhibitors comprise fusion proteins comprising a CR2 portion and a complement inhibitor portion. In certain embodiments, the targeted complement inhibitors comprise fusion proteins comprising a targeting portion and a complement inhibitor portion. In certain embodiments, the complement inhibitor portion comprises full-length human (SEQ ID NO:3) or mouse (SEQ ID NO:8 or SEQ ID NO:9) CD59 protein or a biologically active fragment or homolog thereof. In certain embodiments, the complement inhibitor portion comprises full-length mouse Crry protein (SEQ ID NO:4) or a biologically active fragment or homolog thereof. In certain embodiments, the complement inhibitor portion comprises full-length human (SEQ ID NO:5) or mouse (SEQ ID NO:10) factor H (SEQ ID NO:5) or a biologically active fragment or homolog thereof. In certain embodiments, the complement inhibitor portion comprises human complement receptor 1 (CR1) (SEQ ID NO:11) or a biologically active fragment or homolog thereof. In certain embodiments, the complement inhibitor portion comprises human membrane cofactor protein (MCP) (SEQ ID NO:12) or a biologically active fragment or homolog thereof. In certain embodiments, the complement inhibitor portion comprises full-length human (SEQ ID NO:13) or mouse (SEQ ID NO:14) decay accelerating factor (DAF) or a biologically active fragment or homolog thereof.

In certain embodiments, the CR2 portion comprises full-length CR2 protein (SEQ ID NO:1) or a biologically active fragment thereof. CR2 is a transmembrane protein expressed predominantly on mature B cells and follicular dendritic cells. CR2 is a member of the C3 binding protein family. Natural ligands for CR2 include, for example, iC3b, C3dg, and C3d, and cell-bound breakdown fragments of C3b that bind to the two N-terminal SCR domains of CR2 (SEQ ID NO:2). Cleavage of C3 results initially in the generation of C3b and the covalent attachment of this C3b to the activating cell surface. The C3b fragment is involved in the generation of enzymatic complexes that amplify the complement cascade. On a cell surface, C3b is rapidly converted to inactive iC3b, particularly when deposited on a host surface containing regulators of complement activation (i.e., most host tissue). Even in absence of membrane bound complement regulators, substantial levels of iC3b are formed. iC3b is subsequently digested to the membrane bound fragments C3dg and then C3d by serum proteases, but this process is relatively slow. Thus, the C3 ligands for CR2 are relatively long lived once they are generated and will be present in high concentrations at sites of complement activation. CR2 therefore can serve as a potent targeting vehicle for bringing molecules to the site of complement activation.

CR2 contains an extracellular portion having 15 or 16 repeating units known as short consensus repeats (SCR domains). The SCR domains typically have a framework of highly conserved residues including four cysteines, two prolines, one tryptophan and several other partially conserved glycines and hydrophobic residues. SEQ ID NO:1 represents the full-length human CR2 protein sequence having 15 SCR domains Amino acids 1-20 of SEQ ID NO:1 comprise the leader peptide, amino acids 23-82 of SEQ ID NO:1 comprise SCR1, amino acids 91-146 of SEQ ID NO:1 comprise SCR2, amino acids 154-210 of SEQ ID NO:1 comprise SCR3, amino acids 215-271 of SEQ ID NO:1 comprise SCR4. The active site (C3d binding site) is located in SCR1-2 (the first two N-terminal SCR domains) (SEQ ID NO:2). These SCR domains are separated by short sequences of variable length that serve as spacers. It is understood that species and strain variations exist for the disclosed peptides, polypeptides, and proteins, and that the CR2 or a fragment thereof described herein encompasses all species and strain variations.

In certain embodiments, the CR2 portion comprises a polypeptide that contains some or all of the ligand binding sites of the CR2 protein, and includes, but is not limited to, full-length CR2 proteins (such as human CR2 as shown in SEQ ID NO:1), soluble CR2 proteins (such as a CR2 fragment comprising the extracellular domain of CR2), other biologically active fragments of CR2, a CR2 fragment comprising SCR1-2 (SEQ ID NO:2), or any homolog of a naturally occurring CR2 or fragment thereof, as described in detail below. In some embodiments, the CR2 portion has at least one of the following properties or CR2: (1) the ability to bind to C3d, (2) the ability to bind to iC3b, (3) the ability to bind to C3dg, (4) the ability to bind to C3d, and (5) the ability to bind to one or more cell-bound fragments of C3b that bind to the two N-terminal SCR domains of CR2.

In certain embodiments, the CR2 portion comprises the first two N-terminal SCR domains of CR2 (SEQ ID NO:2). In certain embodiments, the CR2 portion comprises the first three N-terminal SCR domains of CR2. In certain embodiments, the CR2 portion comprises the first four N-terminal SCR domains of CR2. In certain embodiments, the CR2 portion comprises (and in some embodiments consists of or consists essentially of) at least the first two N-terminal SCR domains of CR2, including for example at least any of the first 3, 4, 5, 6, 7, 8, 9, 10, 11, 12, 13, 14, or 15 SCR domains of CR2.

In certain embodiments, the CR2 portion comprises a homolog of a CR2 protein or a biologically active fragment thereof. A homolog of a CR2 protein or a biologically active fragment thereof includes proteins which differ from a naturally occurring CR2 (or CR2 fragment) in that at least one or a few amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol), but that retains the ability to bind one or more naturally-occurring CR2 ligands. In certain embodiments, a CR2 homolog has an amino acid sequence that is at least about 70% identical to the amino acid sequence of a naturally occurring CR2 (e.g., SEQ ID NO:1), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring CR2 (e.g., SEQ ID NO:1). A CR2 homolog or a fragment thereof preferably retains the ability to bind to a naturally occurring ligand of CR2 (e.g., C3d or other C3 fragments with CR2-binding ability). For example, the CR2 homolog (or fragment thereof) may have a binding affinity for C3d that is at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of that of CR2 (or a fragment thereof).

In certain embodiments, the CR2 portion comprises at least the first two N-terminal SCR domains of a human CR2, such as a CR2 portion having an amino acid sequence containing at least amino acids 23 through 146 of the human CR2 (SEQ ID NO:1). In certain embodiments, the CR2 portion comprises at least the first two SCR domains of human CR2 having an amino acid sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to amino acids 23-146 of the human CR2 (SEQ ID NO:1).

In certain embodiments, the CR2 portion comprises at least the first four N-terminal SCR domains of a human CR2, such as a CR2 portion having an amino acid sequence containing at least amino acids 23 through 271 of the human CR2 (SEQ ID NO:1). In certain embodiments, the CR2 portion comprises at least the first four SCR domains of human CR2 having an amino acid sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to amino acids 23-271 of the human CR2 (SEQ ID NO:1).

An amino acid sequence that is at least about, for example, 95% identical to a reference sequence (such as SEQ ID NO:1) is identical to the reference sequence except that the amino acid sequence may include up to five point alterations per each 100 amino acids of the reference sequence. These up to five point alterations may be deletions, substitutions (e.g., conservative substitutions), additions, and may occur anywhere in the sequence, interspersed either individually among amino acids in the reference sequence or in one or more continuous groups within the reference sequence.

In certain embodiments, the CR2 portion comprises part or all of the ligand binding sites of the CR2 protein. In certain embodiments, the CR2 portion further comprises sequences required to maintain the three-dimensional structure of the binding site. Ligand binding sites of CR2 can be readily determined based on the crystal structures of CR2, such as the human and mouse CR2 crystal structures disclosed in U.S. Patent Application Publication No. 2004/0005538. For example, in certain embodiments, the CR2 portion comprises the B strand and B-C loop of SCR2 of CR2. In certain embodiments, the CR2 portion comprises a site on strand B and the B-C loop of CR2 SCR comprising the segment G98-G99-Y100-K101-I102-R103-G104-S105-T106-P107-Y108 with respect to SEQ ID NO:1. In certain embodiments, the CR2 portion comprises a site on the B strand of CR2 SCR2 comprising position K119 with respect to SEQ ID NO:1. In certain embodiments, the CR2 portion comprises a segment comprising V149-F150-P151-L152, with respect to SEQ ID NO:1. In certain embodiments, the CR2 portion comprises a segment of CR2 SCR2 comprising T120-N121-F122. In certain embodiments, the CR2-FH molecule has two or more of these sites. For example, in certain embodiments, the CR2 portion comprises a portion comprising G98-G99-Y100-K101-I102-R103-G104-5105-T106-P107-Y108 and K119 with respect to SEQ ID NO:1. Other combinations of these sites are also contemplated.

In certain embodiments, the targeting portion comprises a non-CR2 targeting portion. In certain embodiments, the non-CR2 targeting portion comprises an antibody or antigen-binding fragment thereof that specifically binds to proteolytic fragments of complement protein C3 (e.g., iC3b, C3dg, and C3d). In certain embodiments, the antibodies are polyclonal antibodies. In certain embodiments, the antibodies are monoclonal antibodies. In certain embodiments, the antibodies are polyclonal or monoclonal antibody fragments selected from the group consisting of Fab, Fab'-SH, Fv, scFv, and (Fab')$_2$ fragments. In certain embodiments, the antibodies or antigen-binding fragments thereof are humanized antibodies. In certain embodiments, the antibodies or antigen-binding fragments thereof are human antibodies.

As used herein, the term "membrane cofactor protein," "MCP," or "CD46" refers to a widely distributed C3b/C4b-binding cell surface glycoprotein which inhibits complement activation on host cells and serves as a cofactor for the factor I-mediated cleavage of C3b and C4b, including homologs thereof. T. J. Oglesby et al., *J. Exp. Med.* (1992) 175:1547-1551. MCP belongs to a family known as the regulators of complement activation ("RCA"). Family members share certain structural features, comprising varying numbers of short consensus repeat (SCR) domains, which are typically between 60 and 70 amino acids in length. MCP comprises four SCRs, a serine/threonine/proline-enriched region, an area of undefined function, a transmembrane hydrophobic domain, a cytoplasmic anchor and a cytoplasmic tail. It is understood that species and strain variations exist for the disclosed peptides, polypeptides, and proteins, and that human MCP or biologically active fragments thereof encompasses all species and strain variations.

SEQ ID NO:12 represents the full-length human MCP amino acid sequence (see, e.g., UniProtKB/Swiss-Prot. Accession No. P15529). Amino acids 1-34 correspond to the signal peptide, amino acids 35-343 correspond to the extracellular domain, amino acids 344-366 correspond to the transmembrane domain, and amino acids 367-392 correspond to the cytoplasmic domain. In the extracellular domain, amino acids 35-96 correspond to SCR 1, amino acids 97-159 correspond to SCR 2, amino acids 160-225 correspond to SCR 3, amino acids 226-285 correspond to SCR 4, and amino acids 302-326 correspond to the serine/threonine-rich domain. It is understood that species and strain variations exist for the disclosed peptides, polypeptides, and proteins, and that MCP or biologically active fragments thereof encompasses all species and strain variations. As used herein, the term "biologically active" fragment of MCP refers to any soluble fragment lacking both the cytoplasmic domain and the transmembrane domain, including fragments comprising, consisting essentially of or consisting of 1, 2, 3, or 4 SCR domains, with or without the serine/threonine-rich domain, having some or all the complement inhibitory activity of the full-length human MCP protein. In certain embodiments, the complement inhibitor portion comprises full-length human MCP (amino acids 35-392 of SEQ ID NO:12), the extracellular domain of human MCP (amino acids 35-343 of SEQ ID NO:12), or SCRs 1-4 of human MCP (amino acids 35-285 of SEQ ID NO:12).

In certain embodiments, the targeted complement inhibitor comprises a CR2 portion and an MCP portion. The CR2 portion of the fusion protein delivers the composition to sites of IRI and/or regeneration (e.g., hepatic sites) by selectively binding to CR2 ligands (i.e., proteolytic fragments of complement protein C3 (e.g., iC3b, C3dg, and C3d)) present at those sites, while the MCP portion of the targeted complement inhibitor inhibits complement activity. In certain embodiments, the targeted complement inhibitor comprises a non-CR2 targeting portion and an MCP portion. The non-CR2 targeting portion of the fusion protein delivers the composition to sites of IRI and/or regeneration (e.g., hepatic sites) by selectively binding to CR2 ligands (i.e., proteolytic fragments of complement protein C3 (e.g., iC3b, C3dg, and C3d)) present at those sites, while the MCP portion of the targeted complement inhibitor inhibits complement activity.

In certain embodiments, the targeted complement inhibitor comprises full-length CR2 protein (SEQ ID NO:1) fused to full-length human MCP protein (amino acids 35-392 of SEQ ID NO:12). In certain embodiments, the targeted complement inhibitor comprises full-length CR2 protein (SEQ ID NO:1) fused to a biologically active fragment of MCP protein comprising the extracellular domain of human MCP (amino acids 35-343 of SEQ ID NO:12). In certain embodiments, the targeted complement inhibitor comprises full-length CR2 protein (SEQ ID NO:1) fused to SCRs 1-4 of human MCP (amino acids 35-285 of SEQ ID NO:12).

In certain embodiments, the targeted complement inhibitor comprises a biologically active fragment of CR2 protein comprising SCR1-2 (SEQ ID NO:2) fused to full-length human MCP protein (amino acids 35-392 of SEQ ID NO:12). In certain embodiments, the targeted complement inhibitor comprises a biologically active fragment of CR2 protein comprising SCR1-2 (SEQ ID NO:2) fused to a biologically active fragment of MCP protein comprising the extracellular domain of human MCP (amino acids 35-343 of SEQ ID NO:12). In certain embodiments, the targeted complement inhibitor comprises a biologically active fragment of CR2 protein comprising SCR1-2 (SEQ ID NO:2) fused to a biologically active fragment of MCP protein comprising SCRs 1-4 of human MCP (amino acids 35-285 of SEQ ID NO:12).

In certain embodiments, the targeted complement inhibitor comprises a non-CR2 targeting portion fused to full-length human MCP protein (amino acids 35-392 of SEQ ID NO:12), to a biologically active fragment of MCP protein comprising the extracellular domain of human MCP (amino acids 35-343 of SEQ ID NO:12), or to a biologically active fragment of MCP protein comprising SCRs 1-4 of human MCP (amino acids 35-285 of SEQ ID NO:12).

In certain embodiments, the non-CR2 targeting portion comprises an antibody or antigen-binding fragment thereof that specifically binds to proteolytic fragments of complement protein C3 (e.g., iC3b, C3dg, and C3d). In certain embodiments, the antibodies are polyclonal antibodies. In certain embodiments, the antibodies are monoclonal antibodies. In certain embodiments, the antibodies are polyclonal or monoclonal antibody fragments selected from the group consisting of Fab, Fab'-SH, Fv, scFv, and (Fab')$_2$ fragments. In certain embodiments, the antibodies or antigen-binding fragments thereof are humanized antibodies. In certain embodiments, the antibodies or antigen-binding fragments thereof are human antibodies.

In certain embodiments, the complement inhibitor portion comprises a homolog of a human MCP protein or a biologically active fragment thereof. A homolog of a human MCP protein or a biologically active fragment thereof includes proteins which differ from a naturally occurring human MCP (or biologically active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). For example, a human MCP homolog may have an amino acid sequence that is at least about 70% identical to the amino acid sequence of a naturally occurring human MCP (e.g., SEQ ID NO:12), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring human MCP (e.g., SEQ ID NO:12). In certain embodiments, a homolog of human MCP (or a biologically active fragment thereof) retains all the alternative complement pathway inhibitory activity of human MCP (or a biologically active fragment thereof). In certain embodiments, the homolog of human MCP (or a biologically active fragment thereof) retains at least about 50%, for example, at least about any of 60%, 70%, 80%, 90%, or 95% of the complement inhibitory activity of human MCP (or a biologically active fragment thereof).

As used herein, the term "decay accelerating factor," "DAF," or "CD55" refers to a seventy kilodalton ("kD") membrane glycoprotein comprising four short consensus repeat (SCR) domains followed by a heavily O-glycosylated serine/threonine-rich domain at the C-terminus that elevates the molecule from the membrane surface, including homologs thereof. DAF is anchored into the cell membrane by a glycosylphosphatidylinositol ("GPI") anchor. DAF protects the cell surface from complement activation by dissociating membrane-bound C3 convertases that are required to cleave complement protein C3 and to amplify the alternative complement cascade.

SEQ ID NO:13 represents the full-length human DAF amino acid sequence (see, e.g., UniProtKB/Swiss-Prot. Accession No. P08173); SEQ ID NO:14 represents the full-length mouse DAF amino acid sequence (see, e.g., UniProtKB/Swiss-Prot. Accession No. Q61475). In the human DAF sequence, amino acids 1-34 correspond to the signal peptide, amino acids 35-353 appear in the mature protein, and amino acids 354-381 are removed from the polypeptide after translation. Within the mature protein, amino acids 35-96 correspond to SCR 1, amino acids 96-160 correspond to SCR 2, amino acids 161-222 correspond to SCR 3, amino acids 223-285 correspond to SCR 4, and amino acids 287-353 correspond to the O-glycosylated serine/threonine-rich domain. The GPI anchor is attached to human DAF at a serine at position 353. In the mouse DAF sequence, amino acids 1-34 correspond to the signal peptide, amino acids 35-362 appear in the mature protein, and amino acids 363-390 are removed from the polypeptide after translation. Within the mature protein, amino acids 35-96 correspond to SCR 1, amino acids 97-160 correspond to SCR 2, amino acids 161-222 correspond to SCR 3, amino acids 223-286 correspond to SCR 4, and amino acids 288-362 correspond to the O-glycosylated serine/threonine-rich domain. The GPI anchor is attached to mouse DAF at a serine at position 362. It is understood that species and strain variations exist for the disclosed peptides, polypeptides, and proteins, and that DAF or biologically active fragments thereof encompasses all species and strain variations. As used herein, the term "biologically active"

fragment of DAF refers to any fragment of DAF lacking a GPI anchor and/or the amino acid to which it is attached (i.e., Ser-353), including any fragments of the full-length DAF protein comprising, consisting essentially of or consisting of 1, 2, 3, or 4 SCR domains, with or without the O-glycosylated serine/threonine-rich domain, having some or all the complement inhibitory activity of the full-length DAF protein.

In certain embodiments, the targeted complement inhibitor comprises a CR2 portion and a DAF portion. The CR2 portion of the fusion protein delivers the composition to sites of IRI and/or regeneration (e.g., hepatic sites) by selectively binding to CR2 ligands (i.e., proteolytic fragments of complement protein C3 (e.g., iC3b, C3dg, and C3d)) present at those sites, while the DAF portion of the targeted complement inhibitor inhibits complement activity. In certain embodiments, the targeted complement inhibitor comprises a non-CR2 targeting portion and a DAF portion. The non-CR2 targeting portion of the fusion protein delivers the composition to sites of IRI and/or regeneration (e.g., hepatic sites) by selectively binding to CR2 ligands (i.e., proteolytic fragments of complement protein C3 (e.g., iC3b, C3dg, and C3d)) present at those sites, while the DAF portion of the targeted complement inhibitor inhibits complement activity.

In certain embodiments, the targeted complement inhibitor comprises full-length CR2 protein (SEQ ID NO:1) fused to full-length human decay-accelerating factor (DAF) (SEQ ID NO:13). In certain embodiments, the targeted complement inhibitor comprises full-length CR2 protein (SEQ ID NO:1) fused to full-length mouse decay-accelerating factor (DAF) (SEQ ID NO:14). In certain embodiments, the targeted complement inhibitor comprises full-length CR2 protein (SEQ ID NO:1) fused to a biologically active fragment of human DAF comprising the mature human DAF protein (amino acids 35-353 of SEQ ID NO:13) without its GPI anchor and/or the amino acid to which it is attached (i.e., Ser-353). In certain embodiments, the targeted complement inhibitor comprises full-length CR2 protein (SEQ ID NO:1) fused to a biologically active fragment of mouse DAF comprising the mature mouse DAF protein (amino acids 35-362 of SEQ ID NO:14) without its GPI anchor and/or the amino acid to which it is attached (i.e., Ser-362). In certain embodiments, the targeted complement inhibitor comprises full-length CR2 protein (SEQ ID NO:1) fused to a biologically active fragment of human DAF comprising short consensus repeat sequences 1-4 (SCRs 1-4) of full-length human DAF (amino acids 35 to 285 of SEQ ID NO:13). In certain embodiments, the targeted complement inhibitor comprises full-length CR2 protein (SEQ ID NO:1) fused to a biologically active fragment of mouse DAF comprising short consensus repeat sequences 1-4 (SCRs 1-4) of full-length mouse DAF (amino acids 35-286 of SEQ ID NO:14).

In certain embodiments, the targeted complement inhibitor comprises a biologically active fragment of CR2 protein comprising SCR1-2 (SEQ ID NO:2) fused to full-length human decay-accelerating factor (DAF) (SEQ ID NO:13). In certain embodiments, the targeted complement inhibitor comprises a biologically active fragment of CR2 protein comprising SCR1-2 (SEQ ID NO:2) fused to full-length mouse decay-accelerating factor (DAF) (SEQ ID NO:14). In certain embodiments, the targeted complement inhibitor comprises a biologically active fragment of CR2 protein comprising SCR1-2 (SEQ ID NO:2) fused to a biologically active fragment of human DAF comprising the mature human DAF protein (amino acids 35-353 of SEQ ID NO:13) without its GPI anchor and/or the amino acid to which it is attached (i.e., Ser-353). In certain embodiments, the targeted complement inhibitor comprises a biologically active fragment of CR2 protein comprising SCR1-2 (SEQ ID NO:2) fused to a biologically active fragment of mouse DAF comprising the mature mouse DAF protein (amino acids 35-362 of SEQ ID NO:14) without its GPI anchor and/or the amino acid to which it is attached (i.e., Ser-362). In certain embodiments, the targeted complement inhibitor comprises a biologically active fragment of CR2 protein comprising SCR1-2 (SEQ ID NO:2) fused to a biologically active fragment of human DAF comprising short consensus repeat sequences 1-4 (SCRs 1-4) of full-length human DAF (amino acids 35-285 of SEQ ID NO:13). In certain embodiments, the targeted complement inhibitor comprises a biologically active fragment of CR2 protein comprising SCR1-2 (SEQ ID NO:2) fused to a biologically active fragment of mouse DAF comprising short consensus repeat sequences 1-4 (SCRs 1-4) of full-length mouse DAF (amino acids 35-286 of SEQ ID NO:14).

In certain embodiments, the targeted complement inhibitor comprises a non-CR2 targeting portion fused to full-length human decay-accelerating factor (DAF) (SEQ ID NO:13), to a biologically active fragment of human DAF comprising the mature human DAF protein (amino acids 35-353 of SEQ ID NO:13) without its GPI anchor and/or the amino acid to which it is attached (i.e., Ser-353), or to a biologically active fragment of human DAF comprising short consensus repeat sequences 1-4 (SCRs 1-4) of full-length human DAF (amino acids 35-285 of SEQ ID NO:13).

In certain embodiments, the targeted complement inhibitor comprises a non-CR2 targeting portion fused to full-length mouse decay-accelerating factor (DAF) (SEQ ID NO:14), to a biologically active fragment of mouse DAF comprising the mature mouse DAF protein (amino acids 35-362 of SEQ ID NO:14) without its GPI anchor and/or the amino acid to which it is attached (i.e., Ser-362), or to a biologically active fragment of mouse DAF comprising short consensus repeat sequences 1-4 (SCRs 1-4) of full-length mouse DAF (amino acids 35-286 of SEQ ID NO:14).

In certain embodiments, the non-CR2 targeting portion comprises an antibody or antigen-binding fragment thereof that specifically binds to proteolytic fragments of complement protein C3 (e.g., iC3b, C3dg, and C3d). In certain embodiments, the antibodies are polyclonal antibodies. In certain embodiments, the antibodies are monoclonal antibodies. In certain embodiments, the antibodies are polyclonal or monoclonal antibody fragments selected from the group consisting of Fab, Fab'-SH, Fv, scFv, and (Fab')$_2$ fragments. In certain embodiments, the antibodies or antigen-binding fragments thereof are humanized antibodies. In certain embodiments, the antibodies or antigen-binding fragments thereof are human antibodies.

In certain embodiments, the complement inhibitor portion comprises a homolog of a human or mouse DAF protein or a biologically active fragment thereof. A homolog of a human or mouse DAF protein or a biologically active fragment thereof includes proteins which differ from a naturally occurring human or mouse DAF (or biologically active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). For example, a human or mouse DAF homolog may have an amino acid sequence that is at least about 70% identical to the amino acid sequence of a naturally occurring human or mouse DAF (e.g., SEQ ID NO:13 or SEQ ID NO:14), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring human or mouse DAF (e.g., SEQ ID NO:13 or SEQ ID NO:14). In certain embodiments, a homolog of human or mouse DAF (or a biologically active fragment thereof) retains all the complement inhibitory activity of human or mouse DAF (or a biologically active fragment thereof). In certain embodiments, the homolog of human or mouse DAF (or a biologically active fragment thereof) retains at least about 50%, for example, at least about any of 60%, 70%, 80%, 90%, or 95% of the complement inhibitory activity of human or mouse DAF (or a biologically active fragment thereof).

As used herein, the term "CD59" refers to a membrane-bound 128 amino acid glycoprotein that potently inhibits the membrane attack complex (MAC) of complement, including homologs thereof. CD59 acts by binding to the C8 and/or C9 components of the MAC during assembly, ultimately preventing incorporation of the multiple copies of C9 required for complete formation of the osmolytic pore at the heart of the MAC. CD59 is both N- and O-glycosylated. The N-glycosylation comprises primarily of bi- or tri-antennary structures with and without lactosamine and outer arm fucose residues, with variable sialylation present at some sites. Like DAF, CD59 is anchored in the cell membrane by a glycosylphosphatidylinositol ("GPI") anchor, which is attached to an asparagine at amino acid 102.

SEQ ID NO:3 represents the full-length human CD59 amino acid sequence (see, e.g., UniProtKB/Swiss-Prot. Accession No. P13987); SEQ ID NO:8 represents the full-length mouse CD59 sequence, isoform A (see, e.g., UniProtKB/Swiss-Prot. Accession No. O55186); SEQ ID NO:9 represents the full-length mouse CD59 sequence, isoform B (see, e.g., UniProtKB/Swiss-Prot. Accession No. P58019). In the human CD59 sequence, amino acids 1-25 of SEQ ID NO:3 correspond to the leader peptide, amino acids 26-102 of SEQ ID NO:3 correspond to the mature protein, and amino acids 103-128 of SEQ ID NO:3 are removed after translation. The GPI anchor is attached to CD59 at an asparagine at position 102 of SEQ ID NO:3. In isoform A of the mouse CD59 sequence, amino acids 1-23 of SEQ ID NO:8 correspond to the leader peptide, amino acids 24-96 of SEQ ID NO:8 correspond to the mature protein, and amino acids 97-123 of SEQ ID NO:8 are removed after translation. The GPI anchor is attached to CD59 at a serine at position 96 of SEQ ID NO:8. In isoform B of the mouse CD59 sequence, amino acids 1-23 of SEQ ID NO:9 correspond to the leader peptide, amino acids 24-104 of SEQ ID NO:9 correspond to the mature protein, and amino acids 105-129 of SEQ ID NO:9 are removed after translation. The GPI anchor is attached to CD59 at an asparagine at position 104 of SEQ ID NO:9. It is understood that species and strain variations exist for the disclosed peptides, polypeptides, and proteins, and that CD59 or biologically active fragments thereof encompasses all species and strain variations. As used herein, the term "biologically active" fragment of human CD59 refers to any fragment of human CD59 lacking a GPI anchor and/or the amino acid to which it is attached (i.e., Asn-102), including any fragments of the full-length human CD59 protein having some or all the complement inhibitory activity of the full-length CD59 protein; and the term "biologically active" fragment of mouse CD59 refers to any fragment of mouse CD59 isoform A or isoform B lacking a GPI anchor and/or the amino acid to which it is attached (i.e., Ser-96 of isoform A, or Asp-104 of isoform B), including any fragments of either full-length mouse CD59 protein isoform having some or all the complement inhibitory activity of the full-length CD59 protein In certain embodiments, the targeted complement inhibitor comprises a CR2 portion and a CD59 portion. The CR2 portion of the targeted complement inhibitor delivers the composition to sites of IRI and/or regeneration (e.g., hepatic sites) by selectively binding to CR2 ligands (e.g., iC3b, C3dg, and C3d) present at those sites, while the CD59 portion of the targeted complement inhibitor inhibits activity of the terminal complement pathway and assembly of the membrane attack complex (MAC). In certain embodiments, the targeted complement inhibitor comprises a non-CR2 targeting portion and a CD59 portion. The non-CR2 targeting portion of the fusion protein delivers the composition to sites of IRI and/or regeneration (e.g., hepatic sites) by selectively binding to CR2 ligands (i.e., proteolytic fragments of complement protein C3 (e.g., iC3b, C3dg, and C3d)) present at those sites, while the CD59 portion of the targeted complement inhibitor inhibits terminal complement and assembly of the MAC.

In certain embodiments, the targeted complement inhibitor comprises full-length CR2 protein (SEQ ID NO:1) fused to full-length human CD59 protein (SEQ ID NO:3), a full-length mouse CD59 protein, isoform A (SEQ ID NO:8), or a full-length mouse CD59 protein, isoform B (SEQ ID NO:9). In certain embodiments, the targeted complement inhibitor comprises full-length CR2 protein (SEQ ID NO:1) fused to a biologically active fragment of CD59 protein comprising the extracellular domain of human CD59 (amino acids 26-102 of SEQ ID NO:3) lacking its GPI anchor and/or the amino acid to which it is attached (i.e., Asn-102), a biologically active fragment of mouse CD59 protein, isoform A comprising the extracellular domain of mouse CD59, isoform A (amino acids 24-96 of SEQ ID NO:8) lacking its GPI anchor and/or the amino acid to which it is attached (i.e., Ser-96), or a biologically active fragment of mouse CD59 protein, isoform B comprising the extracellular domain of mouse CD59, isoform B (amino acids 24-104 of SEQ ID NO:9) lacking its GPI anchor and/or the amino acid to which it is attached (i.e., Asn-104).

In certain embodiments, the targeted complement inhibitor comprises a biologically active fragment of CR2 protein comprising SCR1-2 (SEQ ID NO:2) fused to full-length human CD59 protein (SEQ ID NO:3), a full-length mouse CD59 protein, isoform A (SEQ ID NO:8), or a full-length mouse CD59 protein, isoform B (SEQ ID NO:9). In certain embodiments, the targeted complement inhibitor comprises a biologically active fragment of CR2 protein comprising SCR1-2 (SEQ ID NO:2) fused to a biologically active fragment of CD59 protein comprising the extracellular domain of human CD59 (amino acids 26-102 of SEQ ID NO:3) lacking its GPI anchor and/or the amino acid to which it is attached (i.e., Asn-102), a biologically active fragment of mouse CD59 protein, isoform A comprising the extracellular domain of mouse CD59, isoform A (amino acids 24-96 of SEQ ID NO:8) lacking its GPI anchor and/or the amino acid to which it is attached (i.e., Ser-96), or a biologically active fragment of mouse CD59 protein, isoform B comprising the extracellular domain of mouse CD59, isoform B (amino acids 24-104 of SEQ ID NO:9) lacking its GPI anchor and/or the amino acid to which it is attached (i.e., Asn-104).

In certain embodiments, the targeted complement inhibitor comprises a non-CR2 targeting portion fused to full-length human CD59 protein (SEQ ID NO:3), to a full-length mouse CD59 protein, isoform A (SEQ ID NO:8), or to a full-length mouse CD59 protein, isoform B (SEQ ID NO:9). In certain embodiments, the targeted complement inhibitor comprises a non-CR2 targeting portion fused to a biologically active fragment of CD59 protein comprising the extracellular domain of human CD59 (amino acids 26-102 of SEQ ID NO:3) lacking its GPI anchor and/or the amino acid to which it is attached (i.e., Asn-102), to a biologically active fragment of mouse CD59 protein, isoform A comprising the extracellular domain of mouse CD59, isoform A (amino acids 24-96 of SEQ ID NO:8) lacking its GPI anchor and/or the amino acid to which it is attached (i.e., Ser-96), or to a biologically active fragment of mouse CD59 protein, isoform B comprising the extracellular domain of mouse CD59, isoform B (amino acids 24-104 of SEQ ID NO:9) lacking its GPI anchor and/or the amino acid to which it is attached (i.e., Asn-104).

In certain embodiments, the non-CR2 targeting portion comprises an antibody or antigen-binding fragment thereof that specifically binds to proteolytic fragments of complement protein C3 (e.g., iC3b, C3dg, and C3d). In certain embodiments, the antibodies are polyclonal antibodies. In certain embodiments, the antibodies are monoclonal antibodies. In certain embodiments, the antibodies are polyclonal or monoclonal antibody fragments selected from the group consisting of Fab, Fab'-SH, Fv, scFv, and (Fab')$_2$ fragments. In certain embodiments, the antibodies or antigen-binding fragments thereof are humanized antibodies. In certain embodiments, the antibodies or antigen-binding fragments thereof are human antibodies.

In certain embodiments, the complement inhibitor portion comprises a homolog of a human or mouse CD59 protein or a biologically active fragment thereof. A homolog of a human or mouse CD59 protein or a biologically active fragment thereof includes proteins which differ from a naturally occurring human or mouse CD59 (or biologically active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol), but that retain the ability to inhibit terminal complement (i.e., formation of the MAC). For example, a human or mouse CD59 homolog may have an amino acid sequence that is at least about 70% identical to the amino acid sequence of a naturally occurring human or mouse CD59 (e.g., SEQ ID NO:3, SEQ ID NO:8, or SEQ ID NO:9), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring human or mouse CD59 (e.g., SEQ ID NO:3, SEQ ID NO:8, or SEQ ID NO:9). In certain embodiments, a homolog of human or mouse CD59 (or a biologically active fragment thereof) retains all the alternative complement pathway inhibitory activity of human or mouse CD59 (or a biologically active fragment thereof). In certain embodiments, the homolog of human or mouse CD59 (or a biologically active fragment thereof) retains at least about 50%, for example, at least about any of 60%, 70%, 80%, 90%, or 95% of the complement inhibition activity of human or mouse CD59 (or a biologically active fragment thereof).

As used herein, the term "mouse complement receptor 1-related gene/protein y" or "Crry" refers to a membrane-bound mouse glycoprotein that regulates complement activation, including homologs thereof. Crry regulates complement activation by serving as a cofactor for complement factor I, a serine protease which cleaves C3b and C4b deposited on host tissue. Crry also acts as a decay-accelerating factor, preventing the formation of C4b2a and C3bBb, the amplification convertases of the complement cascade.

SEQ ID NO:4 represents the full-length mouse Crry protein amino acid sequence. Amino acids 1-40 correspond to the leader peptide, amino acids 41-483 of SEQ ID NO:4 correspond to the mature protein, comprising amino acids 41-405 of SEQ ID NO:4, corresponding to the extracellular domain, amino acids 406-426 of SEQ ID NO:4, corresponding to the transmembrane domain, and amino acids 427-483 of SEQ ID NO:4, corresponding to the cytoplasmic domain. In the extracellular domain, amino acids 83-143 of SEQ ID NO:4 correspond to SCR 1, amino acids 144-205 of SEQ ID NO:4 correspond to SCR2, amino acids 206-276 of SEQ ID NO:4 correspond to SCR3, amino acids 277-338 of SEQ ID NO:4 correspond to SCR4, and amino acids 339-400 of SEQ ID NO:4 correspond to SCR5. It is understood that species and strain variations exist for the disclosed peptides, polypeptides, and proteins, and that mouse Crry protein or biologically active fragments thereof encompasses all species and strain variations. As used herein, the term "biologically active" fragment of mouse Crry protein refers to refers to any soluble fragment of mouse Crry lacking the transmembrane domain and the cytoplasmic domain, including fragments comprising, consisting essentially of or consisting of 1, 2, 3, 4, or 5 SCR domains, including any fragments of the full-length mouse Crry protein having some or all the complement inhibitory activity of the full-length Crry protein.

In certain embodiments, the targeted complement inhibitor comprises a CR2 portion and a mouse Crry portion. The CR2 portion of the targeted complement inhibitor delivers the composition to sites of IRI and/or regeneration (e.g., hepatic sites) by selectively binding to CR2 ligands (e.g., iC3d, C3dg, and C3d) present at those sites, while the mouse Crry portion of the targeted complement inhibitor inhibits complement activity. In certain embodiments, the targeted complement inhibitor comprises a non-CR2 targeting portion and a mouse Crry portion. The non-CR2 targeting portion of the fusion protein delivers the composition to sites of IRI and/or regeneration (e.g., hepatic sites) by selectively binding to CR2 ligands (i.e., proteolytic fragments of complement protein C3 (e.g., iC3b, C3dg, and C3d)) present at those sites, while the Crry portion of the targeted complement inhibitor inhibits complement activity.

In certain embodiments, the targeted complement inhibitor comprises full-length CR2 (SEQ ID NO:1) fused to full-length mouse Crry (SEQ ID NO:4). In certain embodiments, the targeted complement inhibitor comprises full-length CR2 (SEQ ID NO:1) fused to a biologically active fragment of mouse Crry protein comprising the extracellular domain of mouse Crry (amino acids 41-405 of SEQ ID NO:4). In certain embodiments, the targeted complement inhibitor comprises full-length CR2 (SEQ ID NO:1) fused to a biologically active fragment of mouse Crry protein comprising SCR1-4 of mouse Crry (amino acids 83-338 of SEQ ID NO:4). In certain embodiments, the targeted complement inhibitor comprises full-length CR2 (SEQ ID NO:1) fused to a biologically active fragment of mouse Crry protein comprising SCR1-5 of mouse Crry (amino acids 83-400 of SEQ ID NO:4).

In certain embodiments, the targeted complement inhibitor comprises a biologically active fragment of CR2 comprising SCR1-2 (SEQ ID NO:2) fused to full-length mouse Crry protein (SEQ ID NO:4). In certain embodiments, the targeted complement inhibitor comprises a biologically active fragment of CR2 comprising SCR1-2 (SEQ ID NO:2) fused to a biologically active fragment of mouse Crry protein comprising the extracellular domain of mouse Crry (amino acids 41-405 of SEQ ID NO:4). In certain embodiments, the targeted complement inhibitor comprises a biologically active fragment of CR2 comprising SCR1-2 (SEQ ID NO:2) fused to a biologically active fragment of mouse Crry protein comprising SCR1-4 of mouse Crry (amino acids 83-338 of SEQ ID NO:4). In certain embodiments, the targeted complement inhibitor comprises a biologically active fragment of CR2 comprising SCR1-2 (SEQ ID NO:2) fused to a biologically active fragment of mouse Crry comprising SCR1-5 of mouse Crry (amino acids 83-400 of SEQ ID NO:4).

In certain embodiments, the targeted complement inhibitor comprises a non-CR2 targeting portion fused to full-length mouse Crry protein (SEQ ID NO:4), to a biologically active fragment of mouse Crry protein comprising the extracellular domain of mouse Crry (amino acids 41-405 of SEQ ID NO:4), to a biologically active fragment of mouse Crry protein comprising SCR1-4 of mouse Crry (amino acids 83-338 of SEQ ID NO:4), or to a biologically active fragment of mouse Crry comprising SCR1-5 of mouse Crry (amino acids 83-400 of SEQ ID NO:4).

In certain embodiments, the non-CR2 targeting portion comprises an antibody or antigen-binding fragment thereof that specifically binds to proteolytic fragments of complement protein C3 (e.g., iC3b, C3dg, and C3d). In certain embodiments, the antibodies are polyclonal antibodies. In certain embodiments, the antibodies are monoclonal antibodies. In certain embodiments, the antibodies are polyclonal or monoclonal antibody fragments selected from the group consisting of Fab, Fab'-SH, Fv, scFv, and (Fab')$_2$ fragments. In certain embodiments, the antibodies or antigen-binding fragments thereof are humanized antibodies. In certain embodiments, the antibodies or antigen-binding fragments thereof are human antibodies.

In certain embodiments, the complement inhibitor portion comprises a homolog of a mouse Crry protein or a biologically active fragment thereof. A homolog of a mouse Crry protein or a biologically active fragment thereof includes proteins which differ from a naturally occurring mouse Crry protein (or biologically active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol), but that retain the ability to inhibit complement. For example, a mouse Crry protein homolog may have an amino acid sequence that is at least about 70% identical to the amino acid sequence of a naturally occurring mouse Crry protein (e.g., SEQ ID NO:4), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring mouse Crry protein (e.g., SEQ ID NO:4). In certain embodiments, a homolog of mouse Crry protein (or a biologically active fragment thereof) retains all the alternative complement pathway inhibitory activity of mouse Crry protein (or a biologically active fragment thereof). In certain embodiments, the homolog of mouse Crry protein (or a biologically active fragment thereof) retains at least about 50%, for example, at least about any of 60%, 70%, 80%, 90%, or 95% of the complement inhibition activity of mouse Crry protein (or a biologically active fragment thereof).

As used herein, the term "complement receptor 1," "CR1," or "CD35" refers to a human gene encoding a protein of 2039 amino acids, with a predicted molecular weight of 220 kilodaltons ("kD"), including homologs thereof. The gene is expressed principally on erythrocytes, monocytes, neutrophils, and B cells, but is also present on some T lymphocytes, mast cells, and glomerular podocytes. CR1 protein is typically expressed at between 100 and 1000 copies per cell. The full-length CR1 protein comprises a 42 amino acid signal peptide, an extracellular domain of 1930 amino acids, a 25 amino acid transmembrane domain, and a 43 amino acid C-terminal cytoplasmic domain. The extracellular domain of CR1 has 25 potential N-glycosylation signal sequences, and comprises 30 short consensus ("SCR") domains, also known as complement control protein (CCP) repeats, or sushi domains, each 60 to 70 amino acids long. The sequence homology between SCRs ranges between 60-99 percent. The 30 SCR domains are further grouped into four longer regions termed long homologous repeats ("LHRs"), each encoding approximately 45 kD segments of the CR1 protein, designated LHR-A, -B, -C, and -D. The first three comprise seven SCR domains each, while LHR-D comprises 9 SCR domains. The active sites on the extracellular domain of CR1 protein include a C4b-binding site with lower affinity for C3b in SCRs 1-4 comprising amino acids 42-295, a C3b-binding site with lower affinity for C4b in SCRs 8-11 comprising amino acids 490-745, a C3b-binding site with lower affinity for C4b in SCRs 15-18 comprising amino acids 940-1196, and a C1q-binding site in SCRs 22-28 comprising amino acids 1394-1842.

SEQ ID NO:11 represents the full-length human CR1 amino acid sequence (see, e.g., UniProtKB/Swiss-Prot. Accession No. P17927). Amino acids 1-41 correspond to the signal peptide, amino acids 42-2039 correspond to the mature protein, comprising amino acids 42-1971, corresponding to the extracellular domain, amino acids 1972-1996, corresponding to the transmembrane domain, and amino acids 1997-2039, corresponding to the cytoplasmic domain. In the extracellular domain, amino acids 42-101 correspond to SCR 1, 102-163 correspond to SCR2, amino acids 164-234 correspond to SCR3, amino acids 236-295 correspond to SCR4, amino acids 295-355 correspond to SCR5, amino acids 356-418 correspond to SCR6, amino acids 419-489 correspond to SCR7, amino acids 491-551 correspond to SCR8, amino acids 552-613 correspond to SCR9, amino acids 614-684 correspond to SCR10, amino acids 686-745 correspond to SCR11, amino acids 745-805 correspond to SCR12, amino acids 806-868 correspond to SCR13, amino acids 869-939 correspond to SCR14, amino acids 941-1001 correspond to SCR15, amino acids 1002-1063 correspond to SCR16, amino acids 1064-1134 correspond to SCR17, amino acids 1136-1195 correspond to SCR18, amino acids 1195-1255 correspond to SCR 19, amino acids 1256-1318 correspond to SCR 20, amino acids 1319-1389 correspond to SCR 21, amino acids 1394-1454 correspond to SCR 22, amino acids 1455-1516 correspond to SCR 23, amino acids 1517-1587 correspond to SCR 24, amino acids 1589-1648 correspond to SCR 25, amino acids 1648-1708 correspond to SCR 26, amino acids 1709-1771 correspond to SCR 27, amino acids 1772-1842 correspond to SCR 28, amino acids 1846-1906 correspond to SCR 29, amino acids 1907-1967 correspond to SCR 30. It is understood that species and strain variations exist for the disclosed peptides, polypeptides, and proteins, and that CR1 protein or biologically active fragments thereof encompasses all species and strain variations. As used herein, the term "biologically active" fragment of CR1 protein refers to refers to any soluble fragment of CR1 lacking the transmembrane domain and the cytoplasmic domain, including fragments comprising, consisting essentially of or consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 SCR domains, including any fragments of the full-length CR1 protein having some or all the complement inhibitory activity of the full-length CR1 protein.

In certain embodiments, the targeted complement inhibitor comprises a CR2 portion and a CR1 portion. The CR2 portion of the targeted complement inhibitor delivers the composition to sites of IRI and/or regeneration (e.g., hepatic sites) by selectively binding to CR2 ligands (e.g., iC3d, C3dg, and C3d) present at those sites, while the CR1 portion of the targeted complement inhibitor inhibits complement activity. In certain embodiments, the targeted complement inhibitor comprises a non-CR2 targeting portion and a CR1 portion. The non-CR2 targeting portion of the fusion protein delivers the composition to sites of IRI and/or regeneration (e.g., hepatic sites) by selectively binding to CR2 ligands (i.e., proteolytic fragments of complement protein C3 (e.g., iC3b, C3dg, and C3d)) present at those sites, while the CR1 portion of the targeted complement inhibitor inhibits complement activity.

In certain embodiments, the targeted complement inhibitor comprises full-length CR2 (SEQ ID NO:1) or SCR1-2 of CR2 (SEQ ID NO:2) fused to full-length human CR1 (SEQ ID NO:11). In certain embodiments, the targeted complement inhibitor comprises full-length CR2 (SEQ ID NO:1) or SCR1-2 of CR2 (SEQ ID NO:2) fused to a biologically active fragment of full-length human CR1 comprising the complete extracellular domain of human CR1 (SCRs 1-30) (amino acids 42-1971 of SEQ ID NO:11). In certain embodiments, the targeted complement inhibitor comprises full-length CR2 (SEQ ID NO:1) or SCR1-2 of CR2 (SEQ ID NO:2) fused to a biologically active fragment of full-length human CR1 comprising SCRs 1-4 (amino acids 42-295 of SEQ ID NO:11). In certain embodiments, the targeted complement inhibitor comprises full-length CR2 (SEQ ID NO:1) or SCR1-2 of CR2 (SEQ ID NO:2) fused to a biologically active fragment of full-length human CR1 comprising SCRs 1-11 (amino acids 42-745 of SEQ ID NO:11). In certain embodiments, the targeted complement inhibitor comprises full-length CR2 (SEQ ID NO:1) or SCR1-2 of CR2 (SEQ ID NO:2) fused to a biologically active fragment of full-length human CR1 comprising SCRs 1-18 (amino acids 42-1195 of SEQ ID NO:11).

In certain embodiments, the targeted complement inhibitor comprises a non-CR2 targeting portion fused to full-length human CR1 (SEQ ID NO:11), to a biologically active fragment of full-length human CR1 comprising the complete extracellular domain of human CR1 (SCRs 1-30) (amino acids 42-1971 of SEQ ID NO:11), to a biologically active fragment of full-length human CR1 comprising SCRs 1-4 (amino acids 42-295 of SEQ ID NO:11), to a biologically active fragment of full-length human CR1 comprising SCRs 1-11 (amino acids 42-745 of SEQ ID NO:11), or to a biologically active fragment of full-length human CR1 comprising SCRs 1-18 (amino acids 42-1195 of SEQ ID NO:11).

In certain embodiments, the non-CR2 targeting portion comprises an antibody or antigen-binding fragment thereof that specifically binds to proteolytic fragments of complement protein C3 (e.g., iC3b, C3dg, and C3d). In certain embodiments, the antibodies are polyclonal antibodies. In certain embodiments, the antibodies are monoclonal antibodies. In certain embodiments, the antibodies are polyclonal or monoclonal antibody fragments selected from the group consisting of Fab, Fab'-SH, Fv, scFv, and (Fab')$_2$ fragments. In certain embodiments, the antibodies or antigen-binding fragments thereof are humanized antibodies. In certain embodiments, the antibodies or antigen-binding fragments thereof are human antibodies.

In certain embodiments, the complement inhibitor portion comprises a homolog of a human CR1 protein or a biologically active fragment thereof. A homolog of a human CR1 protein or a biologically active fragment thereof includes proteins which differ from a naturally occurring human CR1 (or biologically active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). For example, a human CR1 homolog may have an amino acid sequence that is at least about 70% identical to the amino acid sequence of a naturally occurring human CR1 (e.g., SEQ ID NO:11), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring human CR1 (e.g., SEQ ID NO:11). In certain embodiments, a homolog of human CR1 (or a biologically active fragment thereof) retains all the alternative complement pathway inhibitory activity of human CR1 (or a biologically active fragment thereof). In certain embodiments, the homolog of human CR1 (or a biologically active fragment thereof) retains at least about 50%, for example, at least about any of 60%, 70%, 80%, 90%, or 95% of the complement inhibition activity of human CR1 (or a biologically active fragment thereof).

As used herein, the term "complement factor H," "factor H," or "FH" refers to complement factor H, a single polypeptide chain plasma glycoprotein, including homologs thereof. The protein is composed of 20 conserved short consensus repeat (SCR) domains of approximately 60 amino acids, arranged in a continuous fashion like a string of beads, separated by short linker sequences of 2-6 amino acids each. Factor H binds to C3b, accelerates the decay of the alternative pathway C3-convertase (C3bBb), and acts as a cofactor for the proteolytic inactivation of C3b. In the presence of factor H, C3b proteolysis results in the cleavage of C3b. Factor H has at least three distinct binding domains for C3b, which are located within SCRs 1-4, SCRs 5-8, and SCRs 19-20. Each site of factor H binds to a distinct region within the C3b protein: the N-terminal sites bind to native C3b; the second site, located in the middle region of factor H, binds to the C3c fragment and the site located within SCR19 and 20 binds to the C3d region. In addition, factor H also contains binding sites for heparin, which are located within SCR 7, SCRs 5-12, and SCR 20 of factor H and overlap with those of the C3b binding sites. Structural and functional analyses have shown that the domains for the complement inhibitory activity of factor H are located within the first four N-terminal SCR domains.

SEQ ID NO:5 represents the full-length human factor H amino acid sequence (see, e.g., UniProtKB/Swiss-Prot. Accession No. P08603); SEQ ID NO:10 represents the full-length mouse factor H amino acid sequence (see, e.g., UniProtKB/Swiss-Prot. Accession No. P06909). In the human factor H sequence, amino acids 1-18 of SEQ ID NO:5 correspond to the signal peptide, and amino acids 19-1231 of SEQ ID NO:5 correspond to the mature protein. Within that protein, amino acids 21-80 of SEQ ID NO:5 correspond to SCR 1, amino acids 85-141 of SEQ ID NO:5 correspond to SCR 2, amino acids 146-205 of SEQ ID NO:5 correspond to SCR 3, amino acids 210-262 of SEQ ID NO:5 correspond to SCR 4, and amino acids 267-320 of SEQ ID NO:5 correspond to SCR 5. In the mouse factor H sequence, amino acids 1-18 of SEQ ID NO:10 correspond to the signal peptide, and amino acids 19-1234 of SEQ ID NO:10 correspond to the mature protein. Within that protein, amino acids 19-82 of SEQ ID NO:10 correspond to SCR 1, amino acids 83-143 of SEQ ID NO:10 correspond to SCR 2, amino acids 144-207 of SEQ ID NO:10 correspond to SCR 3, amino acids 208-264 of SEQ ID NO:10 correspond to SCR 4, and amino acids 265-322 of SEQ ID NO:10 correspond to SCR 5. It is understood that species and strain variations exist for the disclosed peptides, polypeptides, and proteins, and that factor H or biologically active fragments thereof encompasses all species and strain variations.

As used herein, the term "biologically active" fragment of factor H refers to any portion of a factor H protein having some or all the complement inhibitory activity of the full-length factor H protein, and includes, but is not limited to, factor H fragments comprising SCRs 1-4, SCRs 1-8, SCRs 1-18, SCRs 19-20, or any homolog of a naturally-occurring factor H or fragment thereof, as described in detail below. In certain embodiments, the biologically active fragment of factor H has one or more of the following properties: (1) binding to C-reactive protein (CRP), (2) binding to C3b, (3) binding to heparin, (4) binding to sialic acid, (5) binding to endothelial cell surfaces, (6) binding to cellular integrin receptor, (7) binding to pathogens, (8) C3b co-factor activity, (9) C3b decay-acceleration activity, and (10) inhibiting the alternative complement pathway.

In certain embodiments, the complement inhibitor portion of the targeted complement inhibitor comprises full-length human (SEQ ID NO:5) or mouse (SEQ ID NO:10) factor H. In certain embodiments, the complement inhibitor portion of the targeted complement inhibitor comprises a biologically active fragment of human or mouse factor H. In certain embodiments, the biologically active fragment of human or mouse factor H comprises the first four N-terminal SCR domains of factor H. In certain embodiments, the biologically active fragment of human or mouse factor H comprises the first five N-terminal SCR domains of factor H. In certain embodiments, the biologically active fragment of human or mouse factor H comprises the first six N-terminal SCR domains of factor H. In certain embodiments, the biologically active fragment of human or mouse factor H comprises the first eight N-terminal SCR domains of factor H. In certain embodiments, the biologically active fragment of human or mouse factor H comprises the first eighteen N-terminal SCR domains of factor H. In certain embodiments, the biologically active fragment of human or mouse factor H comprises SCRs 1-4 of factor H. In certain embodiments, the biologically active fragment of human or mouse factor H comprises SCRs 1-5 of factor H. In certain embodiments, the biologically active fragment of human or mouse factor H comprises SCRs 1-8 of factor H. In certain embodiments, the biologically active fragment of human or mouse factor H comprises SCRs 1-18 of factor H. In certain embodiments, the biologically active fragment of human or mouse factor H comprises (and in certain embodiments consists of or consists essentially of) at least the first four N-terminal SCR domains of factor H, including for example, at least any of the first 5, 6, 7, 8, 9, 10, 11, 12, 13, 14, 15, 16, 17, 18, or more N-terminal SCR domains of factor H.

In certain embodiments, the biologically active fragment of factor H is derived from a wild-type factor H. In certain embodiments, the biologically active fragment of factor H is derived from a naturally-occurring protective variant of factor H.

In certain embodiments, the biologically active fragment of factor H lacks a heparin binding site. This can be achieved, for example, by mutation of the heparin binding site on a biologically active fragment of factor H, or by selecting biologically active factor H fragments that do not contain a heparin binding site. In certain embodiments, the biologically active fragment of factor H has a polymorphism that is protective to age-related macular degeneration. Hageman et al., Proc. Nat'l Acad. Sci. USA 102(20):7227.

In certain embodiments, the targeted complement inhibitor comprises a CR2 portion and a human or mouse factor H portion. The CR2 portion of the targeted complement inhibitor delivers the composition to sites of IRI and/or regeneration (e.g., hepatic sites) by selectively binding to CR2 ligands (e.g., iC3b, C3dg, and C3d) present at those sites, while the human or mouse factor H portion of the targeted complement inhibitor inhibits activity of the alternative complement pathway. In certain embodiments, the targeted complement inhibitor comprises a non-CR2 targeting portion and a human or mouse factor H portion. The non-CR2 targeting portion of the fusion protein delivers the composition to sites of IRI and/or regeneration (e.g., hepatic sites) by selectively binding to CR2 ligands (i.e., proteolytic fragments of complement protein C3 (e.g., iC3b, C3dg, and C3d)) present at those sites, while the human or mouse factor H portion of the targeted complement inhibitor inhibits complement activity.

In certain embodiments, the targeted complement inhibitor comprises full-length human CR2 (SEQ ID NO:1) or SCR1-2 of human CR2 (SEQ ID NO:2) fused to full-length human factor H (SEQ ID NO:5). In certain embodiments, the targeted complement inhibitor comprises full-length human CR2 (SEQ ID NO:1) or SCR1-2 of human CR2 (SEQ ID NO:2) fused to a biologically active fragment of human factor H comprising the first four N-terminal SCR domains of human factor H (amino acids 21-262 of SEQ ID NO:5). In certain embodiments, the targeted complement inhibitor comprises full-length human CR2 (SEQ ID NO:1) or SCR1-2 of human CR2 (SEQ ID NO:2) fused to a biologically active fragment of human factor H comprising the first five N-terminal SCR domains of human factor H (amino acids 21-320 of SEQ ID NO:5). In certain embodiments, the targeted complement inhibitor comprises full-length human CR2 (SEQ ID NO:1) or SCR1-2 of human CR2 (SEQ ID NO:2) fused to a biologically active fragment of human factor H comprising the first six N-terminal SCR domains of human factor H (amino acids 21-386 of SEQ ID NO:5). In certain embodiments, the targeted complement inhibitor comprises full-length human CR2 (SEQ ID NO:1) or SCR1-2 of human CR2 (SEQ ID NO:2) fused to a biologically active fragment of human factor H comprising the first eight N-terminal SCR domains of human factor H (amino acids 21-507 of SEQ ID NO:5). In certain embodiments, the targeted complement inhibitor comprises full-length human CR2 (SEQ ID NO:1) or SCR1-2 of human CR2 (SEQ ID NO:2) fused to a biologically active fragment of human factor H comprising the first eighteen N-terminal SCR domains of human factor H (amino acids 21-1104 of SEQ ID NO:5).

In certain embodiments, the targeted complement inhibitor comprises full-length human CR2 (SEQ ID NO:1) or SCR1-2 of human CR2 (SEQ ID NO:2) fused to full-length mouse factor H (SEQ ID NO:10). In certain embodiments, the targeted complement inhibitor comprises full-length human CR2 (SEQ ID NO:1) or SCR1-2 of human CR2 (SEQ ID NO:2) fused to a biologically active fragment of mouse factor H comprising the first four N-terminal SCR domains of mouse factor H (amino acids 19-264 of SEQ ID NO:10). In certain embodiments, the targeted complement inhibitor comprises full-length human CR2 (SEQ ID NO:1) or SCR1-2 of human CR2 (SEQ ID NO:2) fused to a biologically active fragment of mouse factor H comprising the first five N-terminal SCR domains of mouse factor H (amino acids 19-322 of SEQ ID NO:10). In certain embodiments, the targeted complement inhibitor comprises full-length human CR2 (SEQ ID NO:1) or SCR1-2 of human CR2 (SEQ ID NO:2)

fused to a biologically active fragment of mouse factor H comprising the first six N-terminal SCR domains of mouse factor H (amino acids 19-386 of SEQ ID NO:10). In certain embodiments, the targeted complement inhibitor comprises full-length human CR2 (SEQ ID NO:1) or SCR1-2 of human CR2 (SEQ ID NO:2) fused to a biologically active fragment of mouse factor H comprising the first eight N-terminal SCR domains of mouse factor H (amino acids 19-624 of SEQ ID NO:10). In certain embodiments, the targeted complement inhibitor comprises full-length human CR2 (SEQ ID NO:1) or SCR1-2 of human CR2 (SEQ ID NO:2) fused to a biologically active fragment of mouse factor H comprising the first eighteen N-terminal SCR domains of mouse factor H (amino acids 19-1109 of SEQ ID NO:10).

In certain embodiments, the targeted complement inhibitor comprises a non-CR2 targeting portion fused to full-length human factor H (SEQ ID NO:5), to a biologically active fragment of human factor H comprising the first four N-terminal SCR domains of human factor H (amino acids 21-262 of SEQ ID NO:5), to a biologically active fragment of human factor H comprising the first five N-terminal SCR domains of human factor H (amino acids 21-320 of SEQ ID NO:5), to a biologically active fragment of human factor H comprising the first six N-terminal SCR domains of human factor H (amino acids 21-386 of SEQ ID NO:5), to a biologically active fragment of human factor H comprising the first eight N-terminal SCR domains of human factor H (amino acids 21-507 of SEQ ID NO:5), or to a biologically active fragment of human factor H comprising the first eighteen N-terminal SCR domains of human factor H (amino acids 21-1104 of SEQ ID NO:5).

In certain embodiments, the targeted complement inhibitor comprises a non-CR2 targeting portion fused to full-length mouse factor H (SEQ ID NO:10), to a biologically active fragment of mouse factor H comprising the first four N-terminal SCR domains of mouse factor H (amino acids 19-264 of SEQ ID NO:10), to a biologically active fragment of mouse factor H comprising the first five N-terminal SCR domains of mouse factor H (amino acids 19-322 of SEQ ID NO:10), to a biologically active fragment of mouse factor H comprising the first six N-terminal SCR domains of mouse factor H (amino acids 19-386 of SEQ ID NO:10), to a biologically active fragment of mouse factor H comprising the first eight N-terminal SCR domains of mouse factor H (amino acids 19-624 of SEQ ID NO:10), or to a biologically active fragment of mouse factor H comprising the first eighteen N-terminal SCR domains of mouse factor H (amino acids 19-1109 of SEQ ID NO:10).

In certain embodiments, the non-CR2 targeting portion comprises an antibody or antigen-binding fragment thereof that specifically binds to proteolytic fragments of complement protein C3 (e.g., iC3b, C3dg, and C3d). In certain embodiments, the antibodies are polyclonal antibodies. In certain embodiments, the antibodies are monoclonal antibodies. In certain embodiments, the antibodies are polyclonal or monoclonal antibody fragments selected from the group consisting of Fab, Fab'-SH, Fv, scFv, and $(Fab')_2$ fragments. In certain embodiments, the antibodies or antigen-binding fragments thereof are humanized antibodies. In certain embodiments, the antibodies or antigen-binding fragments thereof are human antibodies.

In certain embodiments, the complement inhibitor portion comprises a homolog of a human or mouse factor H protein or a biologically active fragment thereof. A homolog of a human of mouse factor H protein or a biologically active fragment thereof includes proteins which differ from a naturally occurring human or mouse factor H (or biologically active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol), but that retains the ability to inhibit the alternative complement pathway. For example, a human or mouse factor H homolog may have an amino acid sequence that is at least about 70% identical to the amino acid sequence of a naturally occurring human or mouse factor H (e.g., SEQ ID NO:5 or SEQ ID NO:10), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring human or mouse factor H (e.g., SEQ ID NO:5 or SEQ ID NO:10). In certain embodiments, a homolog of human or mouse factor H (or a biologically active fragment thereof) retains all the alternative complement pathway inhibitory activity of human or mouse factor H (or a biologically active fragment thereof). In certain embodiments, the homolog of human or mouse factor H (or a biologically active fragment thereof) retains at least about 50%, for example, at least about any of 60%, 70%, 80%, 90%, or 95% of the complement inhibitory activity of human or mouse factor H (or a biologically active fragment thereof).

In any of the embodiments described herein, the fusion protein comprising a CR2 portion or a biologically active fragment thereof and a complement inhibitor portion comprising human CD59, mouse CD59 isoform A, mouse CD59 isoform B, mouse Crry protein, human factor H, mouse factor H, human CR1, human MCP, human DAF or mouse DAF or a biologically active fragment thereof also includes an amino acid linker sequence linking the CR2 portion and the complement inhibitor portion (e.g., human CD59, mouse CD59 isoform A, mouse CD59 isoform B, mouse Crry protein, human factor H, mouse factor H, human CR1, human MCP, human DAF or mouse DAF or a biologically active fragment thereof). Examples of linker sequences are known in the art, and include, for example, $(Gly_4Ser)$, $(Gly_4Ser)_2$, $(Gly_4Ser)_3$, $(Gly_3Ser)_4$, $(SerGly_4)$, $(SerGly_4)_2$, $(SerGly_4)_3$, and $(SerGly_4)_4$. Linking sequences can also comprise "natural" linking sequences found between different domains of complement factors. For example, VSVFPLE, the linking sequence between the first two N-terminal short consensus repeat domains of human CR2, can be used. In some embodiments, the linking sequence between the fourth and the fifth N-terminal short consensus repeat domains of human CR2 (EEIF) is used.

Non-Targeted Complement Inhibitors

In certain embodiments, the compositions comprise non-targeted complement inhibitors. In certain embodiments, the non-targeted complement inhibitors inhibit the classical complement pathway and the alternative complement pathway. In certain embodiments, the non-targeted complement inhibitor that inhibits the classical complement pathway and the alternative complement pathway is C1-inhibitor protein or a biologically active fragment or homolog thereof.

As used herein, the term "C1-inhibitor" or "C1 esterase inhibitor" refers to a serine protease inhibitor (a "serpin protein") protein of 500 amino acids (human) or 504 amino acids (mouse) that inhibits formation of the classical pathway C3 convertase (C4b2a). C1-inhibitor circulates in blood at levels of around 0.25 g/L, rising to roughly twice that level during inflammation. C1-inhibitor irreversibly binds to and inactivates C1r and C1s proteinases in the C1 complex of classical pathway of complement, and also inactivates MASP-1 and MASP-2 proteinases of the lectin pathway. Thus, C1-inhibitor prevents the proteolytic cleavage of later complement components C4 and C2 by C1 and mannose-binding lectin. See, e.g., UniProtKB/Swiss-Prot. Accession No. P05155 (human C1-inhibitor protein; SEQ ID NO:19) or UniProtKB/Swiss-Prot. Accession No. P97290 (mouse C1-inhibitor protein; SEQ ID NO:20).

In certain embodiments, the non-targeted complement inhibitor comprises a homolog of a human or mouse C1-inhibitor protein or a biologically active fragment thereof. A homolog of a human or mouse C1-inhibitor protein or a biologically active fragment thereof includes proteins which differ from a naturally occurring human or mouse C1-inhibitor (or biologically active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol), but that retains the ability to inhibit the formation of the classical pathway C3 convertase (C4bC2a). For example, a human or mouse C1-inhibitor homolog may have an amino acid sequence that is at least about 70% identical to the amino acid sequence of a naturally occurring human or mouse clusterin (e.g., SEQ ID NO:19 or SEQ ID NO:20), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring human or mouse C1-inhibitor (e.g., SEQ ID NO:19 or SEQ ID NO:20). In certain embodiments, a homolog of human or mouse C1-inhibitor (or a biologically active fragment thereof) retains all the classical complement pathway inhibitory activity of human or mouse C1-inhibitor (or a biologically active fragment thereof). In certain embodiments, the homolog of human or mouse C1-inhibitor (or a biologically active fragment thereof) retains at least about 50%, for example, at least about any of 60%, 70%, 80%, 90%, or 95% of the complement inhibitory activity of human or mouse C1-inhibitor (or a biologically active fragment thereof).

In certain embodiments, the non-targeted complement inhibitor that inhibits the classical complement pathway and the alternative complement pathway is an anti-C3 antibody. In certain embodiments, the anti-C3 antibody or antigen-binding fragment thereof selectively binds to complement protein C3 and prevents cleavage of C3 into C3a and C3b.

As used herein, the term "C3" or "complement protein C3" refers to a component of all three complement pathways that C3 plays a central role in the activation of the complement system. Cleavage of C3 by the classical (C4bC2a) or alternative pathway (C3bBb) convertase is the central reaction in both classical and alternative complement pathways. Cleavage of C3 produces the active fragment C3b, which binds covalently to cell surface carbohydrates or immune aggregates via its reactive thioester. See, e.g., UniProtKB/Swiss-Prot. Accession No. P01024 (human) and UniProtKB/Swiss-Prot. Accession No. P01027 (mouse).

In certain embodiments, the anti-C3 antibody or antigen-binding fragment thereof is of a non-complement activating isotype or subclass. In certain embodiments, the antigen-binding fragment thereof is selected from the group consisting of Fab, Fab'-SH, Fv, scFv, and (Fab')$_2$ fragments. In certain embodiments, the anti-C3 antibody or antigen-binding fragment thereof is a monoclonal antibody, a humanized antibody, or a human antibody.

In certain embodiments, the non-targeted complement inhibitors specifically inhibit the alternative complement pathway. In certain embodiments, the non-targeted complement inhibitor that specifically inhibits the alternative complement pathway comprises an anti-factor B antibody. In certain embodiments, the anti-factor B antibody or antigen-binding fragment thereof selectively binds to factor B within the third short consensus repeat (SCR) domain and prevents formation of a C3bBb complex, as described in U.S. patent application Ser. No. 11/057,047, which is incorporated herein by reference, particularly with respect to its description of anti-factor B antibodies. In certain embodiments, the anti-factor B antibody selectively binds to factor B within the third short consensus repeat (SCR) domain and prevents or inhibits cleavage of factor B by factor D. In another aspect, the antibody or antigen-binding fragment binds to the third short consensus repeat (SCR) domain of human factor B. In certain embodiments, the anti-factor B antibody or antigen binding fragment thereof selectively binds to factor B from multiple mammalian species (e.g., human and an animal selected from the group consisting of non-human primate, mouse, rat, pig, horse and rabbit).

As used herein, the term "factor B" or "FB" refers to a protein component of the alternative complement pathway that factor D cleaves into 2 fragments: Ba and Bb. Bb, a serine protease, then combines with complement protein C3 cleavage product C3b to generate the C3 or C5 convertases. See, e.g., UniProtKB/Swiss-Prot. Accession No. P00751 (human) and UniProtKB/Swiss-Prot. Accession No. P04186 (mouse).

In certain embodiments, the anti-factor B antibody or antigen-binding fragment thereof is of a non-complement activating isotype or subclass. In certain embodiments, the antigen-binding fragment thereof is selected from the group consisting of Fab, Fab'-SH, Fv, scFv, and (Fab')$_2$ fragments. In certain embodiments, the anti-factor B antibody or antigen-binding fragment thereof is a monoclonal antibody, a humanized antibody, or a human antibody. In certain embodiments, the antibody is the monoclonal antibody 1379 (produced by ATCC Deposit No. PTA-6230).

In certain embodiments, the non-targeted complement inhibitor that specifically inhibits the alternative complement pathway comprises an anti-properdin antibody that selectively binds to properdin, such as those described in U.S. Pat. No. 7,423,128, which is incorporated herein by reference, particularly with respect to its description relating to anti-properdin antibodies. As used herein, the term "properdin" or "complement factor P" refers to a component of the alternative complement pathway that complexes with C3b, a proteolytic fragment of complement protein C3, to stabilize the alternative pathway C3 convertase (C3bBb), allowing it to generate still more C3, thereby amplifying the alternative complement cascade. See, e.g., UniProtKB/Swiss-Prot. Accession No. P27918 (human properdin) and Accession No. P11680 (mouse properdin).

In certain embodiments, the anti-properdin antibody inhibits the production of one or more of Bb, C3a, and C5a. In certain embodiments, the anti-properdin antibody or antigen-binding fragment thereof is of a non-complement activating isotype or subclass. In certain embodiments, the antigen-binding fragment thereof is selected from the group consisting of Fab, Fab'-SH, Fv, scFv, and (Fab')$_2$ fragments. In certain embodiments, the anti-properdin antibody or antigen-binding fragment thereof is a monoclonal antibody, a humanized antibody, or a human antibody.

In certain embodiments, the non-targeted complement inhibitor that specifically inhibits the alternative complement pathway comprises an anti-factor D antibody that selectively binds to factor D. As used herein, the term "factor D" refers to a serum protease that cleaves factor B when factor B is bound to factor C3b, activating the alternative pathway convertase (C3bBb). See, e.g., UniProtKB/Swiss-Prot. Accession No. P00746 (human factor D) and Accession No. P03953 (mouse factor D). Factor D performs the same function in the alternative complement pathway as does C1s in the classical complement pathway.

In certain embodiments, the anti-factor D antibody inhibits the production of one or more of Bb, C3a, C5a, and sC5b-9. In certain embodiments, the anti-factor D antibody or antigen-binding fragment thereof is of a non-complement activating isotype or subclass. In certain embodiments, the antigen-binding fragment thereof is selected from the group consisting of Fab, Fab'-SH, Fv, scFv, and (Fab')$_2$ fragments. In certain embodiments, the anti-factor D antibody or antigen-binding fragment thereof is a monoclonal antibody, a humanized antibody, or a human antibody. In certain embodiments, the antibody is the monoclonal antibody (mAb) 166-32 (produced by ATCC Deposit Accession_Number HB-12476).

In certain embodiments, the non-targeted complement inhibitors inhibit terminal complement and formation of the membrane attack complex (MAC). In certain embodiments, the non-targeted complement inhibitor is an anti-C5 antibody or antigen-binding fragment thereof that inhibits activation of terminal complement and formation of the membrane attack complex (MAC). In certain embodiments, the anti-C5 antibody or antigen-binding fragment thereof inhibits cleavage of complement protein C5 (C5). In certain embodiments, the anti-C5 antibody or antigen-binding fragment thereof inhibits assembly of the membrane attack complex (MAC). In certain embodiments, the anti-C5 antibody or antigen-binding fragment thereof is polyclonal, monoclonal, chimeric, or humanized. In certain embodiments, the antigen-binding fragments are selected from the group consisting of Fab, Fab', and F(ab')$_2$ fragments. In certain embodiments, the anti-C5 antibody or antigen-binding fragment thereof is polyclonal. In certain embodiments, the anti-C5 antibody or antigen-binding fragment thereof is monoclonal. In certain embodiments, the anti-C5 antibody or antigen-binding fragment thereof is chimeric. In certain embodiments, the anti-C5 antibody or antigen-binding fragment thereof is humanized. In certain embodiments, the humanized anti-C5 antibody or antigen-binding fragment thereof is eculizumab or pexelizumab.

In certain embodiments, the non-targeted complement inhibitor is the heterodimeric apolipoprotein clusterin. In certain embodiments, the clusterin inhibits terminal complement and assembly of the membrane attack complex (MAC). In certain embodiments, the clusterin inhibits complement protein C9 assembly on C5b-8 and C5b-9 or binds to C5b-7 to prevent membrane attachment.

As used herein, the term "clusterin" refers to an 80 kilo-Dalton (kD) heterdimeric apolipoprotein (e.g., UniProtKB/Swiss-Prot Accession No. P10909 (SEQ ID NO:15) or UniProtKB/Swiss-Prot Accession No. Q06890) (SEQ ID NO:16). Human clusterin is produced as a protein of 449 amino acids, of which amino acids 1-22 constitute the signal peptide, and amino acids 23-449 constitute the mature peptide, which undergoes further processing via proteolytic cleavage between amino acids 227 and 228 to produce the clusterin alpha chain (amino acids 228-449 of SEQ ID NO:15) and the clusterin beta chain (amino acids 23-227 of SEQ ID NO:15). Mouse clusterin is produced as a protein of 448 amino acids, of which amino acids 1-21 constitute the signal peptide, and amino acids 22-448 constitute the mature peptide, which undergoes further processing via proteolytic cleavage between amino acids 226 and 227 to produce the clusterin alpha chain (amino acids 227-447 of SEQ ID NO:16) and the clusterin beta chain (amino acids 22-226 of SEQ ID NO:16).

In certain embodiments, the non-targeted complement inhibitor comprises a homolog of a human or mouse clusterin protein or a biologically active fragment thereof. A homolog of a human or mouse clusterin protein or a biologically active fragment thereof includes proteins which differ from a naturally occurring human or mouse clusterin (or biologically active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol), but that retains the ability to inhibit the terminal complement pathway and assembly of the MAC. For example, a human or mouse clusterin homolog may have an amino acid sequence that is at least about 70% identical to the amino acid sequence of a naturally occurring human or mouse clusterin (e.g., SEQ ID NO:15 or SEQ ID NO:16), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring human or mouse clusterin (e.g., SEQ ID NO:15 or SEQ ID NO:16). In certain embodiments, a homolog of human or mouse clusterin (or a biologically active fragment thereof) retains all the terminal complement pathway inhibitory activity of human or mouse clusterin (or a biologically active fragment thereof). In certain embodiments, the homolog of human or mouse clusterin (or a biologically active fragment thereof) retains at least about 50%, for example, at least about any of 60%, 70%, 80%, 90%, or 95% of the complement inhibitory activity of human or mouse clusterin (or a biologically active fragment thereof).

In certain embodiments, the non-targeted complement inhibitor is the protein vitronectin or a biologically active fragment or homolog thereof. In certain embodiments, the vitronectin inhibits terminal complement and assembly of the membrane attack complex (MAC). In certain embodiments, the vitronectin blocks C5b-7 membrane binding and prevents C9 polymerization.

As used herein, the term "vitronectin" refers to a 75 kDa protein (e.g., UniProtKB/Swiss-Prot. Accession No. P04004 (SEQ ID NO:17); or UniProtKB/Swiss-Prot. Accession No. P29788 (SEQ ID NO:18). Human vitronectin is produced as a protein of 478 amino acids, of which amino acids 1-19 comprise the signal peptide and amino acids 20-478 comprise the mature protein. The mature human protein occurs in a monomeric form as a 75 kDa protein, and as a heterodimeric form resulting from proteolytic processing between amino acids 398 and 399, producing a 65 kDa subunit (amino acids 20-398 of SEQ ID NO:17) and a 10 kDa subunit (amino acids 399-478 of SEQ ID NO:17) held together by disulfide bonds. Mouse vitronectin is also produced as a protein of 478 amino acids, of which amino acids 1-19 comprise the signal peptide and amino acids 20-478 comprise the mature protein. Unlike human vitronectin, however, the mature mouse protein generally occurs in a monomeric form as a 75 kDa protein, comprising amino acids 20-478 of SEQ ID NO:18.

In certain embodiments, the non-targeted complement inhibitor comprises a homolog of a human or mouse vitronectin protein or a biologically active fragment thereof. A homolog of a human or mouse vitronectin protein or a biologically active fragment thereof includes proteins which differ from a naturally occurring human or mouse clusterin (or biologically active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol), but that retains the ability to inhibit the terminal complement pathway and assembly of the MAC. For example, a human or mouse vitronectin homolog may have an amino acid sequence that is at least about 70% identical to the amino acid sequence of a naturally occurring human or mouse vitronectin (e.g., SEQ ID NO:17 or SEQ ID NO:18), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring human or mouse vitronectin (e.g., SEQ ID NO:17 or SEQ ID NO:18). In certain embodiments, a homolog of human or mouse vitronectin (or a biologically active fragment thereof) retains all the terminal complement pathway inhibitory activity of human or mouse vitronectin (or a biologically active fragment thereof). In certain embodiments, the homolog of human or mouse vitronectin (or a biologically active fragment thereof) retains at least about 50%, for example, at least about any of 60%, 70%, 80%, 90%, or 95% of the complement inhibitory activity of human or mouse vitronectin (or a biologically active fragment thereof).

Acylation Stimulating Protein (ASP/C3adesArg) and ASP/C3adesArg Receptor (C5L2) Antagonists As used herein, the terms "acylation stimulating protein," "ASP," "C3adesArg," or "ASP/C3adesArg" refer to an adipose tissue-derived hormone that stimulates adipocyte triglyceride (TG) synthesis and glucose transport. ASP/C3adesArg acts through the receptor C5L2, a G protein-coupled receptor, to stimulate diacylglycerol acyltransferase activity (DGAT), the rate-limiting enzyme in the TG synthesis pathway, and glucose transport. SEQ ID NO:6 represents the amino acid sequence of human ASP/C3adesArg, which lacks the COOH-terminal asparagine present in human C3a, a cleavage product of complement protein C3. The potent anaphylatoxic activity of C3a depends largely on the COOH-terminal asparagine; removal of the asparagine by carboxypeptidase A eliminates that activity.

ASP/C3adesArg is generated through the alternative pathway of complement activation, based on differentiation-dependent expression of adipsin (factor D), complement protein C3, and factor B (FB) in adipose tissue. Baldo, A. D. et al. (1993) *J. Clin. Invest.* 92:1543-57. The alternative pathway C3 convertase, a proteolytic complex formed by the interaction of C3b, FB, and factor D (adipsin), cleaves complement protein C3 into two fragments, C3a and C3b. C3a is a potent anaphylatoxin interacting with its receptor C3aR. However, in the circulation, the terminal arginine of C3a is rapidly cleaved by carboxypeptidase B, inactivating the anaphylatoxic function and generating ASP/C3adesArg. Both ASP/C3adesArg and C3a interact with the ASP/C3adesArg receptor (C5L2) to effectively stimulate TG synthesis in cultured adipocytes.

In certain embodiments, the compositions comprise an ASP/C3adesArg antagonist. In certain embodiments, the ASP/C3adesArg antagonist is selected from the group consisting of an antibody or antigen-binding fragment thereof that specifically binds to ASP/C3adesArg and prevents it from binding to the ASP/C3adesArg receptor (C5L2) and soluble ASP/C3adesArg receptor (C5L2) fragments that specifically bind to ASP/C3adesArg and prevent it from binding to the ASP/C3adesArg receptor (C5L2). In certain embodiments, the ASP/C3adesArg antagonist comprises an antibody or antigen-binding fragment thereof that specifically binds to ASP/C3adesArg and prevents it from binding to the ASP/C3adesArg receptor (C5L2). In certain embodiments, the antibody that specifically binds to ASP/C3adesArg and prevents it from binding to the ASP/C3adesArg receptor (C5L2) is polyclonal, monoclonal, chimeric, or humanized. In certain embodiments, the antigen-binding fragment that specifically binds to ASP/C3adesArg and prevents it from binding to the ASP/C3adesArg receptor (C5L2) is selected from the group consisting of Fab, Fab', and $F(ab')_2$ fragments.

ASP/C3adesArg acts through C5L2, a G protein-coupled receptor (GPCR). As used herein, the term "C5L2," "ASP receptor," or ASP/C3adesArg receptor (C5L2)" refers to a G-protein coupled receptor that specifically binds ASP/C3adesArg and is expressed in human adipose tissue, liver, brain, spleen, intestine, human skin fibroblasts, and 3T3-L1 cells. Gain-of-function studies in human HEK-293 cells stably transfected with human C5L2 showed that TG synthesis and glucose transport were significantly increased upon ASP/C3adesArg stimulation compared to untransfected cells. Loss-of-function studies showed that cells endogenously expressing C5L2 treated with antisense nucleic acid or small interfering RNA specific for C5L2 had decreased ASP/C3adesArg response. In addition, activation of C5L2 by ASP/C3adesArg-induced beta-arrestin translocation to the plasma membrane and phosphorylation of C5L2. Molecules shown to be involved in C5L2 signaling include phosphatidylinositol 3-kinasse, Akt, and protein kinase C.

SEQ ID NO:7 represents the amino acid sequence of the ASP/C3adesArg receptor (C5L2) (see, e.g., UniProtKB/Swiss-Prot. Accession No. Q9P296). The ASP/C3adesArg receptor (C5L2) has a complex structure comprising several extracellular, transmembrane, and intracellular or cytoplasmic domains. Amino acids 1-38 of SEQ ID NO:7 comprise the first extracellular domain (ECD1); amino acids 39-61 of SEQ ID NO:7 comprise the first transmembrane domain (TM1); amino acids 62-72 of SEQ ID NO:7 comprise the first cytoplasmic domain (CPD1); amino acids 73-95 of SEQ ID NO:7 comprise the second transmembrane domain (TM2); amino acids 96-114 of SEQ ID NO:7 comprise the second extracellular domain (ECD2); amino acids 115-137 of SEQ ID NO:7 comprise the third transmembrane domain (TM3); amino acids 138-149 of SEQ ID NO:7 comprise the second cytoplasmic domain (CPD2); amino acids 150-172 of SEQ ID NO:7 comprise the fourth transmembrane domain (TM4); amino acids 173-202 of SEQ ID NO:7 comprise the third extracellular domain (ECD3); amino acids 203-225 of SEQ ID NO:7 comprise the fifth transmembrane domain (TM5); amino acids 226-237 of SEQ ID NO:7 comprise the third cytoplasmic domain (CPD3); amino acids 238-260 of SEQ ID NO:7 comprise the sixth transmembrane domain (TM6); amino acids 261-274 of SEQ ID NO:7 comprise the fourth extracellular domain (ECD4); amino acids 275-294 of SEQ ID NO:7 comprise the seventh transmembrane domain (TM7); and amino acids 295-337 of SEQ ID NO:7 comprise the fourth cytoplasmic domain (CPD4).

In certain embodiments, the ASP/C3adesArg antagonist is a soluble ASP/C3adesArg receptor (C5L2) fragment that specifically binds to ASP/C3adesArg and prevents ASP/C3adesArg from binding to the ASP/C3adesArg receptor (C5L2). In certain embodiments, the soluble ASP/C3adesArg receptor (C5L2) fragment comprises amino acids 1-38 (ECD1) of the ASP/C3adesArg receptor (C5L2) (SEQ ID NO:7). In certain embodiments, the soluble ASP/C3adesArg receptor (C5L2) fragment comprises amino acids 96-114 (ECD2) of the ASP/C3adesArg receptor (C5L2) (SEQ ID NO:7). In certain embodiments, the soluble ASP/C3adesArg receptor (C5L2) fragment comprises amino acids 173-202 (ECD3) of the ASP/C3adesArg receptor (C5L2) (SEQ ID NO:7). In certain embodiments, the soluble ASP/C3adesArg receptor (C5L2) fragment comprises amino acids 261-274 (ECD4) of the ASP/C3adesArg receptor (C5L2) (SEQ ID NO:7).

In certain embodiments, the soluble ASP/C3adesArg receptor (C5L2) fragment comprises amino acids 1-38 (ECD1) and amino acids 96-114 (ECD2) of the ASP/C3adesArg receptor (C5L2) (SEQ ID NO:7). In certain embodiments, the soluble ASP/C3adesArg receptor (C5L2) fragment comprises amino acids 1-38 (ECD1) and amino acids 173-202 (ECD3) of the ASP/C3adesArg receptor (C5L2) (SEQ ID NO:7). In certain embodiments, the soluble ASP/C3adesArg receptor (C5L2) fragment comprises amino acids 1-38 (ECD1) and amino acids 261-274 (ECD4) of the ASP/C3adesArg receptor (C5L2) (SEQ ID NO:7). In certain embodiments, the soluble ASP/C3adesArg receptor (C5L2) fragment comprises amino acids 96-114 (ECD2) and amino acids 173-202 (ECD3) of the ASP/C3adesArg receptor (C5L2) (SEQ ID NO:7). In certain embodiments, the soluble ASP/C3adesArg receptor (C5L2) fragment comprises amino acids 96-114 (ECD2) and amino acids 261-274 (ECD4) of the ASP/C3adesArg receptor (C5L2) (SEQ ID NO:7). In certain embodiments, the soluble ASP/C3adesArg receptor (C5L2) fragment comprises amino acids 173-202 (ECD3) and amino acids 261-274 (ECD4) of the ASP/C3adesArg receptor (C5L2) (SEQ ID NO:7).

In certain embodiments, the soluble ASP/C3adesArg receptor (C5L2) fragment comprises amino acids 1-38 (ECD1), amino acids 96-114 (ECD2), and amino acids 173-202 (ECD3) of the ASP/C3adesArg receptor (C5L2) (SEQ ID NO:7). In certain embodiments, the soluble ASP/C3adesArg receptor (C5L2) fragment comprises amino acids 1-38 (ECD1), amino acids 96-114 (ECD2), amino acids 173-202 (ECD3), and amino acids 261-274 (ECD4) of the ASP/C3adesArg receptor (C5L2) (SEQ ID NO:7). In certain embodiments, the soluble ASP/C3adesArg receptor (C5L2) fragment comprises amino acids 1-38 (ECD1), amino acids 173-202 (ECD3), and amino acids 261-274 (ECD4) of the ASP/C3adesArg receptor (C5L2) (SEQ ID NO:7). In certain embodiments, the soluble ASP/C3adesArg receptor (C5L2) fragment comprises amino acids 96-114 (ECD2), amino acids 173-202 (ECD3), and amino acids 261-274 (ECD4) of the ASP/C3adesArg receptor (C5L2) (SEQ ID NO:7).

In any of the embodiments described herein, the soluble ASP/C3adesArg receptor (C5L2) fragment further comprises one or more amino acid linker sequences linking the ASP/C3adesArg receptor (C5L2) portions together. Examples of linker sequences are known in the art, and include, for example, $(Gly_4Ser)$, $(Gly_4Ser)_2$, $(Gly_4Ser)_3$, $(Gly_3Ser)_4$, $(SerGly_4)$, $(SerGly_4)_2$, $(SerGly_4)_3$, and $(SerGly_4)_4$. Linking sequences can also comprise "natural" linking sequences found between different domains of complement factors. For example, VSVFPLE, the linking sequence between the first two N-terminal short consensus repeat domains of human CR2, can be used.

In certain embodiments, the compositions comprise ASP/C3adesArg receptor (C5L2) antagonists. In certain embodiments, the ASP/C3adesArg receptor (C5L2) antagonist is selected from the group consisting of an antibody or antigen-binding fragment thereof that specifically binds to ASP/C3adesArg receptor (C5L2) and prevents ASP/C3adesArg from binding and ASP/C3adesArg or a fragment thereof that specifically binds to ASP/C3adesArg receptor (C5L2) but does not activate the receptor. In certain embodiments, the ASP/C3adesArg receptor (C5L2) antagonist is an antibody or antigen-binding fragment thereof that specifically binds to ASP/C3adesArg receptor (C5L2) and prevents ASP/C3adesArg from binding. In certain embodiments, the antibody that specifically binds to ASP/C3adesArg receptor (C5L2) and prevents ASP/C3adesArg from binding to the receptor is polyclonal, monoclonal, chimeric, or humanized. In certain embodiments, the antigen-binding fragment that specifically bind to ASP/C3adesArg and prevents it from binding to the ASP/C3adesArg receptor (C5L2) is selected from the group consisting of Fab, Fab', and $F(ab')_2$ fragments. In certain embodiments, the ASP/C3adesArg receptor (C5L2) antagonist is ASP/C3adesArg or a fragment thereof that specifically binds to ASP/C3adesArg receptor (C5L2) but does not activate the receptor.

As used herein, the term "specifically binds to" or "selectively binds to" refers to the specific binding of one protein to another (e.g., an antibody or antigen-binding fragment thereof to an antigen, or a receptor to a ligand), wherein the level of binding, as measured by any standard assay (e.g., an immunoassay), is statistically significantly higher than the background control for the assay. For example, when performing an immunoassay, controls typically include a reaction well or tube that contains an antibody or antigen-binding fragment thereof alone (i.e., in the absence of antigen), wherein an amount of reactivity (e.g., non-specific binding to the well) by the antibody or antigen-binding fragment thereof in the absence of the antigen is considered to be background. Binding can be measured using a variety of methods standard in the art, including, but not limited to: Western blot, immunoblot, enzyme-linked immunosorbant assay ("ELISA"), radioimmunoassay ("RIA"), immunoprecipitation, surface plasmon resonance, chemiluminescence, fluorescent polarization, phosphorescence, immunohistochemical analysis, matrix-assisted laser desorption/ionization time-of-flight ("MALDI-TOF") mass spectrometry, microcytometry, microarray, microscopy, fluorescence activated cell sorting ("FACS"), and flow cytometry.

As used herein, the term "antibody or antigen-binding fragment thereof that specifically binds to ASP/C3adesArg" refers to an antibody that specifically or selectively binds to ASP/C3adesArg, or a fragment of such an antibody that retains the ability to specifically or selectively bind to ASP/C3adesArg, and preferably prevents it from binding to its cognate receptor, ASP/C3adesArg receptor (C5L2). Similarly, as used herein, the term "antibody or antigen-binding fragment thereof that specifically binds to ASP/C3adesArg receptor (C5L2)" refers to an antibody that specifically or selectively binds to ASP/C3adesArg receptor (C5L2), or a fragment of such an antibody that retains the ability to specifically or selectively bind to ASP/C3adesArg receptor (C5L2), and preferably prevents it from binding to its cognate ligand, ASP/C3adesArg.

Antibodies contain immunoglobulin (Ig) domains and are members of the Ig superfamily of proteins. Generally, an antibody molecule comprises two types of chains: a heavy or H chain, and a light or L chain. The light chain contains a variable domain ($V_L$) and a constant domain ($C_L$), while the heavy chain contains a variable domain ($V_H$) and three constant domains ($C_H1$, $C_H2$, and $C_H3$), with the $C_H1$ and $C_H2$ domains separated by a hinge region. The distinctive characteristics of each isotype are defined by sequences in the constant domain of the immunoglobulin. Each antibody molecule typically contains two H chains and two L chains. The two H chains are linked together by disulfide bonds and each H chain is linked to an L chain by a disulfide bond. There are only two types of L chains referred to as lambda (μ) and kappa (κ) chains. In contrast, there are five major H chain classes, referred to as isotypes. The five classes include IgM (λ), IgD (δ), IgG (λ), IgA (α), and IgE (or ε). Human immunoglobulin molecules comprise nine isotypes: IgM, IgD, IgE, four subclasses of IgG including $IgG_1$ ($\gamma_1$), $IgG_2$ ($\gamma_2$), $IgG_3$ ($\gamma_3$) and $IgG_4$ ($\gamma_4$), and two subclasses of IgA including $IgA_1$ ($\alpha_1$) and $IgA_2$ ($\alpha_2$).

Together, one H chain and one L chain form an arm of an immunoglobulin molecule having an immunoglobulin variable region. A complete immunoglobulin molecule comprises two di-sulfide linked arms. Thus, each arm of a whole immunoglobulin comprises a $V_{H+L}$ region, and a $C_{H+L}$ region. As used herein, the variable region or V region refers to a $V_{H+L}$ region (also known as an Fv fragment), a $V_L$ region, or a $V_H$ region of an Ig protein. Also as used herein, the term constant region or C region refers to a $C_{H+L}$ region, a $C_L$ region or a $C_H$ region.

Limited digestion of an Ig protein with different proteases produces a number of fragments, only some of which retain the capacity to bind antigen. The antigen-binding fragments are referred to as Fab, Fab', or F(ab')$_2$ fragments. A fragment lacking the ability to bind to antigen is referred to as an Fc fragment. An Fab fragment comprises one arm of an immunoglobulin molecule containing an L chain ($V_L$+$C_L$ domains) paired with the $V_H$ region and the $C_H$1 region. An Fab' fragment corresponds to an Fab fragment with part of the hinge region attached to the $C_H$1 domain. An F(ab')$_2$ fragment corresponds to two Fab' fragments that are normally covalently linked to each other through a disulfide bond, typically in the hinge region.

The antibodies or antigen-binding fragments thereof described herein may also be "chimeric" antibodies in which a portion of the heavy and/or light chain is identical with or homologous to corresponding sequences in antibodies derived from a particular species (e.g., human or mouse and the like) or belonging to a particular antibody class or subclass (e.g., $IgG_1$ and the like), while the remainder of the chain(s) is(are) identical with or homologous to corresponding sequences in antibodies derived from another species or belonging to another antibody class or subclass, as well as fragments of such antibodies, so long as they exhibit the desired biological activity. U.S. Pat. No. 4,816,567; Morrison et al., Proc. Nat'l Acad. Sci. USA, 81:6851-55 (1984). Chimeric antibodies of interest herein may include, for example, those comprising Fc domains from other immunoglobulin subtypes having shorter or longer circulating plasma half lives than the corresponding non-chimeric antibody.

ASP/C3adesArg antibodies, ASP/C3adesArg receptor (C5L2) antibodies, or fragments of such antibodies described herein may also be humanized antibodies. Humanized antibodies are molecules having an antigen-binding site derived from an immunoglobulin from a non-human species, the remaining immunoglobulin-derived parts of the molecule being derived from a human immunoglobulin, in order to reduce immunogenicity of the protein. The antigen-binding site may comprise either complete variable regions fused onto human constant domains or only the complementarity determining regions (CDRs) grafted onto appropriate human framework regions in the variable domains. Humanized antibodies can be produced, for example, by modeling the antibody variable domains and producing the antibodies using genetic engineering techniques, such as CDR grafting. A description of various techniques for the production of humanized antibodies is found, for example, in Morrison et al., (1984) Proc. Nat'l Acad. Sci. USA 81:6851-55; Whittle et al., (1987) Prot. Eng. 1:499-505; Co et al., (1990) J. Immunol. 148:1149-1154; Co et al., (1992) Proc. Nat'l Acad. Sci. USA 88:2869-2873; Carter et al., (1992) Proc. Nat'l Acad. Sci. USA 89:4285-4289; Routledge et al., (1991) Eur. J. Immunol. 21:2717-2725 and PCT Patent Publication Nos. WO 91/09967; WO 91/09968 and WO 92/113831.

Whole antibodies of the present invention can be polyclonal or monoclonal. Alternatively, functional equivalents of whole antibodies, such as antigen-binding fragments in which one or more antibody domains are truncated or absent (e.g., Fv, Fab, Fab', or F(ab)$_2$ fragments), as well as genetically-engineered antibodies or antigen-binding fragments thereof, including single chain antibodies, humanized antibodies (discussed above), antibodies that can bind to more than one epitope (e.g., bi-specific antibodies), or antibodies that can bind to one or more different antigens (e.g., bi- or multi-specific antibodies), may also be used as targeting groups.

Methods of producing polyclonal antibodies that specifically or selectively bind to a particular antigen (i.e., ASP/C3adesArg or ASP/C3adesArg receptor (C5L2)) are known in the art. Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired (i.e., ASP/C3adesArg or ASP/C3adesArg receptor (C5L2)). Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate to precipitate the antibodies.

Methods of producing monoclonal antibodies that specifically or selectively bind to a particular antigen (i.e., ASP/C3adesArg or ASP/C3adesArg receptor (C5L2)) are known in the art. For example, monoclonal antibodies may be produced according to the methodology of Kohler and Milstein (Nature (1975) 256:495-497). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen, for example in an enzyme-linked immunosorbent assay or other routine method known in the art.

A preferred method to produce antibodies of the present invention includes (a) administering to an animal an effective amount of a protein or peptide (e.g., ASP/C3adesArg protein or peptide, or ASP/C3adesArg receptor (C5L2) protein or peptide) to produce the antibodies and (b) recovering the antibodies. In another method, antibodies of the present invention are produced recombinantly. For example, once a cell line, for example a hybridoma, expressing an antibody according to the invention has been obtained, it is possible to clone therefrom the cDNA and to identify the variable region genes encoding the desired antibody, including the sequences encoding the CDRs. From there, antibodies and antigen-binding fragments according to the invention may be obtained by preparing one or more replicable expression vectors containing at least the DNA sequence encoding the variable domain of the antibody heavy or light chain and optionally other DNA sequences encoding remaining portions of the heavy and/or light chains as desired, and transforming or transfecting an appropriate host cell, in which production of the antibody will occur. Suitable expression hosts include bacteria, (for example, an *E. coli* strain), fungi, (in particular yeasts, e.g., members of the genera *Pichia, Saccharomyces,* or *Kluyveromyces*) and mammalian cell lines, e.g., a non-producing myeloma cell line, such as a mouse NSO line, or CHO cells. In order to obtain efficient transcription and translation, the DNA sequence in each vector should include appropriate regulatory sequences, particularly a promoter and leader sequence operably-linked to the variable domain sequence. Particular methods for producing antibodies in this way are generally well known and routinely used. For example, basic molecular biology procedures are described by Maniatis et al. (Molecular Cloning, Cold Spring Harbor Laboratory, New York, 1989); DNA sequencing can be performed as described in Sanger et al. (*Proc. Nat'l Acad. Sci. USA* (1977) 74:5463) and the Amersham International plc sequencing handbook; and site directed mutagenesis can be carried out according to the method of Kramer et al. (*Nucl. Acids Res.* (1984) 12:9441) and the Anglian Biotechnology Ltd. handbook. Additionally, there are numerous publications, including patent specifications, describing techniques suitable for the preparation of antibodies by manipulation of DNA, creation of expression vectors and transformation of appropriate cells, for example as reviewed by Mountain, A. and Adair, J. R., in BIOTECHNOLOGY AND GENETIC ENGINEERING REVIEWS (ed. Tombs, M P, 10, Chapter 1, 1992, Intercept, Andover, UK).

Pharmaceutical Compositions and Doses

Also provided herein are pharmaceutical compositions comprising any one or more of the targeted complement inhibitors, non-targeted complement inhibitors, ASP/C3adesArg antagonists, or ASP/C3adesArg receptor (C5L2) antagonists described herein, and a pharmaceutically acceptable carrier.

In any of the embodiments described herein, the pharmaceutical compositions are suitable for administration to an individual. In certain embodiments, the individual is a vertebrate. In certain embodiments, the vertebrate is a mammal. In certain embodiments, the mammal is a research animal or a domestic animal. In certain embodiments, the mammal is a human. In any of the embodiments described herein, the pharmaceutical compositions are suitable for a variety of modes of administration, including, for example, systemic or localized administration. In certain embodiments, the pharmaceutical compositions are in the form of injectable solutions and suitable for systemic administration, such as, for example, intravenous administration. In certain embodiments, the pharmaceutical compositions are in the form of injectable solutions and suitable for local administration. In any of the embodiments, the pharmaceutical compositions are in a liquid or solid form suitable for oral administration. In any of the embodiments described herein, the pharmaceutical compositions can be packaged in single unit dosages or in multidosage forms.

In clinical terms, a therapeutically effective dosage for administration of any of the pharmaceutical compositions described herein, including targeted and non-targeted complement inhibitors, may be determined by titration, starting at a low dose and increasing the dosage while monitoring the patient until indications of the desired complement-dependent proliferative response are observed (such as 5-bromo-2'-deoxyuridine (BrdU) incorporation; increased levels of the reduced form of glutathione (GSH); increased glutathione peroxidase (GPX1); decreased malondialdehyde (MDA); increased levels of IL-6; and/or decreased levels of TNFa).

If desired, the clinician may further increase the dosage while monitoring the patient to ensure that the complement-dependent proliferative response is maintained, while further monitoring the patient for the appearance of undesired indications of complement-dependent injury (such as increased serum alanine aminotransferase (ALT) levels; reduced GSH and GPX1; increased MDA; increased liver myeloperoxidase (MPO) content; decreased levels of IL-6; and increased levels of TNFa). When these indications of complement-dependent injury are observed, the clinician may choose to cease increasing the dosage, or even decrease the dosage.

In certain embodiments, the pharmaceutical compositions comprise a targeted complement inhibitor comprising full-length CR2 protein (SEQ ID NO:1) fused to full-length human MCP (amino acids 35-392 of SEQ ID NO:12) and a pharmaceutically acceptable carrier suitable for administration to an individual. In certain embodiments, the pharmaceutical compositions comprise a targeted complement inhibitor comprising full-length CR2 protein (SEQ ID NO:1) fused to a biologically active fragment of MCP protein comprising the extracellular domain of human MCP (amino acids 35-343 of SEQ ID NO:12) and a pharmaceutically acceptable carrier suitable for administration to an individual. In certain embodiments, the pharmaceutical compositions comprise a targeted complement inhibitor comprising full-length CR2 protein (SEQ ID NO:1) fused to SCRs 1-4 of human MCP (amino acids 35-285 of SEQ ID NO:12) and a pharmaceutically acceptable carrier suitable for administration to an individual.

In certain embodiments, the pharmaceutical compositions comprise a targeted complement inhibitor comprising a biologically active fragment of CR2 protein comprising SCR1-2 (SEQ ID NO:2) fused to full-length human MCP (amino acids 35-392 of SEQ ID NO:12) and a pharmaceutically acceptable carrier suitable for administration to an individual. In certain embodiments, the pharmaceutical compositions comprise a targeted complement inhibitor comprising a biologically active fragment of CR2 protein comprising SCR1-2 (SEQ ID NO:2) fused to a biologically active fragment of MCP protein comprising the extracellular domain of human MCP (amino acids 35-343 of SEQ ID NO:12) and a pharmaceutically acceptable carrier suitable for administration to an individual. In certain embodiments, the pharmaceutical compositions comprise a targeted complement inhibitor comprising a biologically active fragment of CR2 protein comprising SCR1-2 (SEQ ID NO:2) fused to SCRs 1-4 of human MCP (amino acids 35-285 of SEQ ID NO:12) and a pharmaceutically acceptable carrier suitable for administration to an individual.

In certain embodiments, the pharmaceutical compositions comprise a targeted complement inhibitor comprising full-length CR2 protein (SEQ ID NO:1) fused to full-length human DAF (SEQ ID NO:13) or to full-length mouse DAF (SEQ ID NO:14) and a pharmaceutically acceptable carrier suitable for administration to an individual. In certain embodiments, the pharmaceutical compositions comprise a targeted complement inhibitor comprising full-length CR2 protein (SEQ ID NO:1) fused to full-length human DAF (SEQ ID NO:13) or to full-length mouse DAF (SEQ ID NO:14) and a pharmaceutically acceptable carrier suitable for administration to an individual. In certain embodiments, the pharmaceutical compositions comprise a targeted complement inhibitor comprising full-length CR2 protein (SEQ ID NO:1) fused to full-length human DAF (SEQ ID NO:13) or to full-length mouse DAF (SEQ ID NO:14) and a pharmaceutically acceptable carrier suitable for administration to an individual.

In certain embodiments, the pharmaceutical compositions comprise a targeted complement inhibitor comprising a biologically active fragment of CR2 protein comprising SCR1-2 (SEQ ID NO:2) fused to full-length human DAF (SEQ ID NO:13) or to full-length mouse DAF (SEQ ID NO:14) and a pharmaceutically acceptable carrier suitable for administration to an individual. In certain embodiments, the pharmaceutical compositions comprise a targeted complement inhibitor comprising a biologically active fragment of CR2 protein comprising SCR1-2 (SEQ ID NO:2) fused to a biologically active fragment of human DAF comprising the mature human DAF protein (amino acids 35-353 of SEQ ID NO:13) without its GPI anchor and/or the amino acid to which it is attached (i.e., Ser-353) or to a biologically active fragment of mouse DAF comprising the mature mouse DAF protein (amino acids 35-362 of SEQ ID NO:14) without its GPI anchor and/or the amino acid to which it is attached (i.e., Ser-362) and a pharmaceutically acceptable carrier suitable for administration to an individual. In certain embodiments, the pharmaceutical compositions comprise a targeted complement inhibitor comprising a biologically active fragment of CR2 protein comprising SCR1-2 (SEQ ID NO:2) fused to a biologically active fragment of human DAF comprising short consensus repeat sequences 1-4 (SCRs 1-4) of full-length human DAF (amino acids 35 to 285 of SEQ ID NO:13) or to a biologically active fragment of mouse DAF comprising short consensus repeat sequences 1-4 (SCRs 1-4) of full-length mouse DAF (amino acids 35 to 286 of SEQ ID NO:14) and a pharmaceutically acceptable carrier suitable for administration to an individual.

In certain embodiments, the pharmaceutical compositions comprise a targeted complement inhibitor comprising full-length CR2 protein (SEQ ID NO:1) fused to full-length human CD59 protein (SEQ ID NO:3), to full-length mouse CD59 protein, isoform A (SEQ ID NO:8), or to full-length mouse CD59 protein, isoform B (SEQ ID NO:9) and a pharmaceutically acceptable carrier suitable for administration to an individual. In certain embodiments, the pharmaceutical compositions comprise a targeted complement inhibitor comprising full-length CR2 protein (SEQ ID NO:1) fused to a biologically active fragment of CD59 protein comprising the extracellular domain of human CD59 (amino acids 26-102 of SEQ ID NO:3) lacking its GPI anchor and/or the amino acid to which it is attached (i.e., Asn-102), to a biologically active fragment of CD59 protein comprising the extracellular domain of full-length mouse CD59 protein, isoform A (amino acids 24-96 of SEQ ID NO:8) lacking its GPI anchor and/or the amino acid to which it is attached (i.e., Ser-96), or to a biologically active fragment of CD59 protein comprising the extracellular domain of full-length mouse CD59 protein, isoform B (amino acids 24-104 of SEQ ID NO:9) lacking its GPI anchor and/or the amino acid to which it is attached (i.e., Asn-104) and a pharmaceutically acceptable carrier suitable for administration to an individual.

In certain embodiments, the pharmaceutical compositions comprise a targeted complement inhibitor comprising a biologically active fragment of CR2 protein comprising SCR1-2 (SEQ ID NO:2) fused to full-length human CD59 protein (SEQ ID NO:3), to full-length mouse CD59 protein, isoform A (SEQ ID NO:8), or to full-length mouse CD59 protein, isoform B (SEQ ID NO:9) and a pharmaceutically acceptable carrier suitable for administration to an individual. In certain embodiments, the pharmaceutical compositions comprise a targeted complement inhibitor comprising a biologically active fragment of CR2 protein comprising SCR1-2 (SEQ ID NO:2) fused to a biologically active fragment of CD59 protein comprising the extracellular domain of human CD59 (amino acids 26-102 of SEQ ID NO:3) lacking its GPI anchor and/or the amino acid to which it is attached (i.e., Asn-102), to a biologically active fragment of CD59 protein comprising the extracellular domain of full-length mouse CD59 protein, isoform A (amino acids 24-96 of SEQ ID NO:8) lacking its GPI anchor and/or the amino acid to which it is attached (i.e., Ser-96), or to a biologically active fragment of CD59 protein comprising the extracellular domain of full-length mouse CD59 protein, isoform B (amino acids 24-104 of SEQ ID NO:9) lacking its GPI anchor and/or the amino acid to which it is attached (i.e., Asn-104) and a pharmaceutically acceptable carrier suitable for administration to an individual.

In certain embodiments, the pharmaceutical compositions comprise a targeted complement inhibitor comprising full-length CR2 (SEQ ID NO:1) fused to full-length mouse Crry (SEQ ID NO:4) and a pharmaceutically acceptable carrier suitable for administration to an individual. In certain embodiments, the pharmaceutical compositions comprise a targeted complement inhibitor comprising full-length CR2 (SEQ ID NO:1) fused to a biologically active fragment of mouse Crry protein comprising the extracellular domain of mouse Crry (amino acids 41-405 of SEQ ID NO:4) and a pharmaceutically acceptable carrier suitable for administration to an individual. In certain embodiments, the pharmaceutical compositions comprise a targeted complement inhibitor comprising full-length CR2 (SEQ ID NO:1) fused to a biologically active fragment of mouse Crry protein comprising SCR1-4 of mouse Crry (amino acids 83-338 of SEQ ID NO:4) and a pharmaceutically acceptable carrier suitable for administration to an individual. In certain embodiments, the pharmaceutical compositions comprise a targeted complement inhibitor comprising full-length CR2 (SEQ ID NO:1) fused to a biologically active fragment of mouse Crry protein comprising SCR1-5 of mouse Crry (amino acids 83-400 of SEQ ID NO:4) and a pharmaceutically acceptable carrier suitable for administration to an individual. In certain embodiments, the pharmaceutical compositions comprise a targeted complement inhibitor comprising a biologically active fragment of CR2 comprising SCR1-2 (SEQ ID NO:2) fused to full-length mouse Crry protein (SEQ ID NO:4) and a pharmaceutically acceptable carrier suitable for administration to an individual. In certain embodiments, the pharmaceutical compositions comprise a targeted complement inhibitor comprising a biologically active fragment of CR2 comprising SCR1-2 (SEQ ID NO:2) fused to a biologically active fragment of mouse Crry protein comprising the extracellular domain of mouse Crry (amino acids 41-405 of SEQ ID NO:4) and a pharmaceutically acceptable carrier suitable for administration to an individual. In certain embodiments, the pharmaceutical compositions comprise a targeted complement inhibitor comprising a biologically active fragment of CR2 comprising SCR1-2 (SEQ ID NO:2) fused to a biologically active fragment of mouse Crry protein comprising SCR1-4 of mouse Crry (amino acids 83-338 of SEQ ID NO:4) and a pharmaceutically acceptable carrier suitable for administration to an individual. In certain embodiments, the pharmaceutical compositions comprise a targeted complement inhibitor comprising a biologically active fragment of CR2 comprising SCR1-2 (SEQ ID NO:2) fused to a biologically active fragment of mouse Crry comprising SCR1-5 of mouse Crry (amino acids 83-400 of SEQ ID NO:4) and a pharmaceutically acceptable carrier suitable for administration to an individual.

In certain embodiments, the pharmaceutical compositions comprise a targeted complement inhibitor comprising full-length CR2 (SEQ ID NO:1) fused to full-length human factor H (SEQ ID NO:5) and a pharmaceutically acceptable carrier suitable for administration to an individual. In certain embodiments, the pharmaceutical compositions comprise a targeted complement inhibitor comprising full-length CR2 (SEQ ID NO:1) fused to a biologically active fragment of factor H comprising the first four N-terminal SCR domains of factor H (amino acids 21-262 of SEQ ID NO:5) and a pharmaceutically acceptable carrier suitable for administration to an individual. In certain embodiments, the pharmaceutical compositions comprise a targeted complement inhibitor comprising full-length CR2 (SEQ ID NO:1) fused to a biologically active fragment of factor H comprising the first five N-terminal SCR domains of factor H (amino acids 21-320 of SEQ ID NO:5) and a pharmaceutically acceptable carrier suitable for administration to an individual. In certain embodiments, the pharmaceutical compositions comprise a targeted complement inhibitor comprising full-length CR2 (SEQ ID NO:1) fused to a biologically active fragment of factor H comprising the first six N-terminal SCR domains of factor H (amino acids 21-386 of SEQ ID NO:5) and a pharmaceutically acceptable carrier suitable for administration to an individual. In certain embodiments, the pharmaceutical compositions comprise a targeted complement inhibitor comprising full-length CR2 (SEQ ID NO:1) fused to a biologically active fragment of factor H comprising the first eight N-terminal SCR domains of factor H (amino acids 21-507 of SEQ ID NO:5) and a pharmaceutically acceptable carrier suitable for administration to an individual. In certain embodiments, the pharmaceutical compositions comprise a targeted complement inhibitor comprising full-length CR2 (SEQ ID NO:1) fused to a biologically active fragment of factor H comprising the first eighteen N-terminal SCR domains of factor H (amino acids 21-1104 of SEQ ID NO:5) and a pharmaceutically acceptable carrier suitable for administration to an individual.

In certain embodiments, the pharmaceutical compositions comprise a targeted complement inhibitor comprising a biologically active fragment of CR2 comprising SCR1-2 (SEQ ID NO:2) fused to full-length human factor H (SEQ ID NO:5) and a pharmaceutically acceptable carrier suitable for administration to an individual. In certain embodiments, the pharmaceutical compositions comprise a targeted complement inhibitor comprising a biologically active fragment of CR2 comprising SCR1-2 (SEQ ID NO:2) fused to a biologically active fragment of factor H comprising the first four N-terminal SCR domains of factor H (amino acids 21-262 of SEQ ID NO:5) and a pharmaceutically acceptable carrier suitable for administration to an individual. In certain embodiments, the pharmaceutical compositions comprise a targeted complement inhibitor comprising a biologically active fragment of CR2 comprising SCR1-2 (SEQ ID NO:2) fused to a biologically active fragment of factor H comprising the first five N-terminal SCR domains of factor H (amino acids 21-320 of SEQ ID NO:5) and a pharmaceutically acceptable carrier suitable for administration to an individual. In certain embodiments, the pharmaceutical compositions comprise a targeted complement inhibitor comprising a biologically active fragment of CR2 comprising SCR1-2 (SEQ ID NO:2) fused to a biologically active fragment of factor H comprising the first six N-terminal SCR domains of factor H (amino acids 21-386 of SEQ ID NO:5) and a pharmaceutically acceptable carrier suitable for administration to an individual. In certain embodiments, the pharmaceutical compositions comprise a targeted complement inhibitor comprising a biologically active fragment of CR2 comprising SCR1-2 (SEQ ID NO:2) fused to a biologically active fragment of factor H comprising the first eight N-terminal SCR domains of factor H (amino acids 21-507 of SEQ ID NO:5) and a pharmaceutically acceptable carrier suitable for administration to an individual. In certain embodiments, the pharmaceutical compositions comprise a targeted complement inhibitor comprising a biologically active fragment of CR2 comprising SCR1-2 (SEQ ID NO:2) fused to a biologically active fragment of factor H comprising the first eighteen N-terminal SCR domains of factor H (amino acids 21-1104 of SEQ ID NO:5) and a pharmaceutically acceptable carrier suitable for administration to an individual.

In certain embodiments, the pharmaceutical compositions comprise a targeted complement inhibitor comprising full-length CR2 protein (SEQ ID NO:1) fused to full-length human CR1 (SEQ ID NO:11) and a pharmaceutically acceptable carrier suitable for administration to an individual. In certain embodiments, the pharmaceutical compositions comprise a targeted complement inhibitor comprising full-length CR2 protein (SEQ ID NO:1) fused to a biologically active fragment of full-length human CR1 comprising the complete extracellular domain of human CR1 (SCRs 1-30) (amino acids 42-1971 of SEQ ID NO:11) and a pharmaceutically acceptable carrier suitable for administration to an individual. In certain embodiments, the pharmaceutical compositions comprise a targeted complement inhibitor comprising full-length CR2 protein (SEQ ID NO:1) fused to a biologically active fragment of full-length human CR1 comprising SCRs 1-4 (amino acids 42-295 of SEQ ID NO:11) and a pharmaceutically acceptable carrier suitable for administration to an individual. In certain embodiments, the pharmaceutical compositions comprise a targeted complement inhibitor comprising full-length CR2 protein (SEQ ID NO:1) fused to a biologically active fragment of full-length human CR1 comprising SCRs 1-11 (amino acids 42-745 of SEQ ID NO:11) and a pharmaceutically acceptable carrier suitable for administration to an individual. In certain embodiments, the pharmaceutical compositions comprise a targeted complement inhibitor comprising full-length CR2 protein (SEQ ID NO:1) fused to a biologically active fragment of full-length human CR1 comprising SCRs 1-18 (amino acids 42-1195 of SEQ ID NO:11) and a pharmaceutically acceptable carrier suitable for administration to an individual.

In certain embodiments, the pharmaceutical compositions comprise a targeted complement inhibitor comprising a biologically active fragment of CR2 protein comprising SCR1-2 (SEQ ID NO:2) fused to full-length human CR1 (SEQ ID NO:11) and a pharmaceutically acceptable carrier suitable for administration to an individual. In certain embodiments, the pharmaceutical compositions comprise a targeted complement inhibitor comprising a biologically active fragment of CR2 protein comprising SCR1-2 (SEQ ID NO:2) fused to a biologically active fragment of full-length human CR1 comprising the complete extracellular domain of human CR1 (SCRs 1-30) (amino acids 42-1971 of SEQ ID NO:11) and a pharmaceutically acceptable carrier suitable for administration to an individual. In certain embodiments, the pharmaceutical compositions comprise a targeted complement inhibitor comprising a biologically active fragment of CR2 protein comprising SCR1-2 (SEQ ID NO:2) fused to a biologically active fragment of full-length human CR1 comprising SCRs 1-4 (amino acids 42-295 of SEQ ID NO:11) and a pharmaceutically acceptable carrier suitable for administration to an individual. In certain embodiments, the pharmaceutical compositions comprise a targeted complement inhibitor comprising a biologically active fragment of CR2 protein comprising SCR1-2 (SEQ ID NO:2) fused to a biologically active fragment of full-length human CR1 comprising SCRs 1-11 (amino acids 42-745 of SEQ ID NO:11) and a pharmaceutically acceptable carrier suitable for administration to an individual. In certain embodiments, the pharmaceutical compositions comprise a targeted complement inhibitor comprising a biologically active fragment of CR2 protein comprising SCR1-2 (SEQ ID NO:2) fused to a biologically active fragment of full-length human CR1 comprising SCRs 1-18 (amino acids 42-1195 of SEQ ID NO:11) and a pharmaceutically acceptable carrier suitable for administration to an individual.

In any of the embodiments described herein, the targeted complement inhibitors comprise a non-CR2 targeting portion. In any of the embodiments described herein, the non-CR2 targeting portion comprises an antibody or antigen-binding fragment thereof that specifically binds to proteolytic fragments of complement protein C3 (e.g., iC3b, C3dg, and C3d). In any of the embodiments described herein, the antibodies are polyclonal antibodies. In any of the embodiments described herein, the antibodies are monoclonal antibodies. In any of the embodiments described herein, the antibodies are polyclonal or monoclonal antibody fragments selected from the group consisting of Fab, Fab'-SH, Fv, scFv, and (Fab')$_2$ fragments. In any of the embodiments described herein, the antibodies or antigen-binding fragments thereof are humanized antibodies. In any of the embodiments described herein, the antibodies or antigen-binding fragments thereof are human antibodies.

In certain embodiments, the pharmaceutical compositions comprise a non-targeted complement inhibitor and a pharmaceutically acceptable carrier suitable for administration to an individual. In certain embodiments, the non-targeted complement inhibitor is human C1-inhibitor protein (SEQ ID NO:19) or mouse C1-inhibitor protein (SEQ ID NO:20). In certain embodiments, the non-targeted complement inhibitor is a homolog of human C1-inhibitor protein or a homolog of mouse C1-inhibitor protein or a biologically active fragment thereof.

In certain embodiments, the pharmaceutical compositions comprise a non-targeted complement inhibitor and a pharmaceutically acceptable carrier suitable for administration to an individual. In certain embodiments, the non-targeted complement inhibitor is an anti-C3 antibody or antigen-binding fragment thereof. In certain embodiments, the anti-C3 antibody or antigen-binding fragment thereof selectively binds to complement protein C3 and prevents cleavage of C3 into C3a and C3b. In certain embodiments, the anti-C3 antibody or antigen-binding fragment thereof is of a non-complement activating isotype or subclass. In certain embodiments, the antigen-binding fragment thereof is selected from the group consisting of Fab, Fab'-SH, Fv, scFv, and (Fab')$_2$ fragments. In certain embodiments, the anti-C3 antibody or antigen-binding fragment thereof is a monoclonal antibody, a humanized antibody, or a human antibody.

In certain embodiments, the pharmaceutical compositions comprise a non-targeted complement inhibitor and a pharmaceutically acceptable carrier suitable for administration to an individual. In certain embodiments, the non-targeted complement inhibitor is an anti-factor B antibody or antigen-binding fragment thereof. In certain embodiments, the anti-factor B antibody or antigen-binding fragment thereof selectively binds to factor B within the third short consensus repeat (SCR) domain and prevents formation of a C3bBb complex. In certain embodiments, the anti-factor B antibody or antigen-binding fragment thereof is of a non-complement activating isotype or subclass. In certain embodiments, the antigen-binding fragment thereof is selected from the group consisting of Fab, Fab'-SH, Fv, scFv, and (Fab')$_2$ fragments. In certain embodiments, the anti-factor B antibody or antigen-binding fragment thereof is a monoclonal antibody, a humanized antibody, or a human antibody. In certain embodiments, the antibody is the monoclonal antibody 1379 (produced by ATCC Deposit No. PTA-6230).

In certain embodiments, the pharmaceutical compositions comprise a non-targeted complement inhibitor and a pharmaceutically acceptable carrier suitable for administration to an individual. In certain embodiments, the non-targeted complement inhibitor is an anti-properdin antibody or antigen-binding fragment thereof. In certain embodiments, the anti-properdin antibody inhibits the production of one or more of Bb, C3a, and C5a. In certain embodiments, the anti-properdin antibody or antigen-binding fragment thereof is of a non-complement activating isotype or subclass. In certain embodiments, the antigen-binding fragment thereof is selected from the group consisting of Fab, Fab'-SH, Fv, scFv, and (Fab')$_2$ fragments. In certain embodiments, the anti-properdin antibody or antigen-binding fragment thereof is a monoclonal antibody, a humanized antibody, or a human antibody.

In certain embodiments, the pharmaceutical compositions comprise a non-targeted complement inhibitor and a pharmaceutically acceptable carrier suitable for administration to an individual. In certain embodiments, the non-targeted complement inhibitor is an anti-factor D antibody or antigen-binding fragment thereof. In certain embodiments, the anti-factor D antibody inhibits the production of one or more of Bb, C3a, C5a, and sC5b-9. In certain embodiments, the anti-factor D antibody or antigen-binding fragment thereof is of a non-complement activating isotype or subclass. In certain embodiments, the antigen-binding fragment thereof is selected from the group consisting of Fab, Fab'-SH, Fv, scFv, and (Fab')$_2$ fragments. In certain embodiments, the anti-factor D antibody or antigen-binding fragment thereof is a monoclonal antibody, a humanized antibody, or a human antibody. In certain embodiments, the antibody is the monoclonal antibody (mAb) 166-32 (produced by ATCC Deposit Accession_Number HB-12476).

In certain embodiments, the pharmaceutical compositions comprise a non-targeted complement inhibitor and a pharmaceutically acceptable carrier suitable for administration to an individual. In certain embodiments, the non-targeted complement inhibitor inhibits terminal complement and formation of the membrane attack complex (MAC). In certain embodiments, the non-targeted complement inhibitor is an anti-C5 antibody or antigen-binding fragment thereof that inhibits activation of terminal complement and formation of the membrane attack complex (MAC). In certain embodiments, the anti-C5 antibody or antigen-binding fragment thereof inhibits cleavage of complement protein C5 (C5). In certain embodiments, the anti-C5 antibody or antigen-binding fragment thereof inhibits assembly of the membrane attack complex (MAC). In certain embodiments, the anti-C5 antibody or antigen-binding fragment thereof is polyclonal, monoclonal, chimeric, or humanized. In certain embodiments, the antigen-binding fragments are selected from the group consisting of Fab, Fab', and F(ab')$_2$ fragments. In certain embodiments, the anti-C5 antibody or antigen-binding fragment thereof is polyclonal. In certain embodiments, the anti-C5 antibody or antigen-binding fragment thereof is monoclonal. In certain embodiments, the anti-C5 antibody or antigen-binding fragment thereof is chimeric. In certain embodiments, the anti-C5 antibody or antigen-binding fragment thereof is humanized. In certain embodiments, the humanized anti-C5 antibody or antigen-binding fragment thereof is eculizumab or pexelizumab.

In certain embodiments, the pharmaceutical compositions comprise a non-targeted complement inhibitor and a pharmaceutically acceptable carrier suitable for administration to an individual. In certain embodiments, the non-targeted complement inhibitor inhibits terminal complement and formation of the membrane attack complex (MAC). In certain embodiments, the non-targeted complement inhibitor is the heterodimeric apolipoprotein clusterin. In certain embodiments, the clusterin inhibits complement protein C9 assembly on C5b-8 and C5b-9 or binds to C5b-7 to prevent membrane attachment. In certain embodiments, the non-targeted complement inhibitor is human clusterin protein (SEQ ID NO:15) or mouse clusterin protein (SEQ ID NO:16). In certain embodiments, the non-targeted complement inhibitor comprises a homolog of a human or mouse clusterin protein or a biologically active fragment thereof.

In certain embodiments, the pharmaceutical compositions comprise a non-targeted complement inhibitor and a pharmaceutically acceptable carrier suitable for administration to an individual. In certain embodiments, the non-targeted complement inhibitor inhibits terminal complement and formation of the membrane attack complex (MAC). In certain embodiments, the non-targeted complement inhibitor is the protein vitronectin or a biologically active fragment or homolog thereof. In certain embodiments, the vitronectin blocks C5b-7 membrane binding and prevents C9 polymerization. In certain embodiments, the non-targeted complement inhibitor is human vitronectin protein (SEQ ID NO:17) or mouse vitronectin protein (SEQ ID NO:18). In certain embodiments, the non-targeted complement inhibitor comprises a homolog of a human or mouse vitronectin protein or a biologically active fragment thereof.

In any of the embodiments described herein, the individual is a vertebrate. In any of the embodiments described herein, the vertebrate is a mammal. In any of the embodiments described herein, the mammal is a research animal or a domestic animal. In any of the embodiments described herein, the mammal is a human. In any of the embodiments described herein, the pharmaceutical compositions are suitable for a variety of modes of administration, including, for example, systemic or localized administration. In any of the embodiments described herein, the pharmaceutical compositions are in the form of injectable solutions and suitable for systemic administration such as, for example, intravenous administration. In any of the embodiments described herein, the pharmaceutical compositions are in the form of injectable solutions and suitable for local administration. In any of the embodiments described herein, the pharmaceutical compositions are in a liquid or solid form suitable for oral administration. In any of the embodiments described herein, the pharmaceutical compositions can be packaged in single unit dosages or in multidosage forms.

In certain embodiments, the pharmaceutical compositions comprise an ASP/C3adesArg antagonist and a pharmaceutically acceptable carrier suitable for administration to an individual. In certain embodiments, the pharmaceutical compositions comprise an ASP/C3adesArg antagonist comprising an antibody or antigen-binding fragment thereof that specifically binds to ASP/C3adesArg and prevents it from binding to the ASP/C3adesArg receptor (C5L2) and a pharmaceutically acceptable carrier suitable for administration to an individual. In certain embodiments, the pharmaceutical compositions comprise an ASP/C3adesArg antagonist comprising a soluble ASP/C3adesArg receptor (C5L2) fragment comprising one or more extracellular domains of ASP/C3adesArg receptor (C5L2) that specifically binds to ASP/C3adesArg and prevent it from binding to the ASP/C3adesArg receptor (C5L2) and a pharmaceutically acceptable carrier suitable for administration to an individual. In certain embodiments, the pharmaceutical compositions comprise an ASP/C3adesArg antagonist comprising any combination of one or more of the soluble ASP/C3adesArg receptor (C5L2) fragments provided herein that specifically binds to ASP/C3adesArg and prevent it from binding to the ASP/C3adesArg receptor (C5L2) and a pharmaceutically acceptable carrier suitable for administration to an individual. In certain embodiments, the pharmaceutical compositions comprise an ASP/C3adesArg receptor (C5L2) antagonist comprising an antibody or antigen-binding fragment thereof that specifically binds to ASP/C3adesArg receptor (C5L2) and prevents ASP/C3adesArg from binding and a pharmaceutically acceptable carrier suitable for administration to an individual. In certain embodiments, the pharmaceutical compositions comprise an ASP/C3adesArg receptor (C5L2) antagonist comprising ASP/C3adesArg or a fragment thereof that specifically binds to ASP/C3adesArg receptor (C5L2) but does not activate the receptor and a pharmaceutically acceptable carrier suitable for administration to an individual.

In certain embodiments, the individual is a vertebrate. In certain embodiments, the vertebrate is a mammal. In certain embodiments, the mammal is a research animal or a domestic animal. In certain embodiments, the mammal is a human. In any of the embodiments described herein, the pharmaceutical compositions are suitable for a variety of modes of administration, including, for example, systemic or localized administration. In certain embodiments, the pharmaceutical compositions are in the form of injectable solutions and suitable for systemic administration such as, for example, intravenous administration. In certain embodiments, the pharmaceutical compositions are in the form of injectable solutions and suitable for local administration. In any of the embodiments, the pharmaceutical compositions are in a liquid or solid form suitable for oral administration. In any of the embodiments described herein, the pharmaceutical compositions can be packaged in single unit dosages or in multidosage forms.

In certain embodiments, any of the pharmaceutical compositions comprising a targeted complement inhibitor described herein are administered a dose between 3.2 mg/kg to approximately 20 mg/kg. In certain embodiments, any of the pharmaceutical compositions comprising a targeted complement inhibitor described herein are administered a dose between 4 mg/kg to approximately 18 mg/kg. In certain embodiments, any of the pharmaceutical compositions comprising a targeted complement inhibitor described herein are administered a dose between 6 mg/kg to approximately 16 mg/kg. In certain embodiments, any of the pharmaceutical compositions comprising a targeted complement inhibitor described herein are administered a dose between 8 mg/kg to approximately 14 mg/kg. In certain embodiments, any of the pharmaceutical compositions comprising a targeted complement inhibitor described herein are administered a dose between 10 mg/kg to approximately 12 mg/kg. In certain embodiments, any of the pharmaceutical compositions comprising a targeted complement inhibitor described herein are administered a dose of 3.2 mg/kg, 3.5 mg/kg, 4 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 11.0 mg/kg, 12.0 mg/kg, 13.0 mg/kg, 14.0 mg/kg, 15.0 mg/kg, 16.0 mg/kg, 17.0 mg/kg, 18.0 mg/kg, 19.0 mg/kg, or 20.0 mg/kg.

In certain embodiments, any of the pharmaceutical compositions comprising an ASP/C3adesArg antagonist described herein are administered a dose between 3.2 mg/kg to approximately 20 mg/kg. In certain embodiments, any of the pharmaceutical compositions comprising an ASP/C3adesArg antagonist described herein are administered a dose between 4 mg/kg to approximately 18 mg/kg. In certain embodiments, any of the pharmaceutical compositions comprising an ASP/C3adesArg antagonist described herein are administered a dose between 6 mg/kg to approximately 16 mg/kg. In certain embodiments, any of the pharmaceutical compositions comprising an ASP/C3adesArg antagonist described herein are administered a dose between 8 mg/kg to approximately 14 mg/kg. In certain embodiments, any of the pharmaceutical compositions comprising an ASP/C3adesArg antagonist described herein are administered a dose between 10 mg/kg to approximately 12 mg/kg. In certain embodiments, any of the pharmaceutical compositions comprising an ASP/C3adesArg antagonist described herein are administered a dose of 3.2 mg/kg, 3.5 mg/kg, 4 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 11.0 mg/kg, 12.0 mg/kg, 13.0 mg/kg, 14.0 mg/kg, 15.0 mg/kg, 16.0 mg/kg, 17.0 mg/kg, 18.0 mg/kg, 19.0 mg/kg, or 20.0 mg/kg.

In certain embodiments, any of the pharmaceutical compositions comprising an ASP/C3adesArg receptor (C5L2) antagonist described herein are administered a dose between 3.2 mg/kg to approximately 20 mg/kg. In certain embodiments, any of the pharmaceutical compositions comprising an ASP/C3adesArg receptor (C5L2) antagonist described herein are administered a dose between 4 mg/kg to approximately 18 mg/kg. In certain embodiments, any of the pharmaceutical compositions comprising an ASP/C3adesArg receptor (C5L2) antagonist described herein are administered a dose between 6 mg/kg to approximately 16 mg/kg. In certain embodiments, any of the pharmaceutical compositions comprising an ASP/C3adesArg receptor (C5L2) antagonist described herein are administered a dose between 8 mg/kg to approximately 14 mg/kg. In certain embodiments, any of the pharmaceutical compositions comprising an ASP/C3adesArg receptor (C5L2) antagonist described herein are administered a dose between 10 mg/kg to approximately 12 mg/kg. In certain embodiments, any of the pharmaceutical compositions comprising an ASP/C3adesArg receptor (C5L2) antagonist described herein are administered a dose of 3.2 mg/kg, 3.5 mg/kg, 4 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 11.0 mg/kg, 12.0 mg/kg, 13.0 mg/kg, 14.0 mg/kg, 15.0 mg/kg, 16.0 mg/kg, 17.0 mg/kg, 18.0 mg/kg, 19.0 mg/kg, or 20.0 mg/kg.

The liquid compositions are generally formulated as sterile, substantially isotonic solutions in full compliance with all Good Manufacturing Practice (GMP) regulations of the U.S. Food and Drug Administration. In certain embodiments, the composition is free of pathogen. For injection, the pharmaceutical composition can be in the form of liquid solutions, for example in physiologically compatible buffers such as Hank's Balanced Salt Solution, Phosphate-Buffered Saline or Ringer's solution. In addition, the pharmaceutical compositions provided herein can be in solid form and redissolved or resuspended immediately prior to use. Lyophilized compositions are also contemplated.

For oral administration, the pharmaceutical compositions can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

In certain embodiments, the composition is formulated in accordance with routine procedures as a pharmaceutical composition adapted for injection. In certain embodiments, the pharmaceutical compositions provided herein are formulated for intravenous, intraperitoneal, or intraocular injection. Typically, compositions for injection are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions may further comprise additional ingredients, for example preservatives, buffers, tonicity agents, antioxidants and stabilizers, nonionic wetting or clarifying agents, viscosity-increasing agents, and the like.

Suitable preservatives for use in a solution include polyquaternium-1, benzalkonium chloride, thimerosal, chlorobutanol, methyl paraben, propyl paraben, phenylethyl alcohol, disodium-EDTA, sorbic acid, benzethonium chloride, and the like. Typically (but not necessarily) such preservatives are employed at a level of from 0.001% to 1.0% by weight.

Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5.

Suitable tonicity agents include dextran 40, dextran 70, dextrose, glycerin, potassium chloride, propylene glycol, sodium chloride, and the like, such that the sodium chloride equivalent of the injectable solution is in the range 0.9 plus or minus 0.2%.

Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, hydroxyethylcellulose, lanolin, methylcellulose, petrolatum, polyethylene glycol, polyvinyl alcohol, polyvinylpyrrolidone, carboxymethylcellulose and the like.

The pharmaceutical compositions may be suitable for a variety of modes of administration described herein, including for example systemic or localized administration. The pharmaceutical compositions can be in the form of injectable solutions or in a form suitable for oral administration. The pharmaceutical compositions described herein can be packaged in single unit dosages or in multidosage forms. In certain embodiments, the pharmaceutical compositions are suitable for administration to an individual, a vertebrate, a mammal, or a human by any route of administration described herein, including oral administration or intravenous injection.

Methods of Stimulating Liver Regeneration

Provided herein are methods of stimulating liver regeneration in an individual in need thereof. In any of the embodiments described herein, the methods stimulate liver regeneration and decrease ischemia/reperfusion injury in an individual in need thereof. In any of the embodiments described herein, the methods stimulate liver regeneration and decrease hepatic steatosis in an individual in need thereof. In any of the embodiments described herein, the methods stimulate liver regeneration, decrease ischemia/reperfusion injury, and decrease hepatic steatosis in an individual in need thereof.

In any of the embodiments described herein, the individual is a vertebrate. In certain embodiments, the vertebrate is a mammal. In any of the embodiments described herein, the mammal is a research animal or a domestic animal. In any of the embodiments described herein, the mammal is a human. In any of the embodiments described herein, the individual has undergone a partial hepatectomy or liver resection. In any of the embodiments described herein, the partial hepatectomy or liver resection removed 5%, 10%, 15%, 20%, 25%, 30%, 35%, 40%, 45%, 50%, 55%, 60%, 65%, 70%, 75%, 80%, 85%, 90%, or 95% by mass of the individual's liver. In any of the embodiments described herein, the partial hepatectomy or liver resection removed 5%, 10%, 15%, 20%, 25%, 30%, 35%, 40%, 45%, 50%, 55%, 60%, 65%, 70%, 75%, 80%, 85%, 90%, or 95% by volume of the individual's liver. In any of the embodiments described herein, the individual has undergone a liver transplant. In any of the embodiments described herein, the individual has undergone a small-for-size liver transplant. In any of the embodiments described herein, the individual has liver damage caused by toxic injury, traumatic injury, microvesicular steatosis, or macrovesicular steatosis. In any of the embodiments described herein, the toxic injury results from exposure to carbon tetrachloride ($CCl_4$), bacterial endotoxin, use or abuse of intravenous or prescription drugs, chemotherapy, excessive consumption of alcohol, or infection with hepatitis virus A, B, or C. In any of the embodiments described herein, the traumatic injury results from surgical resection or blunt force trauma, such as that occurring in an automobile accident.

As used herein, the term "microvesicular steatosis" refers to a variant form of hepatic fat accumulation whose histologic features contrast with the much more common macrovesicular steatosis. The condition was originally described in association with conditions sharing a number of biochemical and clinical features: acute fatty liver of pregnancy, Reye's syndrome, Jamaican vomiting sickness, sodium valproate toxicity, high-dose tetracycline toxicity and certain congenital defects of urea cycle enzymes. Those disorders were originally thought to constitute the so-called "microvesicular fat diseases." In recent years, microvesicular steatosis has been observed in a wide variety of conditions, including alcoholism, toxicity of several medications, hepatitis delta virus infection (primarily in South America and Central Africa), sudden childhood death, congenital defects of fatty acid beta oxidation, cholesterol ester storage disease, Wolman disease and Alper's syndrome. Not much is known regarding the pathogenesis of microvesicular steatosis, but in many instances the primary defect could be a mitochondrial lesion, although inhibition of the mitochondrial beta oxidation of fatty acids has been the most frequently implicated defect. See, e.g., M. L. Hautekeete et al., (1990) *Acta Clin. Belg.* 45(5):311-326.

As used herein, the term "macrovesicular steatosis" refers to abnormal retention of lipids within a cell, reflecting an impairment of the normal processes of fatty acid and/or triglyceride synthesis and elimination. Excess lipid accumulates in vesicles that displace the cytoplasm. In "macrovesicular steatosis," the vesicles become large enough to distort the cell's nucleus. The condition is not particularly detrimental to the cell in mild cases, large accumulations can disrupt cell constituents, and in severe cases cells may even burst. Many different mechanisms can disrupt normal lipid movement through the cell and cause steatosis. Those mechanisms can be classified based on whether they result in an oversupply of lipid or a failure of lipid breakdown. Oversupply of lipid may result from, among other conditions, obesity, insulin resistance, or alcoholism. Certain toxins, such as alcohols, carbon tetrachloride, aspirin, and diptheria toxin, among others, interfere with cellular machinery involved in lipid metabolism. In addition, certain metabolic diseases are characterized by defects in lipid metabolism. For example, in Gaucher's disease, the lysosomes fail to degrade glycolipids, resulting in steatosis.

As used herein, the term "partial hepatectomy," "surgical resection," or "liver resection" refers to a surgical procedure in which a portion of the liver is removed, typically because of cancer or other serious injury to the liver. The extent of the hepatectomy or resection will depend on the size, number, and location of the cancerous lesions, or on the extent of other liver injury. It also depends on whether liver function is still adequate. The surgeon may remove a part of the liver that contains the tumor, an entire lobe, or an even larger portion of the liver. In a partial hepatectomy, the surgeon typically leaves a margin of healthy liver tissue to maintain the functions of the liver.

As used herein, the term "small-for-size" liver transplant or "SFS" liver transplant refers to a surgical technique in which a donor liver is split into two or more fragments, each of which is subsequently transplanted into a different recipient. Adequate hepatic regeneration is essential for recovery of patients receiving SFS transplants, most of whom are chronically ill with severely compromised liver function to begin with. Inadequate regeneration can result in "small-for-size graft syndrome," characterized by poor bile production, intractable ascites, and prolonged cholestasis, and closely associated with surgical and septic complications.

In certain embodiments, the method of stimulating liver regeneration in an individual in need thereof comprises administering to the individual a composition in an amount effective to reduce the circulating concentration of acylation stimulating protein (ASP/C3adesArg) in the individual. In certain embodiments, the method of stimulating liver regeneration and decreasing ischemia/reperfusion injury in an individual in need thereof comprises administering a composition to the individual in an amount effective to reduce the circulating concentration of acylation stimulating protein (ASP/C3adesArg) in the individual. In certain embodiments, the method of stimulating liver regeneration and decreasing hepatic steatosis in an individual in need thereof comprises administering to the individual a composition in an amount effective to reduce the circulating concentration of acylation stimulating protein (ASP/C3adesArg) in the individual. In certain embodiments, the method of stimulating liver regeneration, decreasing ischemia/reperfusion injury, and decreasing hepatic steatosis in an individual in need thereof comprises administering to the individual a composition in an amount effective to reduce the circulating concentration of acylation stimulating protein (ASP/C3adesArg) in the individual. In certain embodiments, the circulating concentration of ASP/C3adesArg is reduced to between 2 µg/ml and 8 µg/ml. In certain embodiments, the circulating concentration of ASP/C3adesArg is determined in a biological sample taken from the individual. In certain embodiments, the biological sample is blood, plasma, or serum. In certain embodiments, the biological sample is a liver sample obtained by biopsy, and the concentration of ASP/C3adesArg is determined in a liver homogenate. In certain embodiments, the circulating concentration of ASP/C3adesArg is determined by Western blot, immunoblot, enzyme-linked immunosorbant assay ("ELISA"), radioimmunoassay ("RIA"), immunoprecipitation, surface plasmon resonance, chemiluminescence, fluorescent polarization, phosphorescence, or matrix-assisted laser desorption/ionization time-of-flight ("MALDI-TOF") mass spectrometry.

In certain embodiments, the composition is selected from the group consisting of a complement inhibitor, an ASP/C3adesArg antagonist and an ASP/C3adesArg receptor (C5L2) antagonist.

In certain embodiments, the complement inhibitor is a targeted complement inhibitor. In certain embodiments, the targeted complement inhibitor is a fusion protein comprising a complement receptor 2 (CR2) portion comprising CR2 or a biologically active fragment thereof; and a complement inhibitor portion. In certain embodiments, the complement inhibitor portion is selected from the group consisting of CD59, mouse Crry, human factor H, and biologically active fragments thereof. In certain embodiments, the CR2 portion comprises at least the first two N-terminal short consensus repeat (SCR) domains of CR2. In certain embodiments, the CR2 portion comprises at least the first four N-terminal SCR domains of CR2. In certain embodiments, the complement inhibitor portion comprises full-length human CD59. In certain embodiments, the complement inhibitor portion comprises the extracellular domain of human CD59 lacking its GPI anchor. In certain embodiments, the complement inhibitor portion comprises the extracellular domain of human CD59 lacking its GPI anchor and/or the amino acid to which it is attached (i.e., Asn-102). In certain embodiments, the complement inhibitor portion comprises the complete extracellular domain of mouse Crry protein. In certain embodiments, the complement inhibitor portion comprises SCRs 1-4 of mouse Crry protein. In certain embodiments, the complement inhibitor portion comprises SCRs 1-5 of mouse Crry protein. In certain embodiments, the complement inhibitor portion comprises full-length human factor H. In certain embodiments, the complement inhibitor portion comprises SCRs 1-4 of human factor H. In certain embodiments, the complement inhibitor portion comprises SCRs 1-5 of human factor H. In certain embodiments, the complement inhibitor portion comprises SCRs 1-8 of human factor H. In certain embodiments, the complement inhibitor portion comprises SCRs 1-18 of human factor H.

In certain embodiments, the targeted complement inhibitor comprises a fusion protein comprising at least the first two N-terminal SCR domains of CR2 and the extracellular domain of human CD59 lacking its GPI anchor. In certain embodiments, the targeted complement inhibitor comprises a fusion protein comprising at least the first two N-terminal SCR domains of CR2 and the extracellular domain of human CD59 lacking its GPI anchor and/or the amino acid to which it is attached (i.e., Asn-102). In certain embodiments, the targeted complement inhibitor comprises a fusion protein comprising at least the first four N-terminal SCR domains of CR2 and the extracellular domain of human CD59 lacking its GPI anchor. In certain embodiments, the targeted complement inhibitor comprises a fusion protein comprising at least the first four N-terminal SCR domains of CR2 and the extracellular domain of human CD59 lacking its GPI anchor and/or the amino acid to which it is attached (i.e., Asn-102). In certain embodiments, the targeted complement inhibitor comprises a fusion protein comprising at least the first two N-terminal SCR domains of CR2 and the complete extracellular domain of mouse Crry protein. In certain embodiments, the targeted complement inhibitor comprises a fusion protein comprising at least the first two N-terminal SCR domains of CR2 and SCRs 1-4 of mouse Crry protein. In certain embodiments, the targeted complement inhibitor comprises a fusion protein comprising at least the first two N-terminal SCR domains of CR2 and SCRs 1-5 of mouse Crry protein. In certain embodiments, the targeted complement inhibitor comprises a fusion protein comprising at least the first four N-terminal SCR domains of CR2 and the complete extracellular domain of mouse Crry protein. In certain embodiments, the targeted complement inhibitor comprises a fusion protein comprising at least the first four N-terminal SCR domains of CR2 and SCRs 1-4 of mouse Crry protein. In certain embodiments, the targeted complement inhibitor comprises a fusion protein comprising at least the first four N-terminal SCR domains of CR2 and SCRs 1-5 of mouse Crry protein.

In certain embodiments, the targeted complement inhibitor comprises a fusion protein comprising at least the first two N-terminal SCR domains of CR2 and full-length human factor H. In certain embodiments, the targeted complement inhibitor comprises a fusion protein comprising at least the first two N-terminal SCR domains of CR2 and SCRs 1-4 of human factor H. In certain embodiments, the targeted complement inhibitor comprises a fusion protein comprising at least the first two N-terminal SCR domains of CR2 and SCRs 1-5 of human factor H. In certain embodiments, the targeted complement inhibitor comprises a fusion protein comprising at least the first two N-terminal SCR domains of CR2 and SCRs 1-8 of human factor H. In certain embodiments, the targeted complement inhibitor comprises a fusion protein comprising at least the first two N-terminal SCR domains of CR2 and SCRs 1-18 of human factor H.

In certain embodiments, the targeted complement inhibitor comprises a fusion protein comprising at least the first four N-terminal SCR domains of CR2 and full-length human factor H. In certain embodiments, the targeted complement inhibitor comprises a fusion protein comprising at least the first four N-terminal SCR domains of CR2 and SCRs 1-4 of human factor H. In certain embodiments, the targeted complement inhibitor comprises a fusion protein comprising at least the first four N-terminal SCR domains of CR2 and SCRs 1-5 of human factor H. In certain embodiments, the targeted complement inhibitor comprises a fusion protein comprising at least the first four N-terminal SCR domains of CR2 and SCRs 1-8 of human factor H. In certain embodiments, the targeted complement inhibitor comprises a fusion protein comprising at least the first four N-terminal SCR domains of CR2 and SCRs 1-18 of human factor H.

In any of the embodiments described herein, the targeted complement inhibitor comprises a non-CR2 targeting portion. In any of the embodiments described herein, the non-CR2 targeting portion comprises an antibody or antigen-binding fragment thereof that specifically binds to proteolytic fragments of complement protein C3 (e.g., iC3b, C3dg, and C3d). In any of the embodiments described herein, the antibodies are polyclonal antibodies. In certain embodiments, the antibodies are monoclonal antibodies. In any of the embodiments described herein, the antibodies are polyclonal or monoclonal antibody fragments selected from the group consisting of Fab, Fab'-SH, Fv, scFv, and (Fab')$_2$ fragments. In any of the embodiments described herein, the antibodies or antigen-binding fragments thereof are humanized antibodies. In any of the embodiments described herein, the antibodies or antigen-binding fragments thereof are human antibodies.

In certain embodiments, the ASP/C3adesArg antagonist is selected from the group consisting of an antibody or antigen-binding fragments thereof that specifically bind to ASP/C3adesArg and soluble ASP/C3adesArg receptor (C5L2) fragments that specifically bind to ASP/C3adesArg and prevent ASP/C3adesArg from binding to the receptor. In certain embodiments, the ASP/C3adesArg antagonist is an antibody or antigen-binding fragments thereof that specifically bind to ASP/C3adesArg and prevent ASP/C3adesArg from binding to the receptor. In certain embodiments, the antibody is a polyclonal, monoclonal, chimeric, or humanized antibody. In certain embodiments, the antigen-binding fragments are selected from the group consisting of Fab, Fab', and F(ab')$_2$ fragments.

In certain embodiments, the ASP/C3adesArg antagonist is a soluble ASP/C3adesArg receptor (C5L2) fragment that specifically binds to ASP/C3adesArg and prevents ASP/C3adesArg from binding to the receptor. In certain embodiments, the ASP/C3adesArg antagonist is a soluble ASP/C3adesArg receptor (C5L2) fragment comprising one or more extracellular domains of ASP/C3adesArg receptor (C5L2) that specifically binds to ASP/C3adesArg and prevent it from binding to the ASP/C3adesArg receptor (C5L2). In certain embodiments, the ASP/C3adesArg antagonist comprises any combination of one or more of the soluble ASP/C3adesArg receptor (C5L2) fragments provided herein that specifically binds to ASP/C3adesArg and prevent it from binding to the ASP/C3adesArg receptor (C5L2).

In certain embodiments, the ASP/C3adesArg receptor (C5L2) antagonist comprises an antibody or antigen-binding fragments thereof that specifically bind to the ASP/C3adesArg receptor (C5L2) and prevent activation of the receptor. In certain embodiments, the antibody is a polyclonal, monoclonal, chimeric, or humanized antibody. In certain embodiments, the antigen-binding fragments are selected from the group consisting of Fab, Fab', and F(ab')$_2$ fragments.

In certain embodiments, the method of stimulating liver regeneration in an individual in need thereof comprises administering a composition in an amount effective to reduce activation of complement. In certain embodiments, the composition is a complement inhibitor. In certain embodiments, the complement inhibitor is a targeted complement inhibitor. In certain embodiments, the complement inhibitor is a non-targeted complement inhibitor.

In any of the embodiments described herein, the individual is a vertebrate. In any of the embodiments described herein, the vertebrate is a mammal. In any of the embodiments described herein, the mammal is a research animal or a domestic animal. In any of the embodiments described herein, the mammal is a human. In any of the embodiments described herein, the individual has undergone a partial hepatectomy or liver resection. In any of the embodiments described herein, the partial hepatectomy or liver resection removed 5%, 10%, 15%, 20%, 25%, 30%, 35%, 40%, 45%, 50%, 55%, 60%, 65%, 70%, 75%, 80%, 85%, 90%, or 95% by mass of the individual's liver. In any of the embodiments described herein, the partial hepatectomy or liver resection removed 5%, 10%, 15%, 20%, 25%, 30%, 35%, 40%, 45%, 50%, 55%, 60%, 65%, 70%, 75%, 80%, 85%, 90%, or 95% by volume of the individual's liver. In any of the embodiments described herein, the individual has undergone a liver transplant. In any of the embodiments described herein, the individual has undergone a small-for-size liver transplant. In any of the embodiments described herein, the individual has liver damage caused by toxic injury, traumatic injury, microvesicular steatosis, or macrovesicular steatosis. In any of the embodiments described herein, the toxic injury results from exposure to carbon tetrachloride ($CCl_4$), bacterial endotoxin, use or abuse of intravenous or prescription drugs, chemotherapy, excessive consumption of alcohol, or infection with hepatitis virus A, B, or C. In any of the embodiments described herein, the traumatic injury results from surgical resection or blunt force trauma, such as that occurring in an automobile accident.

In certain embodiments, the method of stimulating liver regeneration in an individual in need thereof comprises administering to the individual a composition in an amount effective to reduce or prevent activation of one or more of the classical, lectin or alternative complement pathways. In certain embodiments, the composition comprises a targeted complement inhibitor. In certain embodiments, the targeted complement inhibitor comprises full-length CR2 (SEQ ID NO:1) fused to full-length mouse Crry (SEQ ID NO:4). In certain embodiments, the targeted complement inhibitor comprises full-length CR2 (SEQ ID NO:1) fused to a biologically active fragment of mouse Crry protein comprising the extracellular domain of mouse Crry (amino acids 41-405 of SEQ ID NO:4). In certain embodiments, the targeted complement inhibitor comprises full-length CR2 (SEQ ID NO:1) fused to a biologically active fragment of mouse Crry protein comprising SCR1-4 of mouse Crry (amino acids 83-338 of SEQ ID NO:4). In certain embodiments, the targeted complement inhibitor comprises full-length CR2 (SEQ ID NO:1) fused to a biologically active fragment of mouse Crry protein comprising SCR1-5 of mouse Crry (amino acids 83-400 of SEQ ID NO:4).

In certain embodiments, the targeted complement inhibitor comprises a biologically active fragment of CR2 comprising SCR1-2 (SEQ ID NO:2) fused to full-length mouse Crry protein (SEQ ID NO:4). In certain embodiments, the targeted complement inhibitor comprises a biologically active fragment of CR2 comprising SCR1-2 (SEQ ID NO:2) fused to a biologically active fragment of mouse Crry protein comprising the extracellular domain of mouse Crry (amino acids 41-405 of SEQ ID NO:4). In certain embodiments, the targeted complement inhibitor comprises a biologically active fragment of CR2 comprising SCR1-2 (SEQ ID NO:2) fused to a biologically active fragment of mouse Crry protein comprising SCR1-4 of mouse Crry (amino acids 83-338 of SEQ ID NO:4). In certain embodiments, the targeted complement inhibitor comprises a biologically active fragment of CR2 comprising SCR1-2 (SEQ ID NO:2) fused to a biologically active fragment of mouse Crry comprising SCR1-5 of mouse Crry (amino acids 83-400 of SEQ ID NO:4).

In certain embodiments, the targeted complement inhibitor comprises a non-CR2 targeting portion fused to full-length mouse Crry protein (SEQ ID NO:4), to a biologically active fragment of mouse Crry protein comprising the extracellular domain of mouse Crry (amino acids 41-405 of SEQ ID NO:4), to a biologically active fragment of mouse Crry protein comprising SCR1-4 of mouse Crry (amino acids 83-338 of SEQ ID NO:4), or to a biologically active fragment of mouse Crry comprising SCR1-5 of mouse Crry (amino acids 83-400 of SEQ ID NO:4). In certain embodiments, the non-CR2 targeting portion comprises an antibody or antigen-binding fragment thereof that specifically binds to proteolytic fragments of complement protein C3 (e.g., iC3b, C3dg, and C3d). In certain embodiments, the antibodies are polyclonal antibodies. In certain embodiments, the antibodies are monoclonal antibodies. In certain embodiments, the antibodies are polyclonal or monoclonal antibody fragments selected from the group consisting of Fab, Fab'-SH, Fv, scFv, and (Fab')$_2$ fragments. In certain embodiments, the antibodies or antigen-binding fragments thereof are humanized antibodies. In certain embodiments, the antibodies or antigen-binding fragments thereof are human antibodies.

In certain embodiments, the composition comprises a non-targeted complement inhibitor. In certain embodiments, the non-targeted complement inhibitor is human C1-inhibitor protein (SEQ ID NO:19) or mouse C1-inhibitor protein (SEQ ID NO:20). In certain embodiments, the non-targeted complement inhibitor is a homolog of human C1-inhibitor protein or a homolog of mouse C1-inhibitor protein or a biologically active fragment thereof.

In certain embodiments, the non-targeted complement inhibitor comprises an anti-C3 antibody or antigen-binding fragment thereof. In certain embodiments, the anti-C3 antibody or antigen-binding fragment thereof selectively binds to complement protein C3 and prevents cleavage of C3 into C3a and C3b. In certain embodiments, the anti-C3 antibody or antigen-binding fragment thereof is of a non-complement activating isotype or subclass. In certain embodiments, the antigen-binding fragment thereof is selected from the group consisting of Fab, Fab'-SH, Fv, scFv, and (Fab')$_2$ fragments. In certain embodiments, the anti-C3 antibody or antigen-binding fragment thereof is a monoclonal antibody, a humanized antibody, or a human antibody.

In certain embodiments, the method of stimulating liver regeneration in an individual in need thereof comprises administering to the individual a composition in an amount effective to reduce or prevent activation of the alternative complement pathway. In certain embodiments, the composition comprises a targeted complement inhibitor. In certain embodiments, the targeted complement inhibitor comprises full-length human CR2 (SEQ ID NO:1) or SCR1-2 of human CR2 (SEQ ID NO:2) fused to full-length human factor H (SEQ ID NO:5). In certain embodiments, the targeted complement inhibitor comprises full-length human CR2 (SEQ ID NO:1) or SCR1-2 of human CR2 (SEQ ID NO:2) fused to a biologically active fragment of human factor H comprising the first four N-terminal SCR domains of human factor H (amino acids 21-262 of SEQ ID NO:5). In certain embodiments, the targeted complement inhibitor comprises full-length human CR2 (SEQ ID NO:1) or SCR1-2 of human CR2 (SEQ ID NO:2) fused to a biologically active fragment of human factor H comprising the first five N-terminal SCR domains of human factor H (amino acids 21-320 of SEQ ID NO:5). In certain embodiments, the targeted complement inhibitor comprises full-length human CR2 (SEQ ID NO:1) or SCR1-2 of human CR2 (SEQ ID NO:2) fused to a biologically active fragment of human factor H comprising the first six N-terminal SCR domains of human factor H (amino acids 21-386 of SEQ ID NO:5). In certain embodiments, the targeted complement inhibitor comprises full-length human CR2 (SEQ ID NO:1) or SCR1-2 of human CR2 (SEQ ID NO:2) fused to a biologically active fragment of human factor H comprising the first eight N-terminal SCR domains of human factor H (amino acids 21-507 of SEQ ID NO:5). In certain embodiments, the targeted complement inhibitor comprises full-length human CR2 (SEQ ID NO:1) or SCR1-2 of human CR2 (SEQ ID NO:2) fused to a biologically active fragment of human factor H comprising the first eighteen N-terminal SCR domains of human factor H (amino acids 21-1104 of SEQ ID NO:5).

In certain embodiments, the targeted complement inhibitor comprises full-length human CR2 (SEQ ID NO:1) or SCR1-2 of human CR2 (SEQ ID NO:2) fused to full-length mouse factor H (SEQ ID NO:10). In certain embodiments, the targeted complement inhibitor comprises full-length human CR2 (SEQ ID NO:1) or SCR1-2 of human CR2 (SEQ ID NO:2) fused to a biologically active fragment of mouse factor H comprising the first four N-terminal SCR domains of mouse factor H (amino acids 19-264 of SEQ ID NO:10). In certain embodiments, the targeted complement inhibitor comprises full-length human CR2 (SEQ ID NO:1) or SCR1-2 of human CR2 (SEQ ID NO:2) fused to a biologically active fragment of mouse factor H comprising the first five N-terminal SCR domains of mouse factor H (amino acids 19-322 of SEQ ID NO:10). In certain embodiments, the targeted complement inhibitor comprises full-length human CR2 (SEQ ID NO:1) or SCR1-2 of human CR2 (SEQ ID NO:2) fused to a biologically active fragment of mouse factor H comprising the first six N-terminal SCR domains of mouse factor H (amino acids 19-386 of SEQ ID NO:10). In certain embodiments, the targeted complement inhibitor comprises full-length human CR2 (SEQ ID NO:1) or SCR1-2 of human CR2 (SEQ ID NO:2) fused to a biologically active fragment of mouse factor H comprising the first eight N-terminal SCR domains of mouse factor H (amino acids 19-624 of SEQ ID NO:10). In certain embodiments, the targeted complement inhibitor comprises full-length human CR2 (SEQ ID NO:1) or SCR1-2 of human CR2 (SEQ ID NO:2) fused to a biologically active fragment of mouse factor H comprising the first eighteen N-terminal SCR domains of mouse factor H (amino acids 19-1109 of SEQ ID NO:10).

In certain embodiments, the targeted complement inhibitor comprises a non-CR2 targeting portion fused to full-length human factor H (SEQ ID NO:5), to a biologically active fragment of human factor H comprising the first four N-terminal SCR domains of human factor H (amino acids 21-262 of SEQ ID NO:5), to a biologically active fragment of human factor H comprising the first five N-terminal SCR domains of human factor H (amino acids 21-320 of SEQ ID NO:5), to a biologically active fragment of human factor H comprising the first six N-terminal SCR domains of human factor H (amino acids 21-386 of SEQ ID NO:5), to a biologically active fragment of human factor H comprising the first eight N-terminal SCR domains of human factor H (amino acids 21-507 of SEQ ID NO:5), or to a biologically active fragment of human factor H comprising the first eighteen N-terminal SCR domains of human factor H (amino acids 21-1104 of SEQ ID NO:5).

In certain embodiments, the non-targeted complement inhibitor comprises an anti-factor B antibody or antigen-binding fragment thereof. In certain embodiments, the anti-factor B antibody or antigen-binding fragment thereof selectively binds to factor B within the third short consensus repeat (SCR) domain and prevents formation of a C3bBb complex.

In certain embodiments, the anti-factor B antibody or antigen-binding fragment thereof is of a non-complement activating isotype or subclass. In certain embodiments, the antigen-binding fragment thereof is selected from the group consisting of Fab, Fab'-SH, Fv, scFv, and (Fab')$_2$ fragments. In certain embodiments, the anti-factor B antibody or antigen-binding fragment thereof is a monoclonal antibody, a humanized antibody, or a human antibody. In certain embodiments, the antibody is the monoclonal antibody 1379 (produced by ATCC Deposit No. PTA-6230).

In certain embodiments, the non-targeted complement inhibitor comprises an anti-properdin antibody or antigen-binding fragment thereof. In certain embodiments, the anti-properdin antibody inhibits the production of one or more of Bb, C3a, and C5a. In certain embodiments, the anti-properdin antibody or antigen-binding fragment thereof is of a non-complement activating isotype or subclass. In certain embodiments, the antigen-binding fragment thereof is selected from the group consisting of Fab, Fab'-SH, Fv, scFv, and (Fab')$_2$ fragments. In certain embodiments, the anti-properdin antibody or antigen-binding fragment thereof is a monoclonal antibody, a humanized antibody, or a human antibody.

In certain embodiments, the non-targeted complement inhibitor comprises an anti-factor D antibody or antigen-binding fragment thereof. In certain embodiments, the anti-factor D antibody inhibits the production of one or more of Bb, C3a, C5a, and sC5b-9. In certain embodiments, the anti-factor D antibody or antigen-binding fragment thereof is of a non-complement activating isotype or subclass. In certain embodiments, the antigen-binding fragment thereof is selected from the group consisting of Fab, Fab'-SH, Fv, scFv, and (Fab')$_2$ fragments. In certain embodiments, the anti-factor D antibody or antigen-binding fragment thereof is a monoclonal antibody, a humanized antibody, or a human antibody. In certain embodiments, the antibody is the monoclonal antibody (mAb) 166-32 (produced by ATCC Deposit Accession_Number HB-12476).

In certain embodiments, the method of stimulating liver regeneration in an individual in need thereof comprises administering to the individual a composition in an amount effective to reduce or prevent activation of terminal complement and formation of the membrane attack complex (MAC) in the individual. In certain embodiments, the composition is a targeted complement inhibitor. In certain embodiments, the targeted complement inhibitor comprises full-length CR2 protein (SEQ ID NO:1) fused to full-length human CD59 protein (SEQ ID NO:3), a full-length mouse CD59 protein, isoform A (SEQ ID NO:8), or a full-length mouse CD59 protein, isoform B (SEQ ID NO:9). In certain embodiments, the targeted complement inhibitor comprises full-length CR2 protein (SEQ ID NO:1) fused to a biologically active fragment of CD59 protein comprising the extracellular domain of human CD59 (amino acids 26-102 of SEQ ID NO:3) lacking its GPI anchor and/or the amino acid to which it is attached (i.e., Asn-102), a biologically active fragment of mouse CD59 protein, isoform A comprising the extracellular domain of mouse CD59, isoform A (amino acids 24-96 of SEQ ID NO:8) lacking its GPI anchor and/or the amino acid to which it is attached (i.e., Ser-96), or a biologically active fragment of mouse CD59 protein, isoform B comprising the extracellular domain of mouse CD59, isoform B (amino acids 24-104 of SEQ ID NO:9) lacking its GPI anchor and/or the amino acid to which it is attached (i.e., Asn-104).

In certain embodiments, the targeted complement inhibitor comprises a biologically active fragment of CR2 protein comprising SCR1-2 (SEQ ID NO:2) fused to full-length human CD59 protein (SEQ ID NO:3), a full-length mouse CD59 protein, isoform A (SEQ ID NO:8), or a full-length mouse CD59 protein, isoform B (SEQ ID NO:9). In certain embodiments, the targeted complement inhibitor comprises a biologically active fragment of CR2 protein comprising SCR1-2 (SEQ ID NO:2) fused to a biologically active fragment of CD59 protein comprising the extracellular domain of human CD59 (amino acids 26-102 of SEQ ID NO:3) lacking its GPI anchor and/or the amino acid to which it is attached (i.e., Asn-102), a biologically active fragment of mouse CD59 protein, isoform A comprising the extracellular domain of mouse CD59, isoform A (amino acids 24-96 of SEQ ID NO:8) lacking its GPI anchor and/or the amino acid to which it is attached (i.e., Ser-96), or a biologically active fragment of mouse CD59 protein, isoform B comprising the extracellular domain of mouse CD59, isoform B (amino acids 24-104 of SEQ ID NO:9) lacking its GPI anchor and/or the amino acid to which it is attached (i.e., Asn-104).

In certain embodiments, the targeted complement inhibitor comprises a non-CR2 targeting portion fused to full-length human CD59 protein (SEQ ID NO:3), to a full-length mouse CD59 protein, isoform A (SEQ ID NO:8), or to a full-length mouse CD59 protein, isoform B (SEQ ID NO:9). In certain embodiments, the targeted complement inhibitor comprises a non-CR2 targeting portion fused to a biologically active fragment of CD59 protein comprising the extracellular domain of human CD59 (amino acids 26-102 of SEQ ID NO:3) lacking its GPI anchor and/or the amino acid to which it is attached (i.e., Asn-102), to a biologically active fragment of mouse CD59 protein, isoform A comprising the extracellular domain of mouse CD59, isoform A (amino acids 24-96 of SEQ ID NO:8) lacking its GPI anchor and/or the amino acid to which it is attached (i.e., Ser-96), or to a biologically active fragment of mouse CD59 protein, isoform B comprising the extracellular domain of mouse CD59, isoform B (amino acids 24-104 of SEQ ID NO:9) lacking its GPI anchor and/or the amino acid to which it is attached (i.e., Asn-104).

In certain embodiments, the composition is a non-targeted complement inhibitor. In certain embodiments, the non-targeted complement inhibitor inhibits terminal complement and formation of the membrane attack complex (MAC). In certain embodiments, the non-targeted complement inhibitor is an anti-C5 antibody or antigen-binding fragment thereof that inhibits activation of terminal complement and formation of the membrane attack complex (MAC). In certain embodiments, the anti-C5 antibody or antigen-binding fragment thereof inhibits cleavage of complement protein C5 (C5). In certain embodiments, the anti-C5 antibody or antigen-binding fragment thereof inhibits assembly of the membrane attack complex (MAC). In certain embodiments, the anti-C5 antibody or antigen-binding fragment thereof is polyclonal, monoclonal, chimeric, or humanized. In certain embodiments, the antigen-binding fragments are selected from the group consisting of Fab, Fab', and F(ab')$_2$ fragments. In certain embodiments, the anti-C5 antibody or antigen-binding fragment thereof is polyclonal. In certain embodiments, the anti-C5 antibody or antigen-binding fragment thereof is monoclonal. In certain embodiments, the anti-C5 antibody or antigen-binding fragment thereof is chimeric. In certain embodiments, the anti-C5 antibody or antigen-binding fragment thereof is humanized. In certain embodiments, the humanized anti-C5 antibody or antigen-binding fragment thereof is eculizumab or pexelizumab.

In certain embodiments, the non-targeted complement inhibitor inhibits terminal complement and formation of the membrane attack complex (MAC). In certain embodiments, the non-targeted complement inhibitor is the heterodimeric apolipoprotein clusterin. In certain embodiments, the clusterin inhibits complement protein C9 assembly on C5b-8 and C5b-9 or binds to C5b-7 to prevent membrane attachment. In certain embodiments, the non-targeted complement inhibitor is human clusterin protein (SEQ ID NO:15) or mouse clusterin protein (SEQ ID NO:16). In certain embodiments, the non-targeted complement inhibitor comprises a homolog of a human or mouse clusterin protein or a biologically active fragment thereof.

In certain embodiments, the non-targeted complement inhibitor inhibits terminal complement and formation of the membrane attack complex (MAC). In certain embodiments, the non-targeted complement inhibitor is the protein vitronectin or a biologically active fragment or homolog thereof. In certain embodiments, the vitronectin blocks C5b-7 membrane binding and prevents C9 polymerization. In certain embodiments, the non-targeted complement inhibitor is human vitronectin protein (SEQ ID NO:17) or mouse vitronectin protein (SEQ ID NO:18). In certain embodiments, the non-targeted complement inhibitor comprises a homolog of a human or mouse vitronectin protein or a biologically active fragment thereof.

In any of the embodiments described herein, the individual is a vertebrate. In any of the embodiments described herein, the vertebrate is a mammal. In any of the embodiments described herein, the mammal is a research animal or a domestic animal. In any of the embodiments described herein, the mammal is a human.

In any of the embodiments described herein, the non-CR2 targeting portion comprises an antibody or antigen-binding fragment thereof that specifically binds to proteolytic fragments of complement protein C3 (e.g., iC3b, C3dg, and C3d). In any of the embodiments described herein, the antibodies are polyclonal antibodies. In certain embodiments, the antibodies are monoclonal antibodies. In any of the embodiments described herein, the antibodies are polyclonal or monoclonal antibody fragments selected from the group consisting of Fab, Fab'-SH, Fv, scFv, and (Fab')$_2$ fragments. In any of the embodiments described herein, the antibodies or antigen-binding fragments thereof are humanized antibodies. In any of the embodiments described herein, the antibodies or antigen-binding fragments thereof are human antibodies.

In any of the embodiments described herein, the compositions administered to an individual are pharmaceutical compositions suitable for administration to an individual by any commonly used route of administration, including those described herein.

Sequences
[complete amino acid sequence of complement receptor 2 (CR2)]:
SEQ ID NO: 1
MGAAGLLGVFLALVAPGVLGISCGSPPPILNGRISYYSTPIAVGTVIRY

SCSGTFRLIGEKSLLCITKDKVDGTWDKPAPKCEYFNKYSSCPEPIVPG

GYKIRGSTPYRHGDSVTFACKTNFSMNGNKSVWCQANNMWGPTRLPTCV

SVFPLECPALPMIHNGHHTSENVGSIAPGLSVTYSCESGYLLVGEKIIN

CLSSGKWSAVPPTCEEARCKSLGRFPNGKVKEPPILRVGVTANFFCDEG

YRLQGPPSSRCVIAGQGVAWTKMPVCEEIFCPSPPPILNGRHIGNSLAN

VSYGSIVTYTCDPDPEEGVNFILIGESTLRCTVDSQKTGTWSGPAPRCE

LSTSAVQCPHPQILRGRMVSGQKDRYTYNDTVIFACMFGFTLKGSKQIR

CNAQGTWEPSAPVCEKECQAPPNILNGQKEDRHMVRFDPGTSIKYSCNP

GYVLVGEESIQCTSEGVWTPPVPQCKVAACEATGRQLLTKPQHQFVRPD

VNSSCGEGYKLSGSVYQECQGTIPWFMEIRLCKEITCPPPPVIYNGAHT

GSSLEDFPYGTTVTYTCNPGPERGVEFSLIGESTIRCTSNDQERGTWSG

PAPLCKLSLLAVQCSHVHIANGYKISGKEAPYFYNDTVTFKCYSGFTLK

GSSQIRCKRDNTWDPEIPVCEKGCQPPPGLHHGRHTGGNTVFFVSGMTV

DYTCDPGYLLVGNKSIHCMPSGNWSPSAPRCEETCQHVRQSLQELPAGS

RVELVNTSCQDGYQLTGHAYQMCQDAENGIVVFKKIPLCKVIHCHPPPV

IVNGKHTGMMAENFLYGNEVSYECDQGFYLLGEKNCSAEVILKAWILER

AFPQCLRSLCPNPEVKHGYKLNKTHSAYSHNDIVYVDCNPGFIMNGSRV

IRCHTDNTWVPGVPTCIKKAFIGCPPPPKTPNGNHTGGNIARFSPGMSI

LYSCDQGYLVVGEPLLLCTHEGTWSQPAPHCKEVNCSSPADMDGIQKGL

EPRKMYQYGAVVTLECEDGYMLEGSPQSQCQSDHQWNPPLAVCRSRSLA

PVLCGIAAGLILLTFLIVITLYVISKHRERNYYTDTSQKEAFHLEAREV

YSVDPYNPAS

[amino acid sequence of short consensus repeat (SCR) domains 1 and 2 of CR2]:
SEQ ID NO: 2
ISCGSPPPILNGRISYYSTPIAVGTVIRYSCSGTFRLIGEKSLLCITKD

VDGTWDKPAPKCEYFNKYSSCPEPIVPGGYKIRGSTPYRHGDSVTFACK

TNFSMNGNKSVWCQANNMWGPTRLPTCVS

[amino acid sequence of human CD59 protein]:
SEQ ID NO: 3
MGIQGGSVLFGLLLVLAVFCHSGHSLQCYNCPNPTADCKTAVNCSSDFD

ACLITKAGLQVYNKCWKFEHCNFNDVTTRLRENELTYYCCKKDLCNFNE

QLENGGTSLSEKTVLLLVTPFLAAAWSLHP

[amino acid sequence of mouse complement receptor 1-related gene/protein y (Crry)]:
SEQ ID NO: 4
MEVSSRSSEPLDPVWLLVAFGRGGVKLEVLLLFLLPFTLGELRGGLGKH

GHTVHREPAVNRLCADSKRWSGLPVSAQRPFPMGHCPAPSQLPSAKPIN

LTDESMFPIGTYLLYECLPGYIKRQFSITCKQDSTWTSAEDKCIRKQCK

TPSDPENGLVHVHTGIQFGSRINYTCNQGYRLIGSSSAVCVITDQSVDW

DTEAPICEWIPCEIPPGIPNGDFFSSTREDFHYGMVVTYRCNTDARGKA

LFNLVGEPSLYCTSNDGEIGVWSGPPPQCIELNKCTPPPYVENAVMLSE

NRSLFSLRDIVEFRCHPGFIMKGASSVHCQSLNKWEPELPSCFKGVICR

LPQEMSGFQKGLGMKKEYYYGENVTLECEDGYTLEGSSQSQCQSDGSWN

PLLAKCVSRSISGLIVGIFIGIIVFILVIIVFIWMILKYKKRNTTDEKY

KEVGIHLNYKEDSCVRLQSLLTSQENSSTTSPARNSLTQEVS

[amino acid sequence of human factor H]:
SEQ ID NO: 5
MRLLAKIICLMLWAICVAEDCNELPPRRNTEILTGSWSDQTYPEGTQAI

YKCRPGYRSLGNVIMVCRKGEWVALNPLRKCQKRPCGHPGDTPFGTFTL

TGGNVFEYGVKAVYTCNEGYQLLGEINYRECDTDGWTNDIPICEVVKCL

PVTAPENGKIVSSAMEPDREYHFGQAVRFVCNSGYKIEGDEEMHCSDDG

FWSKEKPKCVEISCKSPDVINGSPISQKIIYKENERFQYKCNMGYEYSE

RGDAVCTESGWRPLPSCEEKSCDNPYIPNGDYSPLRIKHRTGDEITYQC
RNGFYPATRGNTAKCTSTGWIPAPRCTLKPCDYPDIKHGGLYHENMRRP
YFPVAVGKYYSYYCDEHFETPSGSYWDHIHCTQDGWSPAVPCLRKCYFP
YLENGYNQNYGRKFVQGKSIDVACHPGYALPKAQTTVTCMENGWSPTPR
CIRVKTCSKSSIDIENGFISESQYTYALKEKAKYQCKLGYVTADGETSG
SITCGKDGWSAQPTCIKSCDIPVFMNARTKNDFTWFKLNDTLDYECHDG
YESNTGSTTGSIVCGYNGWSDLPICYERECELPKIDVHLVPDRKKDQYK
VGEVLKFSCKPGFTIVGPNSVQCYHFGLSPDLPICKEQVQSCGPPPELL
NGNVKEKTKEEYGHSEVVEYYCNPRFLMKGPNKIQCVDGEWTTLPVCIV
EESTCGDIPELEHGWAQLSSPPYYYGDSVEFNCSESFTMIGHRSITCIH
GVWTQLPQCVAIDKLKKCKSSNLIILEEHLKNKKEFDHNSNIRYRCRGK
EGWIHTVCINGRWDPEVNCSMAQIQLCPPPPQIPNSHNMTTTLNYRDGE
KVSVLCQENYLIQEGEEITCKDGRWQSIPLCVEKIPCSQPPQIEHGTIN
SSRSSQESYAHGTKLSYTCEGGFRISEENETTCYMGKWSSPPQCEGLPC
KSPPEISHGVVAHMSDSYQYGEEVTYKCFEGFGIDGPAIAKCLGEKWSH
PPSCIKTDCLSLPSFENAIPMGEKKDVYKAGEQVTYTCATYYKMDGASN
VTCINSRWTGRPTCRDTSCVNPPTVQNAYIVSRQMSKYPSGERVRYQCR
SPYEMFGDEEVMCLNGNWTEPPQCKDSTGKCGPPPPIDNGDITSFPLSV
YAPASSVEYQCQNLYQLEGNKRITCRNGQWSEPPKCLHPCVISREIMEN
YNIALRWTAKQKLYSRTGESVEFVCKRGYRLSSRSHTLRTTCWDGKLEY
PTCAKR

[amino acid sequence of human ASP/C3adesArg]:
SEQ ID NO: 6
SVQLTEKRMDKVGKYPKELRKCCEDGMRENPMRFSCQRRTRFISLGEAC
KKVFLDCCNYITELRRQHARASHLGLA

[amino acid sequence of the human ASP/C3adesArg
receptor (C5L2)]:
SEQ ID NO: 7
MGNDSVSYEYGDYSDLSDRPVDCLDGACLAIDPLRVAPLPLYAAIFLVG
VPGNAMVAWVAGKVARRRVGATWLLHLAVADLLCCLSLPILAVPIARGG
HWPYGAVGCRALPSIILLTMYASVLLLAALSADLCFLALGPAWWSTVQR
ACGVQVACGAAWTLALLLTVPSAIYRRLHQEHFPARLQCVVDYGGSSST
ENAVTAIRFLFGFLGPLVAVASCHSALLCWAARRCRPLGTAIVVGFFVC
WAPYHLLGLVLTVAAPNSALLARALRAEPLIVGLALAHSCLNPMLFLYF
GRAQLRRSLPAACHWALRESQGQDESVDSKKSTSHDLVSEMEV

[amino acid sequence of mouse CD59A protein]:
SEQ ID NO: 8
MRAQRGLILLLLLLAVFCSTAVSLTCYHCFQPVVSSCNMNSTCSPDQDS
CLYAVAGMQVYQRCWKQSDCHGEIIMDQLEETKLKFRCCQFNLCNKSDG
SLGKTPLLGTSVLVAILNLCFLSHL

[amino acid sequence of mouse CD59B protein]:
SEQ ID NO: 9
MRAQRGLILLLLLLAVFCSTAVSLKCYNCFQFVSSCKINTTCSPNLDSC
LYAVAGRQVYQQCWKLSDCNSNYIMSRLDVAGIQSKCCQWGLCNKNLDG
LEEPNNAETSSLRKTALLGTSVLVAILKFCF

[amino acid sequence of mouse factor H]:
SEQ ID NO: 10
MRLSARIIWLILWTVCAAEDCKGPPPRENSEILSGSWSEQLYPEGTQAT
YKCRPGYRTLGTIVKVCKNGKWVASNPSRICRKKPCGHPGDTPFGSFRL
AVGSQFEFGAKVVYTCDDGYQLLGEIDYRECGADGWINDIPLCEVVKCL
PVTELENGRIVSGAAETDQEYYFGQVVRFECNSGFKIEGHKEIHCSENG
LWSNEKPRCVEILCTPPRVENGDGINVKPVYKENERYHYKCKHGYVPKE
RGDAVCTGSGWSSQPFCEEKRCSPPYILNGIYTPHRIIHRSDDEIRYEC
NYGFYPVTGSTVSKCTPTGWIPVPRCTLKPCEFPQFKYGRLYYEESLRP
NFPVSIGNKYSYKCDNGFSPPSGYSWDYLRCTAQGWEPEVPCVRKCVFH
YVENGDSAYWEKVYVQGQSLKVQCYNGYSLQNGQDTMTCTENGWSPPPK
CIRIKTCSASDIHIDNGFLSESSSIYALNRETSYRCKQGYVTNTGEISG
SITCLQNGWSPQPSCIKSCDMPVFENSITKNTRTWFKLNDKLDYECLVG
FENEYKHTKGSITCTYYGWSDTPSCYERECSVPTLDRKLVVSPRKEKYR
VGDLLEFSCHSGHRVGPDSVQCYHFGWSPGFPTCKGQVASCAPPLEILN
GEINGAKKVEYSHGEVVKYDCKPRFLLKGPNKIQCVDGNWTTLPVCIEE
ERTCGDIPELEHGSAKCSVPPYHHGDSVEFICEENFTMIGHGSVSCISG
KWTQLPKCVATDQLEKCRVLKSTGIEAIKPKLTEFTHNSTMDYKCRDKQ
EYERSICINGKWDPEPNCTSKTSCPPPPQIPNTQVIETTVKYLDGEKLS
VLCQDNYLTQDSEEMVCKDGRWQSLPRCIEKIPCSQPPTIEHGSINLPR
SSEERRDSIESSSHEHGTTFSYVCDDGFRIPEENRITCYMGKWSTPPRC
VGLPCGPPPSIPLGTVSLELESYQHGEEVTYHCSTGFGIDGPAFIICEG
GKWSDPPKCIKTDCDVLPTVKNAIIRGKSKKSYRTGEQVTFRCQSPYQM
NGSDTVTCVNSRWIGQPVCKDNSCVDPPHVPNATIVTRTKNKYLHGDRV
RYECNKPLELFGQVEVMCENGIVVTEKPKCRDSTGKCGPPPPIDNGDIT
SLSLPVYEPLSSVEYQCQKYYLLKGKKTITCTNGKWSEPPTCLHACVIP
ENIMESHNIILKWRHTEKIYSHSGEDIEFGCKYGYYKARDSPPFRTKCI
NGTINYPTCV

[amino acid sequence of human complement receptor
1 (CR1)]:
SEQ ID NO: 11
MGASSPRSPEPVGPPAPGLPFCCGGSLLAVVVLLALPVAWGQCNAPEWL
PFARPTNLTDEFEFPIGTYLNYECRPGYSGRPFSIICLKNSVWTGAKDR
CRRKSCRNPPDPVNGMVHVIKGIQFGSQIKYSCTKGYRLIGSSSATCII
SGDTVIWDNETPICDRIPCGLPPTITNGDFISTNRENFHYGSVVTYRCN
PGSGGRKVFELVGEPSIYCTSNDDQVGIWSGPAPQCIIPNKCTPPNVEN
GILVSDNRSLFSLNEVVEFRCQPGFVMKGPRRVKCQALNKWEPELPSCS
RVCQPPPDVLHAERTQRDKDNFSPGQEVFYSCEPGYDLRGAASMRCTPQ
GDWSPAAPTCEVKSCDDFMGQLLNGRVLFPVNLQLGAKVDFVCDEGFQL
KGSSASYCVLAGMESLWNSSVPVCEQIFCPSPPVIPNGRHTGKPLEVFP
FGKAVNYTCDPHPDRGTSFDLIGESTIRCTSDPQGNGVWSSPAPRCGIL
GHCQAPDHFLFAKLKTQTNASDFPIGTSLKYECRPEYYGRPFSITCLDN
LVWSSPKDVCKRKSCKTPPDPVNGMVHVITDIQVGSRINYSCTTGHRLI -continued

GHSSAECILSGNAAHWSTKPPICQRIPCGLPPTIANGDFISTNRENFHY
GSVVTYRCNPGSGGRKVFELVGEPSIYCTSNDDQVGIVVSGPAPQCIIP
NKCTPPNVENGILVSDNRSLFSLNEVVEFRCQPGFVMKGPRRVKCQALN
KWEPELPSCSRVCQPPPDVLHAERTQRDKDNFSPGQEVFYSCEPGYDLR
GAASMRCTPQGDWSPAAPTCEVKSCDDFMGQLLNGRVLFPVNLQLGAKV
DFVCDEGFQLKGSSASYCVLAGMESLWNSSVPVCEQIFCPSPPVIPNGR
HTGKPLEVFPFGKAVNYTCDPHPDRGTSFDLIGESTIRCTSDPQGNGVW
SSPAPRCGILGHCQAPDHFLFAKLKTQTNASDFPIGTSLKYECRPEYYG
RPFSITCLDNLVWSSPKDVCKRKSCKTPPDPVNGMVHVITDIQVGSRIN
YSCTTGHRLIGHSSAECILSGNTAHWSTKPPICQRIPCGLPPTIANGDF
ISTNRENFHYGSVVTYRCNLGSRGRKVFELVGEPSIYCTSNDDQVGIWS
GPAPQCIIPNKCTPPNVENGILVSDNRSLFSLNEVVEFRCQPGFVMKGP

RRVKCQALNKWEPELPSCSRVCQPPPEILHGEHTPSHQDNFSPGQEVFY

SCEPGYDLRGAASLHCTPQGDWSPEAPRCAVKSCDDFLGQLPHGRVLFP

LNLQLGAKVSFVCDEGFRLKGSSVSHCVLVGMRSLWNNSVPVCEHIFCP

NPPAILNGRHTGTPSGDIPYGKEISYTCDPHPDRGMTFNLIGESTIRCT

SDPHGNGVWSSPAPRCELSVRAGHCKTPEQFPFASPTIPINDFEFPVGT

SLNYECRPGYFGKMFSISCLENLVWSSVEDNCRRKSCGPPPEPFNGMVH

INTDTQFGSTVNYSCNEGFRLIGSPSTTCLVSGNNVTWDKKAPICEIIS

CEPPPTISNGDFYSNNRTSFHNGTVVTYQCHTGPDGEQLFELVGERSIY

CTSKDDQVGVWSSPPPRCISTNKCTAPEVENAIRVPGNRSFFSLTEIIR

FRCQPGFVMVGSHTVQCQTNGRWGPKLPHCSRVCQPPPEILHGEHTLSH

QDNFSPGQEVFYSCEPSYDLRGAASLHCTPQGDWSPEAPRCTVKSCDDF

LGQLPHGRVLLPLNLQLGAKVSFVCDEGFRLKGRSASHCVLAGMKALWN

SSVPVCEQIFCPNPPAILNGRHTGTPFGDIPYGKEISYACDTHPDRGMT

FNLIGESSIRCTSDPQGNGVWSSPAPRCELSVPAACPHPPKIQNGHYIG

GHVSLYLPGMTISYTCDPGYLLVGKGFIFCTDQGIVVSQLDHYCKEVNC

SFPLFMNGISKELEMKKVYHYGDYVTLKCEDGYTLEGSPWSQCQADDRW

DPPLAKCTSRAHDALIVGTLSGTIFFILLIIFLSWIILKHRKGNNAHEN

PKEVAIHLHSQGGSSVHPRTLQTNEENSRVLP

[amino acid sequence of human membrane cofactor protein (MCP)]:

SEQ ID NO: 12

MEPPGRRECPFPSWRFPGLLLAAMVLLLYSFSDACEEPPTFEAMELIGK

PKPYYEIGERVDYKCKKGYFYIPPLATHTICDRNHTWLPVSDDACYRET

CPYIRDPLNGQAVPANGTYEFGYQMHFICNEGYYLIGEEILYCELKGSV

AIVVSGKPPICEKVLCTPPPKIKNGKHTFSEVEVFEYLDAVTYSCDPAP

GPDPFSLIGESTIYCGDNSVWSRAAPECKVVKCRFPVVENGKQISGFGK

KFYYKATVMFECDKGFYLDGSDTIVCDSNSTWDPPVPKCLKVLPPSSTK

PPALSHSVSTSSTTKSPASSASGPRPTYKPPVSNYPGYPKPEEGILDSL

DVWVIAVIVIAIVVGVAVICVVPYRYLQRRKKKGTYLTDETHREVKFTS

L

-continued

[amino acid sequence of human decay accelerating factor (DAF/CD55)]:

SEQ ID NO: 13

MTVARPSVPAALPLLGELPRLLLLVLLCLPAVWGDCGLPPDVPNAQPAL

EGRTSFPEDTVITYKCEESFVKIPGEKDSVICLKGSQWSDIEEFCNRSC

EVPTRLNSASLKQPYITQNYFPVGTVVEYECRPGYRREPSLSPKLTCLQ

NLKWSTAVEFCKKKSCPNPGEIRNGQIDVPGGILFGATISFSCNTGYKL

FGSTSSFCLISGSSVQWSDPLPECREIYCPAPPQIDNGIIQGERDHYGY

RQSVTYACNKGFTMIGEHSIYCTVNNDEGEWSGPPPECRGKSLTSKVPP

TVQKPTTVNVPTTEVSPTSQKTTTKTTTPNAQATRSTPVSRTTKHFHET

TPNKGSGTTSGTTRLLSGHTCFTLTGLLGTLVTMGLLT

[amino acid sequence of mouse decay accelerating factor (DAF/CD55)]:

SEQ ID NO: 14

MIRGRAPRTRPSPPPPLLPLLSLSLLLLSPTVRGDCGPPPDIPNARPIL

GRHSKFAEQSKVAYSCNNGFKQVPDKSNIVVCLENGQWSSHETFCEKSC

VAPERLSFASLKKEYLNMNFFPVGTIVEYECRPGFRKQPPLPGKATCLE

DLVWSPVAQFCKKKSCPNPKDLDNGHINIPTGILFGSEINFSCNPGYRL

VGVSSTFCSVTGNTVDWDDEFPVCTEIHCPEPPKINNGIMRGESDSYTY

SQVVTYSCDKGFILVGNASIYCTVSKSDVGQWSSPPPRCIEKSKVPTKK

PTINVPSTGTPSTPQKPTTESVPNPGDQPTPQKPSTVKVSATQHVPVTK

TTVRHPIRTSTDKGEPNTGGDRYIYGHTCLITLTVLHVMLSLIGYLT

[amino acid sequence of human clusterin protein]:

SEQ ID NO: 15

MMKTLLLFVGLLLTWESGQVLGDQTVSDNELQEMSNQGSKYVNKEIQNA

VNGVKQIKTLIEKTNEERKTLLSNLEEAKKKKEDALNETRESETKLKEL

PGVCNETMMALWEECKPCLKQTCMKFYARVCRSGSGLVGRQLEEFLNQS

SPFYFWMNGDRIDSLLENDRQQTHMLDVMQDHFSRASSIIDELFQDRFF

TREPQDTYHYLPFSLPHRRPHFFFPKSRIVRSLMPFSPYEPLNFHAMFQ

PFLEMIHEAQQAMDIHFHSPAFQHPPTEFIREGDDDRTVCREIRHNSTG

CLRMKDQCDKCREILSVDCSTNNPSQAKLRRELDESLQVAERLTRKYNE

LLKSYQWKMLNTSSLLEQLNEQFNWVSRLANLTQGEDQYYLRVTTVASH

TSDSDVPSGVTEVVVKLFDSDPITVTVPVEVSRKNPKFMETVAEKALQE

YRKKHREE

[amino acid sequence of mouse clusterin protein]:

SEQ ID NO: 16

MKILLLCVALLLIWDNGMVLGEQEVSDNELQELSTQGSRYINKEIQNAV

QGVKHIKTLIEKTNAERKSLLNSLEEAKKKKEDALEDTRDSEMKLKAFP

EVCNETMMALWEECKPCLKHTCMKFYARVCRSGSGLVGQQLEEFLNQSS

PFYFWMNGDRIDSLLESDRQQSQVLDAMQDSFARASGIIDTLFQDRFFA

RELHDPHYFSPIGFPHKRPHFLYPKSRLVRSLMSPSHYGPPSFHNMFQP

FFEMIHQAQQAMDVQLHSPAFQFPDVDFLREGEDDRTVCKEIRRNSTGC

LKMKGQCEKCQEILSVDCSTNNPAQANLRQELNDSLQVAERLTEQYKEL

LQSFQSKMLNTSSLLEQLNDQFNWVSQLANLTQGEDKYYLRVSTVTTHS

SDSEVPSRVTEVVVKLFDSDPITVVLPEEVSKDNPKFMDTVAEKALQEY

RRKSRAE

-continued

[amino acid sequence of human vitronectin protein]:
SEQ ID NO: 17
MAPLRPLLILALLAWVALADQESCKGRCTEGFNVDKKCQCDELCSYYQS

CCTDYTAECKPQVTRGDVFTMPEDEYTVYDDGEEKNNATVHEQVGGPSL

TSDLQAQSKGNPEQTPVLKPEEEAPAPEVGASKPEGIDSRPETLHPGRP

QPPAEEELCSGKPFDAFTDLKNGSLFAFRGQYCYELDEKAVRPGYPKLI

RDVWGIEGPIDAAFTRINCQGKTYLFKGSQYWRFEDGVLDPDYPRNISD

GFDGIPDNVDAALALPAHSYSGRERVYFFKGKQYWEYQFQHQPSQEECE

GSSLSAVFEHFAMMQRDSWEDIFELLFWGRTSAGTRQPQFISRDWHGVP

GQVDAAMAGRIYISGMAPRPSLAKKQRFRHRNRKGYRSQRGHSRGRNQN

SRRPSRATWLSLFSSEESNLGANNYDDYRMDWLVPATCEPIQSVFFFSG

DKYYRVNLRTRRVDTVDPPYPRSIAQYWLGCPAPGHL

[amino acid sequence of mouse vitronectin protein]:
SEQ ID NO: 18
MAPLRPFFILALVAWVSLADQESCKGRCTQGFMASKKCQCDELCTYYQS

CCADYMEQCKPQVTRGDVFTMPEDDYWSYDYVEEPKNNTNTGVQPENTS

PPGDLNPRTDGTLKPTAFLDPEEQPSTPAPKVEQQEEILRPDTTDQGTP

EFPEEELCSGKPFDAFTDLKNGSLFAFRGQYCYELDETAVRPGYPKLIQ

DVWGIEGPIDAAFTRINCQGKTYLFKGSQYWRFEDGVLDPGYPRNISEG

FSGIPDNVDAAFALPAHRYSGRERVYFFKGKQYWEYEFQQQPSQEECEG

SSLSAVFEHFALLQRDSWENIFELLFWGRSSDGAREPQFISRNWHGVPG

KVDAAMAGRIYVTGSLSHSAQAKKQKSKRRSRKRYRSRRGRGHRRSQSS

NSRRSSRSIWFSLFSSEESGLGTYNNYDYDMDWLVPATCEPIQSVYFFS

GDKYYRVNLRTRRVDSVNPPYPRSIAQYWLGCPTSEK

[amino acid sequence of human C1-inhibitor protein]:
SEQ ID NO: 19
MASRLTLLTLLLLLLAGDRASSNPNATSSSSQDPESLQDRGEGKVATTV

ISKMLFVEPILEVSSLPTTNSTTNSATKITANTTDEPTTQPTTEPTTQP

TIQPTQPTTQLPTDSPTQPTTGSFCPGPVTLCSDLESHSTEAVLGDALV

DFSLKLYHAFSAMKKVETNMAFSPFSIASLLTQVLLGAGENTKTNLESI

LSYPKDFTCVHQALKGFTTKGVTSVSQIFHSPDLAIRDTFVNASRTLYS

SSPRVLSNNSDANLELINTWVAKNTNNKISRLLDSLPSDTRLVLLNAIY

LSAKWKTTFDPKKTRMEPFHFKNSVIKVPMMNSKKYPVAHFIDQTLKAK

VGQLQLSHNLSLVILVPQNLKHRLEDMEQALSPSVFKAIMEKLEMSKFQ

PTLLTLPRIKVTTSQDMLSIMEKLEFFDFSYDLNLCGLTEDPDLQVSAM

QHQTVLELTETGVEAAAASAISVARTLLVFEVQQPFLFVLWDQQHKFPV

FMGRVYDPRA

[amino acid sequence of mouse C1-inhibitor protein]:
SEQ ID NO: 20
MASRLTPLTLLLLLLAGDRAFSDPEATSHSTQDPLEAQAKSRESFPERD

DSWSPPEPTVLPSTWPTTSVAITITNDTMGKVANESFSQHSQPAAQLPT

DSPGQPPLNSSSQPSTASDLPTQATTEPFCPEPLAQCSDSDRDSSEAKL

SEALTDFSVKLYHAFSATKMAKTNMAFSPFSIASLLTQVLLGAGDSTKS

NLESILSYPKDFACVHQALKGFSSKGVTSVSQIFHSPDLAIRDTYVNAS

QSLYGSSPRVLGPDSAANLELINTWVAENTNHKIRKLLDSLPSDTRLVL

LNAVYLSAKWKITFEPKKMMAPFFYKNSMIKVPMMSSVKYPVAQFDDHT

LKAKVGQLQLSHNLSFVIVVPVFPKHQLKDVEKALNPTVFKAIMKKLEL

SKFLPTYLTMPHIKVKSSQDMLSVMEKLEFFDFTYDLNLCGLTEDPDLQ

VSAMKHETVLELTESGVEAAAASAISFGRSLPIFEVQRPFLFLLWDQQH

RFPVFMGRVYDPRG

EXAMPLES

Example 1

Complement Inhibition with the Targeted Complement Inhibitor CR2-Crry Improves Liver Regeneration in Mouse Models of Warm Hepatic IRI, 70% PHx, and PHx+IRI Materials and Methods
Animal Studies.

$C3^{-/-}$ mice and wild-type controls were obtained from the Jackson Laboratory (Bar Harbor, Me.). $C5L2^{-/+}$ heterozygous mice were provided by Regeneron Pharmaceuticals Inc., courtesy of Dr. Joseph Sorrentino (Tarrytown, N.Y.) and $C5L2^{-/-}$ and wild-type littermates determined by PCR genotyping. All mice were on C57BL/6 background and were used when 8-10 weeks old and weighing between 22.5 g-25 g. Mice were fed a pellet diet with water ad libitum and kept on a 12-hour-light/dark cycle. For all procedures, mice were anesthetized with a intraperitoneal injection of 0.05 ml/10 g body weight of a "ketamine cocktail" consisting of ketamine (13 mg/ml), xylazine (2.6 mg/ml) and acepromazine (0.15 mg/ml) in sterile normal saline. Animals were subjected to one of the following three different procedures: (i) Hepatic IRI; (ii) 70% partial hepatectomy (PHx); and (iii) combined IRI and PHx.

Hepatic IRI.

Mice were subjected to total warm hepatic ischemia and reperfusion (I/R) as previously described (43). The portal vein and hepatic artery were occluded for 30 minutes with a microaneurysm clamp to induce hepatic ischemia, followed by a 6 hour period of reperfusion. For some experiments, we also used a model of partial warm hepatic IRI (see supplemental data). Mice were subjected to occlusion of the left lateral and median lobes of the liver by applying an atraumatic microvascular clamp to the vascular pedicle (44). After 90 minutes of partial warm ischemia, the clamp was removed, initiating hepatic reperfusion. In all IRI studies, CR2-Crry or normal saline (NS) was administered i.p. immediately after ischemia. Mice were sacrificed at predetermined time points after reperfusion for serum and liver sampling. 70% partial hepatectomy (PHx). Surgery was performed as previously described (45, 46) with resection of the median and left lateral liver lobes. Combined I/R and PHx. A model was developed incorporating both of the above hepatic I/R and PHx procedures. The portal vein and hepatic artery were occluded for 30 minutes and during the ischemic period 70% PHx was performed. Following surgeries, mice were sacrificed and livers harvested at 6 hours after reperfusion in IRI model and at 48 hours following resection in PHx and IRI+PHx models. Blood was also collected from the vena cava for serum preparation at the time of sacrifice and at 6 hours in the PHx and IRI+PHx models. Harvested livers were weighted to assess regeneration, and portions of liver tissue were either fixed in 10% neutralized formalin for histological evaluation or were snap-frozen in liquid nitrogen and maintained at −80° C. until homogenization for various biochemical assays. In therapeutic protocols with complement inhibition, CR2-Crry or normal saline (NS) was administered by intraperitoneal (i.p.) injection immediately after surgery. CR2-Crry was administered at a dose of 0.25 mg, based on effective protection in previous studies of intestinal and cerebral IRI (47, 48), and at one third the dose, 0.08 mg. CR2-Crry was prepared as previously described (47). Based on a previous study done in rats (49), IL-6 blockade was accomplished using goat anti-mouse-IL-6 antibody (R&D Systems, Minneapolis, Minn.) injected i.p at 200 µg/kg body weight. The IL-6 antibody or normal goat IgG (control) was injected i.p. immediately after surgery and just prior to CR2-Crry administration.

Acylation-Stimulating Protein/C3adesArg Reconstitution.

Recombinant human ASP/C3adesArg was prepared and purified by a modification of the original procedure (50), using a His-tag at the amino terminal with initial purification on a Ni-Sepharose column followed by HPLC. No denaturing agents were used at any step in the purification to avoid ASP/C3adesArg inactivation. ASP/C3adesArg was administered at a dose of either 15 µg or 50 µg per mouse in 200 µl saline by i.p. injection immediately after PHx. Endotoxin levels in the ASP/C3adesArg preparation were analyzed by the *Limulus Amebocyte* Lysate assay (E-Toxate kit; Sigma Chemicals, St. Louis, Mo.), and 25 µg/µl ASP/C3adesArg (100 times higher concentration than used) tested endotoxin-negative. Mouse ASP/C3adesArg and human ASP/C3adesArg are not identical, but it has been shown that human ASP/C3adesArg interacts with mouse ASP/C3adesArg receptor (C5L2), activates mouse cells and enhances postprandial triglyceride clearance in wild-type and $C3^{-/-}$ mouse models (26).

Microscopy.

For histological examination, tissue blocks were placed in 10% buffered formaldehyde solution for 48 hours before embedding in paraffin. Liver histology was assessed by light microscopy (Olympus BH-2 Olympus America, Melville, N.Y.) of hematoxylin- and eosin-stained (H&E-stained) 4-µm sections in a blinded fashion. Ten random fields on each slide were assessed for necrosis by standard morphologic criteria (loss of architecture, vacuolization, karyolysis, increased eosinophilia) and the extent of necrosis was semi-quantitatively estimated by assigning a severity score on a scale of 0-4 as previously described (51) (absent, 0; mild, 1; moderate, 2; severe, 3; and total necrotic destruction of the liver, 4). The score was used to compare the liver damage after IRI and/or PHx between different study groups. Steatosis was assessed by Oil Red 0 staining as previously described (52). C3 deposition in liver samples was determined by immunofluorescence using anti-mouse C3d-FITC antibody (DakoCytomation, Carpenteria, Calif.) as described (18)

Biochemical and Immunological Assays.

Serum levels of alanine aminotransferase (ALT) and total bilirubin were determined using analytical kits from Sigma Chemicals (St. Louis, Mo.) according to manufacturer's instructions. Serum levels of TNFa and IL-6 were measured by ELISA using kits from eBiosciences (San Diego, Calif.). For measurement of hepatic TNFa and IL-6 levels, frozen liver samples were homogenized in extraction buffer (50 mmol/L Tris, pH 7.2, 150 mmol/L NaCl, Triton X-100, and a protease inhibitor cocktail). The homogenate was centrifuged at 10,000 g and 4° C. for 8 minutes, and TNFa and IL-6 levels in supernatants were measured by ELISA using a kit from eBiosciences (San Diego, Calif.). For quantitative assessment of neutrophil infiltration into the liver parenchyma, liver myeloperoxidase content was assessed using the Hbt mouse MPO ELISA Kit from Hycult Biotechnology (Uden, Netherlands) according to manufacturer's instructions. Liver samples were prepared and hepatic triglyceride content of samples were determined using a triglyceride test kit as described by the manufacturer (Stanbio, Boerne, Tex.). The reduced form of glutathione (GSH) and malondialdehyde (MDA) levels in liver samples were determined spectrophotometrically by commercially available kits (OXISResearch, Portland, Oreg.), as reported previously (43). The calculated concentrations of lipid peroxidation products were normalized by protein concentration and expressed as nmol/mg protein.

Assessment of Liver Regeneration.

Three independent markers for hepatic regeneration were used. Reconstitution of liver weight was expressed as percentage of regenerated liver mass relative to total liver weight and was calculated as described (53). For assessment of hepatic proliferation, 5-bromo-2'-deoxyuridine (BrdU) was injected i.p. (50 mg/kg) 2 hrs prior to harvesting of liver. BrdU incorporation in liver sections was determined by immunohistochemical staining as described (54). Positive and negative cells were counted in 10 randomly selected fields by light microscopy using a 40× objective lens. Constantly proliferating intestinal crypt epithelium served as a positive control for BrdU incorporation and staining. The mitotic index was determined in H&E-stained sections using previously reported criteria for mitosis as follows: complete absence of cell membrane, slight eosinophilic staining of nucleus, nuclear spindle matrix formation, absence of a nucleolus, and slight increase in cell size (55). The mitotic index was expressed as the rate of positive cells per 1000 hepatocytes/HPF. All analyses were performed with the operator blinded to the experimental groups.

Assessment of Morbidity.

Clinical scores of morbidity were assessed 48 hours after PHx as previously described (56). Each mouse was graded from 0 to 3 (0, normal; 1, slight effect; 2, moderate effect; and 3, severe effect) for posture, coat, and activity. Scores were combined to produce a final score on a scale from 0 to 9.

Measurement of Liver ATP Content.

Approximately 50 mg frozen liver tissue was homogenized in 500 µl ice-cold tissue lysis buffer (Sigma-Aldrich Inc., St. Louis, Mo.) with a protease inhibitor cocktail (Pierce, Rockford, Ill.). The homogenates were centrifuged at 10,000×g for 8 minutes at 4° C., and ATP in supernatants was extracted using 1.5% trichloroacetic acid. Supernatants were then diluted 1:150 in Tris-acetate buffer (pH 7.85) and to 100 µl of diluted sample was added 100 µl reconstituted luciferin-luciferase solution (Enliten®, Promega, Madison, Wis.). Luciferase activity was immediately evaluated luminometrically. ATP content in the samples was determined by comparison to a concurrent standard curve. Protein concentration was also determined and the calculated concentrations of ATP content were normalized by protein concentration and expressed as mmol/mg protein.

Western Blot Analysis of GPX1 and STAT3 and Akt Activation.

Liver samples were homogenized on ice in lysis buffer (Sigma-Aldrich Inc., St. Louis, Mo.) containing protease inhibitor cocktail (Pierce, Rockford, Ill.). Homogenates were sonicated and centrifuged at 10,000×g, 4° C. to remove cellular debris. Protein concentrations were determined. Samples containing equal amounts of protein in equal volumes of sample buffer were separated in a 4%-15% Tris-HCl polyacrylamide gradient gel and transferred to polyvinylidene difluoride (PVDF) membrane (BIO-RAD, Hercules, Calif.). Nonspecific binding sites were blocked with Tris-buffered saline containing 5% nonfat dry milk for 1 hour at room temperature. Membranes were then incubated with antibodies to GPX1, Akt, phospho-Akt, STAT3, phospho-STAT3 (all fromCell Signaling Technology, Danvers, Mass.) or GAPDH (Santa Cruz Biotechnology Inc., Santa Cruz, Calif.) in Tris-buffered saline with 0.1% Tween 20. Membranes were washed and incubated with secondary antibodies conjugated to horseradish peroxidase. Immunoreactive proteins were detected via enhanced chemiluminescence.

Statistical Analysis.

Data is expressed as mean±SD. Significant differences between groups were determined by analysis of variance (ANOVA) with a Bonferrroni correction for continuous variable and multiple groups. Student's T-Test was used for the comparison of a normally distributed continuous variable between two groups. For the survival studies, Kaplan-Meier log-rank analysis was performed. All differences were considered statistically significant at the p-value of <0.05.

Results

Hepatic Ischemia Reperfusion Injury.

Figure 1:
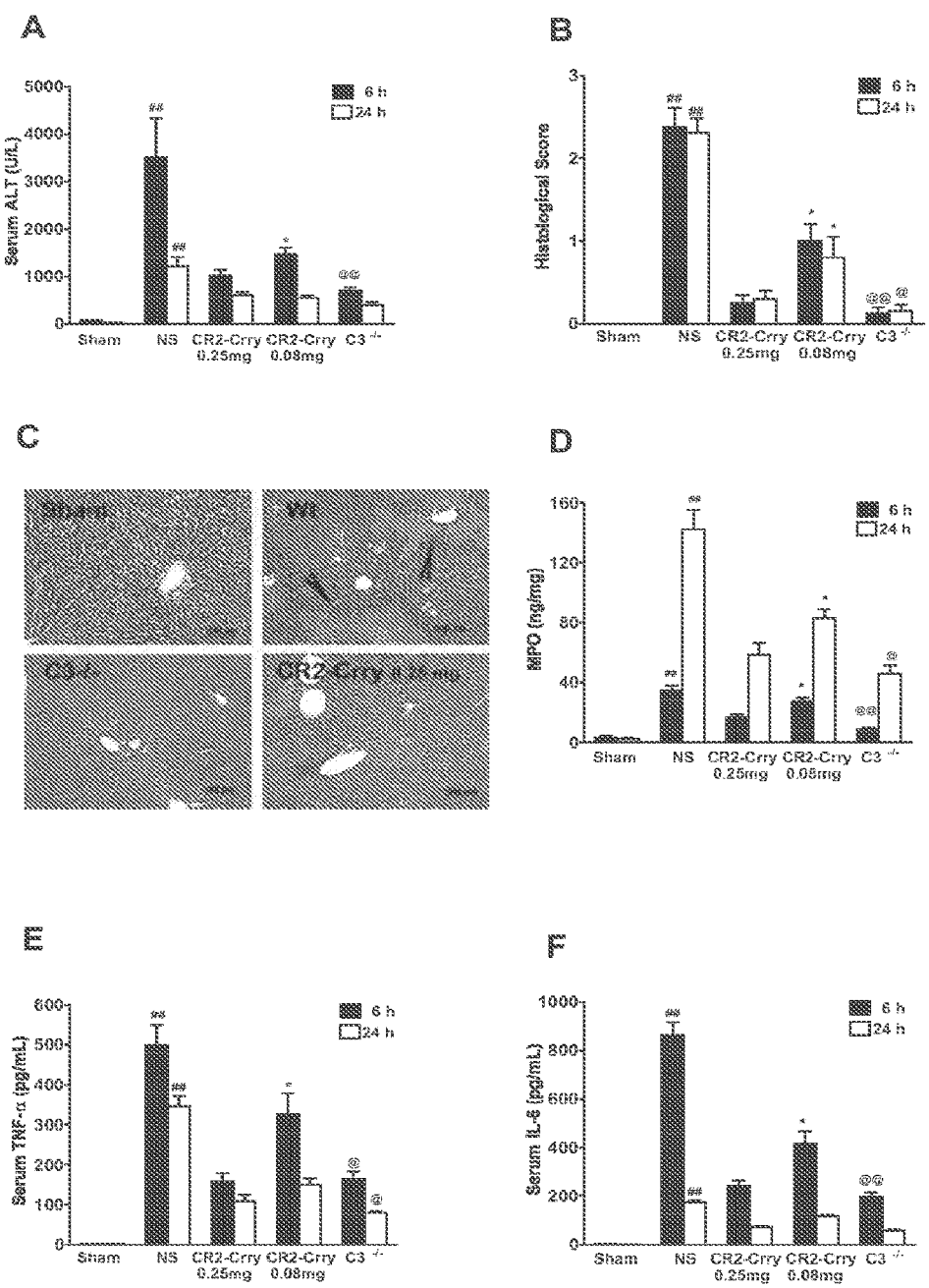
FIG. 1 shows that complement deficiency and inhibition protects against hepatic injury and inflammation following ischemia and reperfusion. Determinations were performed using liver or serum samples prepared after 30 minutes ischemia and either 6 or 24 hours reperfusion in C3$^{-/-}$ mice or wild-type mice treated with normal saline (NS) or CR2-Crry (either 0.25 mg or 0.08 mg dose). (A) Serum alanine aminotransferase (ALT) levels. (B) Histological quantification of hepatic necrosis and injury determined 6 hours after reperfusion on scale of 0-4. (C) Representative hematoxylin- and eosin-stained (H&E-stained) sections 6 hours after reperfusion with arrow outlined area showing wide spread hepatic necrosis in wild-type mice. (D) myeloperoxidase (MPO) content in liver samples normalized by total protein content. (E) Serum concentration of tumor necrosis factor alpha (TNFa). (F) Serum concentration of interleukin-6 (IL-6). Serum ALT levels, histological scores, liver MPO levels and serum TNFa and IL-6 levels were all raised significantly in all groups undergoing I/R compared to sham operated mice. Results expressed as Mean±SD, n=4 for all groups. ($^{\#}$P<0.05, $^{\#\#}$P<0.01 vs. other IRI groups, respectively; *P<0.05 vs. CR2-Crry 0.25 mg group; $^{@}$P<0.05, $^{@@}$P<0.01 vs. CR2-Crry 0.08 mg group).

The role of complement in murine hepatic IRI was investigated using $C3^{-/-}$ mice and in wild-type mice treated with different doses of the complement inhibitor CR2-Crry (either 0.08 mg or 0.25 mg). Following 30 minutes of hepatic ischemia and either 6 hours or 24 hours of reperfusion, survival, liver injury and local inflammation was assessed. All mice survived for the observed periods post-reperfusion. Serum alanine aminotransferase (ALT) levels were determined as a measure of liver function. ALT levels were raised significantly in all groups undergoing I/R compared to baseline or to sham operated mice (FIG. 1A). However, ALT levels were significantly higher post-reperfusion in wild-type mice following I/R compared to $C3^{-/-}$ mice or mice treated with either dose of inhibitor. A 0.08 mg dose of CR2-Crry was less protective than a 0.25 mg dose at 6 hours post-reperfusion, although ALT levels were not significantly different at 24 hours post-reperfusion. Histological assessment of injury was also significantly lower in $C3^{-/-}$ and complement inhibited mice at both 6 hours and 24 hours post-I/R (FIG. 1B-C), with high dose inhibition providing better protection at both time points of analysis. To assess the effect of complement activation on neutrophil recruitment, myeloperoxidase (MPO) levels in liver homogenates were determined. Levels of MPO were elevated in all post-reperfusion samples compared to baseline and sham operated controls, but MPO levels were significantly lower in C3 deficient and complement inhibited mice compared to control wild-type mice at both 6 hours and 24 hours post-reperfusion (FIG. 1D). MPO levels were, however, higher at 24 hours compared to 6 hours post-reperfusion in all groups, which did not correlate with reduced ALT and injury scores at 24 hours compared to 6 hours post-reperfusion. Levels of the inflammatory cytokines, TNFa and IL-6, were also significantly reduced in C3 deficient and complement inhibited mice compared to wild-type controls at both time points post-reperfusion, with significantly lower levels at 24 hours compared to 6 hours post-reperfusion (FIG. 1E-F). An overall comparison of injury and recovery markers at 6 and 24 hours post-I/R indicate that C3 deficiency and high dose complement inhibition delays recovery and repair compared to low dose complement inhibition. For clinical relevance, we used a model of total hepatic ischemia similar to the Pringle maneuver, a clinical procedure often used in hepatic surgery. Nevertheless, these data show that complement deficiency and inhibition also protects against IRI in a model of partial hepatic ischemia that does not carry the risk of intestinal venous congestion, a condition that may activate complement and may cause endotoxemia (FIG. 12).

Partial Hepatectomy and Liver Regeneration.

Figure 2:
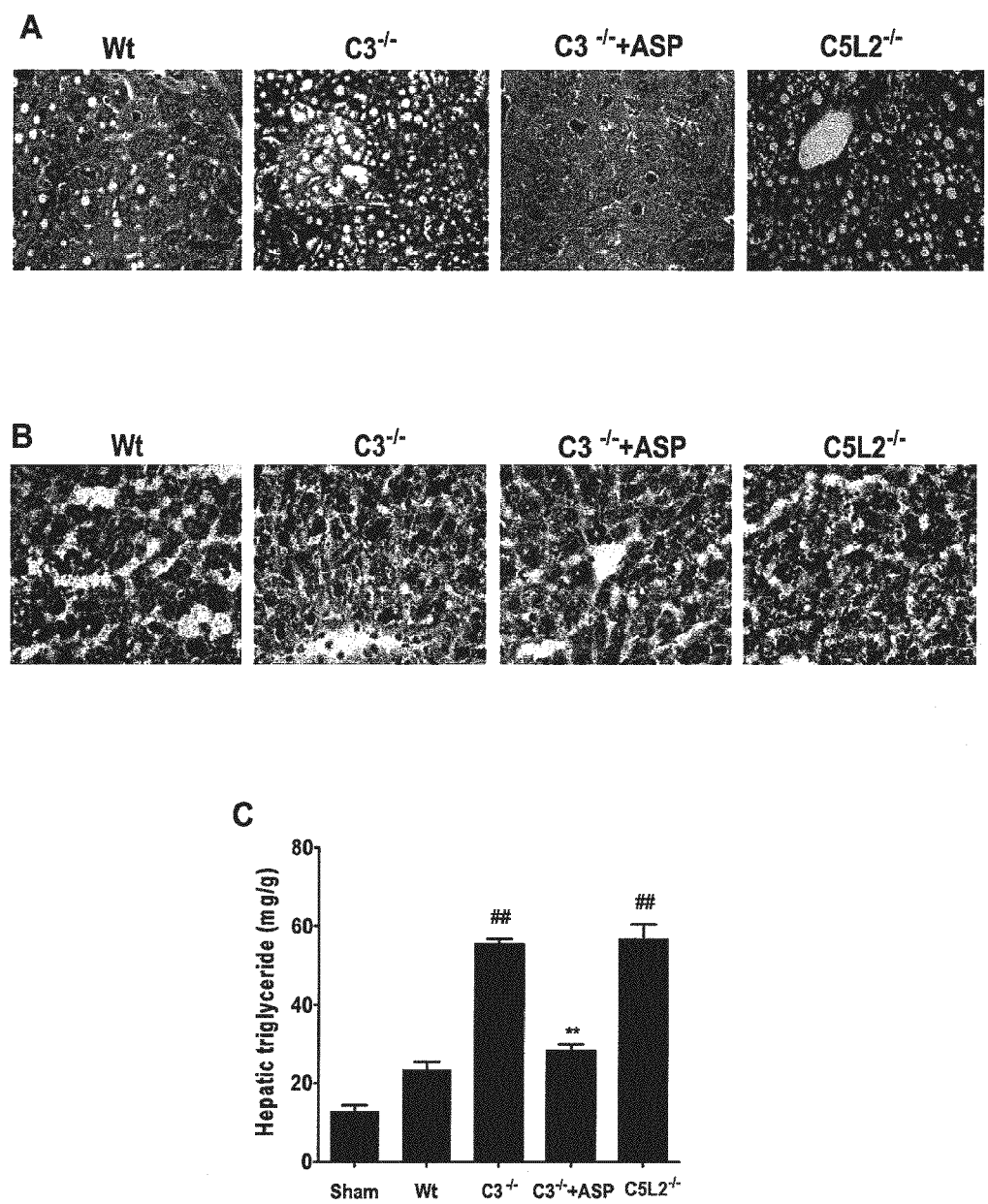
FIG. 2 shows hepatic steatosis in C3$^{-/-}$ and C5L2$^{-/-}$ mice following partial hepatectomy (PHx). All analyses are from liver samples isolated 48 hours post-PHx. (A) Representative H&E stained sections showing C3 and C5L2 deficiency is associated with a significant increase in necrosis with hepatic micro- and macrovesicular steatosis, whereas wild-type mice and C3$^{-/-}$ mice treated with 15 μg acylation stimulating protein (ASP/C3adesArg) exhibit much less apparent steatosis. (B) Representative Oil Red 0 stained sections. C3$^{-/-}$ and C5L2$^{-/-}$ mice have increased micro- and macrovesicular steatosis compared to wild-type and C3$^{-/-}$ mice treated with 15 μg ASP. (C) Quantification of hepatic triglyceride accumulation ($^{\#\#}$P<0.01 vs. wild-type groups; **P<0.01 vs. C3$^{-/-}$ groups). Results expressed as Mean±SD, n=4-6.

In broad agreement with previously published data (14), these data demonstrated that C3 deficiency results in increased injury following 70% PHx as measured by increased serum ALT, bilirubin, focal liver necrosis and mortality. In addition, an impaired regenerative response in $C3^{-/-}$ mice was demonstrated by significantly reduced BrdU incorporation, decreased mitotic index score and reduced restitution of liver weight (FIG. 13). A significant increase in liver steatosis in $C3^{-/-}$ mice post-PHx compared to wild-type mice, as assessed by histological examination and by triglyceride content, was also observed. Liver regeneration is associated with transient accumulation of hepatic lipids, and mild macrovesicular steatosis developed in wild-type mice following PHx. However, C3 deficiency was associated with the development of moderate to severe macrovesicular and microvesicular steatosis (FIG. 2). This suggests a possible mechanistic link between complement, steatosis and regeneration, particularly in view of the fact that C3a has been shown to play an important role in liver regeneration (14), and its degraded form, C3adesArg (also known as acylation stimulating protein or ASP/C3adesArg), plays a role in lipid metabolism. ASP/C3adesArg increases fat storage in adipocytes through increased triglyceride synthesis and decreased intracellular lipolysis (19).

Figure 3:
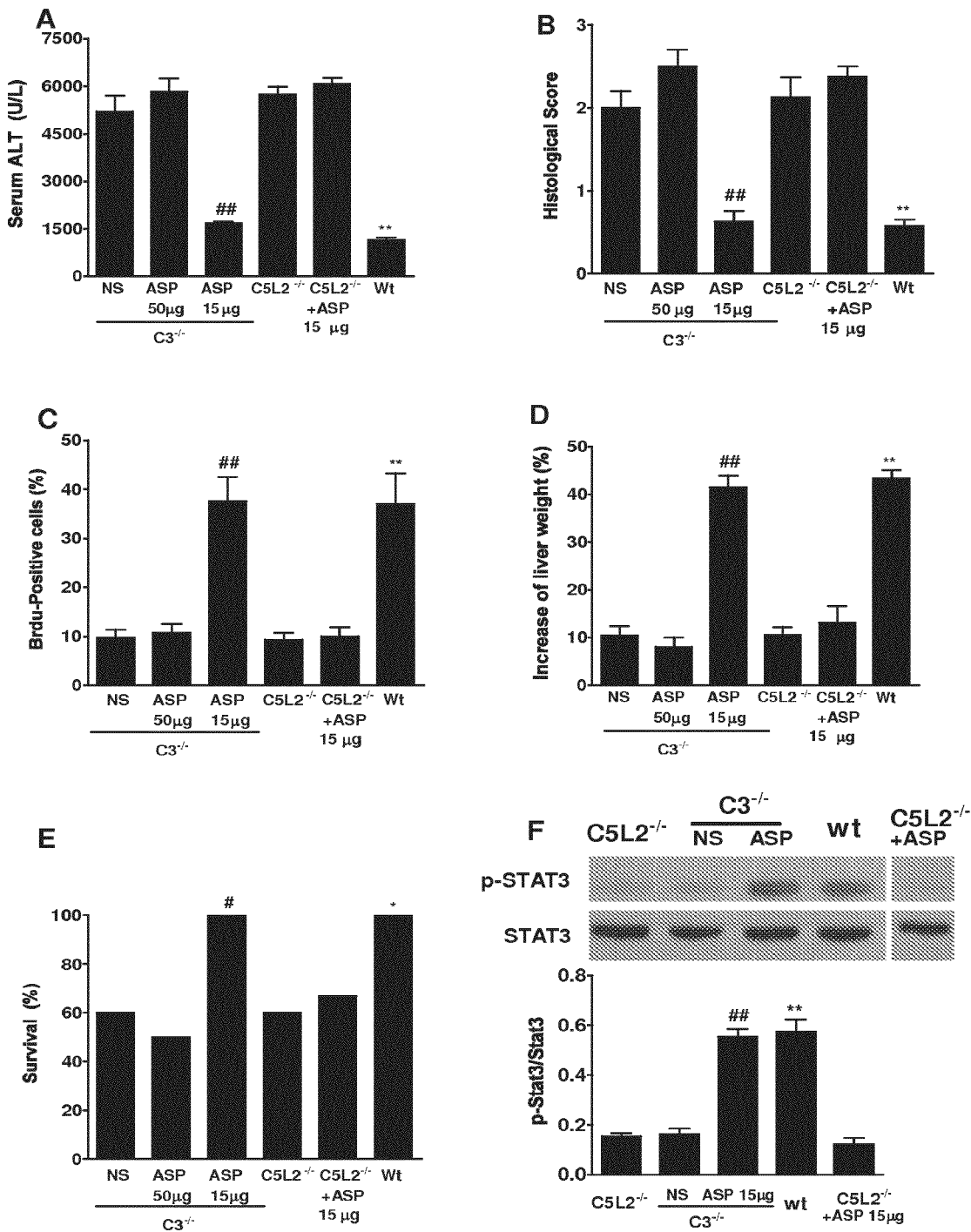
FIG. 3 shows that reconstitution of C3$^{-/-}$ mice with ASP following PHx enhances either regeneration or injury depending on dose, and C5L2 deficiency (ASP/C3adesArg receptor) increases injury and impairs regeneration. A 15 μg or 50 μg dose of ASP/C3adesArg was administered to C3$^{-/-}$ mice immediately after surgery, and all determinations made at 48 hours post-PHx. (A) Serum ALT levels, (B) Histopathological scores, (C) Assessment of regeneration by bromodeoxyuridine (BrdU) incorporation, (D) Restitution of liver weight, (E) 48 hour survival, (F) Western blot assay for phosphorylated form of STAT3 at 3 hours post-PHx. Reconstitution of C3$^{-/-}$ mice with low dose ASP/C3adesArg, but not high dose ASP/C3adesArg significantly increase 2 day survival. Note that p-STAT3 levels are strongly reduced in both C5L2$^{-/-}$ and C3$^{-/-}$ mice compared to wild-type mice. Low dose ASP reconstitution restored activation of STAT3. $^{\#}$P<0.05, $^{\#\#}$P<0.01 vs. the C3$^{-/-}$ NS group; *P<0.05, **P<0.01 vs. the C5L2$^{-/-}$ and C3$^{-/-}$ NS (similar to C3$^{-/-}$) group, respectively. For survival study, n=10 each group; all other studies n=4-6.

Since mice deficient in C3 (and therefore unable to generate ASP/C3adesArg) have delayed triglyceride clearance (20-22), we administered ASP/C3adesArg to $C3^{-/-}$ mice following PHx to assess the effect of ASP/C3adesArg on liver regeneration and steatosis. Reconstitution of $C3^{-/-}$ mice with a 15 µg dose of recombinant ASP/C3adesArg significantly reduced steatosis and hepatic injury, completely restored the proliferative response as measured by BrdU incorporation and restitution of liver weight, and significantly improved survival (FIGS. 2 and 3). TNFa and IL-6 are cytokines involved in the priming events of liver regeneration via their effects on NF-κB and STAT3 activation. Confirming previous data (14), C3 deficiency significantly reduced STAT3 activation following PHx (FIG. 3F). However, reconstitution of $C3^{-/-}$ mice with 15 µg ASP/C3adesArg restored STAT3 activation to wild-type levels, identifying a putative pathway through which ASP/C3adesArg may modulate liver regeneration.

The only identified receptor for ASP/C3adesArg is C5L2 (23-26), and C5L2 plays an important role in triglyceride synthesis and clearance (25, 26). To investigate a role for C5L2 in liver regeneration and a putative link between ASP/C3adesArg and C5L2 in regeneration, we determined the effect of C5L2 deficiency on liver injury and regeneration following PHx. $C5L2^{-/-}$ mice responded to PHx similarly to $C3^{-/-}$ mice, and compared to wild-type mice displayed significantly increased hepatic injury, increased mortality and impaired liver regeneration (FIG. 3). $C5L2^{-/-}$ mice also developed moderate to severe hepatic steatosis following PHx (FIG. 2). Also similar to $C3^{-/-}$ mice, STAT3 activation was significantly reduced in $C5L2^{-/-}$ mice following PHx compared to wild-type mice and ASP/C3adesArg-reconstituted mice. We further determined the effect of ASP/C3adesArg administration to $C5L2^{-/-}$ mice following PHx. Treatment of $C5L2^{-/-}$ mice with 15 µg ASP/C3adesArg following PHx had no effect on any parameter of injury or regeneration in these mice (FIG. 3A-E), and did not affect STAT3 signaling (FIG. 3F). Collectively, the data are consistent with the hypothesis that ASP/C3adesArg modulates regeneration via a mechanism involving C5L2 modulation of STAT3 activation. Nevertheless, previous studies have indicated a key role for C5a and C5aR signaling in STAT3 activation and liver regeneration (14), and importantly, complement activation was similar in C5L2$^{-/-}$ and wild-type mice following PHx, as determined by C3 deposition in liver sections (FIG. 14). Unexpectedly, reconstitution of C3$^{-/-}$ mice with a high dose of ASP/C3adesArg (50 μg) following PHx failed to restore the regenerative response and did not protect against injury (FIG. 3). It was not clear why low vs. high dose ASP/C3adesArg had opposing effects in liver regeneration and injury in C3$^{-/-}$ mice following PHx. However, while the complement activation products C3a and C5a have been shown to play a key role in the priming stages of liver regeneration via their effect on TNFa and IL-6 expression, these cytokines can play dual roles in hepatocyte regeneration and injury, and increased and prolonged expression of these inflammatory cytokines is associated with hepatic injury (27-29).

Figure 4:
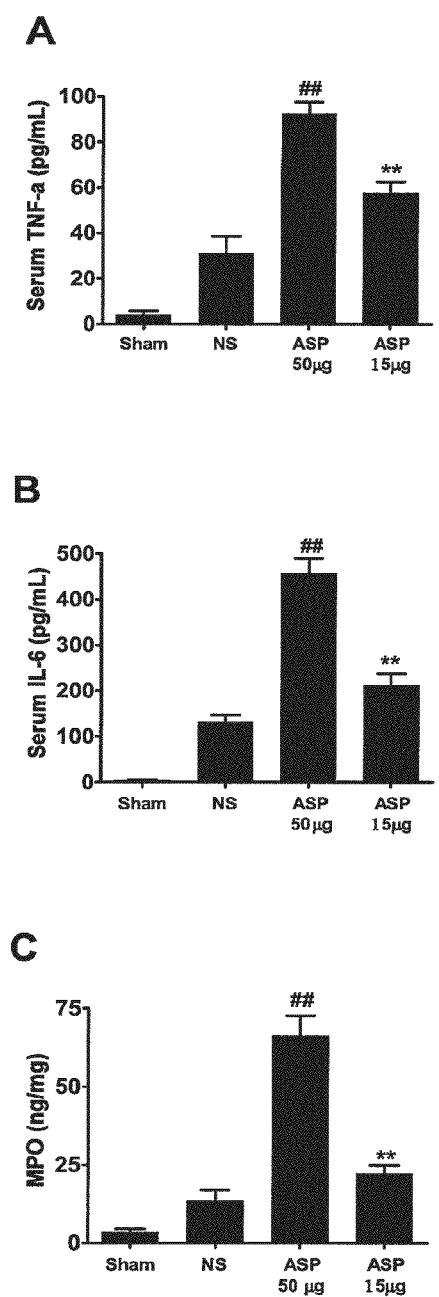
FIG. 4 shows that reconstitution of C3$^{-/-}$ mice with high dose ASP/C3adesArg enhances inflammation and injury after PHx. Either a 15 μg or 50 μg dose of ASP/C3adesArg was administered to C3$^{-/-}$ mice immediately after surgery, and cytokine and MPO determinations measured at 6 hours post-PHx. (A) Serum TNFa levels. (B) Serum IL-6 levels. (C) MPO content in liver samples. $^{\#\#}$P<0.01 vs. NS group; **P<0.01 vs. 50 μg ASP/C3adesArg group. Results expressed as Mean±SD, n=4-6 for all groups.

We therefore investigated the effect of high vs. low dose ASP/C3adesArg on TNFa and IL-6 expression levels and on hepatic neutrophil infiltration (MPO activity) following PHx. At 6 hours post-PHx. TNFa and IL-6 levels were significantly elevated in C3$^{-/-}$ mice treated with either high or low dose ASP/C3adesArg compared to saline treated C3$^{-/-}$ mice (FIG. 4). However, levels of both cytokines were significantly higher in mice treated with 50 μg ASP/C3adesArg compared to mice treated with 15 μg ASP/C3adesArg. High dose ASP/C3adesArg also correlated with significantly increased neutrophil infiltration post-PHx as determined by MPO activity. Thus, high dose ASP/C3adesArg is associated with a significantly higher inflammatory burden post-PHx. We also determined that treatment of wild-type mice with either a low or high dose of ASP/C3adesArg following PHx significantly increased injury and impaired the proliferative response, with the higher dose of ASP/C3adesArg having a more profound effect on injury and regeneration (data not shown). Together, the above data indicate that ASP/C3adesArg is a key factor in liver regeneration following PHx, but ASP/C3adesArg at levels higher than normally generated endogenously due to PHx-induced complement activation results in increased hepatic inflammation and injury, and an impaired regenerative response. These data suggest that there is a threshold of complement activation and C3a/ASP/C3adesArg production for optimal liver regeneration following PHx.

Complement Inhibition and Liver Regeneration.

Figure 5:
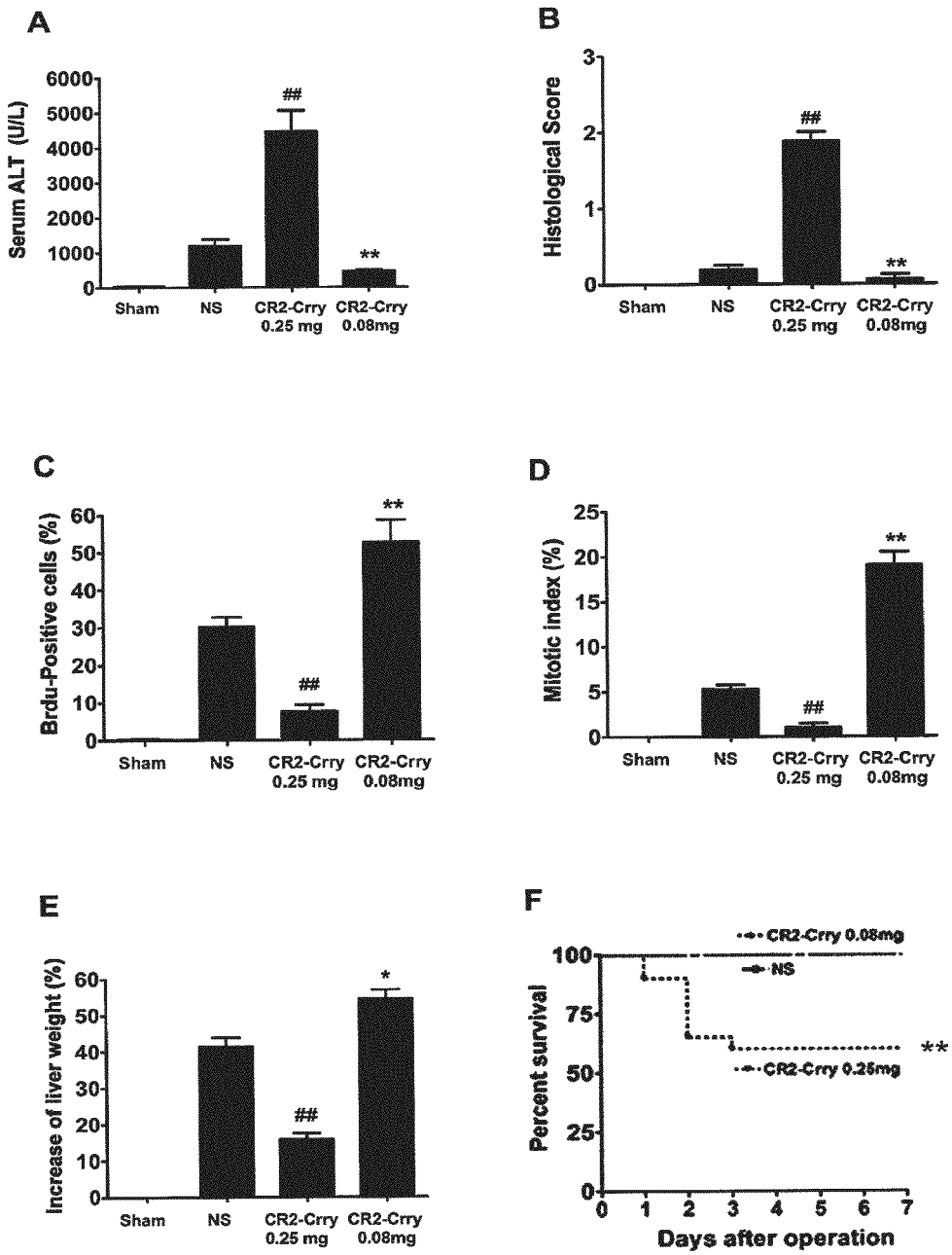
FIG. 5 shows the opposing effects of high and low dose complement inhibition on hepatic injury and regeneration following PHx. Wild-type mice were treated with normal saline or CR2-Crry at a dose of either 0.25 mg or 0.08 mg immediately after surgery. All determinations were made at 48 hours post-PHx. (A) Serum ALT levels. (B) Histological quantification of hepatic necrosis and injury determined on scale of 0-4. (C) Assessment of regeneration by BrdU incorporation. (D) Mitotic index evaluated by calculating percentage of hepatocytes undergoing mitosis in H&E-stained sections. (E) Restitution of liver weight expressed as percentage of regenerated liver mass relative to total liver weight. (F)

To put the above results in a more clinical context, we investigated the effect of different doses of a complement inhibitor on liver injury and regeneration following PHx in wild-type mice. For these studies we used CR2-Crry at a dose of 0.08 mg or 0.25 mg, the same doses used in the above IRI studies. Similar to the results with C3$^{-/-}$ mice (shown in FIG. 13), wild-type mice treated with a 0.25 mg dose of CR2-Crry after PHx showed significantly increased liver injury and impaired proliferative response compared to saline treated controls (FIG. 5). There was also a high mortality of these complement inhibited mice compared to control treated mice (40% vs. 0%, respectively, monitored over a 7 day period). As might be expected given the important role for complement activation in liver regeneration, the lower dose of CR2-Crry resulted in less injury and increased BrdU incorporation compared to high dose CR2-Crry treatment.

Unexpectedly, however, low dose complement inhibition resulted in significantly less hepatic injury and a significantly enhanced proliferative response compared to saline treated controls (FIG. 5). Additional data demonstrated that low dose CR2-Crry treatment resulted in improved and accelerated regeneration at multiple time points after PHx. By 7 days post-PHx, restoration of liver to normal weight was almost complete, and there was no significant difference between mice treated with saline or low dose CR2-Crry (FIG. 15A-B). There was no mortality in mice treated with 0.08 mg of CR2-Crry or saline, but there was some minor injury in control mice following PHx, based on elevated ALT and histology scores. There was also a higher morbidity score in control mice compared to low dose Crry-treated mice (FIG. 15C). ALT levels had dropped to normal by 72 hours post-PHx (FIG. 15D). ALT levels were significantly lower at 24 and 48 hours post-PHx in low dose CR2-Crry-treated mice compared to saline-treated controls.

Anti-C3d immunofuorescence microscopy of liver sections was used to correlate the effect of the different doses of CR2-Crry with the level of complement activation and liver injury/regeneration. C3d was deposited predominantly on hepatocyte membranes and sinusoidal endothelium within livers isolated from wild-type mice 48 hours post-PHx. C3d was deposited with a greater intensity and was more widely distributed in samples from wild-type mice compared to samples from mice treated with 0.08 mg CR2-Crry. There was no detectable C3d deposition in samples from mice treated with 0.25 mg CR2-Crry (FIG. 6).

Together, these data support the concept of a balance between complement-dependent injury and a complement-dependent proliferative response in liver regeneration following PHx. Thus, it is possible that in a clinical setting, impaired liver regeneration following resection or small for size transplantation may be a consequence of excessive complement activation and inflammation following IRI.

Complement Inhibition in a Combined Model of Ischemia Reperfusion Injury and Partial Hepatectomy.

Since hepatic I/R results in a significant level of complement activation and complement-dependent injury (refer to FIG. 1), we investigated the effect of complement inhibition in a model that incorporates both IRI and 70% PHx, a model mimicking the procedure used for massive liver resection under the Pringle maneuver. Wild-type or C3$^{-/-}$ mice were subjected to 30 minutes hepatic ischemia, during which time 70% PHx was performed. Wild-type mice were treated with either 0.08 mg CR2-Crry or 0.25 mg CR2-Crry immediately after surgery. Only 20% of C3$^{-/-}$ mice survived for 48 hours following surgery, compared to 90% survival of wild-type mice (FIG. 7A). Compared to wild-type mice, surviving C3$^{-/-}$ mice had significantly increased hepatic injury and an impaired proliferative response (FIG. 7B-E). Notably, wild-type mice that underwent the combined surgery had a worse outcome in terms of hepatic injury and hepatocyte proliferation than wild-type mice that underwent 70% PHx alone (refer to FIG. 3). Treatment of wild-type mice with 0.25 mg CR2-Crry, a dose that was highly protective against IRI, also resulted in a significantly poorer outcome in the combined model, with increased hepatic injury, decreased BrdU incorporation and lower liver weights at 48 hours post-surgery compared to control animals (FIG. 7). In contrast, low dose CR2-Crry treatment resulted in no mortality and a significantly improved outcome in terms of hepatic injury and liver regeneration when compared to all other groups including, importantly, wild-type control. The level of hepatic injury correlated with neutrophil infiltration as measured by MPO activity (FIG. 7F). We also investigated the effect of complement inhibition on TNFa and IL-6 levels. At 6 hours after reperfusion in this combined model, serum TNFa levels positively correlated with hepatic injury. Serum IL-6 levels, on the other hand, were negatively correlated with injury, with significantly higher IL-6 levels seen in mice treated with 0.08 mg CR2-Crry compared to all other groups (FIG. 8A-B). This is consistent with the important role for IL-6 in the regenerative response, and although TNFa levels were lower in 0.08 mg CR2-Crry treated mice compared to other test groups, they were still significantly elevated compared to sham-operated mice.

Interestingly, at 48 hours post-reperfusion, the situation for IL-6 was reversed, with serum IL-6 levels in low dose CR2-Crry treated mice being significantly lower than in $C3^{-/-}$ mice or mice treated with high dose CR2-Crry. Serum TNFa levels remained significantly lower in low dose CR2-Crry treated mice compared to all other groups (FIG. 8C-D). TNFa and IL-6 are considered important for the priming phase of the regenerative response, and hepatic expression of these cytokines peak at around 1-2 hours and 3-6 hours post-PHx, respectively. We therefore also determined hepatic levels of TNFa and IL-6 at 3 hours post-IRI+PHx. Compared to wild-type mice, C3 deficiency and high dose complement inhibition resulted in significantly reduced levels of TNFa and IL-6 in the liver (FIG. 8E-F). In contrast, low dose CR2-Crry correlated with significantly increased hepatic levels of both cytokines relative to all other groups, including wild-type. Thus, low dose complement inhibition and enhanced liver regeneration is associated with increased early hepatic production of these cytokines, and with diminished systemic levels of the inflammatory cytokines by 48 hours post-PHx compared to all other groups.

Effect of complement deficiency and complement inhibition on signaling pathways, ATP levels and oxidative injury following IRI and PHx. Additional studies were performed to further elucidate potential mechanisms of hepatoprotection and regeneration in CR2-Crry treated mice. In addition to regulating the activation of STAT3, IL-6 also activates the PI3K/Akt survival pathway, a pathway that has been shown to play an important role in the early regenerative response following PHx and that regulates progression of the G1 phase during regeneration (30). We therefore determined whether the high levels of early IL-6 expression associated with low dose complement inhibition correlated with increased STAT3 and Akt activation. Phosphorylation of STAT3 and Akt after IRI+PHx was determined in livers isolated from complement-deficient and complement-inhibited mice. C3 deficiency and high dose complement inhibition markedly reduced STAT3 activation following IRI+PHx compared to saline-treated mice and mice treated with low dose complement inhibition (FIG. 9A). Furthermore, there was an increase in STAT3 activation in low dose CR2-Crry treated mice compared to saline controls at both 3 and 6 hours post-IRI+PHx. Low dose CR2-Crry treatment was also associated with an increase in Akt phosphorylation at 6 hours post-IRI+PHx (FIG. 9A).

Mitochondrial dysfunction and oxidative injury occurs in the liver after I/R and also after massive resection. Also, cellular ATP stores have been shown to play an important role in liver regeneration by supplying energy and regulating post-transcriptional activation of cyclin D-1/cdk complexes (31-33). To investigate whether the effect of complement inhibition on hepatoprotection and liver regeneration was associated with hepatic ATP levels, ATP concentrations were measured in liver samples from all groups at various time points post-IRI+PHx. There was a marked reduction in hepatic ATP in all groups at 6 hours post-IRI+PHx (FIG. 9B). While ATP levels remained low in $C3^{-/-}$ mice and mice treated with high dose CR2-Crry, however, ATP stores recovered to near pre-operation levels by 48 hours after IRI+PHx in mice treated with low dose CR2-Crry.

The production of reactive oxygen species and lipid peroxidation is considered a major mechanism of heptic injury following I/R and extreme liver resection. The effect of complement inhibition on oxidative injury to the liver following IRI+PHx was examined by measuring levels of hepatic glutathione (GSH), glutathione peroxidase (GPX1) and malondialdehyde (MDA). There were reduced levels of GSH (antioxidant) and increased levels of MDA (index of lipid peroxidation) in saline-treated animals after IRI+PHx indicating the organs were under oxidative stress (FIG. 10A,B). Levels of the free radical scavenger GPX1 were also reduced in saline-treated animals following IRI+PHx (FIG. 10C). In contrast, treatment of mice with 0.08 mg CR2-Crry post-IRI+PHx protected against oxidative stress as indicated by significantly increased levels of GSH and GPX1 and decreased levels of MDA.

IL-6 Blockade and Complement Inhibition Following IRI+PHx.

Finally, since low dose complement inhibition increased IL-6 levels post-IRI+PHx, and since IL-6 signaling is essential for the priming phase of liver regeneration, we sought to clarify whether there was a link between the hepatoprotective and proregenerative effect of low dose complement inhibition and IL-6 expression. IL-6 blockade by administration of anti-IL-6 antibodies together with CR2-Crry treatment reduced hepatic levels of IL-6 by about 65% at 3 hours post-IRI+PHx, and reduced serum levels of IL-6 by about 50% at 6 hours post-IRI+PHx (FIGS. 11A-B). Further, IL-6 blockade significantly reduced levels of phosphorylated STAT3 following IRI+PHx, indicating a direct relationship between increased levels of IL-6 and STAT3 activation (FIG. 11C). IL-6 blockade resulted in significantly increased liver injury (assayed by serum ALT) and a significantly impaired regenerative response (assayed by BrdU incorporation) in mice subjected to IRI+PHx and treated with low dose CR2-Crry (FIGS. 11D-E). In addition, only 4 out of 10 mice receiving anti-IL-6 antibody and CR2-Crry survived for more than 48 hours post-IRI+PHx (data not shown). Thus, the protective effect of low dose complement inhibition following IRI+PHx was lost when complement inhibitor treatment was combined with IL-6 blockade. Taken together, these results suggest that the hepatoprotective effect of low dose (but not high dose) complement inhibition is due to the role of complement in IL-6 expression and subsequent priming of the regenerative response.

Example 2

Complement Inhibition with the Targeted Complement Inhibitor CR2-CD59 Improves Liver Regeneration in Mouse Models of Warm Hepatic IRI, 70% PHx, 90% PHx, Ethanol-Induced Liver Injury, and Ethanol-Induced Injury+70% PHx Materials and Methods
Animal Studies.
8-10 week-old wild-type C57BL/6 mice, C3 deficient ($C3^{-/-}$) and CD59 deficient ($CD59^{-/-}$) C57BL/6 mice were used in this study. Mice were fed a pellet diet and water ad libitum, and kept on a 12-hour-light/dark cycle. Mice were anesthetized by intraperitoneal (i.p.) injection of 0.05 ml/10 g body weight of a "ketamine cocktail" consisting of ketamine (13 mg/ml), xylazine (2.6 mg/ml) and acepromazine (0.15 mg/ml) in sterile normal saline. Animals were subjected to one of the following four different procedures: (i) hepatic IRI;

(ii) 70% partial hepatectomy (PHx); (iii) 90% PHx; and (iv) ethanol-induced injury followed by 70% PHx.

Hepatic IRI.

Mice were subjected to total warm hepatic ischemia and reperfusion (I/R) as previously described. Briefly, mice were anesthetized and laparotomy performed with a small vertical incision. Following surgical exposure of the liver, the portal vein and hepatic artery were occluded for 30 minutes with a microaneurysm clamp to induce hepatic ischemia, followed by a 6 hour period of reperfusion. 70% partial hepatectomy (PHx). Surgery was performed as previously described. Briefly, laparotomy was performed with a midline incision and the median and left lateral liver lobes resected. 90% PHx. Ninety percent hepatectomy was performed as previously described. The was procedure performed with removed the left lateral and median lobes using a single ligature (70% PH), afterwards resected the right lateral lobe (20%) and left only the caudate lobe. Ethanol-induced injury followed by 70% PHx. Wild-type, factor $B^{-/-}$, $C3^{-/-}$, and $CD59^{-/-}$ mice were allowed free access to an ethanol-containing diet at increasing concentrations of ethanol as follows: (1) 1% (v/v) for two days; (2) 2% (v/v) for 2 days; (3) 4% (v/v) ethanol for 7 days; and finally (4) 5% (v/v) ethanol for a further 4 weeks. After five weeks and four days, the wild-type, factor $B^{-/-}$, $C3^{-/-}$, and $CD59^{-/-}$ ethanol-fed animals were subjected to 70% PHx.

Following surgeries, mice were sacrificed at different time points and liver and blood samples were collected. Harvested livers were weighted to assess regeneration, and portions of liver tissue were either fixed in 10% neutralized formalin for histological evaluation or were snap frozen in liquid nitrogen and maintained at −80° C. until homogenization for various biochemical assays. In therapeutic protocols with complement inhibition, CR2-Crry, CR2-CD59 or normal saline (NS) was administered i.p. immediately after surgery.

Therapeutic Protocols with Complement Inhibitors.

For clinical relevance and the fact that limited or temporary complement inhibition may have a different effect, we also performed parallel experiments in wild-type mice treated with the complement inhibitors, CR2-Crry, which inhibits complement at the level of C3, and CR2-CD59, which inhibits terminal complement at the level of MAC formation. The inhibitor was prepared as previously described. The effect of complement deficiency and inhibition on regeneration was analyzed as described below. Inhibitors (CR2-Crry and CR2-CD59) or normal saline (NS) were administered immediately after surgery. The dose of inhibitors was administered as described below.

Results

Role of Terminal Complement in Hepatic IRI and Regeneration.

Activation of the terminal complement pathway results in the sequential assembly of complement proteins C6, C7, C8 and $(C9)_n$ to form the cytolytic membrane attack complex (MAC), which causes direct cell lysis, and, when formed at sub-lytic levels also stimulates cells to release proinflammatory molecules. Until now, there have been no reports on the role of MAC in liver IRI and regeneration. Control of the terminal complement pathway and MAC formation in host cell membranes is provided by the activity of CD59. CD59 functions by binding to C8 and C9 during assembly of the MAC (C5b-9) and preventing the unfolding and membrane insertion of C9.

These experiments investigated the role of the MAC in IRI and liver regeneration using $CD59^{-/-}$ mice. The absence of CD59 results in uncontrolled activation of the terminal portion of the complement system. $CD59^{-/-}$ mice subjected to 30 minutes of ischemia and 6 hours of reperfusion, showed a significant increase in ALT level and liver injury compared to wild-type animals. Treatment of the $CD59^{-/-}$ animals with 0.4 mg of CR2-CD59 significantly reduced those injuries (FIGS. 16-17). ALT levels in CR2-CD59 treated wild-type mice were significantly reduced compared to NS control animals (p<0.01).

Furthermore, $CD59^{-/-}$ mice subjected to 70% PHx showed severe impairment of liver regeneration, characterized by significantly increased serum ALT levels (FIG. 18), extensive necrosis, increased inflammatory cell infiltration (FIG. 19), abolition of BrdU incorporation (FIG. 20) and a significantly higher mortality rate (FIG. 21). Treatment with 0.2 mg CR2-CD59, a dose sufficient to reconstitute CD59 expression, significantly reduced hepatic injury and improved regeneration, as shown by serum ALT levels (FIG. 18), liver pathology (FIG. 19), BrdU incorporation (FIG. 20) and overall survival (FIG. 21). These data suggest that the terminal pathway, specifically the MAC, plays an important role in liver regeneration and IRI, and that excessive complement activation significantly hampers the regenerative process within the liver.

Effect on Liver Regeneration Selectively Inhibited at Different Points in the Complement Pathway.

Data obtained using complement deficient mice is not always in agreement with results obtained from studies in which complement has been temporarily inhibited. We next investigated the effect of reduced complement activation in wild-type mice treated with the complement inhibitor CR2-Crry, which inhibits complement at the level of C3, and with the complement inhibitor CR2-CD59, which inhibits terminal complement, preventing assembly of the MAC. We first performed parallel experiments for hepatic IRI, using wild-type mice treated with a 0.25 mg dose of CR2-Crry, and 0.2 mg CR2-CD59. Animals were subjected to 30 minutes of total hepatic warm ischemia and 6 hours of reperfusion, after which survival, liver injury and local inflammation were assessed. ALT levels in complement-inhibited wild-type mice using treatment with CR2-Crry or CR2-CD59 were significantly reduced compared to NS control (FIG. 22). No significant difference was observed between groups treated with CR2-Crry and with CR2-CD59.

Infiltration of ischemic tissue by innate immune effector cells following reperfusion is well-described. To assess to what extent complement plays a role in neutrophil recruitment within the liver, we quantified MPO levels in liver homogenates. MPO levels were elevated in all post-reperfusion samples at 6 hours compared to baseline and sham-operated controls. Complement inhibition with both CR2-Crry and CR2-CD59 was associated with a significant decrease in MPO compared to NS control (p<0.05, respectively), with MPO levels of 34.8±6.5 ng/mg in NS controls, compared to 16.8±4.0 ng/mg in animals treated with 0.25 mg CR2-Crry, and 7.9±2.8 ng/mg in animals treated with 0.2 mg CR2-CD59, respectively.

In regeneration studies, mice treated with CR2-Crry at a dose of 0.25 mg administered i.p. immediately after 70% PHx developed severe liver damage (FIGS. 23-24) and displayed impaired liver regeneration (FIG. 24). Surprisingly, however, mice treated with CR2-Crry at a dose of 0.08 mg administered by i.p. injection immediately after PHx developed significantly less hepatic damage (FIGS. 23-24) and showed a marked increase BrdU incorporation compared to wild-type controls (FIG. 25). More interestingly, mice treated with both 0.45 mg and 0.15 mg CR2-CD59 displayed significantly reduced liver injury and dramatically improved liver regeneration (FIGS. 23-25).

Prevention of Acute Liver Failure in Wild-Type Mice Following 90% PHx with CR2-CD59.

Massive liver resection often leads to liver failure and death and is a major limitation to therapeutic liver resection for patients with liver tumors. Using a mouse model of 90% PHx, we tested the ability of terminal complement inhibition to improve outcomes. Mice were subjected to 90% PHx, and then treated with 0.1 mg CR2-CD59, 0.08 mg CR2-Crry or NS by i.p. injection immediately post-surgery. In NS control mice, 90% PHx induced early, severe liver injury and dysfunction, demonstrated by high serum ALT levels (FIG. 26), extensive necrosis of hepatic parenchyma, severe microvesicular steatosis (FIG. 27), abolition of BrdU incorporation (FIG. 28), and 100% mortality within 3 days (FIG. 29). CR2-CD59 treatment resulted in reduced biochemical and histological evidence of liver injury as well as increased BrdU incorporation and significantly improved survival (FIGS. 26-29). Surprisingly, treatment with CR2-Crry had no therapeutic impact, with an injury profile not significantly different from NS-treated animals.

Aggravated Complement Activation is Involved in Liver Injury in a Model of Alcoholic Liver Disease (ALD).

The complement system is known to be activated in alcoholic liver disease (ALD), but its role in the pathogenesis of alcoholic liver injury remains obscure. Here we investigated the role of activation of complement in alcoholic liver injury. Wild-type mice and mice lacking factor B ($FB^{-/-}$), C3 ($C3^{-/-}$), or CD59 ($CD59^{-/-}$), were fed ethanol-containing diets. Mice were allowed free access to an ethanol-containing diet with increasing concentrations of ethanol as follows: 1% (v/v) ethanol for two days, 2% (v/v) ethanol for 2 days, 4% (v/v) ethanol for 7 days, and finally 5% (v/v) ethanol for a further 4 weeks), each pair-fed a control diets, and the effect of complement reconstitution and targeted complement inhibition was investigated. Ethanol-fed wild-type mice developed hepatic steatosis characterized by mild microvesicular and macrovesicular lipid accumulation and increased triglyceride content, increased serum ALT level (FIGS. 30-31). $FB^{-/-}$ and $C3^{-/-}$ mice on the ethanol diet did not develop steatosis, and only showed a slight increase in ALT levels. In contrast, $CD59^{-/-}$ mice on the ethanol-containing diet developed greater hepatic steatosis, increased levels of hepatic triglyceride and developed more severe hepatic injury compared to wild-type mice (FIGS. 30-31).

In a second set of experiments, the effect of targeted complement inhibitors on liver regeneration was examined in wild-type mice fed the same ethanol-containing diet and in control animals undergoing 70% PHx. An 0.08 μg dose of the targeted complement inhibitor CR2-Crry was administered immediately after surgery by i.p. injection, and hepatic regeneration was assessed by hematoxylin- and eosin-staining. Hepatic regeneration was significantly suppressed in steatotic liver in ethanol-fed wild-type mice as compared to pair-fed mice receiving a normal diet. Interestingly, targeted complement inhibition resulted in improved survival and a significantly enhanced proliferative response compared to control mice (FIG. 32).

Discussion

Identification of mechanisms that limit hepatic regeneration after toxic injury or PHx holds the key to expanding the limits of small-for-size liver transplantation and massive liver resection. Massive liver resection and small-for-size liver transplantation pose a clinical challenge due to increased susceptibility of the remnant/graft to ischemia reperfusion injury (IRI) and suppression of liver regeneration. Complement is implicated in both processes. In a mouse model of warm hepatic IRI, we have shown that CD59 deficiency results in extensive injury compared to wild-type mice. Treatment with CR2-CD59 significantly reduces liver injury in $CD59^{-/-}$ mice and wild-type mice following IRI, as shown by a decrease in ALT levels and histology scores.

Wild-type mice can tolerate 70% hepatectomy, and are capable of undergoing sufficient hepatic regeneration to recover completely from the resection. In contrast, liver regeneration was severely impaired in $CD59^{-/-}$ mice after 70% PHx, as shown by a significant increase in serum ALT levels, extensive necrosis of hepatic parenchyma, an increase in inflammatory cell infiltration, abolition of BrdU incorporation, and significantly increased deposition of C9. Reconstitution with CR2-CD59 significantly decreased parenchyma damage, increased liver regenerative responses and improved survival in $CD59^{-/-}$ mice after 70% PHx. Both CR2-Crry and CR2-CD59 treatment significantly reduced the injury induced by IRI procedure in wild-type mice. Like C3-deficient mice, wild-type mice treated with 0.25 mg CR2-Crry by i.p. injection after 70% PHx displayed impaired liver regeneration. However, a lower dose of 0.08 mg CR2-Crry significantly improved liver regeneration in wild-type mice after 70% PHx compared to NS controls. Surprisingly, however, wild-type mice treated with both 0.45 mg and 0.15 mg CR2-CD59 by i.p. injection following 70% PHx demonstrated significantly reduced liver injury and dramatically improved liver regeneration.

Finally, after 90% PHx, wild-type mice developed severe hepatic steatosis characterized by microvesicular lipid accumulation, increased triglyceride levels, marked increased in serum ALT levels, and severely impaired liver regeneration in liver remnants. In contrast, after 70% PHx, wild-type mice developed mild macrovesicular steatosis and only slight increased ALT levels. Interestingly, blockade of terminal complement (i.e., MAC assembly) with CR2-CD59 significantly increased survival and restored liver regeneration in wild-type mice following 90% PHx. In fact, liver remnants retrieved from CR2-CD59 treated wild-type mice in the first hours after surgery displayed increased expression of regeneration-promoting cytokines TNFα and IL-6, as well as increased STAT3 activation.

This data highlights a central role for terminal complement and MAC assembly in modulation of cell death-promoting mechanisms associated with massive hepatectomy, suggesting blockade of terminal complement and MAC assembly with the targeted complement inhibitor CR2-CD59 as a novel strategy to promote regeneration in the massively-injured liver.

Example 3

Toxicology Studies and Determination of a Human Equivalent Dose

The pharmaceutical compositions exemplified herein were administered to mice at doses ranging from approximately 3.2 mg/kg to approximately 20 mg/kg.

Further toxicological studies are performed in mice to determine the no observed adverse effect level—the highest dose level that does not produce a significant adverse effect—in mice, both sham operated and after varying degrees of PHx and toxic injury. Thus, groups of wild-type C57BL/6 mice are obtained from the Jackson Laboratory (Bar Harbor, Me.) or other commercial source. Mice are fed a pellet diet with free access to water and kept on a 12-hour light/dark cycle. Mice are used at 8-10 weeks old, weighing between 22.5 g-25 g. Mice are placed into groups of an appropriate number (i.e., n=5-10 or more), subjected to IRI, 70% PHx or IRI+70% PHx as described above, then treated with escalating doses of targeted complement inhibitor (e.g., CR2-CD59, CR2-Crry, or CR2-FH), ASP/C3adesArg antagonist, or ASP/C3adesArg receptor (C5L2) antagonist administered by the desired route (e.g., intra-peritoneal injection) immediately following surgery. After an appropriate period of time, mice are exsanguinated, toxicity assessed, and the highest dose level that does not produce a significant adverse effect, defined as impaired liver regeneration and increased hepatic injury assessed by measuring serum ALT, MPO, and BrdU incorporation, is determined. From that data, the no observed adverse effect level (NOAEL) is determined for mice. The mouse NOAEL is then converted to the human equivalent dose based on body surface area. See, e.g., Rick Ng, DRUGS: FROM DISCOVERY TO APPROVAL (2d ed., John Wiley & Sons, Hoboken, N.J.), at p. 158-161. The calculated human NOAEL is used as a starting point to determine appropriate dosing for toxicology and efficacy studies which are conducted in humans.

REFERENCES CITED

1. Helling, T. S. 2006. Liver failure following partial hepatectomy. *HPB (Oxford)* 8:165-174.
2. Helling, T. S., Dhar, A., Helling, T. S., Jr., Moore, B. T., and VanWay, C. W. 2004. Partial hepatectomy with or without endotoxin does not promote apoptosis in the rat liver. *J Surg Res* 116:1-10.
3. Clavien, P. A., Petrowsky, H., DeOliveira, M. L., and Graf, R. 2007. Strategies for safer liver surgery and partial liver transplantation. *N Engl J Med* 356:1545-1559.
4. Kadry, Z., Selzner, N., Selzner, M., and Clavien, P. A. 2004. Liver regeneration after adult living donor and deceased donor split-liver transplants. *Liver Transpl* 10:1078.
5. Dutkowski, P., Furrer, K., Tian, Y., Graf, R., and Clavien, P. A. 2006. Novel short-term hypothermic oxygenated perfusion (HOPE) system prevents injury in rat liver graft from non-heart beating donor. *Ann Surg* 244:968-976; discussion 976-967.
6. Humar, A., Kosari, K., Sielaff, T. D., Glessing, B., Gomes, M., Dietz, C., Rosen, G., Lake, J., and Payne, W. D. 2004. Liver regeneration after adult living donor and deceased donor split-liver transplants. *Liver Transpl* 10:374-378.
7. Dahm, F., Georgiev, P., and Clavien, P. A. 2005. Small-for-size syndrome after partial liver transplantation: definition, mechanisms of disease and clinical implications. *Am J Transplant* 5:2605-2610.
8. Chavez-Cartaya, R. E., DeSola, G. P., Wright, L., Jamieson, N. V., and White, D. J. 1995. Regulation of the complement cascade by soluble complement receptor type 1. Protective effect in experimental liver ischemia and reperfusion. *Transplantation* 59:1047-1052.
9. Lehmann, T. G., Koeppel, T. A., Munch, S., Heger, M., Kirschfink, M., Klar, E., and Post, S. 2001 Impact of inhibition of complement by sCR1 on hepatic microcirculation after warm ischemia. *Microvasc Res* 62:284-292.
10. Lehmann, T. G., Koeppel, T. A., Kirschfink, M., Gebhard, M. M., Herfarth, C., Otto, G., and Post, S. 1998. Complement inhibition by soluble complement receptor type 1 improves microcirculation after rat liver transplantation. *Transplantation* 66:717-722.
11. Arumugam, T. V., Woodruff, T. M., Stocks, S. Z., Proctor, L. M., Pollitt, S., Shiels, I. A., Reid, R. C., Fairlie, D. P., and Taylor, S. M. 2004. Protective effect of a human C5a receptor antagonist against hepatic ischaemia-reperfusion injury in rats. *J Hepatol* 40:934-941.
12. Fondevila, C., Shen, X. D., Tsuchihashi, S., Uchida, Y., Freitas, M. C., Ke, B., Busuttil, R. W., and Kupiec-Weglinski, J. W. 2008. The membrane attack complex (C5b-9) in liver cold ischemia and reperfusion injury. *Liver Transpl* 14:1133-1141.
13. Markiewski, M. M., Mastellos, D., Tudoran, R., DeAngelis, R. A., Strey, C. W., Franchini, S., Wetsel, R. A., Erdei, A., and Lambris, J. D. 2004. C3a and C3b activation products of the third component of complement (C3) are critical for normal liver recovery after toxic injury. *J Immunol* 173:747-754.
14. Strey, C. W., Markiewski, M., Mastellos, D., Tudoran, R., Spruce, L. A., Greenbaum, L. E., and Lambris, J. D. 2003. The proinflammatory mediators C3a and C5a are essential for liver regeneration. *J Exp Med* 198:913-923.
15. Mastellos, D., Papadimitriou, J. C., Franchini, S., Tsonis, P. A., and Lambris, J. D. 2001. A novel role of complement: mice deficient in the fifth component of complement (C5) exhibit impaired liver regeneration. *J Immunol* 166:2479-2486.
16. Clark, A., Weymann, A., Hartman, E., Turmelle, Y., Carroll, M., Thurman, J. M., Holers, V. M., Hourcade, D. E., and Rudnick, D. A. 2008. Evidence for non-traditional activation of complement factor C3 during murine liver regeneration. *Mol Immunol* 45:3125-3132.
17. Fausto, N. 2006. Involvement of the innate immune system in liver regeneration and injury. *J Hepatol* 45:347-349.
18. Atkinson, C., Song, H., Lu, B., Qiao, F., Burns, T. A., Holers, V. M., Tsokos, G. C., and Tomlinson, S. 2005. Targeted complement inhibition by C3d recognition ameliorates tissue injury without apparent increase in susceptibility to infection. *J Clin Invest* 115:2444-2453.
19. Van Harmelen, V., Reynisdottir, S., Cianflone, K., Degerman, E., Hoffstedt, J., Nilsell, K., Sniderman, A., and Arner, P. 1999. Mechanisms involved in the regulation of free fatty acid release from isolated human fat cells by acylation-stimulating protein and insulin. *J Biol Chem* 274:18243-18251.
20. Murray, I., Havel, P. J., Sniderman, A. D., and Cianflone, K. 2000. Reduced body weight, adipose tissue, and leptin levels despite increased energy intake in female mice lacking acylation-stimulating protein. *Endocrinology* 141:1041-1049.
21. Murray, I., Sniderman, A. D., and Cianflone, K. 1999. Mice lacking acylation stimulating protein (ASP) have delayed postprandial triglyceride clearance. *J Lipid Res* 40:1671-1676.
22. Xia, Z., Sniderman, A. D., and Cianflone, K. 2002. Acylation-stimulating protein (ASP) deficiency induces obesity resistance and increased energy expenditure in ob/ob mice. *J Biol Chem* 277:45874-45879.
23. Kalant, D., MacLaren, R., Cui, W., Samanta, R., Monk, P. N., Laporte, S. A., and Cianflone, K. 2005. C5L2 is a functional receptor for acylation-stimulating protein. *J Biol Chem* 280:23936-23944.
24. Kalant, D., Cain, S. A., Maslowska, M., Sniderman, A. D., Cianflone, K., and Monk, P. N. 2003. The chemoattractant receptor-like protein C5L2 binds the C3a des-Arg77/acylation-stimulating protein. *J Biol Chem* 278:11123-11129.
25. Paglialunga, S., Schrauwen, P., Roy, C., Moonen-Kornips, E., Lu, H., Hesselink, M. K., Deshaies, Y., Richard, D., and Cianflone, K. 2007. Reduced adipose tissue triglyceride synthesis and increased muscle fatty acid oxidation in C5L2 knockout mice. *J Endocrinol* 194:293-304.
26. Maslowska, M., Wang, H. W., and Cianflone, K. 2005. Novel roles for acylation stimulating protein/C3adesArg: a review of recent in vitro and in vivo evidence. *Vitam Horm* 70:309-332.

27. Jin, X., Zimmers, T. A., Perez, E. A., Pierce, R. H., Zhang, Z., and Koniaris, L. G. 2006. Paradoxical effects of short- and long-term interleukin-6 exposure on liver injury and repair. *Hepatology* 43:474-484.
28. Wullaert, A., van Loo, G., Heyninck, K., and Beyaert, R. 2007. Hepatic tumor necrosis factor signaling and nuclear factor-kappaB: effects on liver homeostasis and beyond. *Endocr Rev* 28:365-386.
29. Teoh, N., Field, J., Sutton, J., and Farrell, G. 2004. Dual role of tumor necrosis factor-alpha in hepatic ischemia-reperfusion injury: studies in tumor necrosis factor-alpha gene knockout mice. *Hepatology* 39:412-421.
30. Jackson, L. N., Larson, S. D., Silva, S. R., Rychahou, P. G., Chen, L. A., Qiu, S., Rajaraman, S., and Evers, B. M. 2008. PI3K/Akt activation is critical for early hepatic regeneration after partial hepatectomy. *Am J Physiol Gastrointest Liver Physiol* 294:G1401-1410.
31. Satoh, S., Tanaka, A., Hatano, E., Inomoto, T., Iwata, S., Kitai, T., Shinohara, H., Tsunekawa, S., Chance, B., and Yamaoka, Y. 1996. Energy metabolism and regeneration in transgenic mouse liver expressing creatine kinase after major hepatectomy. *Gastroenterology* 110:1166-1174.
32. Crumm, S., Cofan, M., Juskeviciute, E., and Hoek, J. B. 2008. Adenine nucleotide changes in the remnant liver: An early signal for regeneration after partial hepatectomy. *Hepatology* 48:898-908.
33. Jin, X., Zhang, Z., Beer-Stolz, D., Zimmers, T. A., and Koniaris, L. G. 2007. Interleukin-6 inhibits oxidative injury and necrosis after extreme liver resection. *Hepatology* 46:802-812.
34. Scola, A. M., Johswich, K. O., Morgan, B. P., Klos, A., and Monk, P. N. 2009. The human complement fragment receptor, C5L2, is a recycling decoy receptor. *Mol Immunol* 46:1149-1162.
35. Johswich, K., Martin, M., Thalmann, J., Rheinheimer, C., Monk, P. N., and Klos, A. 2006. Ligand specificity of the anaphylatoxin C5L2 receptor and its regulation on myeloid and epithelial cell lines. *J Biol Chem* 281:39088-39095.
36. Kildsgaard, J., Zsigmond, E., Chan, L., and Wetsel, R. A. 1999. A critical evaluation of the putative role of C3adesArg (ASP) in lipid metabolism and hyperapobetalipoproteinemia. *Mol Immunol* 36:869-876.
37. MacLaren, R., Cui, W., and Cianflone, K. 2008. Adipokines and the immune system: an adipocentric view. *Adv Exp Med Biol* 632:1-21.
38. Arumugam, T. V., Magnus, T., Woodruff, T. M., Proctor, L. M., Shiels, I. A., and Taylor, S. M. 2006. Complement mediators in ischemia-reperfusion injury. *Clin Chim Acta* 374:33-45.
39. Tian, Y., Jochum, W., Georgiev, P., Moritz, W., Graf, R., and Clavien, P. A. 2006. Kupffer cell-dependent TNF-alpha signaling mediates injury in the arterialized small-for-size liver transplantation in the mouse. *Proc Natl Acad Sci USA* 103:4598-4603.
40. Taub, R. 2004. Liver regeneration: from myth to mechanism. *Nat Rev Mol Cell Biol* 5:836-847.
41. Iimuro, Y., Nishiura, T., Hellerbrand, C., Behrns, K. E., Schoonhoven, R., Grisham, J. W., and Brenner, D. A. 1998. NFkappaB prevents apoptosis and liver dysfunction during liver regeneration. *J Clin Invest* 101:802-811.
42. Camargo, C. A., Jr., Madden, J. F., Gao, W., Selvan, R. S., and Clavien, P. A. 1997. Interleukin-6 protects liver against warm ischemia/reperfusion injury and promotes hepatocyte proliferation in the rodent. *Hepatology* 26:1513-1520.
43. He, S. Q., Zhang, Y. H., Venugopal, S. K., Dicus, C. W., Perez, R. V., Ramsamooj, R., Nantz, M. H., Zern, M. A., and Wu, J. 2006. Delivery of antioxidative enzyme genes protects against ischemia/reperfusion-induced liver injury in mice. *Liver Transpl* 12:1869-1879.
44. Duranski, M. R., Greer, J. J., Dejam, A., Jaganmohan, S., Hogg, N., Langston, W., Patel, R. P., Yet, S. F., Wang, X., Kevil, C. G., et al. 2005. Cytoprotective effects of nitrite during in vivo ischemia-reperfusion of the heart and liver. *J Clin Invest* 115:1232-1240.
45. Greene, A. K., and Puder, M. 2003. Partial hepatectomy in the mouse: technique and perioperative management. *J Invest Surg* 16:99-102.
46. Higgins, G. M., and Anderson, R. M. 1931. Experimental pathology of the liver. 1. Restoration of the liver of the white rat following partial surgical removal. *Arch. Pathol.* 12:186-202.
47. Harada, N., Okajima, K., Kushimoto, S., Isobe, H., and Tanaka, K. 1999. Antithrombin reduces ischemia/reperfusion injury of rat liver by increasing the hepatic level of prostacyclin. *Blood* 93:157-164.
48. Atkinson, C., Zhu, H., Qiao, F., Varela, J. C., Yu, J., Song, H., Kindy, M. S., and Tomlinson, S. 2006. Complement-dependent P-selectin expression and injury following ischemic stroke. *J Immunol* 177:7266-7274.
49. Yamaji, K., Ochiai, Y., Ohnishi, K., Yawata, A., Chikuma, T., and Hojo, H. 2008. Up-regulation of hepatic heme oxygenase-1 expression by locally induced interleukin-6 in rats administered carbon tetrachloride intraperitoneally. *Toxicol Lett* 179:124-129.
50. Murray, I., Parker, R. A., Kirchgessner, T. G., Tran, J., Zhang, Z. J., Westerlund, J., and Cianflone, K. 1997. Functional bioactive recombinant acylation stimulating protein is distinct from C3a anaphylatoxin. *J Lipid Res* 38:2492-2501.
51. Sigala, F., Kostopanagiotou, G., Andreadou, I., Kavatzas, N., Felekouras, E., Sigalas, P., Bastounis, E., and Papalambros, E. 2004. Histological and lipid peroxidation changes after administration of 2-acetylaminofluorene in a rat liver injury model following selective periportal and pericentral damage. *Toxicology* 196:155-163.
52. Fiorini, R. N., Kirtz, J., Periyasamy, B., Evans, Z., Haines, J. K., Cheng, G., Polito, C., Rodwell, D., Shafizadeh, S. F., Zhou, X., et al. 2004. Development of an unbiased method for the estimation of liver steatosis. *Clin Transplant* 18:700-706.
53. Selzner, M., and Clavien, P. A. 2000. Failure of regeneration of the steatotic rat liver: disruption at two different levels in the regeneration pathway. *Hepatology* 31:35-42.
54. Zhong, Z., Theruvath, T. P., Currin, R. T., Waldmeier, P. C., and Lemasters, J. J. 2007. NIM811, a mitochondrial permeability transition inhibitor, prevents mitochondrial depolarization in small-for-size rat liver grafts. *Am J Transplant* 7:1103-1111.
55. Fabrikant, J. I. 1968. The kinetics of cellular proliferation in regenerating liver. *J Cell Biol* 36:551-565.
56. La Flamme, A. C., MacDonald, A. S., Huxtable, C. R., Carroll, M., and Pearce, E. J. 2003. Lack of C3 affects Th2 response development and the sequelae of chemotherapy in schistosomiasis. *J Immunol* 170:470-476.
57. Habermann, J. K., Roblick U. J., Luke, B. T., Prieto, D. A., Finlay, W. J., Podust, V. N., Roman, J. M., Oevermann, E., Schiedeck, T., Homann, N., Duchrow, M., Conrads, T. P., Veenstra, T. D., Burt, S. K., Bruch, H. P., Auer, G., and Ried, T., "Increased serum levels of complement C3a anaphylatoxin indicate the presence of colorectal tumors," *Gastroenterol.* 131(4):1020-1029 (2006).

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

We claim:

1. A method of stimulating liver regeneration after partial hepatectomy in an individual in need thereof, the method comprising administering to the individual a complement inhibitor that inhibits complement activation at the C3 level,
    wherein the complement inhibitor is administered in a dose therapeutically effective to increase IL-6 levels in the priming phase in regeneration but not sufficient to substantially deplete cell surface C3d deposition in the individual; and
    wherein the complement inhibitor is a complement receptor 2 (CR2)-factor H (FH) molecule comprising:
    i) a CR2 portion comprising at least the first two N-terminal short consensus repeat (SCR) domains of human CR2, and
    ii) a FH portion comprising at least the first four N-terminal SCR domains of human FH.

2. The method of claim 1, wherein the individual is a mammal.

3. The method of claim 2, wherein the mammal is a human.

4. The method of claim 1, wherein the individual has undergone a 70% partial hepatectomy.

5. The method of claim 1, wherein the individual has undergone a liver transplant.

6. The method of claim 5, wherein the liver transplant is a small-for-size liver transplant.

7. The method of claim 1, wherein the individual is a live liver donor.

8. The method of claim 1, wherein the CR2 portion comprises a full-length human CR2 (SEQ ID NO:1).

9. The method of claim 1, wherein the CR2 portion comprises the amino acid sequence of SEQ ID NO:2.

10. The method of claim 1, wherein the CR2 portion comprises at least the first four N-terminal SCR domains of human CR2 (amino acids 23-271 of SEQ ID NO:1).

11. The method of claim 1, wherein the FH portion comprises at least a full-length human FH (SEQ ID NO:5).

12. The method of claim 1, wherein the FH portion comprises amino acids 21-262 of SEQ ID NO:5.

13. The method of claim 1, wherein the FH portion comprises at least the first five N-terminal SCR domains of human FH (amino acids 21-320 of SEQ ID NO:5).

14. The method of claim 1, wherein the CR2 portion comprises SEQ ID NO:2 and the FH portion comprises at least amino acids 21 to 262 of SEQ ID NO:5.

15. The method of claim 1, wherein the CR2 portion comprises at least the first two N-terminal SCR domains of CR2 and the FH portion comprises at least the first five N-terminal SCR domains of FH.

16. The method of claim 1, wherein the CR2 portion comprises SEQ ID NO:2 and the FH portion comprises at least amino acids 21 to 320 of SEQ ID NO:5.

17. The method of claim 1, wherein the CR2-FH molecule is a fusion protein.

18. The method of claim 1, wherein said dose is therapeutically effective to reduce hepatic ischemia reperfusion injury, decrease serum alanine aminotransferase (ALT) levels and histological scores, decrease myeloperoxidase (MPO) levels, increase BrdU incorporation and mitotic index, restore liver weight, decrease mortality, activate STAT3 and PI3K/Akt, restore hepatic ATP levels, and/or protect against oxidative stress.

19. The method of claim 1, wherein said dose is between about 3.2 mg/kg to about 20 mg/kg.

* * * * *